(12) United States Patent
Weinstein et al.

(10) Patent No.: US 12,310,752 B2
(45) Date of Patent: May 27, 2025

(54) SYSTEMS FOR MEASURING PATIENT PHYSIOLOGIC PARAMETERS

(71) Applicant: UCHU Biosensors, Inc., Cambridge, MA (US)

(72) Inventors: Daniel Weinstein, Lincoln, MA (US); Noah William Hill, Tacoma, WA (US); William Gorman, South Hamilton, MA (US); Saam Bozorg, West Hartford, CT (US); J. Christopher Flaherty, Auburndale, FL (US)

(73) Assignee: UCHU Biosensors, Inc., Cambridge, MA (US)

( * ) Notice: Subject to any disclaimer, the term of this patent is extended or adjusted under 35 U.S.C. 154(b) by 373 days.

(21) Appl. No.: 17/815,834

(22) Filed: Jul. 25, 2022

(65) Prior Publication Data
US 2023/0082672 A1    Mar. 16, 2023

Related U.S. Application Data

(63) Continuation of application No. PCT/US2021/015899, filed on Jan. 29, 2021.
(Continued)

(51) Int. Cl.
*A61B 5/145* (2006.01)
*A61B 5/00* (2006.01)

(52) U.S. Cl.
CPC .......... *A61B 5/682* (2013.01); *A61B 2562/12* (2013.01); *A61B 2562/166* (2013.01)

(58) Field of Classification Search
CPC ....... A61C 7/08; A61B 5/682; A61B 2562/12; A61B 2562/166
See application file for complete search history.

(56) References Cited

U.S. PATENT DOCUMENTS

| 4,319,578 A | 3/1982 | Enger |
|---|---|---|
| 4,629,424 A | 12/1986 | Lauks et al. |

(Continued)

FOREIGN PATENT DOCUMENTS

| CA | 2239397 A1 | 12/1998 |
|---|---|---|
| CN | 202311935 U | 7/2012 |

(Continued)

OTHER PUBLICATIONS

Arakawa et al., "Mouthguard biosensor with telemetry system for monitoring of saliva glucose: A novel cavitas sensor," Biosensors and Bioelectronics, 84:106-111 (2016).
(Continued)

*Primary Examiner* — Ralph A Lewis
(74) *Attorney, Agent, or Firm* — Dana M. Gordon; Stephen J. Kenny; Foley Hoag LLP

(57) ABSTRACT

A method of forming an oral device to measure biological variables includes providing a mold configured to impart a contour of an oral retainer sized to extend about a plurality of teeth. The method includes removing the first layer of the retainer from the mold. The method includes attaching at least one sensor to the retainer, the sensor having a profile and defining a boundary edge. The method includes trimming to form a lip of the first layer of material extending beyond the boundary edge of the at least one sensor component. The method includes attaching the first layer of the retainer and at least one sensor component to the mold, forming a second layer of the retainer with the mold, wherein the first layer of retainer retains the mold contour, and wherein the at least one sensor component is disposed between the first and second layer.

20 Claims, 90 Drawing Sheets

Related U.S. Application Data

(60) Provisional application No. 62/967,326, filed on Jan. 29, 2020, provisional application No. 63/041,212, filed on Jun. 19, 2020, provisional application No. 63/112,091, filed on Nov. 10, 2020.

(56) References Cited

U.S. PATENT DOCUMENTS

| | | | |
|---|---|---|---|
| 6,239,705 | B1 | 5/2001 | Glen |
| 6,607,387 | B2 | 8/2003 | Mault |
| 11,638,535 | B2* | 5/2023 | Weinstein ............ G01N 27/414 433/27 |
| 2004/0158194 | A1 | 8/2004 | Wolff et al. |
| 2007/0083094 | A1 | 4/2007 | Colburn et al. |
| 2007/0106138 | A1 | 5/2007 | Beiski et al. |
| 2007/0282226 | A1 | 12/2007 | Longley |
| 2008/0182218 | A1 | 7/2008 | Chen et al. |
| 2011/0172826 | A1 | 7/2011 | Amodei et al. |
| 2011/0184663 | A1 | 7/2011 | Mack et al. |
| 2012/0148971 | A1 | 6/2012 | Yamamoto et al. |
| 2013/0109932 | A1 | 5/2013 | Saadat et al. |
| 2014/0210640 | A1 | 7/2014 | Rahman et al. |
| 2015/0127377 | A1 | 5/2015 | Hashemian |
| 2015/0170504 | A1 | 6/2015 | Jooste |
| 2016/0015321 | A1 | 1/2016 | Hashemian |
| 2016/0338626 | A1 | 11/2016 | Wang et al. |
| 2016/0367188 | A1 | 12/2016 | Malik et al. |
| 2017/0056131 | A1 | 3/2017 | Alauddin et al. |
| 2017/0347953 | A1 | 12/2017 | Suri et al. |
| 2018/0000563 | A1* | 1/2018 | Shanjani ................ H04B 5/70 |
| 2018/0368961 | A1 | 12/2018 | Shanjani et al. |
| 2019/0223751 | A1* | 7/2019 | Weinstein .............. A61B 5/746 |
| 2020/0093436 | A1 | 3/2020 | Lee |
| 2023/0030704 | A1* | 2/2023 | Weinstein .............. A61B 5/682 |
| 2023/0082672 | A1* | 3/2023 | Weinstein .............. A61B 5/682 433/6 |
| 2024/0057886 | A1* | 2/2024 | Weinstein .............. G16H 40/63 |

FOREIGN PATENT DOCUMENTS

| | | |
|---|---|---|
| EP | 3097411 A1 | 11/2016 |
| JP | 2007/064796 A | 3/2007 |
| WO | WO-2005/115225 A2 | 12/2005 |
| WO | WO-2011/117357 A2 | 9/2011 |
| WO | WO-2017/218947 A1 | 12/2017 |
| WO | WO-2021/155285 A1 | 8/2021 |

OTHER PUBLICATIONS

Brierley et al., "How Accurate are TheraMon® Microsensors at Measuring Intraoral Wear-time? Recorded vs. Actual Wear Times in Five Volunteers," Journal of Orthodontics, 44(4):241-248 (2017).

Choi, "Continuous measurement of intra-oral pH and temperature: development, validation of an appliance and a pilot study," 42(8):563-570 (2015).

Davidson, "In-Mouth Measurement of pH and Conductivity during Eating," J Agric. Food Chem., 46(12): 5210-5214 (1998).

Extended European Search Report for EP Application No. 19740972.5 dated Sep. 30, 2021.

Farella et al., "Simultaneous wireless assessment of intra-oral pH and temperature," Journal of Dentistry, 51:49-55 (2016).

Fujii et al., "Roughness and pH changes of enamel surface induced by soft drinks in vitroapplications of stylus profilometry, focus variation 3D scanning microscopy and micro pH sensor," Dental Materials Journal, 30(3):404-410 (2011).

Gou et al., "Carbon Nanotube Chemiresistor for Wireless pH Sensing," Scientific Reports, 4(4468):1-6 (2014).

International Search Report and Written Opinion for International Application No. PCT/US2021/015899 dated Jun. 3, 2021.

International Search Report and Written Opinion for International Application No. PCT/US19/14630 dated Jun. 25, 2019.

Kitasako et al., "The clinical application of surface pH measurements to longitudinally assess white spot enamel lesions," Journal of Dentistry, 38(7):584-590 (2010).

Kolahi et al., "Bluetooth technology for prevention of dental caries," Medical Hypotheses, 73:1067-1068 (2009).

Ma et al., "A wireless system for continuous in-mouth pH monitoring," 2017 IEEE Biomedical Circuits and Systems Conference (BioCAS), Oct. 19-21, 2017.

Machacek, "'Tasting device monitors sodium intake in hypertension patients,'" retrieved Mar. 13, 2019 from https://phys.org/news/2016-01-device-sodium-intake-hypertension-patients.html (2016).

Mahendran, "Bluetoolh for While Tooth," Journal of Operative Dentistry and Endodontics, 2(2):61-64 (2017).

Mannoor et al., "Graphene-based wireless bacteria detection on tooth enamel," Nature Communications, 3(763):1-9 (2012).

Mayanagi et al., "pH Response and Tooth Surface Solubility at the Tooth/Bacteria Interface," Caries Research, 51(2):160-166 (2017).

Moritsuka et al., "Quantitative assessment for stimulated saliva flow rate and buffering capacity in relation to different ages," Journal of Dentistry, 34(9):716-720 (2006).

National Institutes of Health, Fact Sheet—Salivary Diagnostics, National Institutes of Health Updated Oct. 2010, pp. 1-2.

Potyrailo et al., Battery-free radio frequency identification (RFID) sensors for food quality and safety, J Agric Food Chem., 60(35):8535-8543 (2012).

Potyrailo et al., "Passive multivariable RFID pH sensors," 2011 IEEE International Conference on RFID-Technologies and Applications, Sep. 15-16, 2011.

Tsuruzoe et al., "Development of the pH measurement sensor to be mounted on the oral measurement device," 2016 International Symposium on Micro-NanoMechatronics and Human Science (MHS), Nov. 28-30, 2016.

Yamada et al., "A Microftuidic pH Measurement Device with a Flowing Liquid Junction," Sensors, 17(7):1563 (2017).

* cited by examiner

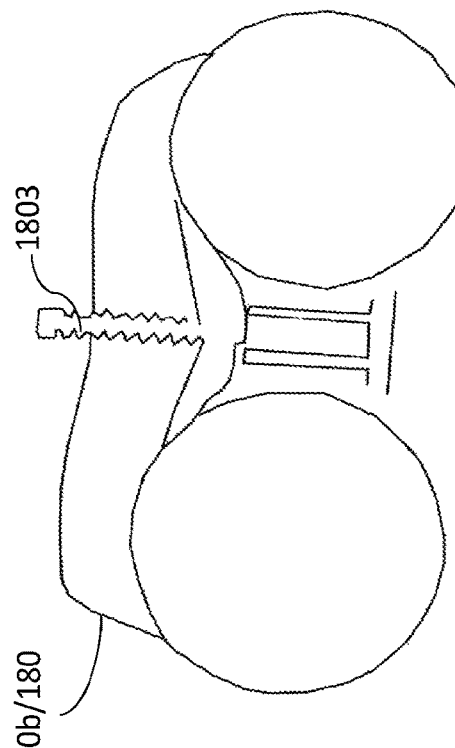
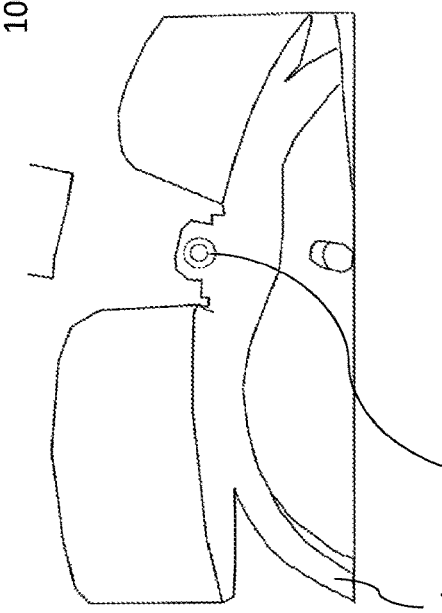
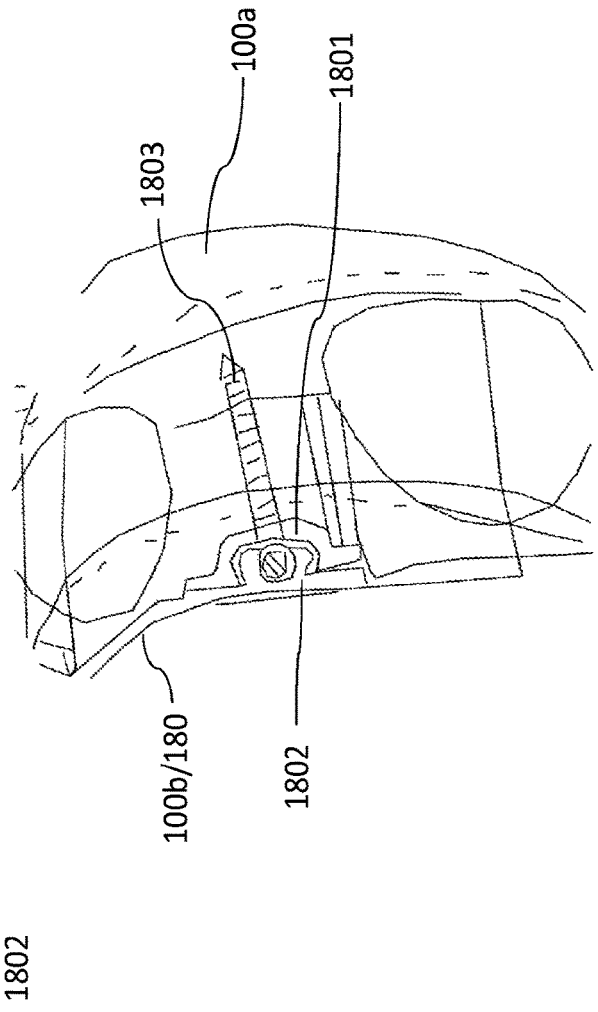
Fig. 15A
Fig. 15B
Fig. 15C 1801　　　1802
Fig. 16A 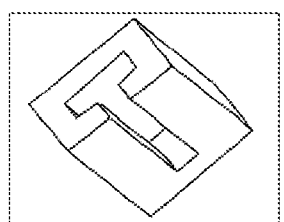 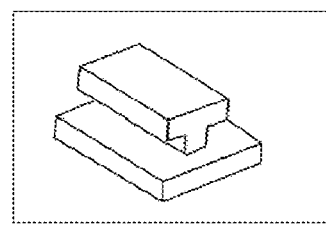 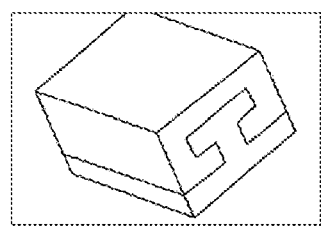
Fig. 16B 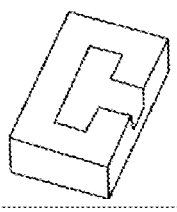 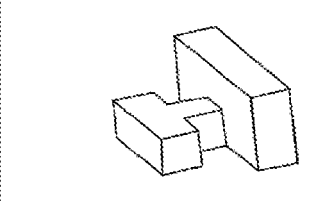 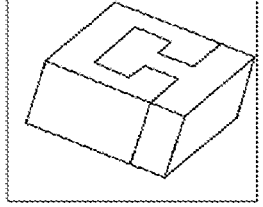
Fig. 16C 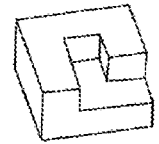 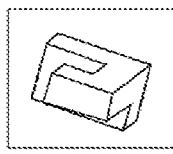 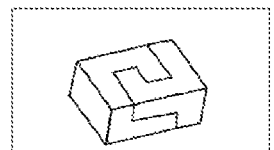
Fig. 16D 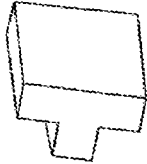 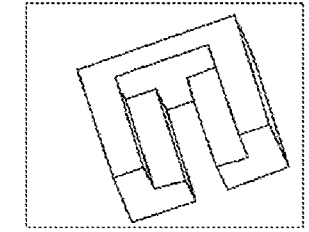 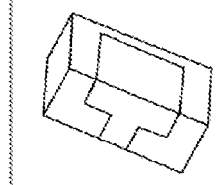
Fig. 16E 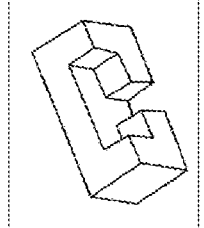 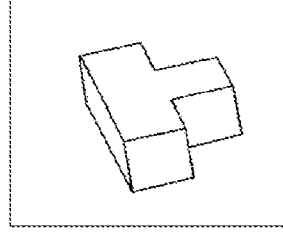 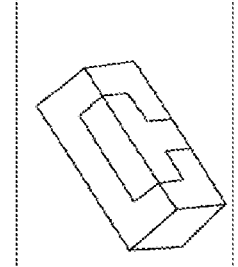
Fig. 16F 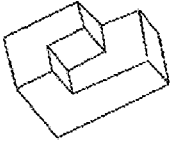 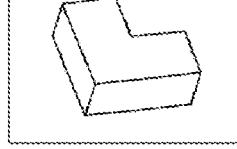 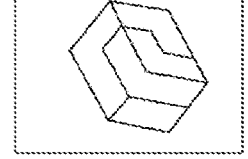

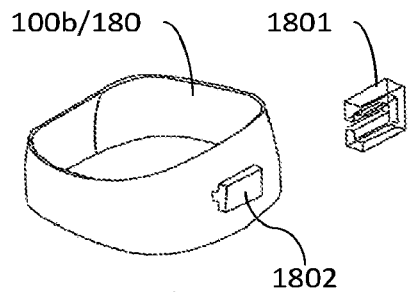
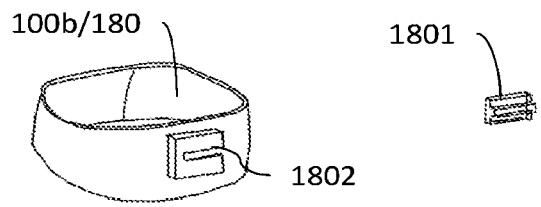
Fig. 17A Fig. 17B
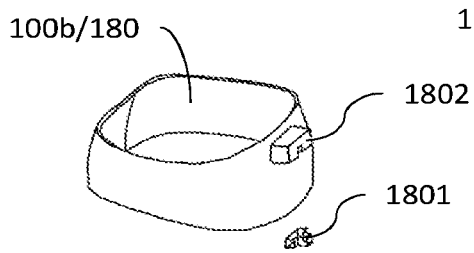
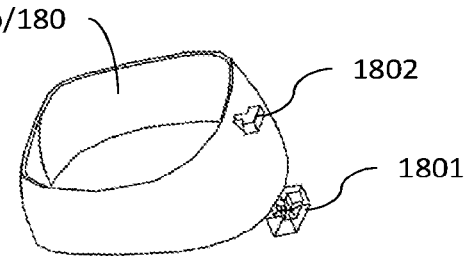
Fig. 17C Fig. 17D
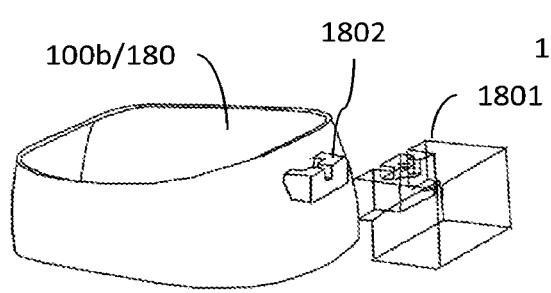
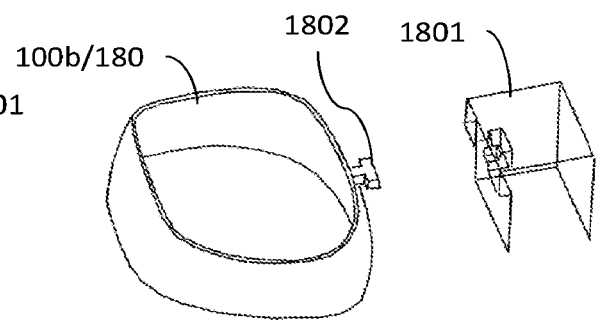
Fig. 17E Fig. 17F
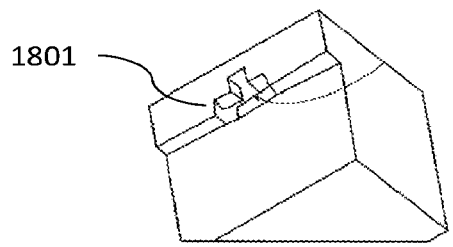
Fig. 17G

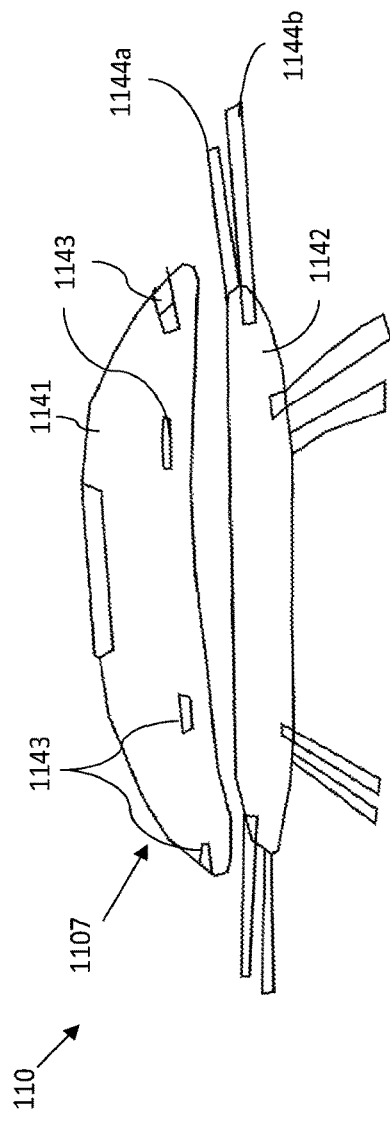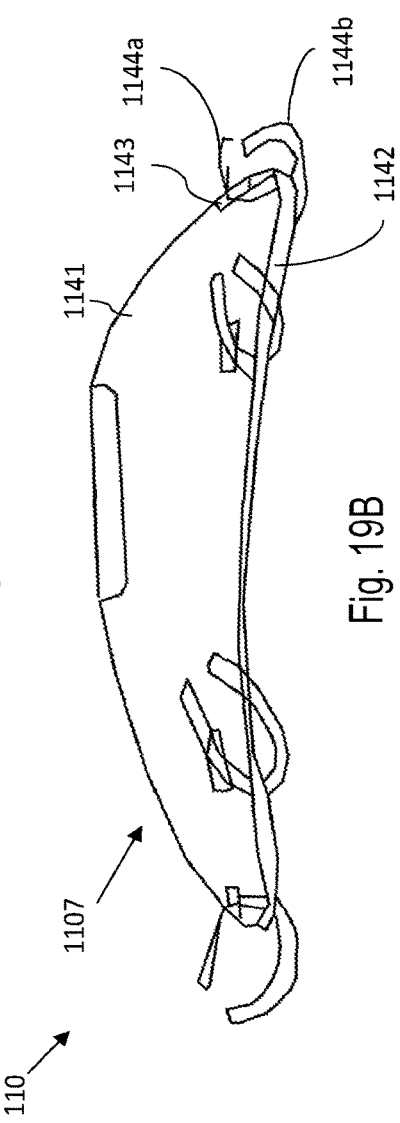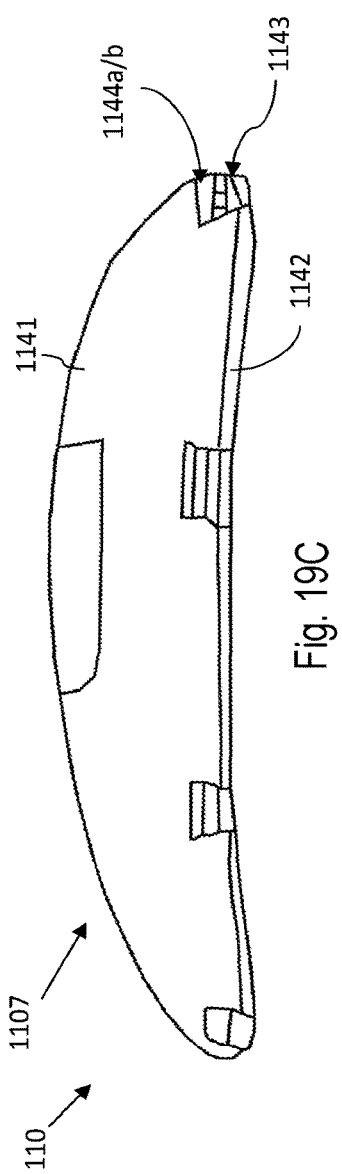

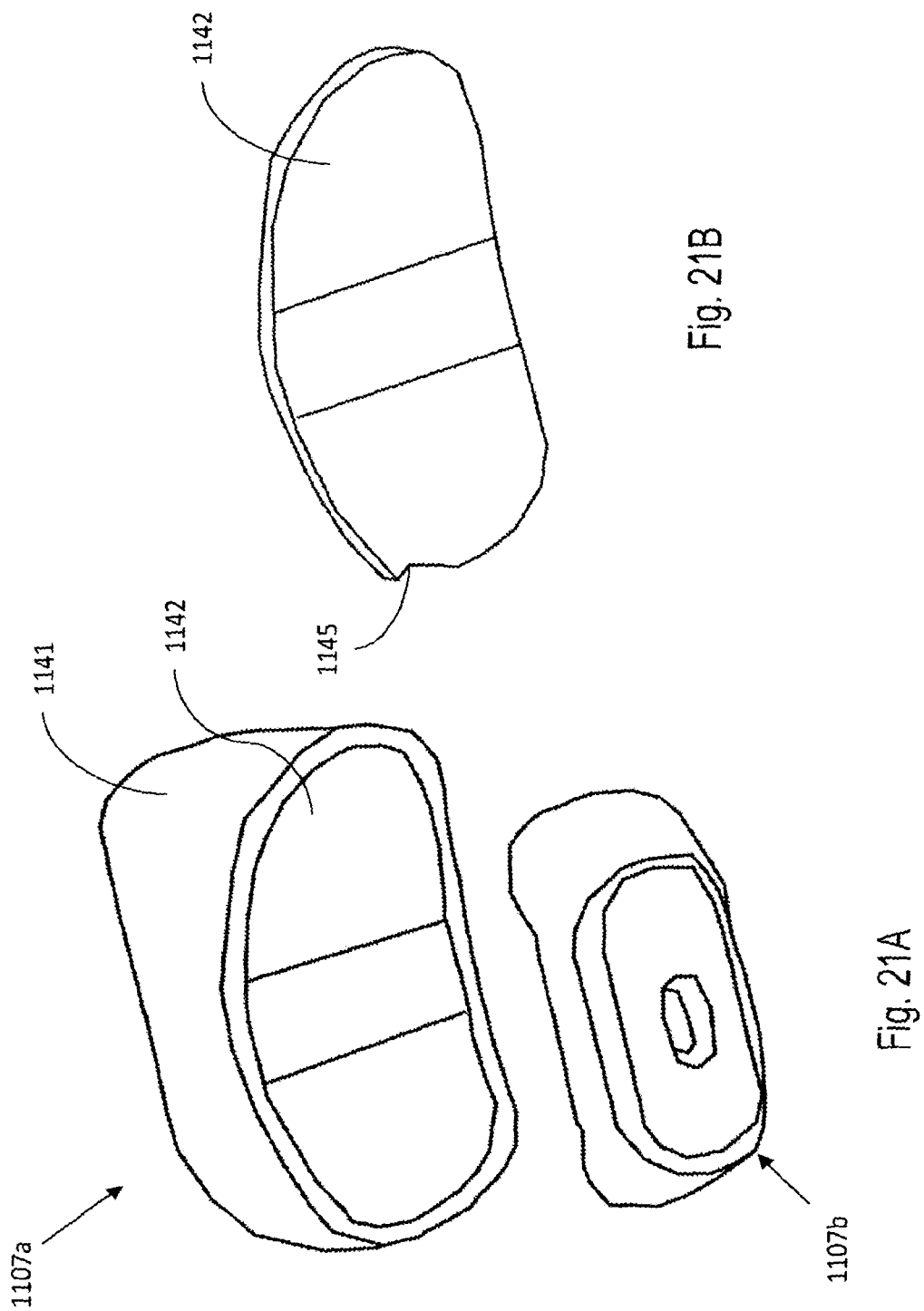

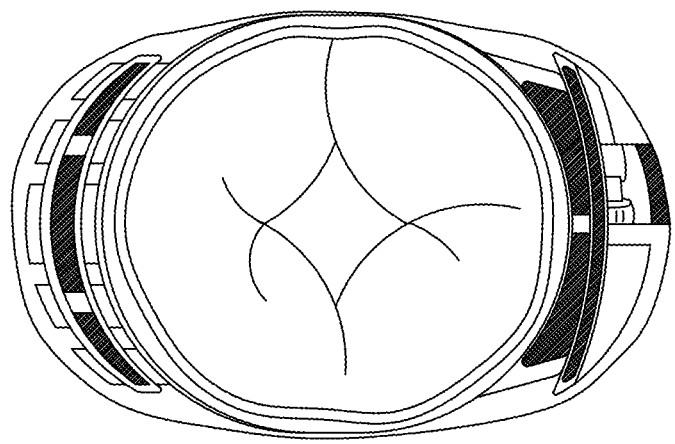
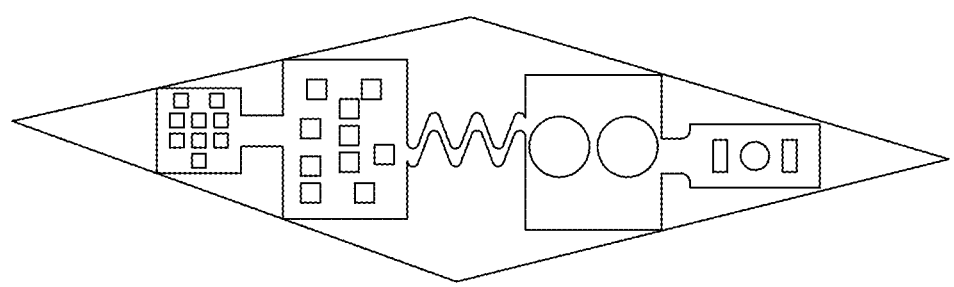
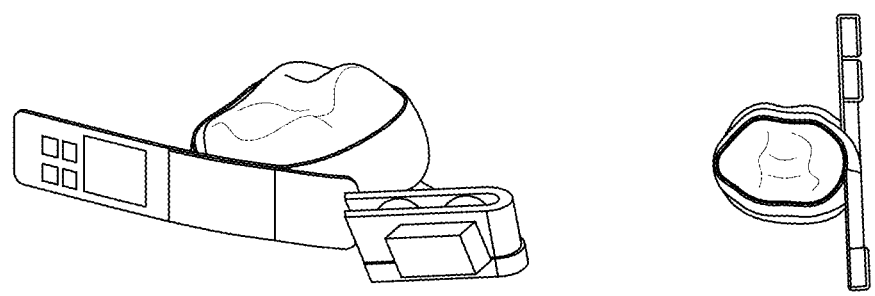
FIG. 22A

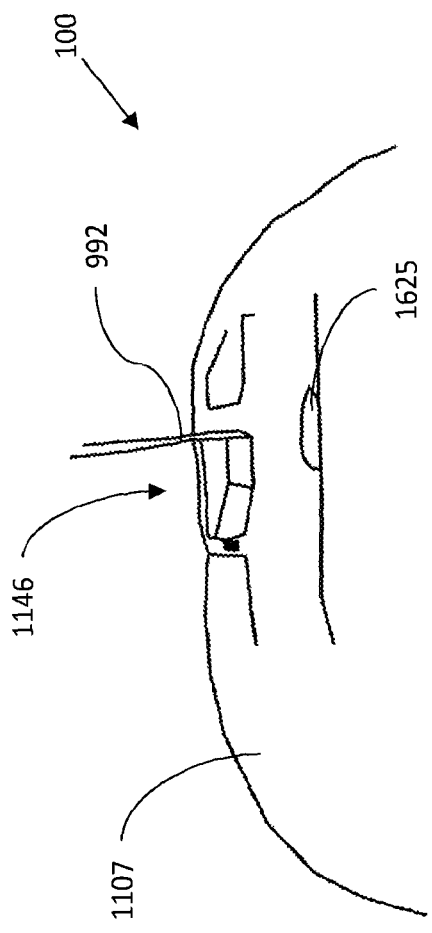
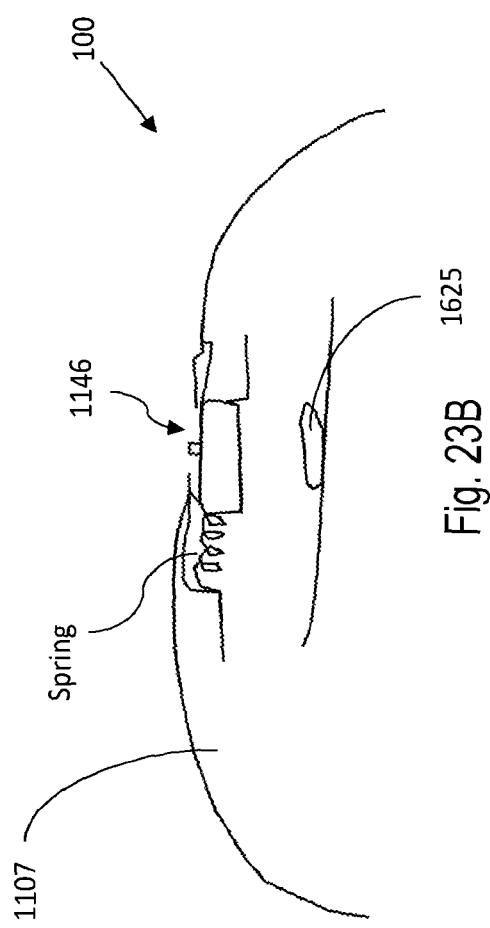

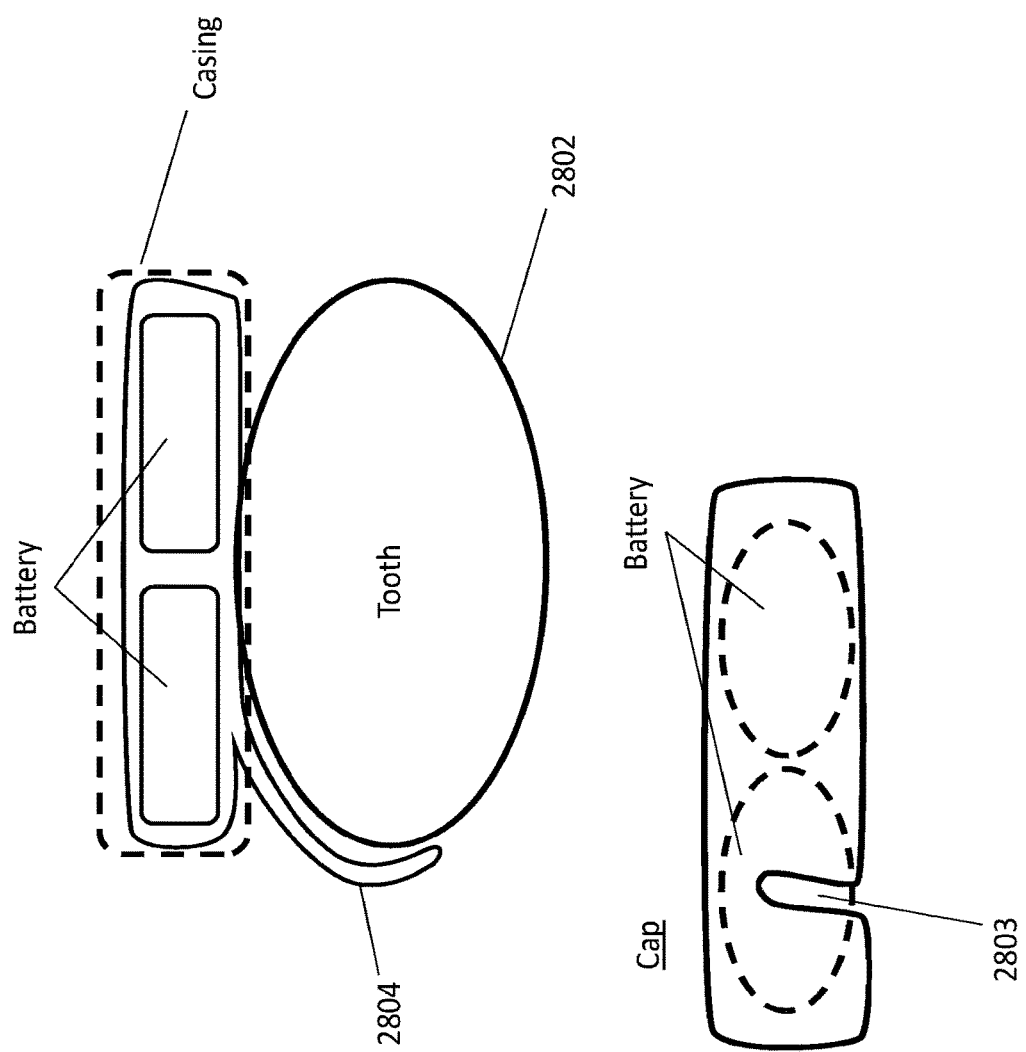

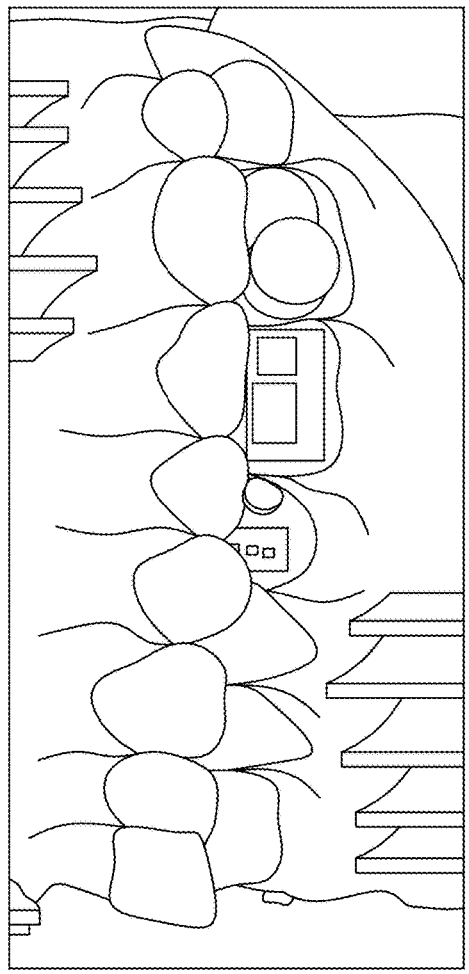
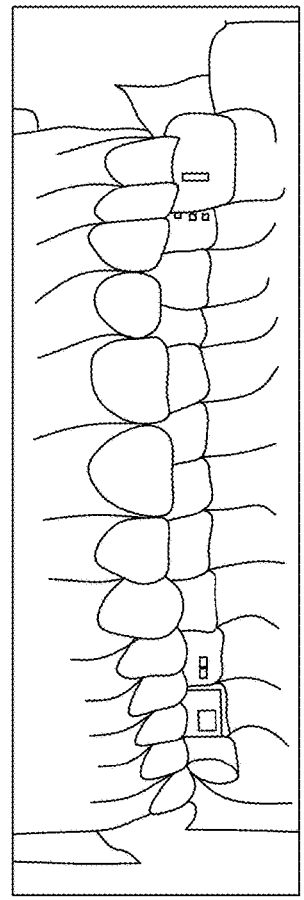
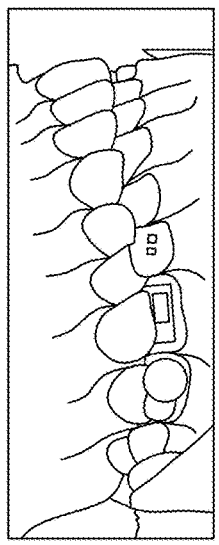
FIG. 49A
FIG. 49B
FIG. 49C

SYSTEMS FOR MEASURING PATIENT PHYSIOLOGIC PARAMETERS

CROSS-REFERENCE TO RELATED APPLICATIONS

This application is a Continuation of and claims the benefit of PCT Patent Application PCT/US21/15899, filed on Jan. 29, 2021, which claims the benefit of U.S. Provisional Patent Application No. 62/967,326, filed on Jan. 29, 2020, U.S. Provisional Patent Application No. 63/041,212, filed on Jun. 19, 2020, and U.S. Provisional Patent Application No. 63/112,091, filed on Nov. 10, 2020, each of which is hereby incorporated by reference in its entirety.

BACKGROUND

Embodiments of the present disclosure generally relate to electronic devices for use within the oral cavity to measure biological or chemical variables, including pH, temperature or analyte concentrations, such as to wirelessly transmit the measurements to a separate device.

BRIEF SUMMARY

Apparatuses, systems, and methods are provided for measuring biological or chemical variables within the oral cavity of a user. In various embodiments, an apparatus includes a band configured to wrap around a perimeter of a tooth, a processor disposed on the band, a sensor assembly disposed on the band and coupled to the processor, a transceiver disposed on the band and coupled to the processor, and a power supply disposed on the band and coupled to the processor, the sensor assembly and the transceiver. The sensor assembly includes one or more sensing elements for measuring a physiologic parameter of a patient.

In various embodiments, a system for measuring a physiologic parameter of a patient includes the apparatus and an external device for receiving patient data from the transceiver of the apparatus.

In various embodiments, a method of measuring one or more analyte within a mouth of a user includes providing the system for measuring a physiologic parameter of a patient. The apparatus is releasably attached to a tooth of the user. One or more measurements of the one or more analyte is recorded via the sensor. While the external device is in communication proximity with the apparatus, the one or more measurements of the one or more analyte is received at the external device.

In various embodiments, a method of forming an oral device to measure biological variables includes providing a mold. The mold is configured to impart a contour of an oral retainer sized to extend about a plurality of teeth. A first layer of a retainer is formed with the mold. The first layer of retainer retains the mold contour. The first layer of the retainer is removed from the mold. At least one sensor component is attached to the first layer of the retainer. The at least one sensor component has a profile and defines a boundary edge. The first layer of the retainer is trimmed at a location(s) spaced from the boundary edge of the at least one sensor component to form a lip of the first layer of material extending beyond the boundary edge of the at least one sensor component. The first layer of the retainer and at least one sensor component are attached to the mold. A second layer of the retainer is formed with the mold. The first layer of retainer retains the mold contour. The at least one sensor component is disposed between the first and second layer.

BRIEF DESCRIPTION OF THE DRAWINGS

FIGS. 15A-15C illustrate various views of an intraoral sensor according to embodiments of the present disclosure.

FIGS. 16A-16F illustrate various perspective views of a first connector and a second connector according to embodiments of the present disclosure.

FIGS. 17A-17G illustrate various perspective views of a first connector and a second connector according to embodiments of the present disclosure.

FIGS. 19A-19C illustrate steps of a method of manufacturing a sensor assembly according to embodiments of the present disclosure.

FIGS. 21A-21B illustrate perspective views of a sensor device according to embodiments of the present disclosure.

FIGS. 22A-22C illustrate schematic views of a sensor device attached to a tooth according to embodiments of the present disclosure.

FIGS. 23A-23B illustrate side views of a sensor device with a spring-loaded housing closing feature according to embodiments of the present disclosure.

FIG. 28 illustrate a slit in a PCB according to embodiments of the present disclosure.

FIGS. 46A-50C are schematic representations of an additional exemplary embodiments of the intraoral monitor (with retainer structure omitted) according to embodiments of the present disclosure.

DETAILED DESCRIPTION

Figure 1:
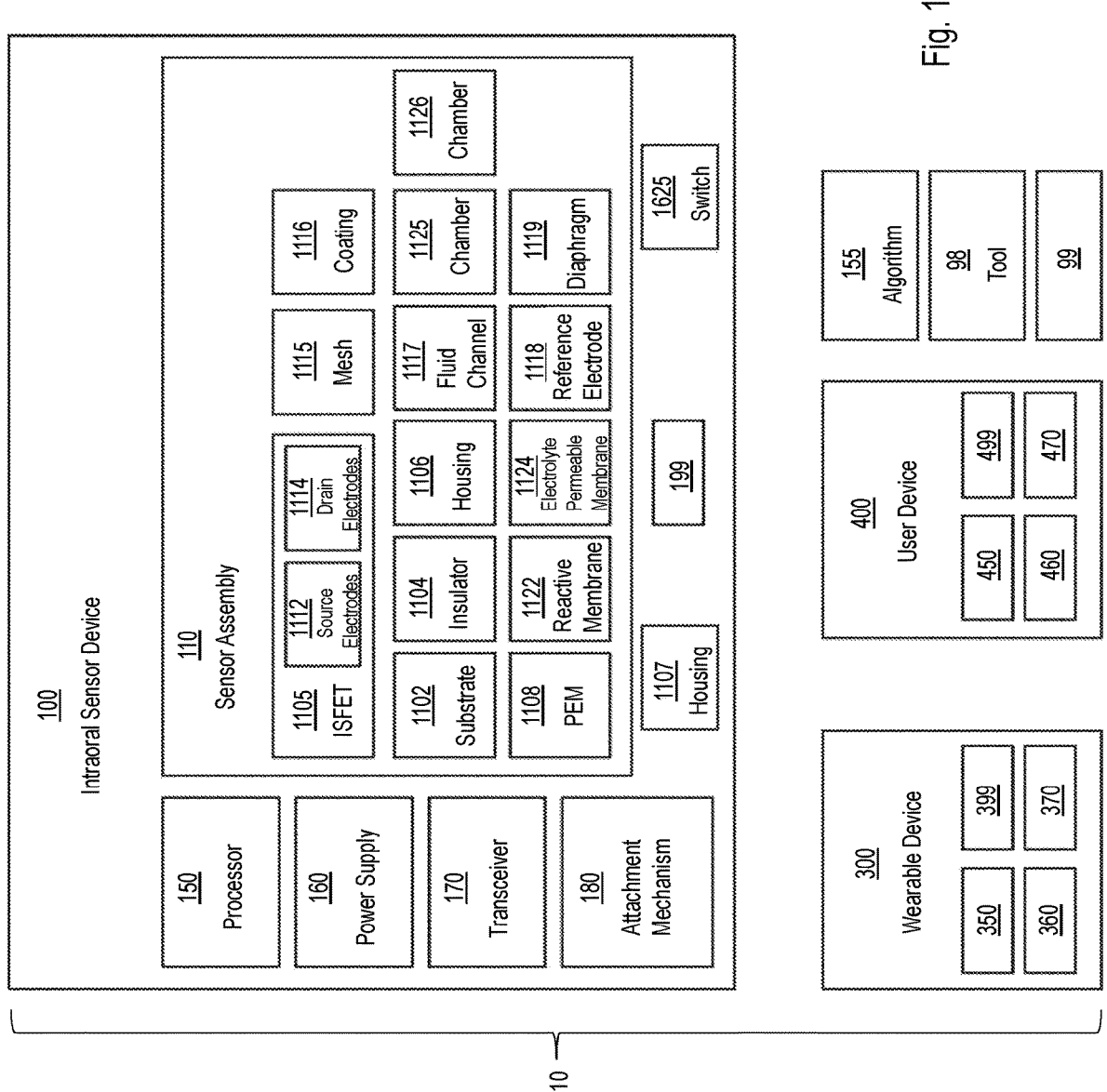
FIG. 1 illustrates a schematic view of a physiologic parameter recording system including a sensor device according to embodiments of the present disclosure.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

As used herein, when a quantifiable parameter is described as having a value "between" a first value X and a second value Y, it shall include the parameter having a value of: at least X, no more than Y, and/or at least X and no more than Y. For example, a length of between 1 and 10 shall include a length of at least 1 (including values greater than 10), a length of less than 10 (including values less than 1), and/or values greater than 1 and less than 10.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "about" or "approximately" shall refer to +/−10% of a stated value.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g., efficacious therapy) and/or to prevent or otherwise reduce (hereinafter "prevent") an undesired event (e.g., a device and/or clinical adverse event). In some embodiments, a system parameter is maintained above a first threshold (e.g., above a first temperature threshold to cause a desired therapeutic effect to tissue) and below a second threshold (e.g., below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or data. Alternatively or additionally, a functional element (e.g. a functional element comprising a sensor) can be configured to record one or more parameters, such as a patient physiologic parameter; a patient anatomical parameter; a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A functional element can comprise a fluid and/or a fluid delivery system. A functional element can comprise a reservoir, such as an expandable balloon or other fluid-maintaining reservoir. A "functional assembly" can comprise an assembly constructed and arranged to perform a function, such as a diagnostic and/or therapeutic function. A functional assembly can comprise one or more functional elements.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as: light (e.g. a transducer comprising a light emitting diode or light bulb), sound (e.g. a transducer comprising a piezo crystal configured to deliver ultrasound energy); pressure (e.g. an applied pressure or force); heat energy; cryogenic energy; chemical energy; mechanical energy (e.g. a transducer comprising a motor or a solenoid); magnetic energy; and/or a different electrical signal (e.g. different than the input signal to the transducer). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "fluid" can refer to a liquid, gas, gel, or any flowable material, such as a material which can be propelled through a lumen and/or opening.

As used herein, the term "material" can refer to a single material, or a combination of two, three, four, or more materials.

As used herein, the term "patient" can refer to any human or other animal, whether healthy, ill, and/or suspected of being ill (e.g. undergoing a diagnostic procedure to identify, gather information related to, and/or to prognose a current or future illness). In some embodiments, the patient comprises a mammal. For example, a mammalian patient can comprise, but is not limited to: human; mouse; rat; rabbit; guinea pig; dog; cat; horse; cow; pig; monkey; chimpanzee; baboon; rhesus monkey; sheep; and/or goat.

As used herein, a "medical procedure" can include a diagnostic procedure and/or a therapeutic procedure.

As used herein, the terms "disorder", "disease", and "condition" can be used interchangeably for one or more medical conditions a patient.

As used herein, the terms "smart device" and "mobile device" can be used interchangeably to mean any portable computing device comprising a processor and a display. For example, mobile device and smart devices include, but are not limited to, mobile phones, smart phones, smart watches, tablets, laptops, and/or other associated devices as described herein.

It is appreciated that certain features of the inventive concepts, which are, for clarity, described in the context of separate embodiments, may also be provided in combination in a single embodiment. Conversely, various features of the inventive concepts which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the inventive concepts have been simplified to focus on elements that are relevant for a clear understanding of the inventive concepts, while eliminating, for purposes of clarity, other elements that those of ordinary skill in the art will appreciate may also comprise a portion of the inventive concepts. However, because such elements are well known in the art, and because they do not necessarily facilitate a better understanding of the inventive concepts, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Saliva is a clinically informative, biological fluid (biofluid) that is useful for novel approaches to prognosis, laboratory or clinical diagnosis, and monitoring and management of patients with both oral and systemic diseases. It is easily collected and stored and ideal for early detection of disease as it contains specific soluble biological markers (biomarkers). Saliva may contain one or more biomarkers which make it useful for multiplexed assays developed as point-of-care (POC) devices, rapid tests, or in more standardized formats for centralized clinical laboratory operations. Ultimately, salivary diagnostics may be incorporated as part of disease diagnosis, clinical monitoring and for making important clinical decisions for patient care.

Salivary diagnostics may be considered a subset of the larger field of molecular diagnostics, now recognized as a central player in a wide variety of biomedical basic and clinical areas. Molecular diagnostics feeds into a wide range of disciplines including drug development, personalized medicine (pharmacogenomics) and plays a major role in discovery of biomarkers for the diagnosis of oral and systemic diseases. This is especially true given that biomarkers present in blood and urine can also be detected in a sample of saliva.

Oral tests may be used for the detection of antibodies to the Human Immunodeficiency Virus (HIV) and may be as sensitive and specific as a blood test. This discovery has led to an increase in HIV testing at a variety of locations including emergency rooms, sexually transmitted diseases (STD) clinics, community health centers, bath houses, and most recently in dental settings. The ability to accurately detect antibodies to HIV strongly suggests the potential to detect antibodies to many other pathogens.

Oral samples that are useful for the diagnosis of systemic diseases include saliva, gingival crevicular fluid (GCF), oral swabs, dental plaque, and volatiles. Indeed, published data indicates the successful use of all of these types of oral samples to detect or predict susceptibility to systemic diseases.

The ability to accurately assess biomarkers in samples obtained from the oral cavity may depend on the biochemical nature of the marker, the source and type of sample being taken, and the mechanism by which the marker enters the oral cavity. One widely-used type of oral sample is a swab that collects a deoxyribonucleic acid (DNA) sample. This has been employed for many years in forensic studies and more recently for single nucleotide polymorphisms (SNP) analyses for mutations associated with specific diseases. While a DNA sample can be collected from a wide range of sites on/in the human body, oral sampling has been used most often because of the ease of the sampling procedure, i.e., a buccal brushing that is placed in a stabilizing transport medium and sent off to a laboratory for evaluation.

Another widely-used type of oral sample is for the quantitation of steroid hormone levels. Assays are commercially available for cortisol, estriol, estrogen, testosterone, and consistently provide accurate detection of these hormones. However, salivary levels do not correlate well with serum levels in the case of conjugated steroid hormones. Thus, while dehydroepiandrosterone (DHEA) can be reliably monitored in saliva and the measurements reflect blood levels of the hormone, the sulfated derivative of the steroid, DHEA-S, can be measured in saliva, but the levels are not correlated with serum levels. The reason for this discrepancy appears to be the route of entry of the hormone into the oral cavity. DHEA as a steroid can readily cross the phospholipid membrane of epithelial cells lining the blood vessels, so that elevated serum levels translate as elevated saliva levels by simple diffusion of the hormone. The addition of the charged sulfate group, however, impedes membrane transport and the substance detected in saliva likely represents leakage from the blood rather than diffusion.

In various embodiments, detectable biomarkers in saliva may correspond to chronic obstructive pulmonary disease (COPD) and cystic fibrosis, acute myocardial infarction, oral cancer, and HIV, TB and Malaria. In various embodiments, detectable biomarkers within saliva may correspond to hormones, steroids (e.g., cortisol, androgens, testosterone, estriol, estrogen, progesterone, aldosterone, DHEAS), antibodies (e.g., IgG, IgA, sIgA, IgM), growth factors (e.g., EGF, NGF, VEGF, IGF), cytokines and chemokines (e.g., IL-1 beta, IL-8, IL-6, MCP-1, CX3CL1, GRO-1 alpha, troponin I, TNF alpha), nucleic acids (e.g., human DNA, microbial DNA, mRNA, siRNA, micro RNA, miR-125a and miR-200a), proteins (e.g., 100s-1000s), and drugs (e.g., drugs of abuse such as NIDA 5, ethanol, therapeutic drugs, anticonvulsants, antipyretic/analgesics, anti-neoplastic agents, antibacterial agents, bronchodilators, cotinine).

In various embodiments, C-reactive protein (CRP) can be monitored in salivary samples. In various embodiments, salivary immunoglobulins levels are known to increase in association with coronary artery disease. In various embodiments, a group of salivary biomarkers can complement findings of an electrocardiogram (ECG) following an acute myocardial infarction, which include CRP, myoglobin and myeloperoxidase, in combination with an ECG. In various embodiments, salivary biomarkers may be incorporated into POC devices for the rapid assessment of cardiovascular disease (CVD) with potential association with distinct disease stages, demonstrating promising results to identify CVD. In various embodiments, elevated salivary lysozyme levels, a biomarker for oral infection and hyperglycemia, may be associated with hypertension, an early stage of CVD.

In various embodiments, salivary markers may be associated with end stage renal disease. In various embodiments, these markers may include cortisol, nitrite, uric acid, sodium, chloride, pH, amylase and/or lactoferrin. In various embodiments, salivary nitrate and uric acid may be monitored. In various embodiments, salivary phosphate may be used as a clinical biomarker for hyperphosphatemia, which is an important contributor to cardiovascular calcification in chronic renal failure (CRF). In various embodiments, both HD and CRF patients may have significantly higher salivary phosphate levels compared with healthy control subjects. In various embodiments, phosphate levels in saliva may have a positive correlation with serum creatinine and the glomerular filtration rate. Thus, salivary phosphate may provide a better marker than serum phosphate for the initiation of treatment of hyperphosphatemia in CRF and HD.

In various embodiments, salivary biomarkers may be used to detect stress and/or pain. In various embodiments, markers for stress or pain may include salivary amylase, cortisol, substance P, lysozyme and secretory IgA. Pain responses in dental pulp have been specifically associated with neuropeptides including calcitonin gene-related peptide (CGRP), substance P, neurokinin A and neurokinin P. In various embodiments, salivary testosterone levels may be associated with increased aggressive behavior and also with athletic activities. In various embodiments, serotonin may be monitored in saliva.

In various embodiments, biomarkers for malignancies may be detected in saliva. In various embodiments, mutations of the tumor suppressor p53 may be detected for salivary gland adenomas or for breast cancer. In various embodiments, elevated levels of the cancer antigen, CA15-3 and the oncogene c-erB2, in woman with breast cancer as compared to controls may be detected. In various embodiments, the tumor marker C125 may be detected in saliva of subjects with malignant ovarian tumors. In various embodiments, down-regulation of the tumor suppressor DMBT1 may be detected in mammary tumors in humans. In various embodiments, four mRNA biomarkers may be detected to distinguish pancreatic cancer subjects from pancreatitis and control subjects.

Because of the large diabetic population, combined with the current epidemic of Type 2 diabetes, an oral test to monitor blood glucose would be highly desirable. Unfortunately, while it is relatively easy to measure salivary glucose, due to the multiple sources of this material in the oral cavity, salivary glucose levels do not correlate with blood glucose levels. In various embodiments, a unique proteomic signature may be determined in saliva from Type-2 diabetics as compared to control saliva (with 65 proteins showing greater than a 2-fold change). Many of these proteins were associated with metabolic and immune regulatory pathways. In various embodiments, exhaled methyl nitrate may be measured to detect Type 1 diabetic hyperglycemia. There may be a correlation between blood glucose levels and exhaled methyl nitrate due to interaction of superoxide dismutase with nitric oxide as a byproduct of elevated oxidative reactions.

In various embodiments, biomarkers may be used to detect major rheumatoid factor diseases include Lupus Erythematosis, Scleroderma, and Sjogren's syndrome. These autoimmune diseases are characterized by the production of auto-antibodies that attack healthy tissue. Sjogren's syndrome is a disease characterized by dryness of the eyes and mouth and it may occur as a primary or a secondary disease. The clinical symptoms in the primary form are more restricted and are associated with lacrimal and salivary gland dryness. In secondary Sjogren's syndrome, patients undergo one of the autoimmune diseases mentioned above before Sjogren's symptoms develop. In contrast, the primary Sjogren's Syndrome (pSS) occurs by itself and it is the third most common autoimmune disease with a reported prevalence between 0.05 and 4.8%, mostly (90%) occurring in women. For decades, the pSS diagnosis has been based on oral examination, detection of blood biomarkers (autoantibodies to self-antigens (SS-A and SS-B), Rheumatoid factor and antinuclear antibodies, and by obtaining a confirmatory salivary gland biopsy. Patients with pSS have forty times higher risk of developing lymphoma, a fatal lymphocytic cancer. In contrast, patients with secondary Sjogren's syndrome tend to have more health problems because they suffer from a primary condition as well as SS. They are also less likely to have the antibodies associated with the pSS. In various embodiments, a panel of salivary biomarkers may be used to distinguish pSS patients from healthy subjects. In various embodiments, whole saliva (i.e., the combination of saliva in the mouth plus saliva from the individual salivary glands) may contain a series of biomarkers that could detect pSS.

In various embodiments, viruses (e.g., at least 23 known viruses) may be identified in salivary samples by specific antibody reactivity, antigen detection, or nucleic acid via PCR. In various embodiments, these viruses include: Herpes viruses, Hepatitis viruses, HIV, Human Papillomavirus (HPV), Influenza virus, and Poliovirus. Fourteen bacterial pathogens were detected (by antibody, antigen or nucleic acid) including *Escherichia coli*, *Mycobacterium tuberculosis*, *Helicobacter pylori*, *Treponema pallidum* and a wide range of streptococcal species. In various embodiments, non-viral and non-bacterial infectious agents including *Candida albicans*, *Toxoplama gondii*, and *Schistosoma mansoni* were detectable, typically by antibodies to these infectious agents. These pathogens are responsible for both systemic and oral diseases.

In various embodiments, the physicochemical and biochemical properties of saliva along with its complex composition endows this fluid with multiple functions, including: anti-bacterial, anti-viral and anti-fungal properties; buffering capacity for plaque acids; digestive activity (amylase, protease, nuclease enzymes) needed for food mastication; mineralizing agents for protection and repair of hard tissues; lubricant and viscoelastic properties essential for the maintenance of oral health; and protective and repairing fluid for mucosal surfaces. Saliva is a hypotonic biofluid composed of 99.5% water and 0.5% ions (e.g., potassium, calcium, chloride, sodium and phosphates), and organic micro- and macro-molecules (e.g., amino acids, histatins, cystatins, defensins, statherins, lysozyme, proline-rich proteins, carbonic anhydrases, peroxidases, lactoferrin, mucins, secretory immunoglobulins, and lipids among others).

In various embodiments, salivary-derived molecules may be used as diagnostic biomarkers for oral diseases including oral cancer, and conditions caused by fungi (*Candida* species), viruses (HPV, Epstein-Barr Virus [EBV], Cytomegalovirus [CMV]) and bacteria (multiple species involved in periodontal diseases and caries). In many instances, pathogen-induced oral diseases have been reported as opportunistic or secondary infections and are referred to as early manifestations of the Acquired Immunodeficiency Syndrome (AIDS) in HIV infected subjects. The frequency of many AIDS-related oral manifestations varies, but increases in the absence of highly active antiretroviral therapy (HAART), and may indicate inadequate HAART treatment, development of drug resistance, or therapeutic failure.

In various embodiments, salivary biomarkers may be used to detect oral squamous cell carcinoma (OSCC). OSCC is the most common malignancy of the oral cavity among oral cancers (e.g., adenocarcinomas, lymphomas, sarcomas, verrucous or mucoepidermoid carcinomas, malignant melanoma, and Kaposi's sarcoma), accounting for more than 90% of clinical cases and ranking among the top ten types of cancers worldwide. However, oral cancers have also been reported with less frequency in the oral mucosa, tongue, pharynx, lips, gums, palate, salivary glands, tonsils and sinuses. In various embodiments, these oral cancer biomarkers include: oncogenes (e.g. C-myc, c-Fos, C-Jun), anti-oncogenes (e.g. p53, p16), cytokines (e.g. TGF-β1, IL-8, and IL-1β), growth factors (e.g. VEGF, EGF and IGF), extracellular matrix-degrading proteinases (MMP1, MMP2, MMP9), hypoxia markers (HIF-α, CA-9), epithelial-mesenchymal transition markers (e.g. E-cadherin, N-cadherin and β-catenin), epithelial tumor factors (CYFRA 21-1), cytokeratins (CK13, 14 and 16), micro RNA molecules and hypermethylation of cancer-related genes (p16 and DAP-K) [43, 82, 83, 84, 85, 86, 87, 88]. These biomarkers have been defined using molecular, transcriptomic, genomic, proteomic, metabolomic and phenotypic techniques.

In various embodiments, the oral cavity of immunocompetent individuals may contain resident microbiota co-existing under a delicate immunophysiological balance and including an important fungal component known as the oral mycobiome. The latter includes culturable and non-culturable fungi, some of which may be pathogenic, causing common oral diseases such as oropharyngeal candidiasis (OPC), frequently observed in immunocompromised individuals. A recent study characterized the oral mycobiome of twenty healthy individuals showing that *Candida* species were the most frequently isolated fungi (present in 75% of participants), followed by *Cladosporium* (65%), *Aureobasidium*, Saccharomycetales (50% for both), *Aspergillus* (35%), *Fusarium* (30%), and *Cryptococcus* (20%). In various embodiments, there are numerous factors that can disturb the balance of microorganisms in the oral microbiome and mycobiome, predisposing individuals to fungal diseases, including: physiological changes that occur in the geriatric and pediatric populations and during pregnancy; disturbances of soft and hard tissues caused by lesions or poor oral hygiene; prolonged use of antibiotics with a broad antimicrobial spectrum; extended use of steroids that impair the immune system; nutritional deficiencies in micro- or macro-nutrients; endocrinological malfunction associated with diseases such as hypothyroidism; chemotherapy and radiotherapy-induced immunosuppression due to cancer; immunodeficiencies caused by pathogens such as the HIV or congenital defects such as thymic aplasia; Xerostomia; autoimmune diseases (Sjogren's syndrome); use of prosthodontic appliances; and diabetes. In various embodiments, biomarkers may be used to detect salivary IgA or IgG antibodies to *Candida*.

In various embodiments, oral diseases caused by viruses may be detected via salivary biomarkers. In various embodiments, these oral diseases include papillomaviruses (HPV associated with oral cancer —OSSC— and oral warts) and herpesviruses (EBV causing Hairy Leukoplakia and is also associated with various types of lymphoid and epithelial malignancies; Cytomegalovirus [CMV] causing opportunistic infections after solid organ transplantation, retinitis, gastrointestinal and neurological disorders, and oral ulcerations; Herpes Simplex Viruses 1 and 2 [HSV-1 and HSV-2] and Varicella Zoster Virus [VZV] also causing oral ulcerations of the aphthous type; and Human Herpesvirus 8 [HHV-8] causing oral and systemic Kaposi's sarcoma). In various embodiments, oral fluids have also been successfully used in lab diagnostics to detect HIV antigen and antibodies in different nucleic- and immunoassay formats such as qRT-PCR, ELISA, rapid test, POC and microfluidic diagnostic devices. In various embodiments, HIV neutralizing innate immune factors such as defensins may be detected in saliva using sophisticated experimental methodologies such as liquid chromatography-tandem mass spectrometry that involves limited sample manipulation and that can be easily automated. In various embodiments, detection of HPV in saliva samples has utilized nucleic acid assays such as HPV DNA amplification by PCR and this methodology has also been used to detect different HPV types. In various embodiments, antibodies to HPV may be detected through oral fluids. In various embodiments, saliva specimens may be used for direct genotyping of CMV strains in a new PCR-restriction fragment length polymorphism (RFLP) method, coupled with capillary electrophoresis fragment detection for genotyping [126]. In various embodiments, reliable detection and quantification of nucleic acids for HSV-1, HSV-2 and VZV may be performed using oral fluids.

Caries and periodontitis are the most commonly known polymicrobial-driven diseases of the oral cavity. Periodontal disease is a chronic inflammatory process of the periodontium in response to bacterial plaque deposited on the adjacent teeth. Bacterial infections forming biofilms, destroy the alveolar bone and periodontal ligament, induce gingivitis, cause apical migration of the epithelial attachment resulting in the formation of periodontal pockets, and induce irreversible loss and exfoliation of the teeth. If left untreated, gingivitis may progress into periodontitis, leading to tooth loss and severe lesions of soft and hard tissues. Periodontitis is also linked to systemic illness, such as CVD and diabetes. Caries is also caused by bacterial plaque that in combination with fermentable carbohydrates produces acids (e.g., lactic acid) that lower the pH at the surface of the tooth compromising the enamel, dentin and cementum, and ultimately affect the structural integrity of the tooth. In various embodiments, biomarkers such as MMP-8 and -9 (matrix metalloproteinases) may be elevated in subjects with advanced periodontitis, which was predicted when assessing multiple combinations of salivary biomarkers (e.g., MMP-8 and -9 and osteoprotegerin) along with red-complex anaerobic periodontal pathogens (e.g., *Porphyromonas gingivalis* or *Treponema denticola*). In various embodiments, disease severity was also predicted when obtaining elevated salivary MMP-8 and *T. denticola* biofilm levels. In various embodiments, biomarkers (genetically determined oligosaccharides profiles present on salivary glycoproteins) for caries risk assessment with prognostic value for caries susceptibility may be detected.

Accordingly, there is a need for a salivary sensor that can be seated in a user's mouth to detect the presence of one or more salivary biomarkers in real time.

The sensor system of the present invention may be seated comfortably on one (or more) tooth, such that the sensor may continually monitor one or more biomarkers (e.g., oral acidity) and transmit data to a mobile application in real time or at a pre-determined time (e.g., when a mobile device is brought within wireless communication range). In various embodiments, patients may receive notifications to monitor oral health in real-time, at the most important moments. In various embodiments, a healthcare provider (e.g., a dentist) may analyze long-term data through a web portal to provide personalized oral health strategies.

The systems of the present inventive concepts include wearable intraoral sensor devices for non-invasive measurement (e.g., continuous measurement), and these systems can provide long-term use in a patient's oral cavity, as well as wireless transmission of measurement data. In some embodiments, the sensor devices include a biosensor transducer configured for measuring pH values, analyte levels, and/or other physiologic parameters of the patient, such as for extended periods of time (e.g., at least months), and in complex oral environments. Design considerations for this sensor device can include the device's specificity and accuracy, size, sensing lifetime, biocompatibility, comfort, and/or power requirements. In some embodiments, the sensor device transduces and transmits pH and/or other physiologic parameter values, while accounting for other variables (e.g., changing variables) such as salivary flow rate, tissue contact, temperature, salivary turbidity, salivary viscosity, ionic strengths, and/or jaw movements. The accuracy of provided pH measurements can be comparable to the accuracy of conventional pH sensors (e.g., glass membrane pH sensors). In some embodiments, the transducer and other components of the sensor device are small enough to fit on the side of a tooth. In some embodiments, the sensor device is able to maintain its accuracy for a period of at least months, and it does not experience significant fouling due to mineral deposition, food deposition, and/or bacterial growth. The sensor device can be comfortable for the patient to wear long term, due to an optimized sensor-gum interface and/or sensor-cheek interface, and by ensuring the sensor device does not occlude or alter the user's bite. In some embodiments, the operational power requirements of the sensor device are small enough to be feasibly powered by a power-supplying component that can also fit onto a tooth of the patient. In some embodiments, the sensor device does not require patient action, thereby eliminating or at least reducing the potential for patient non-compliance.

One aspect of this disclosure provides a sensor device for recording, detecting, monitoring, and/or measuring ("recording", "detecting", "monitoring", or "measuring" used interchangeably herein) pH, one or more analytes, temperature, another physiologic parameter, or a combination thereof. The sensor device can comprise a wearable intraoral sensor device where at least portion (e.g. a sensing portion) is positioned in an oral cavity of a patient for a time period (e.g. at least one day). The sensor device can comprise a dental installation portion, such as an attachment mechanism for attaching to one or more molars or other teeth of the patient. In some embodiments, the attachment mechanism includes a molar band sized to fit around a molar in an oral cavity of a patient. The sensor device also comprises a sensor assembly, which can be coupled to the attachment mechanism, and can comprise a transducer (e.g., including one or more sensors, reference elements, and/or other sensing elements, and the associated circuitry) configured to measure one or more physiologic parameters of the patient (e.g., pH, temperature, one or more analytes, or a combination thereof), in an oral cavity or other location of the patient, and provide the measurement data in the form of a data signal (e.g., a signal suitable for transmission to a separate device). The sensor device can include a data transmitter, operably connected to the sensor assembly, and configured to transmit the data signal (e.g., wirelessly transmit the data signal). The sensor device can include a battery, capacitor, and/or other power supply operably connected to the sensor assembly and the transmitter. In some embodiments, the sensor device further comprises a first housing, enclosing the one or more sensing elements of the sensor assembly, where the sensor assembly includes a semipermeable membrane configured to allow desired molecules to enter one or more chambers of the sensor assembly in which sensing elements are positioned, via one or more openings in the first housing. In some embodiments, the sensor device comprises a proton exchange membrane configured to allow protons to enter the one or more chambers via the first housing. The sensor device can also comprise a second housing sealably coupled to the attachment mechanism (e.g., and surrounding at least a portion of the first housing).

In some embodiments, the sensor device comprises a first housing enclosing sensing elements within one or more chambers of the sensor device, the sensor device further comprising a semi-permeable membrane configured to allow desired molecules to enter the one or more chambers. In some embodiments, the sensor device comprises a first housing enclosing sensing elements within one or more chambers of the sensor device, the sensor device further comprising a proton exchange membrane configured to allow protons to enter the one or more chambers (e.g., to make physical contact with one or more of the sensing elements of the sensor device). In some embodiments, a second housing sealably couples to the attachment mechanism, and seals one or more components within the second housing (e.g., one or more sensing elements, the transmitter, and/or a power supply). In certain embodiments, the second housing sealably couples around a whole molar band, or to a portion of a molar band.

The sensor device first housing unit can define (e.g. provide walls or other surfaces to create) one or more fluid chambers for sensing electronics, such as a first chamber for a reference electrode, and a second chamber for a sensor such as an ISFET transistor. A reference electrode chamber can surround a salt solution, such as a potassium chloride (KCl) salt solution, where the salt solutions contacts the reference electrode (e.g., contact metal of the reference electrode, such as when the metal of the reference electrode comprises Ag/AgCl, and the salt solution comprising a solution or gel, "solution" herein, of saturated or super saturated KCl). The salt solution can be contained within the first chamber using a diaphragm (e.g., a ceramic diaphragm) and/or a semi-permeable membrane (e.g., a sulfonated tetrafluoroethylene-based fluoropolymer-copolymer membrane). The membrane can be configured to allow protons or desired molecules or ions to enter the first chamber. The one or more chambers can each include an opening (e.g., an opening into the second chamber) that is covered by a mesh. The mesh and the internal surface of the first and second chambers can be treated by a surface modification technique such as ion implantation and/or application of a coating (e.g., a hydrophilic coating).

In some embodiments, the sensor device attachment mechanism comprises a molar band that is sized to fit around a molar in an oral cavity of a mammalian patient. Molar bands have numerous advantages over other dental devices, for example, molar bands are relatively non-invasive, most dentists have experience installing molar bands, molar bands can easily be sized to avoid interfering with occlusion in a patient's oral cavity, and molar bands do not need to be custom-made for each patient prior to being installed.

In some embodiments, the sensor device attachment mechanism comprises a dental crown (also called a "dental cap"). In other embodiments, the attachment mechanism comprises a dental implant, bridge, dentures, orthodontic temporary anchorage device (TAD), a removable dental prosthesis, and/or a removable dental appliance including, but not limited to, Herbst appliance, Activator, Bionator, twin block appliance, Pendulum appliance, Forus™ Fatigue Resistant Device, Hyrax appliance, Haas appliance, Hawley-type removable appliance with jackscrew, Quad-helix, W-arch, transpalatal arch, Nance appliance, Lower lingual arch, and/or one or more aligners (e.g., Invisalign™ teeth aligning products).

In some embodiments, the sensor devices of the present inventive concepts are configured to measure pH in an oral cavity of a patient. Periods of elevated acidity within the oral cavity can occur on the span of tens of minutes and can indicate why and/or when teeth are decaying. Existing devices are incapable of adequately (e.g., continually) measuring acidity data, such as for extended time periods, which is critical for monitoring acid attacks and preventing decay and/or crumbling of a tooth or bone, known as "caries". Existing devices (e.g., including mouthguards, retainers, and the like) can be too large to wear in the mouth throughout the day, and require significant effort from the patient to operate or maintain (e.g., which reduces compliance and completeness of data), have short sensor lifetimes, and/or have inadequate durability to survive oral conditions.

In some embodiments, the sensor device measures one or more analytes in an oral cavity of a patient. In some embodiments, the analyte is avian influenza virus, hepatitis B marker HBsAg, cancer marker AFP, human thyroid stimulating hormone, interleukin 8 (IL-8), tumor necrosis factor (TNF-.alpha.), cancer biomarker CYFRA21-1, prostate cancer biomarker PSA, carcinoembryonic antigen (CEA), cardiac troponin I (cTnI), C-reactive protein (CRP), prostate cancer biomarker osteopontin (OPN), interleukin-6 (IL-6), cortisol, lyme disease antigen, Alzheimer biomarker amyloid-.beta., chondroitin sulfate proteoglycan 4, pancreatic cancer biomarker, carbohydrate antigen 19-9 (CA 19-9), prostate specific antigen/1-antichymotrypsin (PSA-ACT) complex, breast cancer biomarkers human epidermal growth factor receptor 2, human immunodeficiency virus (HIV), bladder cancer biomarker, urinary APOA2 protein, prostate cancer biomarker PSA-ACT complex, D-Dimer, biomarker of venous thromboembolism, breast cancer biomarker EGFR, hemoglobin-A1c, insulin, and/or other parameter as described herein. Additional analytes are described in Ana Carolina, Recent Trends in Field-Effect Transistors-Based Immunosensors, Chemosensors 2016, 4, 20, 21 Oct. 2016 (accessed here: http://www.mdpi.com:8080/2227-9040/4/4/20/pdf), which is herein incorporated by reference.

In some embodiments, the analyte detected by the sensor device of the present inventive concepts is an analyte detectable in saliva. In some embodiments, the analyte is a hormone such as cortisol, androgens, testosterone, estriol, estrogen, progesterone, aldosterone, DHEAS. In some embodiments, the analyte is an antibody such as IgG, IgA, IgA, IgM. In some embodiments, the analyte is a growth factor such as EGF, NGF, VEGF, IGF. In some embodiments, the analyte is selected from cytokines and chemokines such as IL-1 beta, IL-8, IL-6, MCP-1, CX3CL1, GRO-1 alpha, troponin I, TNF alpha. In some embodiments, the analyte is selected from nucleic acids such as human DNA, microbial DNA, mRNA, siRNA, micro RNA (miR-125a and miR-200a). In some embodiments, the analyte is a protein detectable in saliva. In some embodiments, the analyte is a drug, including, but not limited to, drugs of abuse, ethanol, therapeutic drugs, anticonvulsants, antipyretic/analgesics, anti-neoplastic agents, anti-bacterial agents, bronchodilators, and cotinine. Additional analytes that can be measured or detected are described in Malamud D, Saliva As A Diagnostic Fluid, Dent Clin North Am. 2011 January; 55(1): 159-78 (accessed here: https://www.ncbi.nlm.nih.gov/pubmed/21094724).

In some embodiments, the analyte detected by a sensor device of the present inventive concepts is selected from analytes that are consumed during eating and drinking. These analytes include nutritional macromolecules such as carbohydrates, proteins, and fats; allergens such as shellfish, peanuts, gluten, etc.; and toxins such as heavy metals, mercury, and the like.

In some embodiments, the sensor device measures temperature in the oral cavity of a patient. In some embodiments, the sensor device measures a combination of two or more of: pH, temperature, and/or one or more analytes in an oral cavity of a patient.

In some embodiments, a sensor device of the present inventive concepts is configured to measure pH, temperature, one or more analytes, or a combination thereof, in an oral cavity of a patient for a time period of at least one week, and/or for a time period of between one day and six months.

The sensor devices of the present inventive concepts can be constructed and arranged to take a patient's comfort into account. A patient's comfort while using the sensor device can be determined by several factors. In some embodiments, the sensor device is constructed and arranged to avoid interfering with user's occlusion (bite), speaking, and/or swallowing. In some embodiments, the sensor device is constructed and arranged to avoid protruding above the bottom molar and/or below the top molar, as this would create a noticeable interference with the user's occlusion. In some embodiments, the one or more surfaces of the sensor device is constructed and arranged to avoid discomfort to the surrounding tissues of the gum, cheek, and/or tongue. In some embodiments, the sensor device comprise a smooth outer surface, free from pockets or rough or jagged spots. In some embodiments, electronic and/or other components of the sensor device are coated with a smooth material, such as a coating which resists degradation in the mouth.

In some embodiments, the sensor devices of the present inventive concepts comprise a sensor assembly coupled to an attachment mechanism comprising a molar band, dental crown, dental implant, bridge, dentures, orthodontic anchor, and/or other dental prosthesis.

The sensing elements of this disclosure, such as those including at least an ion sensitive field effect transistor (ISFET), can be low power, small, easily and inexpensively manufactured, and accurately sense in-vivo conditions, and these sensing elements can produce an easily readable signal. The sensor assembly can comprise conditioning circuitry (also known as "signal processing" circuitry).

In some embodiments, sensing elements of the sensor device include a sensing transistor, such as an ISFET. These ISFET sensors are durable, low-power, inexpensive, and produce a current-based output signal, which can be readily amplified and processed. Additionally, ISFET sensors can be manufactured using CMOS methods, meaning they can be produced directly on an integrated circuit, in a "system on a chip" or SOC configuration. In some embodiments, the sensing assembly includes an ISFET that is fabricated to transduce the analyte ionic potential of protons in saliva to a time changing electrical current. In some embodiments, the sensing assembly is manufactured by depositing a dielectric substrate over a molar band, on which an electrode pattern and thin film or nanotube conductor or semiconductor are deposited. In some embodiments, the sensing assembly further includes a reference electrode. In some embodiments, the sensing assembly includes electrodes that are made of conductive materials like gold, silver, or carbon, and the reference electrode is an Ag/AgCl paste, wire, or ink. The sensing assembly can include one or more fluid transport channels, such as a channel that is a graphene monolayer of a substrate. In some embodiments, a semi-porous hydrogel is added as a transistor gate insulator, positioned on top of semiconductor circuitry with incorporated bioreceptors that are configured to provide specificity towards a certain analyte (e.g. toward a particular physiologic parameter, or other parameter, to be measured).

In some embodiments, the sensor device of the present inventive concept comprises more than one set of analyte sensors. For example, the sensor device can comprise more than one ISFET sensor, wherein each ISFET sensor is configured to measure a different parameter (e.g., pH, temperature, or an analyte). In some embodiments, each ISFET sensor is contained in a chamber (e.g. as defined by walls of a housing), wherein an opening to the chamber is covered by a semi-permeable membrane configured to allow detection of a certain variable by the ISFET sensor. In some embodiments, the ISFET sensor is installed on a substrate, such as a supporting printed circuit board (PCB). In some embodiments, two or more additional ISFET sensors are added to the PCB or other substrate ("PCB" or "substrate" herein) to enable a multiplicity of molecules to be measured. Each ISFET can include a gate that includes a functionalized layer with bioactive elements and/or elements exhibiting preferred binding specificity to a particular analyte of interest. Generally, the membranes described herein (e.g. a membrane covering an ISFET) can comprise a chemically reactive membrane, or other membrane modified by adding inorganic and/or organic chemical or biological receptors such as antibodies, aptamers, and/or small molecules, depending on the analyte to be detected or measured. The selective membrane can enable the sensor device to measure, for example, $Na+$, $Ca2+$, proteins, carbohydrates, fats, allergens, toxins, and other analytes described herein. Further, each ISFET can be positioned in a chamber (e.g. each in a unique chamber) with an opening to the chamber covered by a membrane or filter (e.g. "membrane" herein, each chamber comprising a similar or different membrane). For example, a covering membrane can be configured to selectively or semi-selectively conduct specific molecules into the sensing chamber, which can enable the sensor device to measure, for example, $Na+$, $Ca2+$, proteins, carbohydrates, fats, allergens, toxins, and other analytes described herein. The ability to simultaneously detect a multiplicity of unique analytes may be accomplished by creating an array of functionalized ISFET sensors bonded to conductive pads plated with gold, silver, platinum, etc., and may be commonly serviced with one or more reference electrodes also operating from one or more PCB pads. These pads can be connected to signal processing circuitry using copper (or other) PCB traces which, can be routed on the top, bottom or through one or more layers of the PCB.

In some embodiments, the sensing elements can be encased in a protective housing. In some embodiments, an opening into a chamber comprising a sensing element (e.g. an ISFET and/or reference electrode) is covered by a mesh, a proton exchange membrane, and/or a diaphragm (e.g. a ceramic diaphragm), which can be constructed and arranged to allow fluids, protons, and/or electrolytes to diffuse through the covering to the associated chamber, and to limit the diffusion of larger analytes and undesired particles. The covering can protect the sensing elements within the associated chamber from physical and/or chemical factors in the mouth. In some embodiments, the sensing elements (e.g. electrodes and/or other portions of the sensing elements) are patterned using methods including screen-printing, photolithography, evaporation, electroplating, and/or physical vapor deposition (sputtering). In some embodiments, the semiconducting material of the ISFET can be made using graphene, which can be fabricated using chemical vapor deposition (e.g. a deposition on copper).

In some embodiments, a sensing element is an ISFET, such as an ISFET including a conductive or semi-conductive channel (e.g. gate) material (e.g. graphene), to transduce the ionic potential (e.g. pH) surrounding the ISFET to an electrical signal that can be transmitted.

In some embodiments, the sensor devices of the present inventive concepts measure pH in the oral cavity. In certain embodiments, the sensor device measures pH of saliva in the oral cavity. The pH of saliva can be influenced by various oral environmental factors, including, but not limited to, saliva, biofilm (tooth plaque), intrinsic and extrinsic oral fluids (including vapor), food, and breath.

In some embodiments, a sensing element comprising an ISFET is modified to detect multiple types of molecules in the oral cavity. In some embodiments, the functional groups of an ISFET sensor are modified. Generally, the membranes described herein can be modified by adding inorganic or organic chemical or biological receptors such as antibodies, aptamers, and/or small molecules, depending on the analyte to be detected or measured. Additional analytes are described in Ana Carolina, Recent Trends in Field-Effect Transistors-Based Immunosensors, Chemosensors 2016, 4, 20, 21 Oct. 2016 (accessed here: http://www.mdpi.com:8080/2227-9040/4/4/20/pdf), which is herein incorporated by reference. Additional ISFET modifications are described at Torsi, Organic field-effect transistors sensors: a tutorial review, Chem Soc Rev., 21 Nov. 2013; 42(22):8612-28 (accessed here: https://www.ncbi.nlm.nih.gov/pubmed/24018860); and Lerner, Detecting Lyme disease using antibody-functionalized single-walled carbon nanotube transistors, Biosens Bioelectron. 15 Jul. 2013; 45:163-7 (accessed here https://www.ncbi.nlm.nih.gov/pubmed/23475141) which are incorporated by reference herein.

The sensor devices of the present inventive concepts collect and transmit data reliably. The sensor assemblies can create reliable data with a two-prong approach. First, in static fluid settings, the output of the sensor assembly consistently matches with a given pH value. This consistency can be achieved by testing the sensor assembly with various solutions with known pH values, and then creating a calibration curve. The pH of unknown solutions can then be determined by measuring the sensor assembly output, and then comparing this output to the measured pH value of the solution. Solutions with similar chemical and physical consistencies to saliva can be included in the testing. The second prong is determining whether the sensor assembly is able to measure pH accurately in the dynamic conditions of the mouth. The sensor devices of the present inventive concepts can account for the dynamic conditions of the mouth, including different salivary flow rates, turbidity, and viscosity, different contact from surrounding tissue like cheeks or tongue, as well as talking, yawning, chewing, and swallowing. In some embodiments, the reliability of the sensor device's data is confirmed, during testing, in a simulated mouth environment. Through this two-prong approach, the sensor devices of the present inventive concepts can provide consistently reliable intraoral pH and other measurements.

In some embodiments, the sensor assemblies disclosed herein are designed to wrap around a molar band of an attachment mechanism. In some embodiments, the molar band is metal. The molar band can range in size from molar band size 22 mm to size 43 mm. The bands can range from an upper diameter of around 8 mm and a lower diameter of around 9 mm, to an upper diameter of around 12 mm and a lower diameter of around 14 mm. In some embodiments, electronic components of the sensor device are printed on a flexible substrate (e.g. a flexible PCB) which is adhered to the outer perimeter of the molar band, and/or printed onto the molar band.

The sensor devices of the present inventive concepts can be configured to wirelessly transmit data. Multiple modes of data transmission can be used. The modes of transmission can be passive to the user (e.g. the patient, a family member of the patient, and/or a clinician of the patient), requiring little to no time commitment beyond initial installation of the sensing device to receive data. The modes of transmission can require little to no time commitment for charging or cleaning of the sensor device. The modes of transmission can also avoid requiring an intermediate receiver, which would force users to remember to wear the intermediate receiver, charge it, clean it, etc. In embodiments with an active circuit, energy can be provided by a chemical battery (silver oxide, nickel hydride, lithium polymer, lithium ion, and/or zinc oxide batteries), such as to power a FET, amplify the signal from the FET, and transmit it to a smart device or intermediate receiver, such as a transmission performed via BLE (Bluetooth low energy), WLAN, Wi-Fi or ZigBee or another wireless communication technology described herein. In some embodiments, a transistor signal is sent through analog front end (AFE), to Balun, antenna, and BLE components. Some embodiments comprise a similar electronic pathway with low pass filters to receive more stable readings.

In some embodiments, the sensor devices of the present inventive concepts wirelessly transmits data via Bluetooth technology. In some embodiments, the sensor device wirelessly transmits via a wireless local area network (WLAN), Wi-Fi (wireless fidelity), ZigBee, near-field communication (NFC), ANT, Thread, Zigbee, WiMAX, WWAN, MANET, PAN, Wireless Hart, Z-Wave, MESH, UWB, IrDA, Cellular, Peer-To-Peer, and 802.11 variants. In some embodiments, the sensor device wirelessly transmits via frequencies ranging from sub-sonic to ultraviolet. In some embodiments, the wearable oral sensor wirelessly transmits using modulation methods including, but not limited to, OOK, AM, FM, SSB, FSK, PSK, GFSK, and MSK. In some embodiments, the sensor device wirelessly transmits using Near Field, Mid Field, and/or Far Field magnetic and/or electric field radiation.

The tissue penetration profile of the signals wirelessly transmitted by the sensor device may be determined by passing the signal through real animal tissue or simulated tissue with varying thickness.

In some embodiments, the attachment mechanism comprises a molar band that is configured as an antenna. This antenna configuration is accomplished through use of an impedance matching circuit from the SOC's radio transceiver to the metallic or semi-metallic structure of the molar band. Employing RF instrumentation such as a Vector Network Analyzer (VNA), the components comprising the impedance matching circuit can be adjusted in combination to cause resonance at the frequency of interest and thereby provide the optimal transfer of RF energy either flowing outwards towards the antenna or inwards toward the RF transceiver. This adjustment process (tuning) can be performed in situ, and it can be facilitated through use of external RF instrumentation which measures the radiated field strength from the transmitting device. In various embodiments, metallic material near the antenna may affect antenna performance. In various embodiments, the device may include a non-metallic portion near (e.g., directly above) the antenna. In various embodiments, the non-metallic portion may include a polymer. In various embodiments, the non-metallic portion may be a UV-curable epoxy.

In various embodiments, the casing of the device may be used as the antenna. In various embodiments, the casing includes a metal or combinations of metals (e.g., an alloy). In various embodiments, the printed circuit contains no component antenna, but instead the pads for the Radio Frequency (RF) line may be soldered either directly or via a wire to the inside of the casing. In various embodiments, oscillating voltage is transferred to the casing which produces the electric field. In various embodiments, the inside of the casing where the PCB connection is soldered may be chemically plated with a metal which may be easily soldered to (e.g., nickel, tin, copper, etc.).

In various embodiments, the case may include an antenna cutout and/or waveguide. In various embodiments, as described above, no metal may be disposed near the antenna. In various embodiments, the portion of the case for the antenna may be a hole. In various embodiments, the antenna may be seated such that the antenna is directly pressed against the inside of the casing and into the hole. In various embodiments, the hole may function as a waveguide by directing electromagnetic radiation from the antenna in a specific direction, increasing the intensity in said direction (e.g., towards the cheek).

In some embodiments, a sensor device of the present inventive concepts wirelessly transmits a signal comprising measurement data at intermittent intervals. In some embodiments, the sensor device transmits the data signal on a regular basis, such as once per minute, once every five minutes, once every ten minutes, and/or repeated at intervals between once per minute and once per 30 minutes. In some embodiments, the sensor device wirelessly transmits the data signal immediately after the data signal is generated.

In some embodiments, a second device of the present inventive concepts wirelessly transmits at different intervals depending on measurement time resolution and battery life. These intervals can range from immediate (e.g., once per millisecond) to long term (e.g., once per year), depending upon patient need(s) and the molecule(s) being measured. In some embodiments, in balancing measurement time resolution against battery life, sensor device measurement data is stored in memory and then transmitted together (e.g., in multiple) as a single packet. In some embodiments, in balancing measurement time resolution against battery life, sensor device data is conditionally wirelessly transmitted depending on when and/or how often measurement data deviate from predetermined and/or predicted values.

In some embodiments, the sensor device stores data (e.g., all measured data) in embedded memory and only transfers the data (e.g., all or a portion of the data) through a connection event, such as a connection event that is initiated automatically by the system and/or manually by the user.

The sensor devices of the present inventive concepts can comprise a power source (e.g., a battery and/or a capacitor). The described modes of data transmission can be configured to work with a different powering mode. In embodiments with active circuits, power can be delivered by an onboard battery to supply a source drain voltage and source gate voltage over a FET, amplify the signal, and transmit it.

Figure 27A:
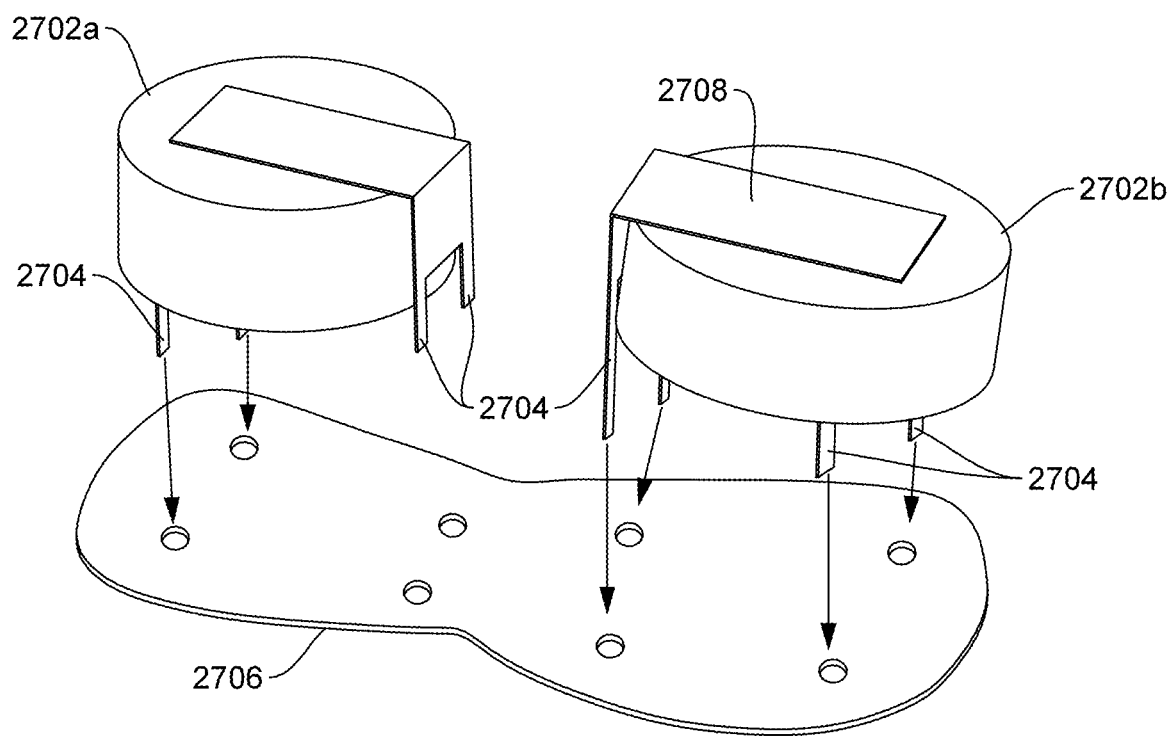
FIGS. 27A-27B illustrate a power source according to embodiments of the present disclosure.
Figure 27B:
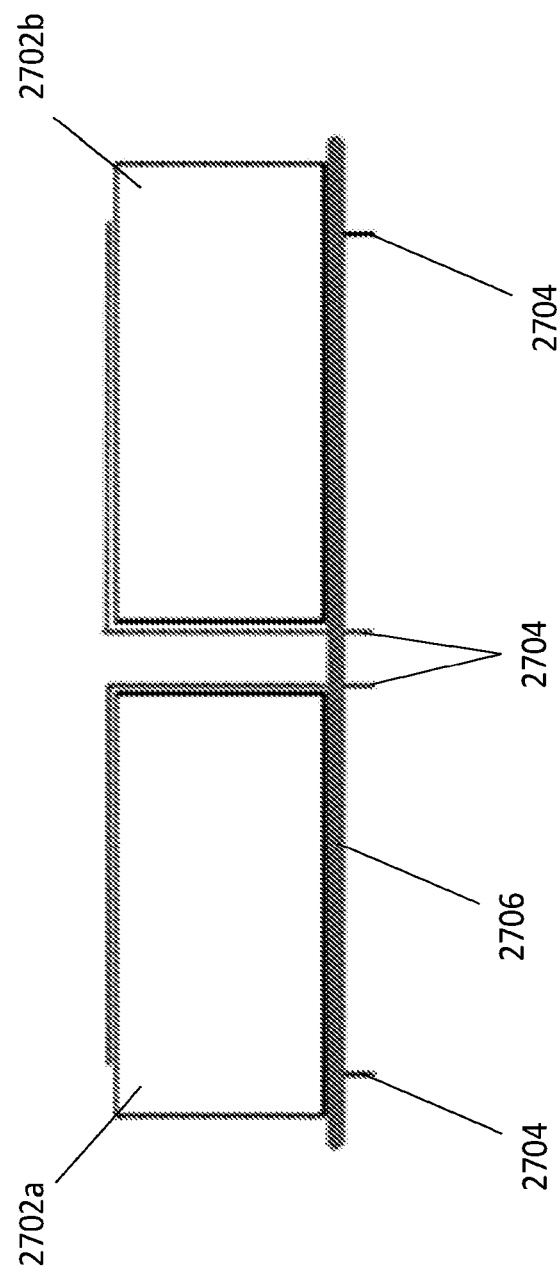

In various embodiments, as shown in FIGS. 27A-27B, the power source (e.g., one or more battery) 1602a, 1602b may include one or more spot-weld tabs 1604 such that the power source 1602a, 1602b can be positioned and soldered on a printed circuit board (PCB) 1606 consistently, accurately, and quickly. In various embodiments, the one or more spot-weld tabs 1604 may be configured such that the power source can be affixed to the PCB 1606 using through-hole soldering. In various embodiments, the spot-weld tabs 1604 may extend from a body 1608 that is affixed to the power source (e.g., at the top of the battery). Exemplary dimensions of the body 1608 may be 0.10 mm thick, 2.25 mm wide, and 2.25 mm long. Exemplary dimensions of the tabs 1604 may be 1.0 mm long, 0.5 mm wide, 0.10 mm thick, and may be spaced away from one another by 1.25 mm. In various embodiments, any electrical components (e.g., the power source, PCB, and/or tabs) may be coated with a coating. For example, the power sources 1602a, 1602b, the tabs 1604 may be coated with parylene to prevent electrical short circuits and/or insulate the electrical components. In various embodiments, the coating may be deposited via chemical vapor deposition. In various embodiments, the thickness of the coating may be from about 5 to about 50 microns thick. In various embodiments, the casing may be designed to take into account power source expansion. For example, when using a lithium ion power source, the power source may expand over its lifetime. In various embodiments, the casing may be designed to provide clearance over a predetermined lifespan of the device.

In view of potential limitations of an included power supply, new devices and methods to wirelessly recharge the power supply (e.g., while in the patient's mouth) have been discovered. In some embodiments, a small plate capacitor is placed on the top of a tooth, which generates current as the user chews. Per Maxwell's equations, a current can be induced by changing the distance between the charged plates of a capacitor over time. Thus, in some embodiments, as the patient chews, a small current is continuously generated and used to recharge the power supply. Alternatively or additionally, the power supply can be recharged by thermal gradients and/or chemical gradients within the mouth. In some embodiments, wireless inductive charging from an external source is used, so the patient doesn't need to remove the power supply (e.g., all or a portion of the sensing device) to recharge the power supply. In some embodiments, at least a portion of the sensor device is removed and placed on a wireless inductive charging plate, similar to a wireless phone charger.

In some embodiments, wireless communications and/or wireless charging of the power supply can be accomplished by employing one or more windings of small diameter magnet wire around the perimeter of a molar band. For charging operations, an electric and/or magnetic field emanated from an external charging device can induce a corresponding electron flow in the winding which would be then rectified into DC current and supplied to the power supply (e.g., battery and/or storage capacitor). For communications operations, the same process can be employed for receiving data, excepting that this energy can be directed towards a radio receiver. For transmitting data, the process is reversed wherein the transmitter induces an electric current in the winding, generating an electric and magnetic field that is sensed by an external device, such as a receiving device described herein.

The sensor devices of the present inventive concepts can be constructed and arranged to withstand damage from a variety of environmental factors, including damage via physical shear forces, damage via chemical corrosion, and/or damage from formation of a biofilm or food layer over the sensing surface in the complex intraoral environment. In some embodiments, the sensing assembly of the sensing device comprises a proton exchange membrane. In such embodiments, the sensing elements (e.g., the ISFET and/or reference electrode) is exposed to salivary analytes only through a proton exchange membrane. The protons must diffuse across the membrane in order to reach the one or more sensing elements. In some embodiments, the sensing element(s) is enclosed in a protective housing which protects the transducer from physical and other forces experienced in the mouth, prolonging sensing lifetime, and reducing noise.

In some embodiments, one or more surfaces (e.g., one or more outer surfaces) of a sensor device of the present inventive concepts is made of an antifouling material that resists biofilm deposition, prolonging the lifetime of the sensor device. In some embodiments, all or a portion of the sensor device outer surface is chemically treated with antibiotics and/or hydrophobic compounds, such as to prevent materials from adhering. In some embodiments, the sensor device comprises an antimicrobial peptide coating. In some embodiments, the all or a portion of the outer surface of the sensor device is smooth, such as with no pockets, jagged edges, gaps, or overhangs in which debris or bacteria can collect. In some embodiments, a physical antifouling surface (e.g., a geometric pattern) is provided on the outside of the sensor device, such as a pattern similar to sharkskin. In various embodiments, the sensor may be protected from biofouling using methods that are known in the art. In various embodiments, if biofouling occurs, any debris can be removed by brushing the device similar to how a tooth would be brushed, or letting the device soak in a cleaning solution such as a denture cleaner.

In some embodiments, a sensor device of the present inventive concepts comprises a biocompatible epoxy which is ISO-10993-4,5,6,10,11 approved. Such a coating can reduce irritation or inflammation of tissue surrounding the sensor in the oral cavity.

Methods of Installation

In some embodiments, the sensor devices of the present inventive concepts are designed to be installed in the mouth of the patient by a dental provider (e.g. a dentist and/or an oral hygienist). In embodiments where the sensor device comprises an attachment assembly including a molar band, and a dental provider can select one molar on each side of the mandible to receive the band. In anticipation of orthodontic band placement, elastomeric separators can be placed through the interproximal contacts of the mandibular (lower) molars to be banded, to create space for the bands to be seated. Next, the correct size band can be selected for the patient. A correctly sized band will not be too loose but will have sufficient space for the placement of band adhesive (e.g. cement). In some embodiments, a band is placed so the slot height of the band is in the middle of the tooth, with the indentation fitting into the mesio-buccal groove of the mandibular molar. Generally, an approximately equal amount of cusp height is visible from the buccal (cheekside) and lingual (tongue side) aspects of the molars that are banded. A band pusher or bite stick can be used to help seat the band. The tooth number and band size can be etched onto the mesial (closer to the anterior midline) surface of the band, and can be noted, by the dental provider, in the patient's records, for future reference. Once the band size is confirmed, the dental provider can choose the appropriate sensor device (e.g., for cementation or other adhesive attachment). In some embodiments, the interior of the band is dried with a cotton roll or gauze and set aside. In some embodiments, pumice is applied to the tooth by way of a prophy cup to remove the pellicle from the surface of the teeth. Next, resin modified glass ionomer cement, zinc oxide eugenol cement, zinc polycaboxylate cement, or resin cement, sometimes with fluoride release and fluoride recharging capability, can be mixed on a glass slab with a mixing spatula. Adhesive (e.g., cement) can then placed, with the mixing spatula, covering the interior of the band. The band can be seated using a band pusher or bite stick as needed. Excess adhesive can be removed with a cotton roll or gauze before the adhesive sets. Once set, excess cement can be removed with a Mitchell trimmer or knotted floss passed through the interproximal contact points.

The present inventive concepts include methods for installing a sensor device comprising an attachment mechanism including a molar band in an oral cavity of a patient. The methods include selecting a molar in the oral cavity of the patient; sizing the selected molar for a molar band; creating space around the molar sufficient to fit the appropriate portion(s) of the sensor device; applying adhesive to the molar band of the sensor device portion; installing the portion around the molar; and wirelessly syncing the sensor device to a receiving device.

In some embodiments, the method further comprises removing excess adhesive from the molar.

In some embodiments, the method further comprises syncing the sensor device to an application installed on a receiving device. The method can further comprise adding identifying information of the patient to the application.

Methods for Measuring pH, Temperature, and Analytes in Patients

The sensor devices of the present inventive concepts can be worn by healthy mammals and/or mammals with various health conditions (either referred to as "patient" herein). Patients who have many cavities and very poor oral health could greatly benefit from using these sensor devices. In some embodiments, the patient is informed throughout the day when their oral pH is approaching critical levels and taught to correct the imbalance in real time. In some embodiments, when a patient receives a notification of low oral pH, he or she will also receive recommendations for how to correct the imbalance in the mobile application (pH correcting mouthwash, pH correcting oral spray, brushing teeth, etc.). Furthermore, in some embodiments, a clinician (e.g. a doctor or other health care provider) of the patient can track the data to identify trends in oral pH levels and better diagnose the source of the disease. If a patient's pH drops below a threshold (e.g. 5.5) at night, caries could be occurring due to xerostomia or conditions that occur while sleeping. If the patient's pH drops after meals, the clinician could recommend different dietary habits. The sensor device can also be used to track the effectiveness of one or more particular treatments, in between dental and/or other clinical visits. The lifespan of permanent restorations, like crowns, root canals and implants will increase significantly if oral pH is maintained at a healthy level. In this way, insurance companies will save on costs associated with re-treatment and dentists will be able to avoid misplaced blame for failing treatment. Individuals with mild and good oral health could also benefit from using this sensor in similar ways. They can be notified (e.g. in real time) whenever oral pH drops below a threshold (e.g. a critical level) and effectively prevent the onset of caries and receive recommendations in the mobile application on how to correct the oral pH (e.g. via mouthwash, brushing teeth, and/or other corrective measures) before carious infections develop. This corrective action can save a great amount of pain and suffering from experiencing cavities, reduce money spent on treating carious infections, and reduce time spent at dentists' offices. If caries does begin to occur, a clinician can monitor the pH levels over time to better assess their origin and provide more personalized and effective treatments.

Another aspect of this disclosure is directed to a method for continually and/or intermittently measuring pH, temperature, one or more analytes, or a combination thereof, in an oral cavity of a patient. The method comprises installing a wearable intraoral sensor of this disclosure in the oral cavity of the patient. This disclosure contemplates wearable intraoral sensors that can be inexpensively and quickly installed.

In some embodiments, the sensor housing comprises one or more sensing elements (e.g. an ISFET and/or a reference electrode), a controller, and a power source. A proton exchange membrane can be included to allow passage of specific materials only (avoiding non-desired materials) to chambers including the sensing elements. A sensor assembly can be connected to an attachment mechanism (e.g. including a band) with a seal. In some embodiments, saliva directly contacts the membrane of the sensor device.

In some embodiments, a sensor device of the present inventive concepts is configured to continually and/or intermittently measure pH in the oral cavity for at least one day, at least one week, at least one month, or at least 3 months.

The methods of the present inventive concepts can also comprise measuring pH, temperature, one or more analytes, or a combination thereof, in the oral cavity of the patient for at least one day, thereby generating measurement data. In some embodiments, the measurement data is pH measurement data, temperature measurement data, analyte measurement data, or a combination thereof.

The methods of the present inventive concepts can also comprise wirelessly transmitting the measurement data from the sensor device at intermittent intervals. In certain embodiments, the measurement data is wirelessly transmitted once per minute, once per five minutes, once per ten minutes, and/or at an interval between once a minute and once every 30 minutes. In some embodiments, the measurement data is wirelessly transmitted immediately after the data signal is generated. In some embodiments, measured data is transmitted when requested by the receiving device at variable, non-defined intervals.

In some embodiments, the attachment mechanism includes a molar band sized to fit around a molar in the oral cavity of the patient. In some embodiments, the attachment mechanism is a dental crown (also called a "dental cap") in the oral cavity of the patient. In some embodiments, the attachment mechanism is a dental implant, bridge, dentures, orthodontic anchor, and/or any dental prosthesis in the oral cavity of the patient.

In some embodiments, the methods of the present inventive concepts include wirelessly transmitting the measurement data from the molar band at intermittent intervals to a receiving device. In some embodiments, the receiving device is a smart device. In certain embodiments, the smart device is a smart phone, a smart watch, a tablet, a smart home device (e.g., an Amazon Echo™ device or other device using Amazon Alexa™ technology, a Google Home™ device, or a smart device manufactured by Apple), and/or a computer. In some embodiments, the smart device is an iPhone or Android phone. In some embodiments, the method further comprises configuring the receiving device and/or smart device to receive the measurement data. In some embodiments, configuring a receiving device or smart device to receive the measurement data comprises installing an application on the receiving device or smart device.

In some embodiments, the methods of the present inventive concepts include wirelessly transmitting measurement data to Apple, Android, Nokia, and/or other smartphones, such as a transmission comprising Bluetooth, WiFi and/or Near Field communications capabilities. In some embodiments, the receiving device is a laptop, PC, and/or other smart device equipped with Bluetooth, WiFi, and/or Near Field communications capabilities. In some embodiments, the receiving device acts as a "relay station" and sends measurement data to the Internet, the "Cloud," and/or to another computer system. In some embodiments, the receiving device is an Apple, Google, or Amazon "Smart Home" device (e.g., a Siri-enabled, Google Home-enabled, or Alexa-enabled device) which, in addition to functioning as a relay station, can interact with the patient in which the sensing device is installed (e.g. in the mouth of the patient).

In some embodiments, the receiving device is a custom product specifically designed for use with the wearable intraoral device. The custom device can provide for a variety of audio, visual, and/or haptic components configured for interaction with the patient. These components can include, but are not limited to, LEDs, speakers, vibrators, and text or graphic displays.

Existing devices and methods do not display patient data measured in the patient's oral cavity. In some embodiments, an application of the present inventive concepts is configured to display measurement data on a display of the receiving device. In some embodiments, the application is configured to display measurement data in graphical form on a display of the receiving device. In some embodiments, the application is configured to display measurement data over time in graphical form on a display of the receiving device. In some embodiments, the application is configured to display pH or other measurement data over time in graphical form with an indication of a critical value (e.g. a critical pH value) on the display of the receiving device.

In some embodiments, the methods of the present inventive concepts comprise transmitting patient data from a receiving device and/or smart device to a medical office, such as a dental office. In some embodiments, the method further comprises transmitting patient data from a receiving device and/or smart device to a research institution and/or a corporation (e.g. a manufacturer of the system of the present inventive concepts), such as to perform data processing or other function. In some embodiments, the method comprises syncing data between the sensor device and the receiving device and/or smart device.

In some embodiments, the methods of the present inventive concepts include orienting a housing of the sensor device buccally to measure pH, temperature, one or more analytes, or a combination thereof, from saliva gathered in the cheek of a patient. In some embodiments, the method comprises orienting the transducer proton exchange membrane buccally.

Long-Term Intraoral Data Measurement Systems

One aspect of the present inventive concepts includes systems for continually and/or intermittently monitoring pH or other parameter, as described herein, in an oral cavity of a patient. Systems comprise a wearable sensor device, as described herein, installed in an oral cavity of a patient. Systems also comprise a receiving device external to the oral cavity of the patient and configured to receive measurement data wirelessly transmitted from the sensor device.

In some embodiments, the receiving device is a mobile device. In some embodiments, the smart device is a smart phone, a smart watch, a tablet, and/or a computer. In some embodiments, the smart device is an iPhone or Android phone.

In some embodiments, the receiving device comprises a display. In some embodiments, the receiving device is configured to display the measurement data, or a manipulation thereof, on a display. In some embodiments, the receiving device is configured to display the measurement data, or a manipulation thereof, in graphical form on a display. In some embodiments, the receiving device is configured to display the measurement data, or a manipulation thereof, in graphical form on a display and to update the measurement data, or manipulation thereof, repeatedly (e.g. in real-time), such as updates performed as measurement data are generated.

In some embodiments, the systems of the present inventive concepts further comprise an application installed on a receiving device for manipulating the measurement data. In some embodiments, the application comprises a user interface configured to interact with a user (e.g. the patient or a clinician of the patient). In some embodiments, the application is configured to display measurement data, or a manipulation thereof (e.g. in graphical form). In some embodiments, the application is configured to enter an alert state (e.g. display an alert or play an audible alert or cause the receiving device to vibrate, or a combination thereof), when measurement data meet certain criteria (e.g. an undesired level of the criteria is achieved, such as when a threshold is exceeded). In some embodiments, the application is configured to determine whether measurement data meet threshold criteria for a disorder or the potential development of a disorder. In some embodiments, pH data is measured within a range of pH 2.0 to pH 10.0, and the threshold pH is set at pH 5.5. In some embodiments, when measured pH is below a pH of 5.5 (e.g. instantaneously and/or for specified periods of time), the application enters an alert state. The specified periods of time can range in duration. For example, a minimum duration can be set to a time ranging from two minutes to 120 minutes.

In some embodiments, the systems of the present inventive concepts are configured to measure macronutrient levels. In some embodiments, the macronutrient data is consumed grams of protein, carbohydrates, fats, and/or calories. In some embodiments, the application is configured to enter an alert state (e.g. play an audible alert or display a message alerting the patient) when specific dietary thresholds are met or approached (e.g. 2000 calories, 100 grams of fat). In some embodiments, allergen data is measured by presence of potential allergen-related molecules. In some embodiments, the application is configured to enter an alert state when a potential allergen has been detected and/or has attained minimum concentration levels (e.g., concentration of peanut proteins increased from 10 ppm to 30 ppm).

In some embodiments, criteria (e.g. criteria used to enter an alert state) comprise criteria for diagnosing caries disease, HIV, viral and bacterial pathogens including herpes, hepatitis, HIV, HPV, influenza, polio, *E. coli, Mycobacterium tuberculosis, Helicobacter pylori, Treponema pallidum, Candida albicans, Toxoplasma gondii*, and *Schistosoma mansoni*, cardiovascular disease (CVD), oral squamous cell carcinoma (OSCC), oral infection, hyperglycemia, hypertension, renal disease, stress, pain, periodontal disease, type 1 and type 2 diabetes, Lupus Erythematosus, oropharyngeal candidiasis (OPC), Scleroderma, Sjogren's syndrome, lymphoma, prostate cancer, breast cancer and tongue cancer.

In some embodiments, criteria (e.g. criteria used to enter an alert state) are customized depending on variables specific to the patient. In some embodiments, the criteria comprise patient-specific risk factors.

In some embodiments, a receiving device is configured to send measurement data to a receiving server. In some embodiments, the receiving device is also configured to send patient-identifying information to a receiving server.

In some embodiments, a system of the present inventive concepts further comprises a receiving server configured to receive measurement data from a receiving device. In some embodiments, the receiving server is configured to determine whether measurement data indicates the development or potential development of a disorder in the patient. In some embodiments, the receiving server comprises criteria for determining whether measurement data indicates the development or potential development of a disorder in a patient. In some embodiments, the receiving server is operably linked to one or more databases, or one or more additional servers, or a combination thereof, for determining whether measurement data indicates the development or potential development of a disorder in the patient. In some embodiments, the receiving server is configured to send a message to the receiving device. In some embodiments, the message comprises information related to the development or potential development of a disorder in the patient. In some embodiments, the message comprises instructions for the application to enter an alert state.

In some embodiments, the criteria are criteria for diagnosing caries disease or the potential for development of caries disease.

In some embodiments, the criteria are customized depending on variables specific to the patient. In some embodiments, the criteria comprise patient-specific risk factors.

In some embodiments of the systems, the sensor device is configured to transmit the measurement data (e.g. to a separate device as described herein) at intermittent intervals. In some embodiments, the measurement data is wirelessly transmitted once per minute, once per five minutes, once per ten minutes, and/or at an interval between once a minute and once every 30 minutes. In some embodiments, the measurement data is wirelessly transmitted immediately after the data signal is generated.

Methods of Diagnosing Disorders

In some embodiments, wireless transmitting of data (e.g. pH or other physiologic parameter data) performed by the sensor device requires no human effort and is continual. In some embodiments, the system of the present inventive concepts compares the measurement data to criteria related to one or more medical conditions, wherein the medical condition is diagnosed when the measurement data matches the criteria for a medical condition. In certain embodiments, the criteria can be customized depending on variables specific to the patient. In some embodiments, the method does not require any action by the patient.

In some embodiments, a method of the present inventive concepts comprises measuring pH, temperature, one or more analytes, or a combination thereof, in an oral cavity of a patient for at least one week. In some embodiments, the method comprises measuring pH, temperature, one or more analytes, or a combination thereof, in an oral cavity of a patient for a defined time period, such as a time period between one day and six months.

In some embodiments, the system of the present inventive concepts is configured to gather data related to: caries disease; GERD; heart disease; hypoglycemia; hyperglycemia; hormonal imbalance; HIV; herpes; hepatitis; HIV; HPV; influenza; polio; *E. coli; Mycobacterium tuberculosis; Helicobacter pylori; Treponema pallidum; Candida albicans; Toxoplasma gondii; Schistosoma mansoni*; cardiovascular disease (CVD); oral squamous cell carcinoma (OSCC); oral infection; hyperglycemia; hypertension; renal disease; stress; pain; periodontal disease; type 1 and type 2 diabetes; Lupus Erythematosus; oropharyngeal candidiasis (OPC); Scleroderma; Sjogren's syndrome; lymphoma; prostate cancer; breast cancer; and/or tongue cancer.

In some embodiments, a method of the present inventive concepts further comprises identifying a time period that the pH measured in the oral cavity was below a threshold value on a plurality of days. In some embodiments, the method further comprises identifying patterns of pH measured falling below a threshold value.

In some embodiments, the systems of the present inventive concepts are configured to provide automated computer-implemented methods of sending a message comprising a suggested product, the method comprising, receiving at a server, measurement data measured in the oral cavity of a patient over a time period of at least one day, where the measurement data is sent from an application installed on a mobile device; identifying a disorder or the potential for a disorder to develop in the patient based on the measurement data; identifying a product for treating the identified disorder; preparing a message comprising information about the product and sending the message to the mobile device.

Saliva is increasingly recognized as a valuable diagnostic fluid. Each year, more diagnostic assays are using saliva to infer the health of an individual, and there are already over one thousand conditions detected and monitored using saliva (Malamud D, Saliva As A Diagnostic Fluid, Dent Clin North Am. 2011 January; 55(1):159-78 (accessed here: https://www.ncbi.nlm.nih.gov/pubmed/21094724).) This disclosure provides details on the design features and production methods on a novel wearable oral sensor to measure and transmit analyte concentrations in saliva in a continual manner.

Caries disease (cavities) is a widespread health problem in the United States. According to the CDC, 60% of American children ages 2 through 18 have this disease, making it the most common chronic disease in kids. 92% of adults ages 19 through 64 experience caries at some point in their lives and 25% of adults over 65 years of age do not have any teeth left, due to untreated decay. Low salivary pH is directly related to caries disease. Caries is caused by the action of acids on the surface of teeth, which slowly demineralize the enamel once the plaque pH drops below 5.5. The acid is produced when sugars from food and drink interact with bacteria present in the dental biofilm (plaque) on the surface of teeth. A healthy patient's salivary pH ranges between 6.2 and 7.6 with occasional drops following eating or drinking. Once the pH drops below 5.5 (the critical pH of enamel) the oral environment is under-saturated with mineral ions relative to tooth's mineral content and enamel begins to dissolve and lose calcium and phosphate in a process known as demineralization. Saliva plays an important role in buffering plaque acids and halting demineralization by providing a reservoir of minerals from which the enamel can re-mineralize and "heal". The demineralization and remineralization of enamel occurs many times throughout the day. Caries progresses only when demineralization exceeds remineralization. The typical treatment option for caries is to drill out the decay and put in a filling (restoration). Patients with extensive caries need a crown, root canal treatment, or extraction of the tooth. If left untreated, infections can develop and spread systemically to vital organs such as the eye, causing blindness, and to the brain or heart where they can be lethal.

Research suggests the need for a major shift in the way tooth decay is managed by dentists. There is a movement towards a more preventive approach compared to the formerly practiced paradigm of just "drilling and filling." Preventative, evidence-based Caries Risk Assessment (CRA) protocols have become the standard of care for prevention and official policy in dental education. The goals of such protocols are to stop or reverse caries by catching them at the earliest stages, i.e., before damage becomes irreversible and restorative intervention is necessary. Caries risk assessment is the current standard for providing preventative care. The existing standardized caries risk assessment methods, like those established by the American Dental Association (ADA), American Academy of Pediatric Dentistry (AAPD), and Caries Management by Risk Assessment (CAMBRA), are time-consuming, and rely on subjective surveys and questionnaires, thus rendering them inaccurate and underused outside of dental school clinics. All risk factors assessed by protocols such as CAMBRA are meant to help the dentist determine when and for how long a patient's oral pH is critically low which provides insight into when and for how long demineralization is out-weighing remineralization; the basis of determining a patient's caries risk level. However, there is no objective tool capable of measuring a patient's risk. There is currently no effective method of monitoring saliva characteristics or pH over time to provide a sufficient understanding of a patient's risk.

Salivary pH testing is part of CAMBRA protocol. Currently, dentists use a one time, color changing, paper pH strip. The dentist dips the pH strip into a sample of resting saliva and may infer the pH of the saliva using the color of the strip and a color calibration guide. However, the single use, high user input level, and analog reading methods of the pH strips make them underused in dental settings. Furthermore, a one-time reading of salivary pH does not convey sufficient information regarding the conditions of the oral cavity, the potential development of caries disease, or the development of caries disease.

Saliva contains information beyond just risk of caries disease. It can be used as a diagnostic fluid, and may be tested to gain insights on thousands of other health conditions.

All of the recent approaches to measure concentration of oral analytes or pH present many problems that limit their effectiveness, usability, and commercialization. Blood tests are invasive, can cause pain, and require samples to be sent to a laboratory. Salivary samples are a snapshot in time and must be sent to a laboratory. Some intraoral devices require wires exiting the mouth for data transmission, some are uncomfortable and irritate tissue in the patient's mouth, some interfere with a patient's occlusion, some disrupt a patient's daily routine, some require significant patient compliance, some are only applicable for short term pH measurement, some require new application methods unfamiliar to dentists, and some must be uniquely fabricated for a patient's mouth. Methods and devices for long term, continual, salivary monitoring that are comfortable, inexpensive, safe, and do not affect a patient's daily routine are needed to help patients and dentists identify the cause and severity of caries progression.

Components of the systems, devices, and assemblies of the present inventive concepts described in reference to the figures can be described in reference to their relative position on the page (e.g. above, below, to the right, to the left, and the like).

Referring now to FIG. 1, a schematic view of a physiologic parameter recording system including a sensor device is illustrated, consistent with the present inventive concepts. System 10 can be configured to measure one or more physiologic parameters of a patient such as a human, other mammal, and/or other animal. System 10 comprises one or more sensor devices, sensor device 100 shown. Sensor device 100 can comprise an intraoral device configured for placement within the mouth of a patient, such as for continuously and/or intermittently monitoring one or more physiologic parameters of the patient (e.g. one or more physiologic parameters present in and/or otherwise determined by an analysis of the patient's saliva). For example, device 100 can record, detect, and/or measure ("record", "detect" or "measure" used interchangeably herein) one, two, three, or more physiologic parameters selected from the group consisting of: pH; temperature; analytes, such avian influenza virus; hepatitis B markers, such as HBsAg; cancer markers, such as AFP; human thyroid stimulating hormones; interleukin 8 (IL-8); tumor necrosis factor (TNF-alpha); cancer biomarkers, such as CYFRA21-1; prostate cancer biomarkers, such as PSA; carcinoembryonic antigen (CEA); cardiac troponin I (cTnI); C-reactive protein (CRP); prostate cancer biomarkers, such as osteopontin (OPN); interleukin-6 (IL-6) cortisol; Lyme disease antigens; Alzheimer's disease biomarkers, such as amyloid-beta; chondroitin sulfate proteoglycan 4; pancreatic cancer biomarkers, such as carbohydrate antigen 19-9 (CA 19-9); prostate specific antigen/1-antichymotrypsin (PSA-ACT) complex; breast cancer biomarkers; human epidermal growth factor receptor 2; human immunodeficiency virus (HIV); bladder cancer biomarkers, such as urinary APOA2 protein; prostate cancer biomarkers, such as PSA-ACT complex; D-Dimer; biomarkers of venous thromboembolism; breast cancer biomarkers, such as EGFR; hemoglobin-A1c; insulin; cortisol; androgens; testosterone; estriol; estrogen; progesterone; aldosterone; DHEAS; antibodies, such as IgG, IgA, sIgA, IgM; growth factors, such as EGF, NGF, VEGF, IGF; cytokines and chemokines, such as IL-1 beta, IL-8, IL-6, MCP-1, CX3CL1, GRO-1 alpha, troponin I, TNF alpha; nucleic acids, such as human DNA, microbial DNA, mRNA, siRNA, micro RNA (miR-125a and miR-200a); and combinations thereof. In some embodiments, device 100 can record a protein (e.g. a protein detectable in saliva). In some embodiments, device 100 can record a drug, such as a drug including, but not limited to: drugs of abuse; ethanol; a therapeutic drug; an anticonvulsants; an antipyretic/analgesic; an anti-neoplastic agent; an anti-bacterial agent; a bronchodilators; cotinine; a carbohydrates; a protein; a fat; an allergen such as shellfish, peanuts, and/or gluten; and/or a toxin such as mercury or other heavy metal. Sensor device 100 can be configured to record physical parameters such as salivary flow rate, tissue contact, temperature, salivary turbidity, salivary viscosity, ionic strengths, and/or jaw movements. Device 100 and/or another component of system 10 can include one or more algorithms, such as algorithm 155 shown. In some embodiments, system 10 further includes wearable device 300 and/or user device 400, each as shown.

Sensor Device 100 can include various components, such as sensor assembly 110, processor 150, power supply 160, transceiver 170, attachment mechanism 180, housing 1107, chamber 1126, and/or functional element 199, each as shown and described in detail herein. In the exemplary embodiment shown, the device 100 is configured to wrap entirely around the outer surface of a single tooth so as to circumscribe the tooth. Additionally or alternatively, the device can wrap around a plurality of teeth, e.g., two adjacent molars, to increase the surface area of the band and thereby provide more flexibility and spacing between components of the device. Also, the exemplary embodiment depicts a tapered band having its largest dimension (or height) proximate housing 1106, as shown in FIG. 1D, but other shapes/sizes (e.g., band with uniform height) will be understood by artisans to be within the scope of this disclosure.

Device 100 can include one or more sensor assemblies, such as sensor assembly 110 shown. Sensor device 100 can comprise an assembly for positioning within the patient's mouth (e.g. an assembly temporarily mounted to one or more molars and/or other teeth of the patient). Sensor assembly 110 can comprise various electrical, mechanical, optical, acoustic, and/or fluidic components (e.g. "electromechanical components" herein). Sensor assembly 110 can comprise one or more components for measuring (e.g. providing a signal related to) one or more physiologic parameters of the patient, as described herein. Sensor assembly 110 can comprise substrate 1102, insulator 1104, ISFET 1105, housing 1106, proton exchange membrane (PEM) 1108, mesh 1115, coating 1116, fluid channel 1117, reference electrode 1118, diaphragm 1119, reactive membrane 1122, electrolyte permeable membrane 1124, and/or chamber 1125, each as shown and described in detail herein.

Sensor device 100 can include one or more attachment devices, attachment mechanism 180 shown. Attachment mechanism 180 can be configured to attach all or a portion of sensor assembly 110 (all or simply a portion of sensor assembly 110 referred to as "sensor assembly 110" herein) to one or more molars and/or other teeth of the patient. Attachment mechanism 180 can be fixedly attached to sensor device 100, it can be attachable to sensor device 100, and/or it can be removably attached or attachable to sensor device 100. Attachment mechanism 180 can comprise one or more bands, such as one or more malleable and/or resiliently biased bands for surrounding one or more teeth of the patient. Attachment element 180 can comprise a band comprising a metal such as stainless steel, and/or a non-metal such as; plastic; polytetrafluoroethylene (PTFE); rubber; silicon; and/or shape memory alloy. In some embodiments, attachment mechanism 180 comprises glue, cement, and/or other adhesive ("adhesive" herein), for attaching a band or other component of attachment mechanism 180 to a patient's tooth. Attachment mechanism 180 can comprise a "clip on" and/or "snap on" feature (e.g., a feature that attaches a first portion of sensor device 100 to a second portion of sensor device 100, such as is described in reference to FIGS. 2A-2B herein). Attachment mechanism 180 can comprise a band (e.g., a band that frictionally engages a molar or other tooth of the patient) that is positioned for a limited period of time (e.g., less than one year) and then discarded (e.g., after use of system 10 is complete and/or to be replaced by a new band). The band can provide prolonged use of sensor device 100 (e.g., at least one day or at least one week), such as to provide valuable measurements of the physiologic parameters of the patient (e.g., measurement datasets used to diagnose a patient medical condition, such as for use in allergen monitors and nutritional monitors, where lapses in datasets may need to be avoided).

In some embodiments, attachment mechanism 180 comprises an adjustable attachment mechanism. For example, mechanism 180 can be comprise an adjustable band, such as a band that can be twisted to cause a diameter reduction, and then crimped onto a tooth to provide optimized sizing. In some embodiments, one or more excess portions attachment mechanisms 180 can be trimmed, such as during a trimming procedure after attachment mechanism 180 is secured to a tooth of the patient.

Sensor device 100, and/or another component of system 10, can include one or more algorithms, algorithm 155 shown. Algorithm 155 can comprise one or more algorithms which analyze recordings made by sensor assembly 110, such as to determine the level of a physiologic parameter of the patient based on the recordings. All or a portion of algorithm 155 can be included in any component of system 10. In some embodiments, algorithm 155 is configured to determine if system 10 should be in an alert state, as described herein.

System 10 can include user device 400 as shown. User device 400 can comprise one, two, or more devices selected from the group consisting of: a phone such as a smart phone; a watch such as a smart watch; a computer such as a laptop computer; a computer network; a tablet; a smart home device (e.g. an Amazon Echo™ device, a Google Home™ device, a smart device manufactured by Apple); and combinations thereof. User device 400 can include one or more batteries, capacitors, and/or other energy storage elements, power supply 460 shown. User device 400 can include one or more receivers, and/or one or more transmitters, transceiver 470 shown. User device 400 can comprise user interface 450, such as a user interface comprising one or more user input and/or user output components selected from the group consisting of: display; touchscreen display; keyboard; mouse; joystick; microphone; speaker; vibrational transducer; light such as an LED; and combinations of these. User device 400 can be configured to receive data from sensor device 100 (e.g. wirelessly receive data), as described herein. User device 400 can comprise at least a portion of algorithm 155.

System 10 can include wearable device 300 shown. Wearable device 300 can comprise one, two or more devices selected from the group consisting of: a user activity sensor; a heart monitor; an infusion device such as a pump; a skin attached device comprising one or more electrodes; a patient body position sensing device; and combinations of these. Wearable device 300 can include one or more batteries, capacitors, and/or other energy storage elements, power supply 360 shown. Wearable device 300 can include one or more receivers, and/or one or more transmitters, transceiver 370 shown. Wearable device 300 can comprise user interface 350, such as a user interface comprising one or more user input and/or user output components selected from the group consisting of: display; touchscreen display; keyboard; mouse; joystick; microphone; speaker; vibrational transducer; light such as an LED; and combinations of these. Wearable device 300 can be configured to receive data from sensor device 100 (e.g. receive data wirelessly and/or via tissue conductance), via transceiver 370, as described herein. Wearable device 300 can be configured to send data to user device 400, such as via a wired and/or wireless connection, such as via transceiver 370. Wearable device 300 can comprise at least a portion of algorithm 155. In some embodiments, user device 400 and wearable device 300 comprise a single device.

User device 400 and/or wearable device 300 can comprise a smart device, and/or a mobile device, as described herein.

Sensor device 100 can comprise a one or more microprocessors, microcontrollers, and/or other processing units, processor 150 shown. Processor 150 can include electronic components and/or assemblies selected from the group consisting of: memory storage circuitry; analog to digital converters; digital to analog converters; state machines; signal processing circuitry; signal filtering circuitry; and combinations of these. Processor 150 can be positioned within housing 1106 and/or 1107, each as described herein.

Device 100 can include one or more power supplies, such as power supply 160 shown. Power supply 160 can comprise one or more batteries, capacitors, and/or other energy supplying components. In some embodiments, power supply 160 comprises a replaceable and/or rechargeable power supply. In some embodiments, power supply 160 comprises a microbattery or other battery, such as a battery with a chemistry selected from the group consisting of: lithium polymer; lithium-ion; nickel metal hydride; silver oxide; and combinations of these.

Device 100 can include one or more data transmission modules, transceiver 170 shown. Transceiver 170 can comprise a wireless receiver and/or transmitter.

Figure 1A:
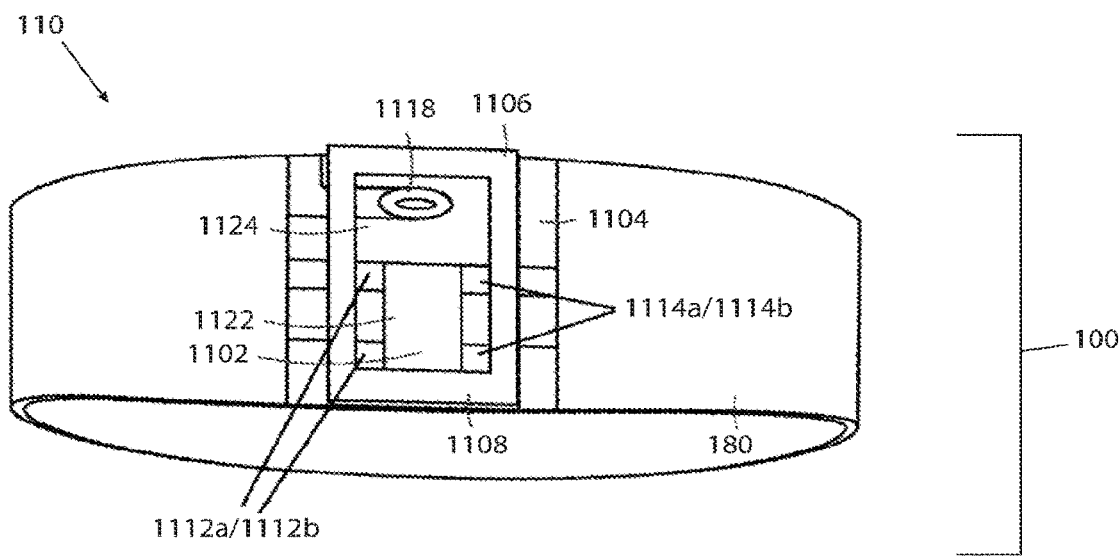
FIGS. 1A-1Q illustrate various views of a physiologic parameter recording system, its components, methods, and test data according to embodiments of the present disclosure.
Figure 1B:
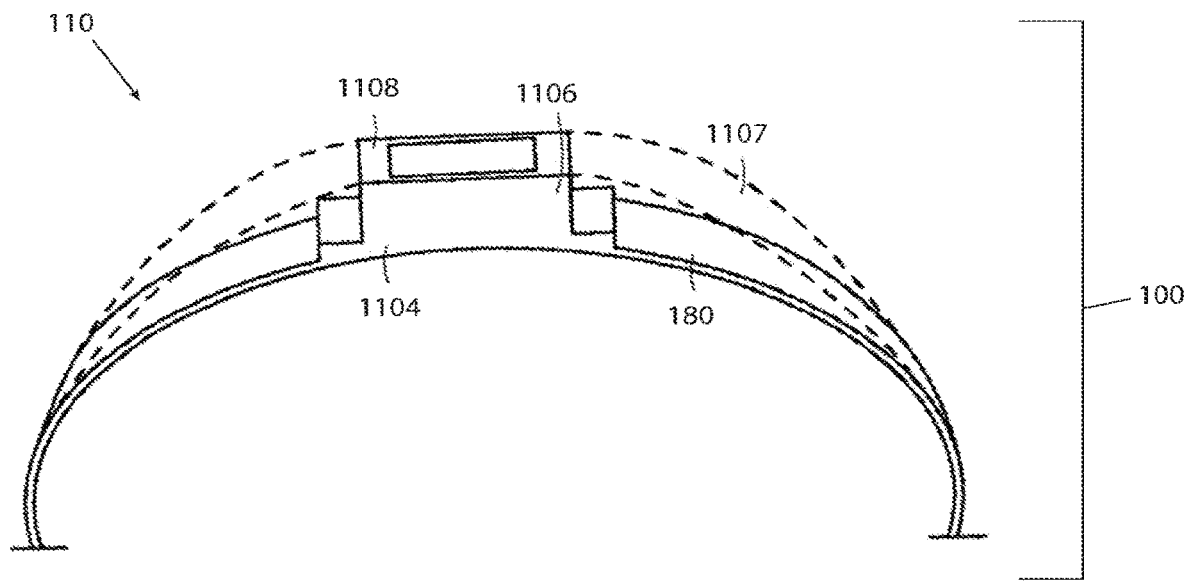
Figure 1C:
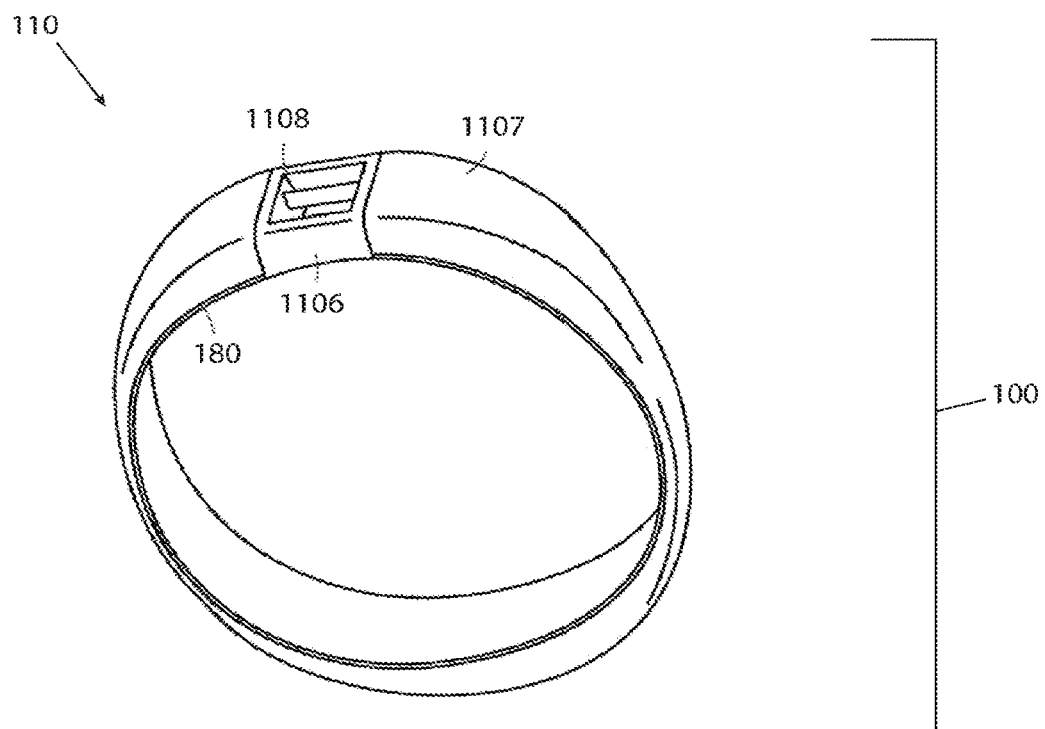
Figure 1D:
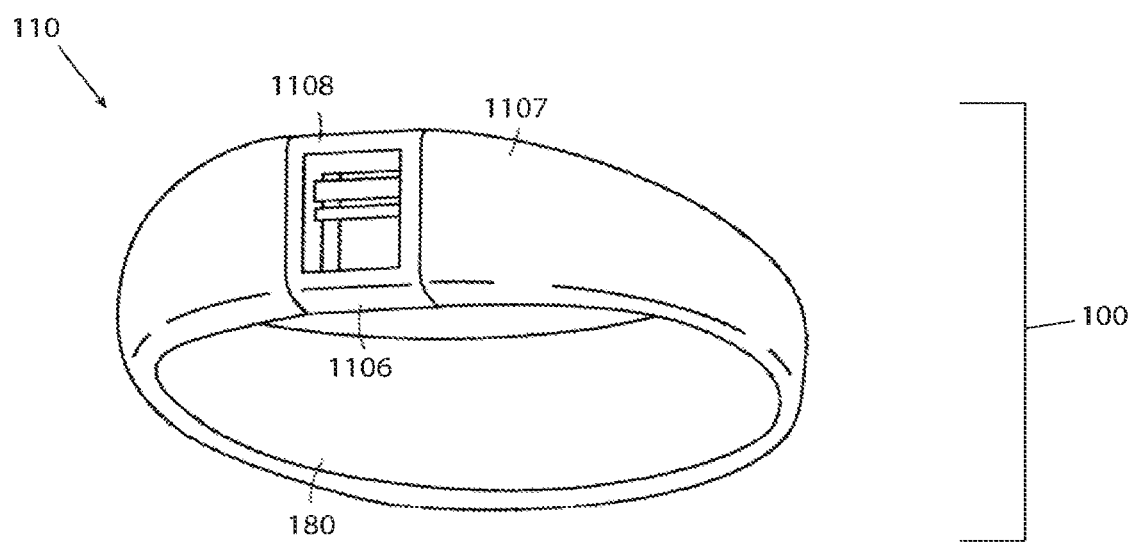
Figure 1E:
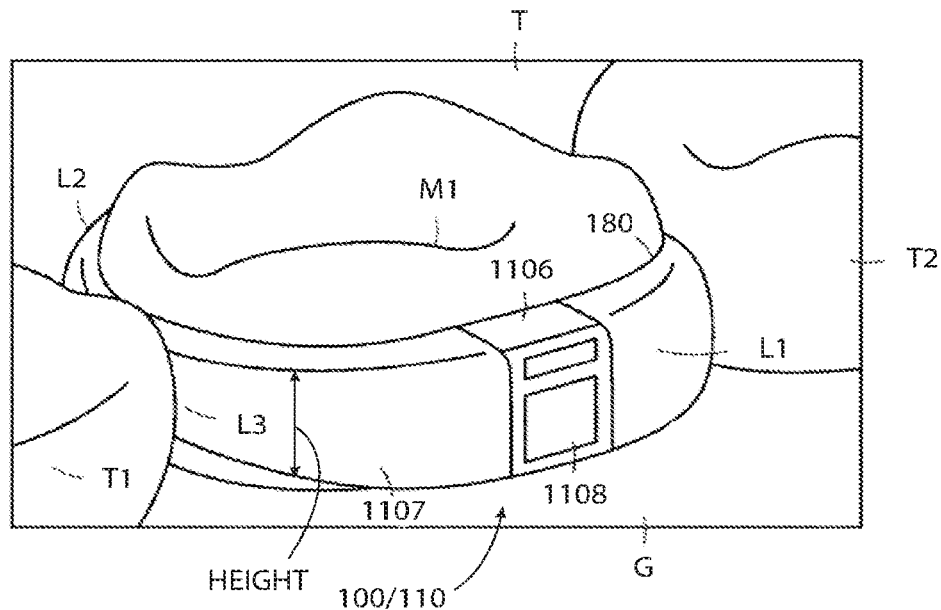
Figure 1F:
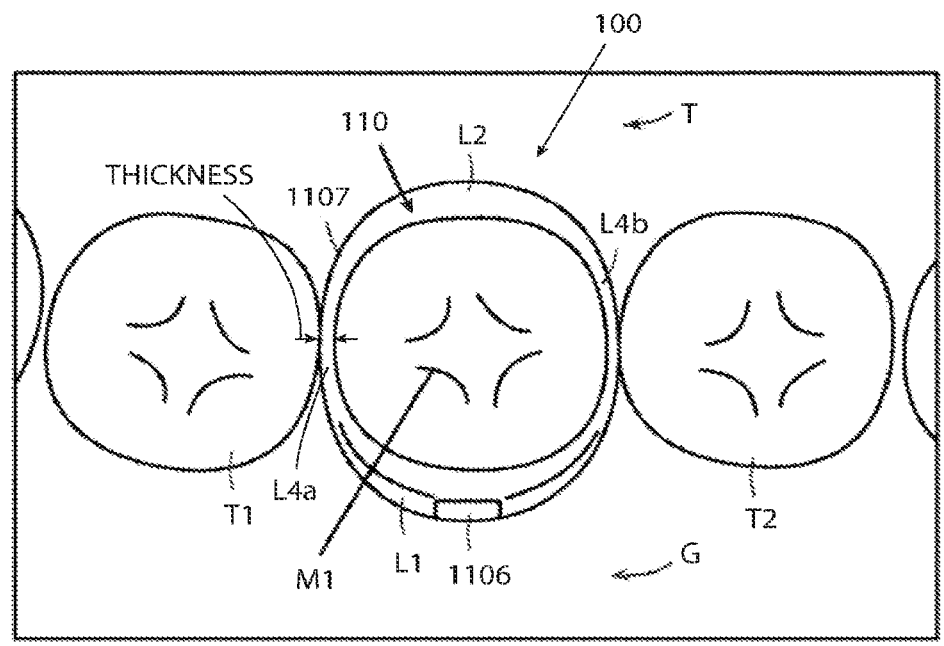
Figure 1G:
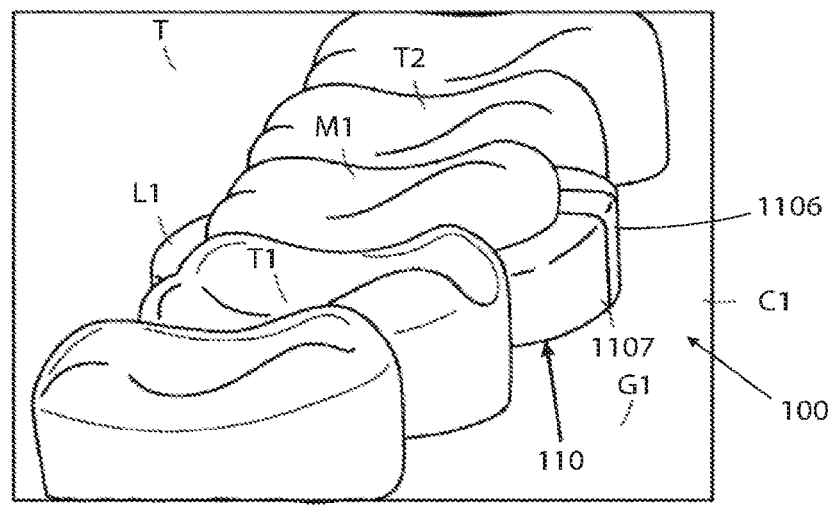
Figure 1H:
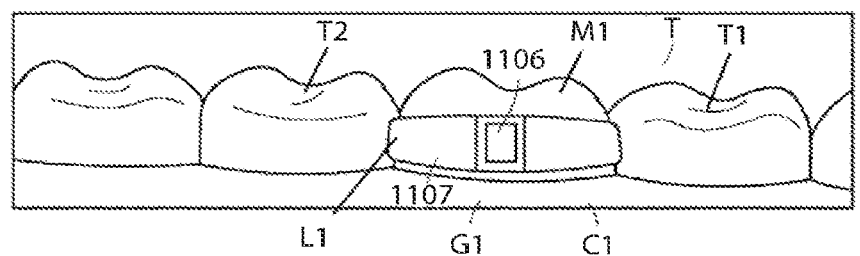
Figure 1I:
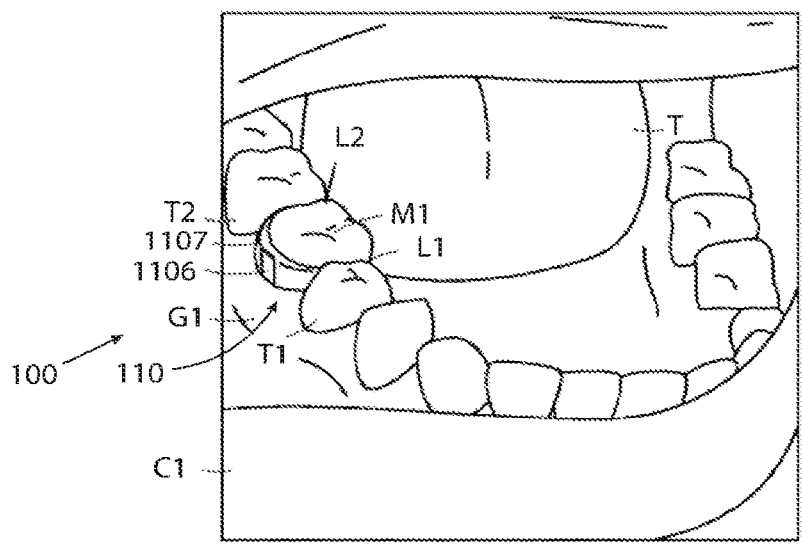
Figure 1J:
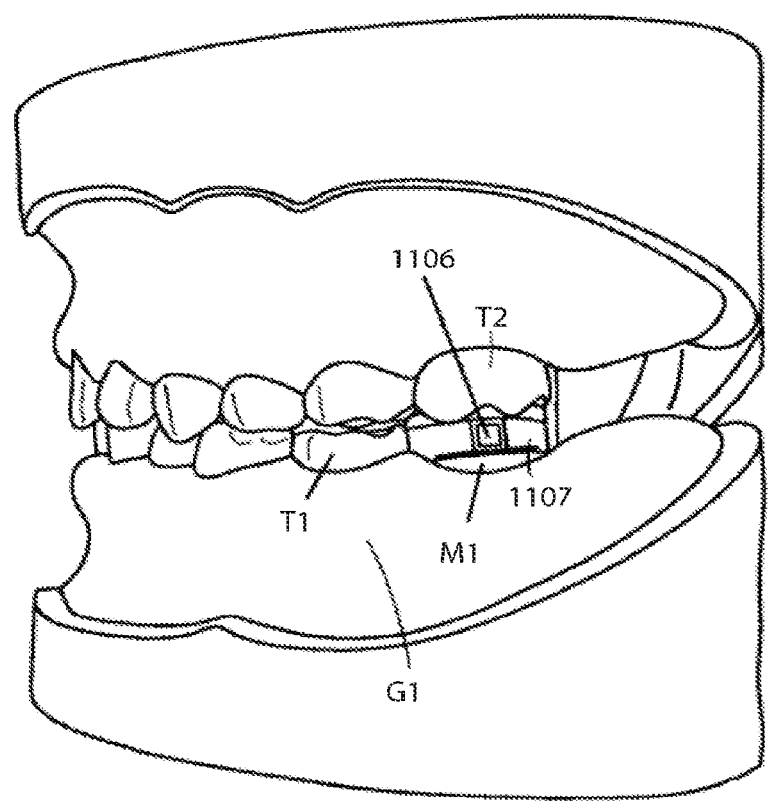
Figure 1K:
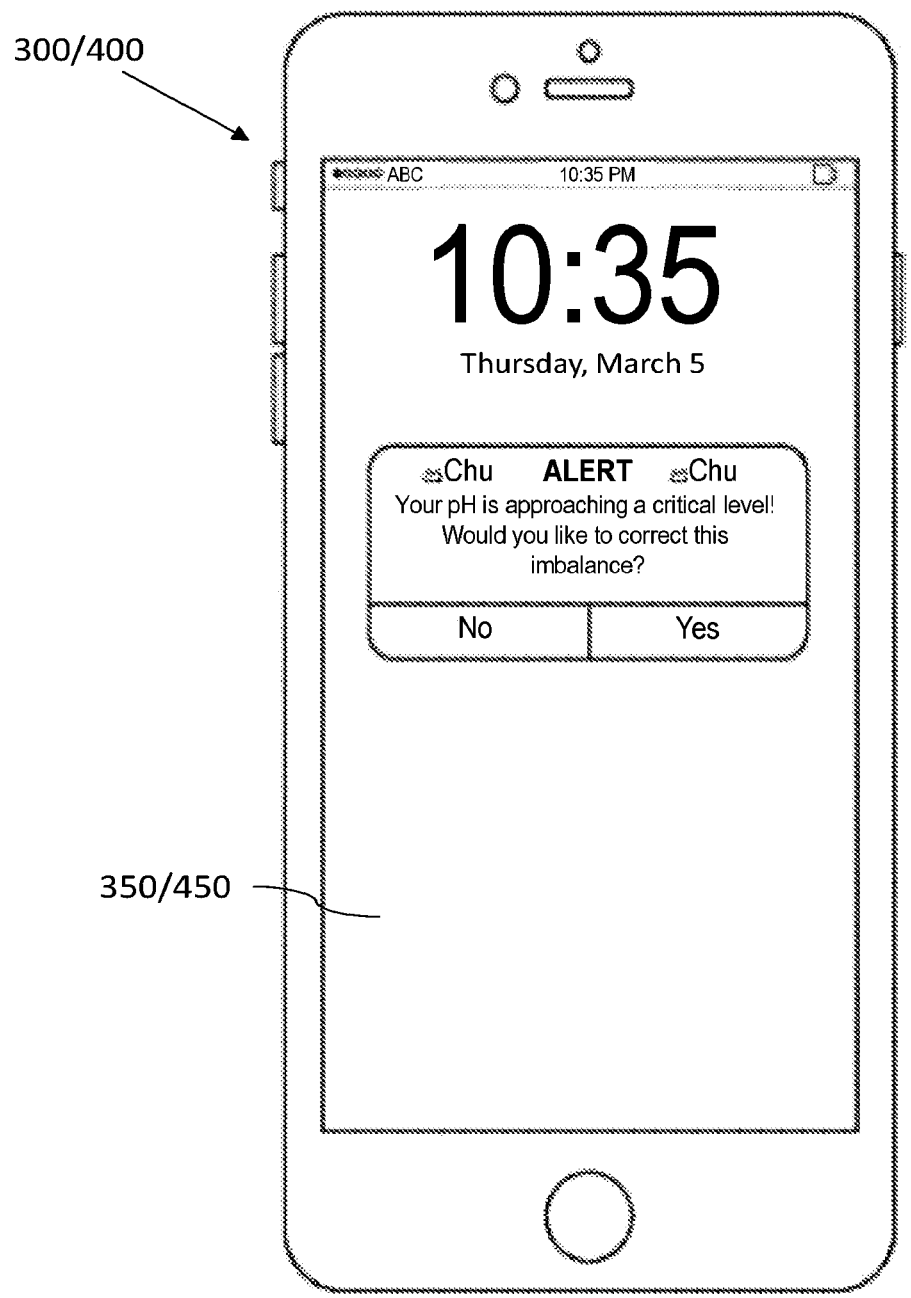
Figure 1L:
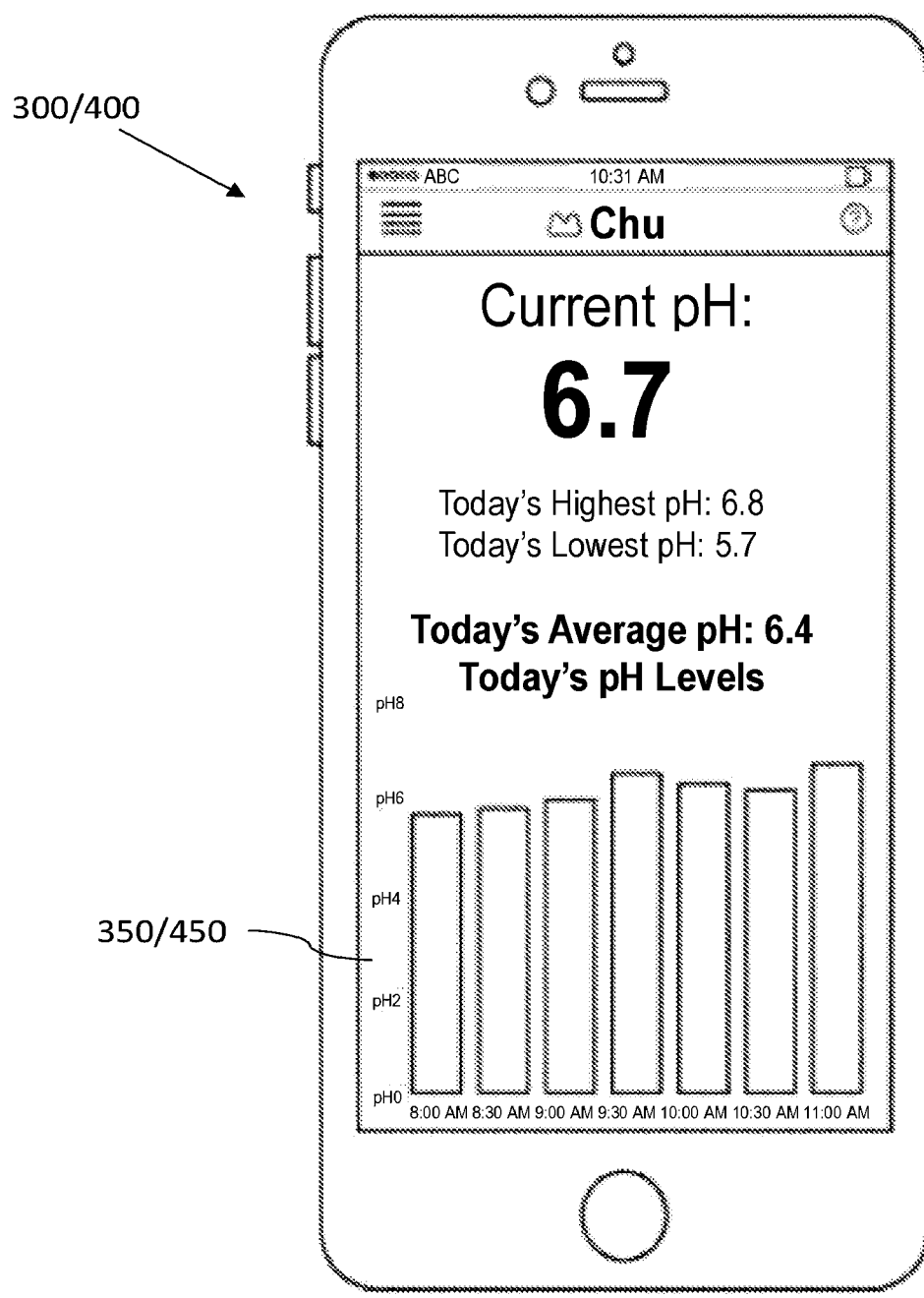
Figure 1M:
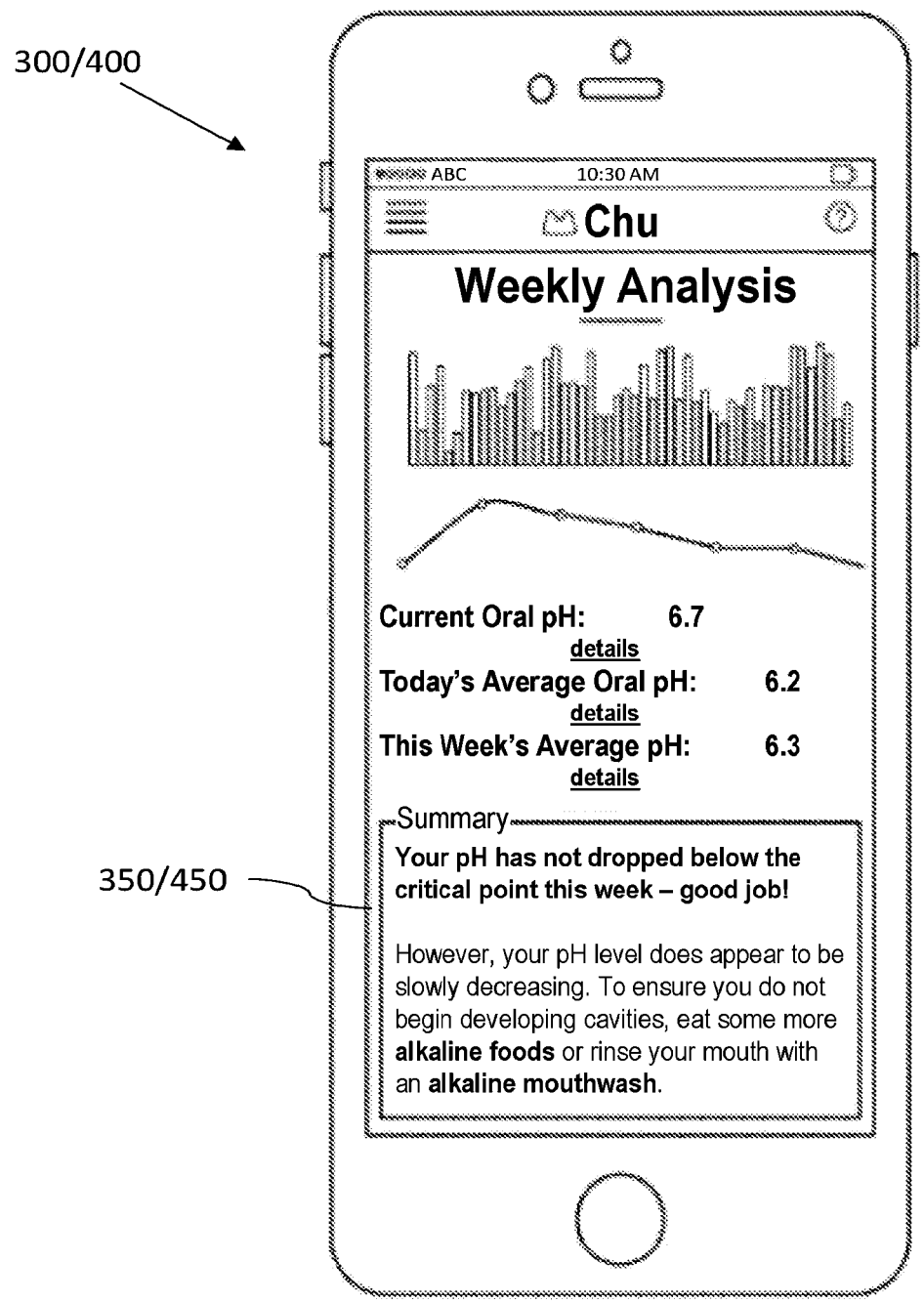
Figure 1N:
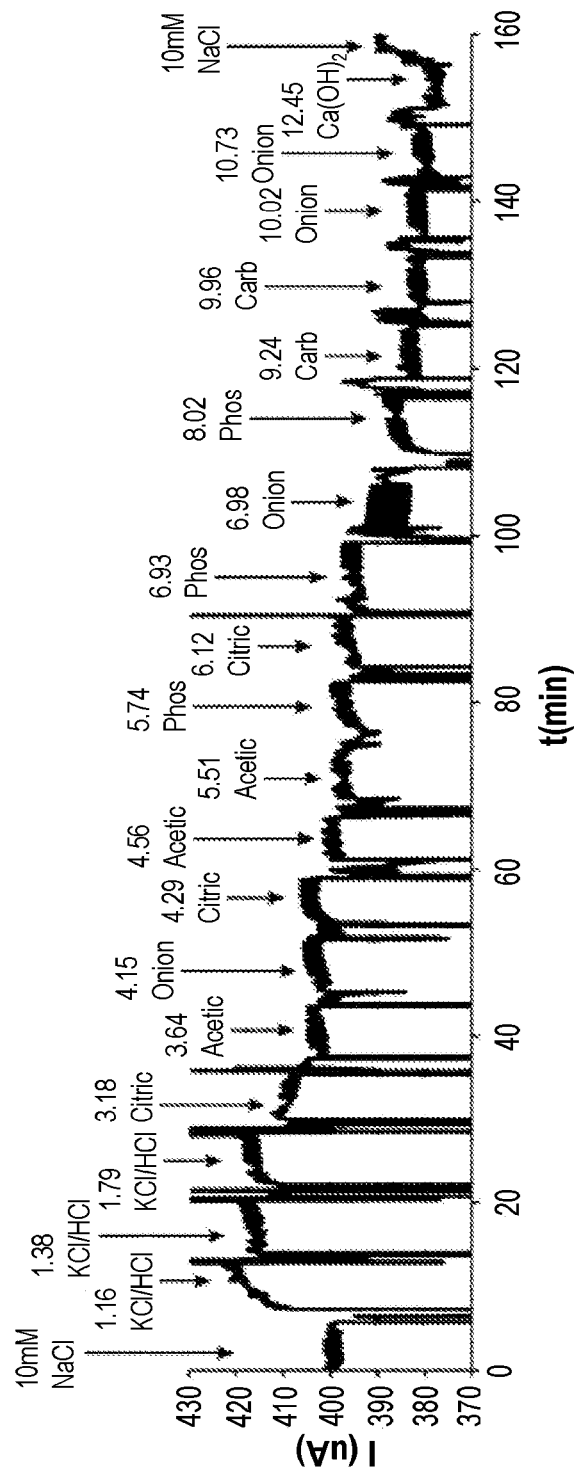
Figure 10:
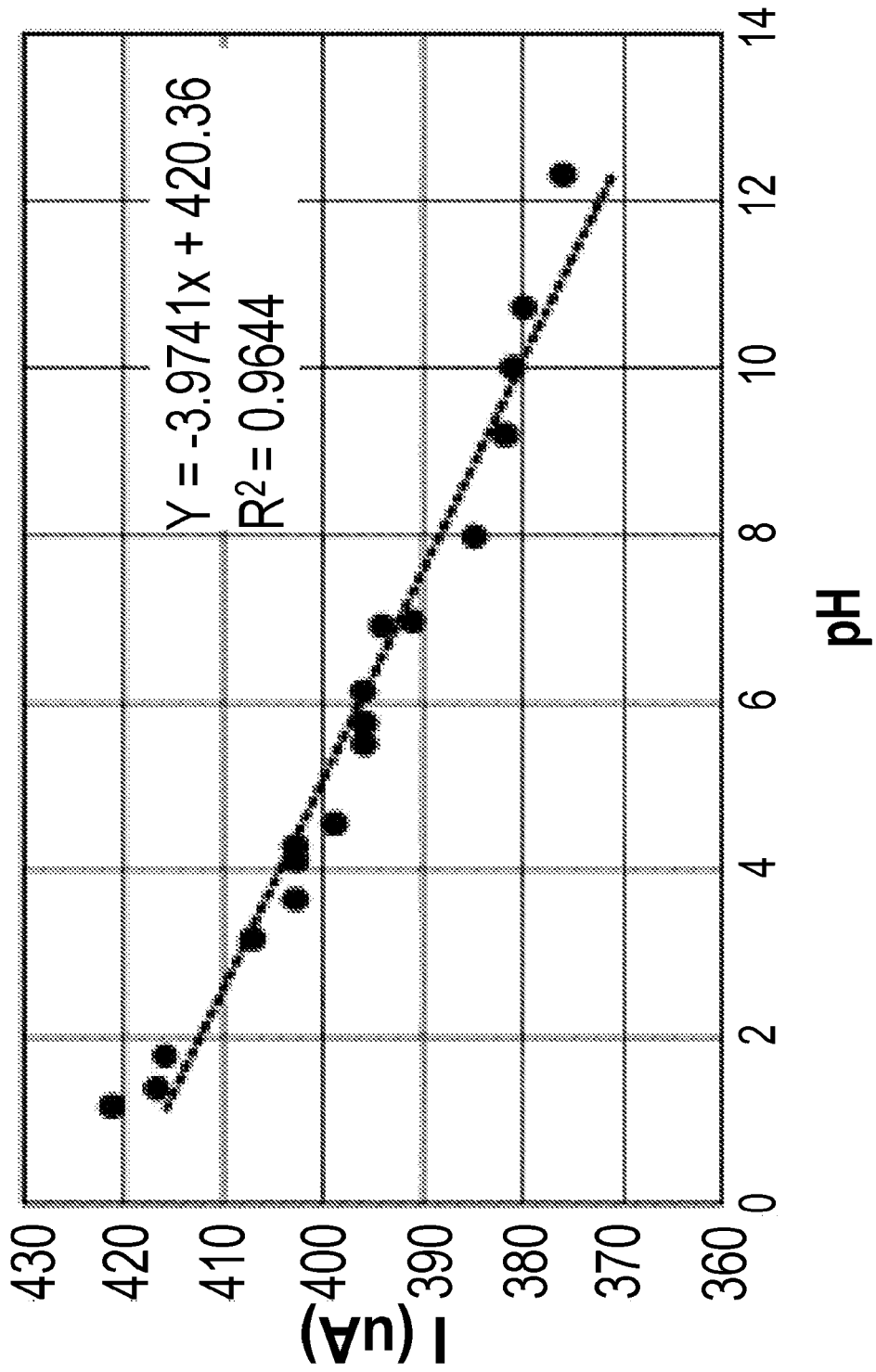
FIGS. 10A-10B illustrate an anatomical view of a sensor device positioned on a molar, and a side view of an electronic assembly of the sensor device, respectively according to embodiments of the present disclosure.
Figure 1P:
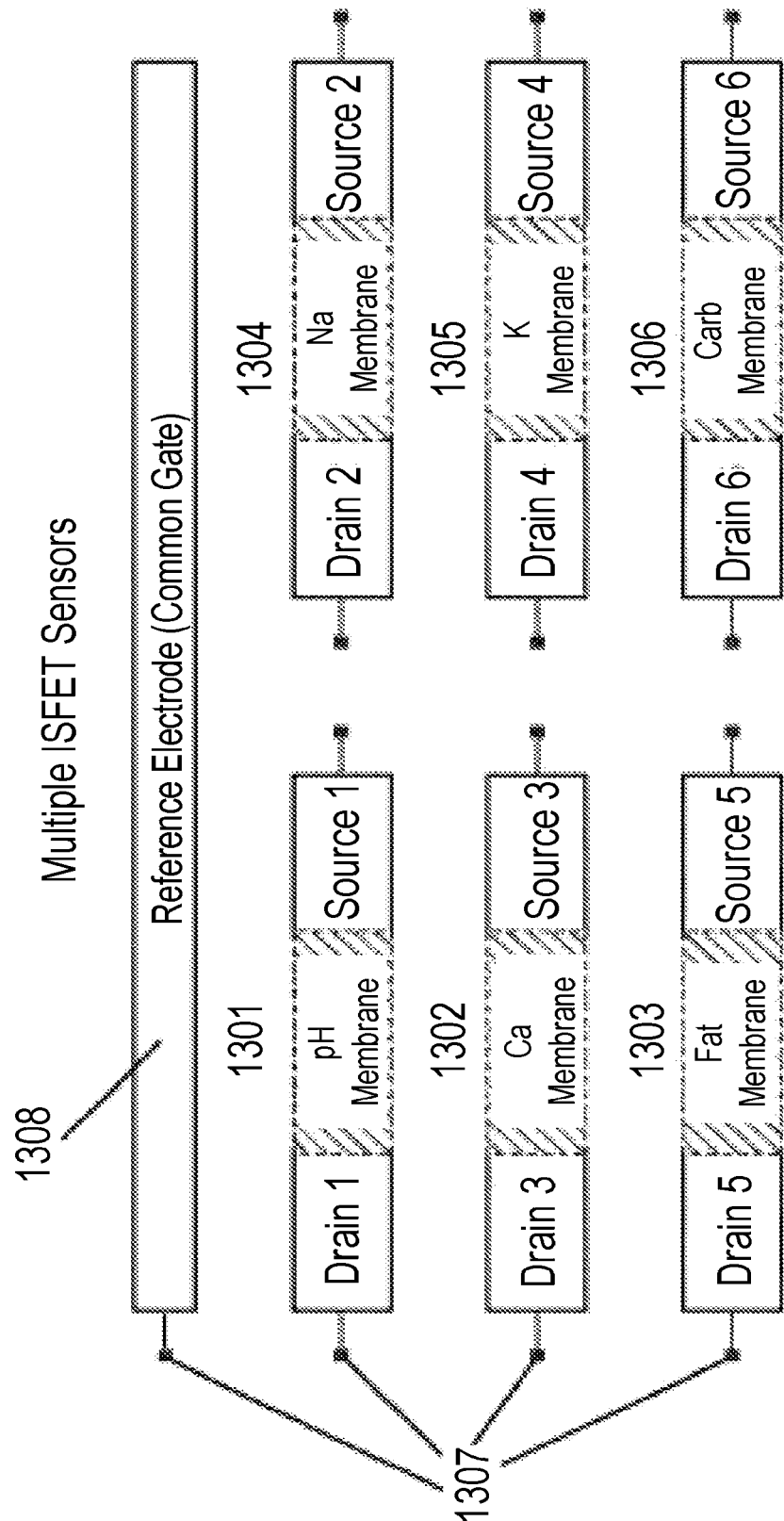
Figure 1Q:
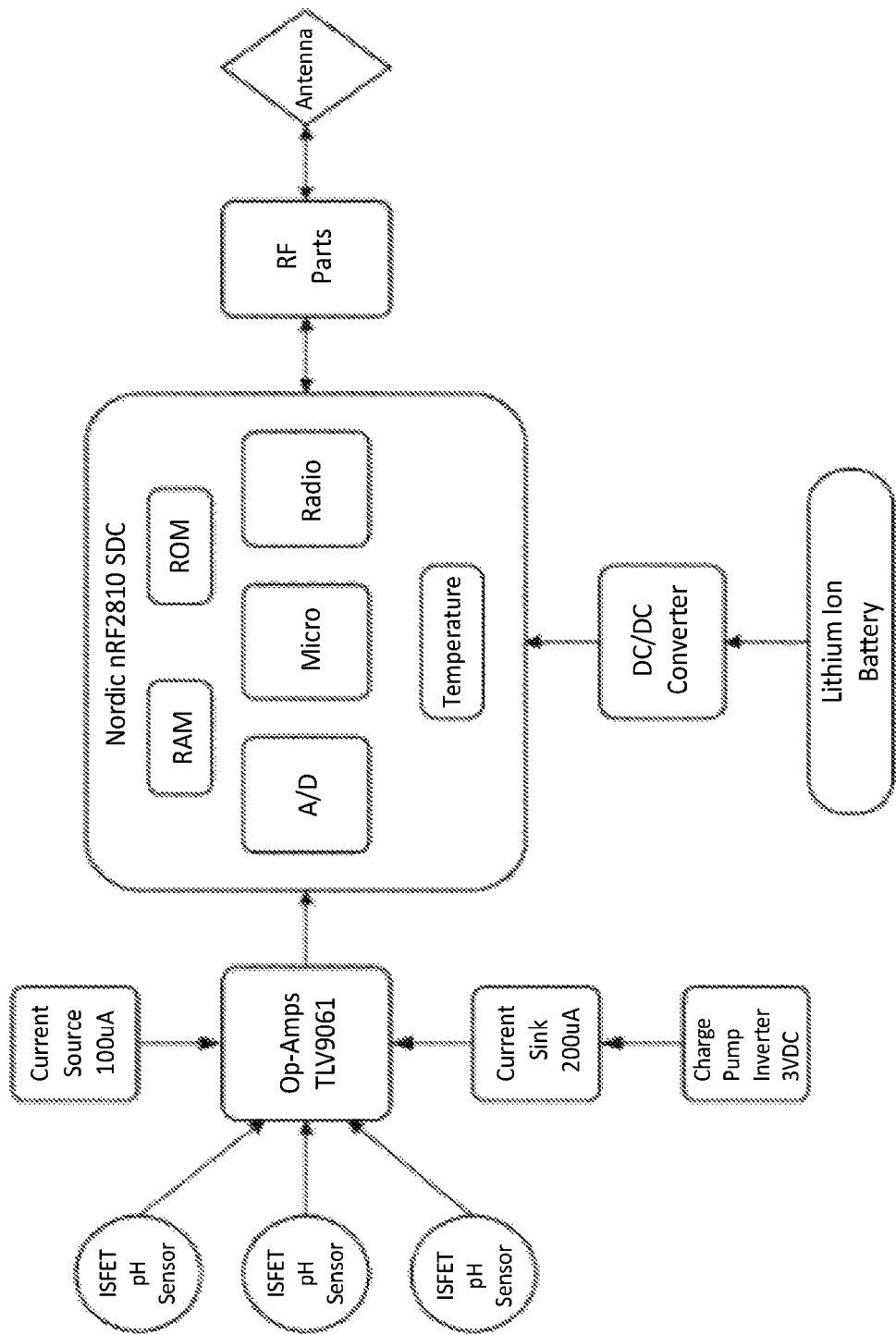

In some embodiments, sensor device 100 and/or other components of system 10, are constructed and arranged as shown in FIGS. 1A-1Q as described herein. Sensor device 100 can include a second enclosure, housing 1107 (shown in phantom in FIG. 1B), which couples to attachment assembly 180 and encloses (e.g. surrounds at least a portion of) housing 1106.

Referring additionally to FIGS. 1A-1D, device 100 can include one or more enclosures (e.g. plastic or metal enclosures including walls surrounding chambers and/or components of device 100), such as housing 1106 of sensor assembly 110, and/or housing 1107 of device 100, each as shown. Housings 1106 and/or 1107 can surround transceiver 170, power supply 160, processor 150, and/or other electronics or other components of sensor assembly 110 and/or sensor device 100. Housings 1106 and/or 1107 can define one or more chambers, such as chambers 1125 and 1126 described herein. In some embodiments, housing 1106 and housing 1107 comprise a single component (e.g. a single housing) that couples to attachment mechanism 180 and surrounds (e.g. seals) one or more components of sensor assembly 110 within a chamber of sensor assembly 110.

ISFET 1105 (e.g. one or more ion sensitive field effect transistors) can comprise one or more source electrodes, source electrode 1112 (e.g. source electrodes 1112a and 1112b shown in FIG. 1A). ISFET 1105 can comprise one or more drain electrodes, drain electrode 1114 (e.g. drain electrodes 1114a and 1114b shown in FIG. 1A). ISFET 1105 can also comprise a gate (e.g. a gate electrode).

In some embodiments, sensor assembly 110 comprises one or more components configured to protect (e.g. physically, electrically, and/or chemically protect) ISFET 1105 from damage. Sensor assembly can include one or more protection elements configured to protect ISFET 1105 from mechanical forces such as scratching, brushing, pressing, and/or other potentially destructive forces (e.g. while still preserving the chemical function of ISFET 1105, such as to continue to allow ions to diffuse to the surface of ISFET 1105). For example, sensor assembly 110 can comprise one or more ISFET 1105 protecting elements selected from the group consisting of: a mechanical protection element (e.g. relatively rigid walls of epoxy or other material, such that an external force would be applied to the walls rather than ISFET 1105); a membrane made from an ionomer such as a Nafion membrane (proton exchange membrane) configured as a protection element; a ceramic protection element; and combinations thereof.

Sensor assembly 110 can comprise one or more semiconductors, PCBs (e.g. flexible and/or rigid PCBs), and/or other substrates, substrate 1102 shown. Source electrode 1112 can comprise one or more source electrodes (e.g. two) positioned on one side of substrate 1102, while drain electrode 1114 comprises one or more drain electrodes (e.g. two) positioned on an opposite side of substrate 1102. A gate voltage can be set by one or more reference electrodes, reference electrode 1118. Sensor assembly 110 can be mounted on insulating material, insulator 1104, which can be positioned between attachment mechanism 180 and sensor assembly 110. An enclosure, housing 1106, protects a fluid channel of sensor assembly 110 (e.g., graphene or doped silicon channel of substrate 1102 or other portion of sensor assembly 110) from tissue contact, microorganisms, and/or other undesired particles. Reference electrode 1118 is positioned in a chamber (chamber 1125 described herein) that is sealed from the environment of the patient's mouth (e.g. the patient's saliva), such as a seal provided via a proton exchange membrane, PEM 1108 (e.g. a sulfonated tetrafluoroethylene-based fluoropolymer-copolymer membrane), which allows protons to selectively cross the membrane, such as to affect the gate voltage of reference electrode 1118.

In some embodiments, reference electrode 1118 comprises an element selected from the group consisting of: a wire; a liquid chamber; a gel chamber; a solid-state component; and combinations of these.

Figure 7A:
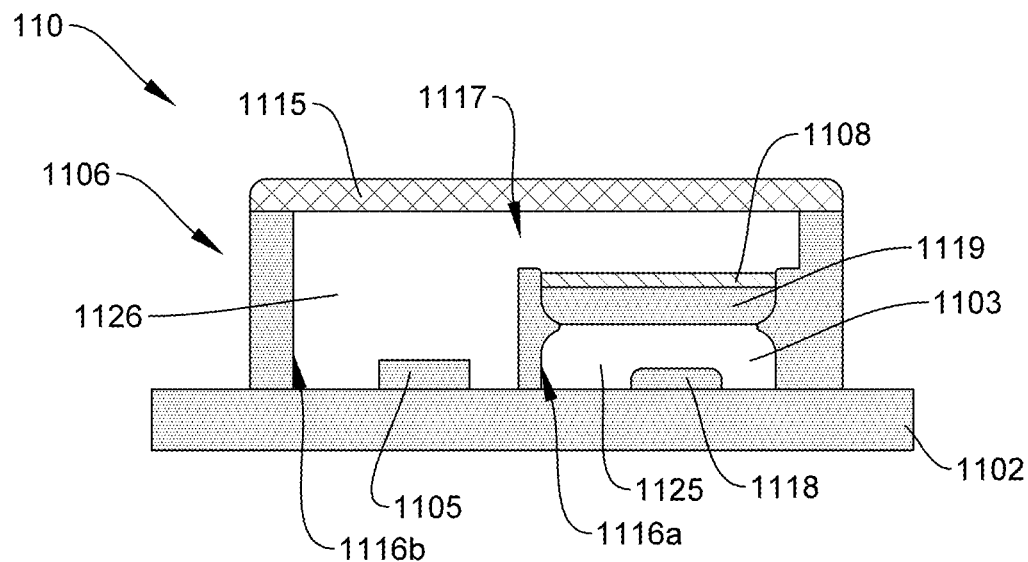
FIGS. 7A-7B illustrate side sectional and top transparent views, respectively, of a sensor assembly according to embodiments of the present disclosure.
Figure 7B:
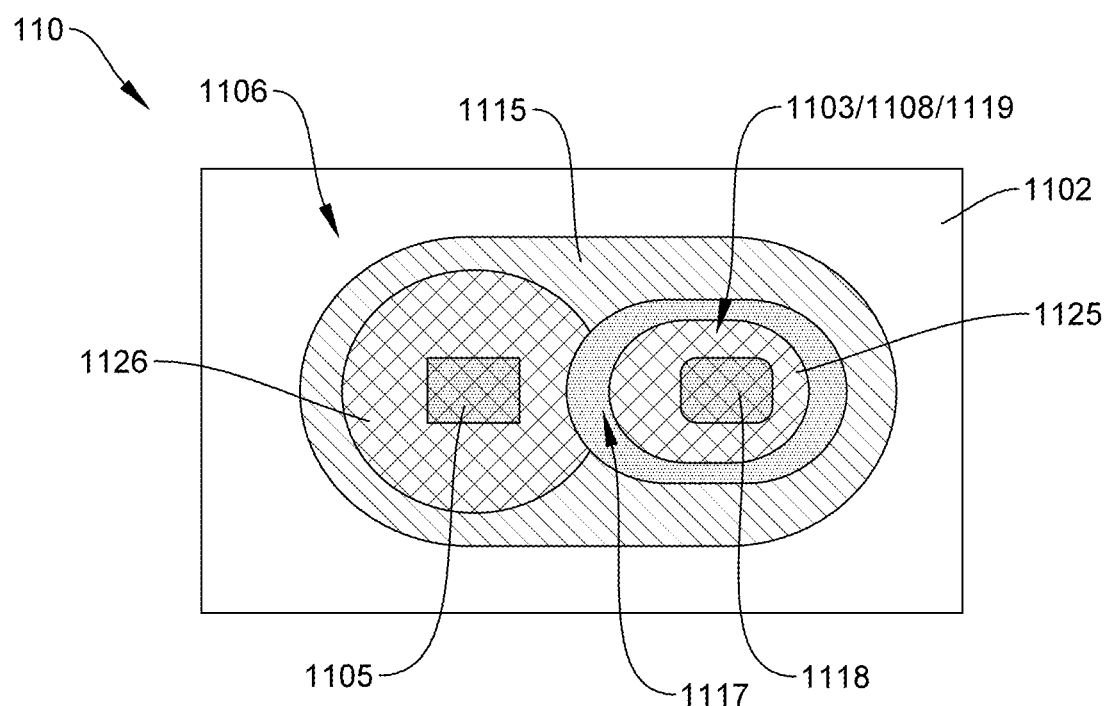
Figure 8:
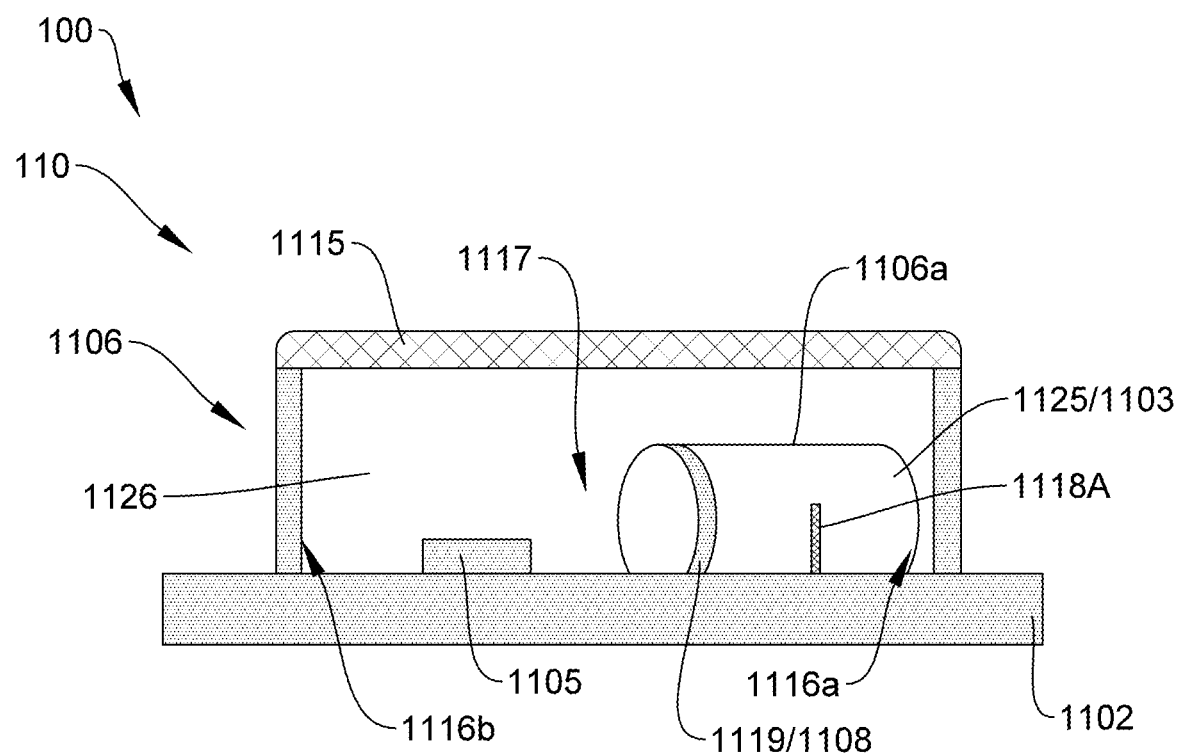
FIG. 8 illustrates a side sectional view of a sensor device according to embodiments of the present disclosure.

Chamber 1125 can comprise a chamber surrounded by: walls (e.g. walls of a housing); diaphragm 1119 (e.g. a ceramic or other diaphragm containing pore sizes of between 0.1 to 25 microns in diameter); a PEM 1108 (e.g. positioned on top of diaphragm 1119); and/or a mesh, mesh 1115 (e.g. a grate or other permeable covering). A fluid channel, channel 1117, can be positioned between chamber 1126 (a chamber in which ISFET 1105 is located) and chamber 1125 (a chamber in which reference electrode 1118 is located). Channel 1117 can be positioned external to PEM 1108 and diaphragm 1119, but sealed underneath mesh 1115 (e.g. as shown in FIGS. 7A-B and 8), allowing fluid that permeates mesh 1115 to enter both chambers 1125 and 1126 (e.g. thus contacting ISFET 1105 and reference electrode 1118, respectively). Channel 1117 can comprise a groove or other channel positioned in a wall of a housing (e.g. housings 1106 and/or 1107), and/or a groove or other channel positioned in a semiconductor substrate or other substrate (e.g. substrate 1102).

Mesh 1115 can be made of stainless steel (e.g. 304 or 316 stainless steel alloy to feature better anti-corrosion and durability properties), and/or non-metals (e.g. polytetrafluoroethylene, a material similar to Kevlar™ material, nylon, and/or plastic). Mesh 1115 can protect ISFET 1105 and reference electrode 1118 from being exposed to mechanical forces present in the mouth.

The surfaces of one more sensor assembly 110 components, such as mesh 1115, PEM 1108, diaphragm 1119, and/or surfaces of housing 1106 and 1107, can include a coating and/or a surface modification ("coating" herein), such as coating 1116 shown. Coating 1116 can comprise one, two or more surface modifications and/or other coatings selected from the group consisting of: a surface modification, such as a surface modification comprising ion implantation; a hydrophilic coating; a super hydrophilic coating; a sulfonated tetrafluoroethylene-based fluoropolymer-copolymer coating; a zwitterion coating; and/or a hydrogel coating. Surfaces of components of sensor assembly 110 can be modified to change the surface energy levels and increase the hydrophilicity. This type of modification can be configured to cause increased saliva and/or other fluid transfer around and/or through the membranes, diaphragms, meshes, and/or other components of sensor assembly 110 (e.g. membrane 1115 and/or PEM 1108), allowing oral fluids to more easily contact ISFET 1105 and/or reference electrode 1118. In some embodiments, sensor assembly 110 comprises a coating (e.g. coating 1116), that is configured to exhibit antifouling and/or antimicrobial properties.

A chemically reactive membrane, membrane 1122, can be placed above the gate of ISFET 1105, such as a membrane that is configured to accept and/or donate hydrogen ions, such as to establish pH equilibrium with the proximate environment. An electrolyte permeable membrane, membrane 1124, can be included to create a sealed chamber above reference electrode 1118, such as a membrane that blocks, or at least partially blocks ("blocks" herein) certain analytes from entering the chamber surrounding electrode 1118 (e.g. chamber 1125 herein). In some embodiments, such as when measuring pH, PEM 1108 and membrane 1124 are the same membrane. In some embodiments, PEM 1108 and membrane 1124 comprise two separate membranes that perform different functions (e.g. when sensor device 100 is configured to detect a peanut allergen, and membrane 1124 is specific to that allergen). Membrane 1124 can be configured as an affinity column, with embedded particles that bind to specific first types of molecules, and/or let pass through specific second types of molecules. In some embodiments, an antifouling membrane (not shown) is placed above PEM 1108 to prevent material deposition and biofilm growth on PEM 1108.

Electrodes 1112 and 1114 of ISFET 1105 are supplied voltages by processor 150 (e.g. via energy supplied by power supply 160), and the source drain current is sent through analog frequency filters into the analog input of a transmission unit of processor 150.

In some embodiments, system 10 is of similar construction and arrangement as applicant's co-pending U.S. patent application Ser. No. 16/254,501, entitled "Long-Term, Continual, Wireless, Intraoral Monitor", filed Jan. 22, 2019—the entire contents of which are hereby incorporated by reference.

As shown in FIG. 1E, sensor device 100 can be installed around a molar, molar M1, between surrounding teeth T1 and T2 as shown. PEM 1108 is oriented buccally such that it can be exposed to saliva pooling between molar M1, teeth T1 and T2, gum G1 (each as shown), and a cheek (not shown) of the patient. Device 100 includes housings 1106 and 1107 as shown and described herein. In some embodiments, conditioning circuitry (e.g. components 1127 described herein in reference to FIGS. 10A-10B) is positioned within sensor assembly 110, such as near location L1 as shown (e.g. to be near sensing electronics of sensor assembly 110 on the buccal side of attachment mechanism 180). In some embodiments, transmission, powering, and/or data storage electronics of device 100 are oriented lingually towards tongue T, and are located within sensor device 100 at or near location L2.

As shown in FIG. 1F, sensor device 100 can be installed around a molar, molar M1, between surrounding teeth T1 and T2 as shown. Housing 1106 is oriented buccally such that it can be exposed to saliva pooling between gum G1 and a cheek (not shown) of the patient. Device 100 includes housings 1106 and 1107 as shown and described herein. In some embodiments, conditioning circuitry (e.g. components 1127 described herein in reference to FIGS. 10A-10B) is positioned within sensor assembly 110, such as near location L1 as shown (e.g. to be near sensing electronics of sensor assembly 110 on the buccal side of attachment mechanism 180). In some embodiments, transmission, powering, and/or data storage electronics located within sensor device 100, are positioned at or near location L2 such that they are oriented lingually towards tongue T.

As shown in FIG. 1G, sensor device 100 can be installed around a molar, molar M1, between surrounding teeth T1 and T2 as shown. Housing 1106 is oriented buccally such that it can be exposed to saliva pooling between gum G1 and cheek C1 as shown. Device 100 includes housings 1106 and 1107 as shown and described herein. In some embodiments, conditioning circuitry (e.g. components 1127 described herein in reference to FIGS. 10A-10B) is positioned within sensor assembly 110 on the buccal side of sensor assembly 110. In some embodiments, transmission, powering, and/or data storage electronics located within sensor device 100 are oriented lingually towards tongue T and positioned at or near location L1.

As shown in FIG. 1I1, sensor device 100 can be installed around a molar, molar M1, between surrounding teeth T1 and T2 as shown. Housing 1106 is oriented buccally such that it can be exposed to saliva pooling between gum G1 and cheek C1 as shown. Device 100 includes housings 1106 and 1107 as shown and described herein. In some embodiments, conditioning circuitry (e.g. components 1127 described herein in reference to FIGS. 10A-10B) is positioned within sensor assembly 110 on the buccal side of sensor assembly 110. In some embodiments, transmission, powering, and/or data storage electronics located within sensor device 100 are oriented lingually towards tongue T.

As shown in FIG. 1I, sensor device 100 can be installed around a molar, molar M1, between surrounding teeth T1 and T2 as shown. Housing 1106 is oriented buccally such that it can be exposed to saliva pooling between gum G1 and cheek C1 as shown. Device 100 includes housings 1106 and 1107 as shown and described herein. In some embodiments, conditioning circuitry (e.g. components 1127 described herein in reference to FIGS. 10A-10B) is positioned within sensor assembly 110 on the buccal side of sensor assembly 110. In some embodiments, transmission, powering, and/or data storage electronics located within sensor device 100 at or near location L1 are oriented lingually towards tongue T.

In FIG. 1J, a model of an oral cavity is illustrated, including sensor device 100 installed around a molar, M1. Also shown in FIG. 1J are adjacent tooth T1 and opposing tooth T2. In some embodiments, sensor device 100 does not protrude above molar M1 as shown, and/or does not occlude the bite of the patient (e.g. does not interfere with opposing tooth T2 when chewing or biting down, such as is described in reference to FIGS. 9 and 9A herein). Housing 1106 is oriented buccally such that it can be exposed to saliva pooling between gum G1 and a cheek (not shown). Device 100 includes housings 1106 and 1107 as shown and described herein. In some embodiments, conditioning circuitry (e.g. components 1127 described herein in reference to FIGS. 10A-10B) is positioned within sensing electronics of sensor assembly 110 on the buccal side of sensor assembly 110. In some embodiments, conditioning circuitry is included within sensing electronics of sensor assembly 110, such as circuitry positioned on the lingual side of sensor assembly 110. In some embodiments, transmission, powering, and/or data storage electronics located within sensor device 100 are oriented lingually towards the patient's tongue. In some embodiments, transmission, powering, and/ or data storage electronics is included within sensor device 100, such as componentry that is oriented on the buccal side of sensor assembly 110.

As described herein, housing 1107 and/or other portions of sensor device 100 can comprise a size and/or a geometry that is constructed and arranged to improve comfort and/or cosmesis for the patient. For example, housing 1107 can include one or more tapers, thinned sections, rounded edge, chamfers, and/or fillets ("tapers" herein), such as to improve comfort and/or cosmesis for the patient. For example, the height of housing 1107 can taper (e.g. as it nears location L3 in FIG. 1E). Alternatively or additionally, the thickness of housing 1107 can be reduced at locations between molar M1 and tooth T1 and/or between molar M1 and tooth T2 (e.g. at locations L4a and L4b, respectively, on FIG. 1F). Housing 1107 can include one or more edges that include a rounded edge and/or a chamfer. Housing 1107 can comprise a size and/or geometry that prevents interference with any teeth of the patient, such as teeth that come into close proximity with device 100 during chewing and/or biting.

In various embodiments, a pocket may form between the PCB and the band if the interproximal PCB exits the case on the battery side directly from the edge, which may prevent the interproximal PCB from being fully sealed during laser welding. In various embodiments, as shown in FIG. 28, the PCB 2804 may be inserted into the lingual battery section through a slit 2803 in the middle of the band 2802 thereby allowing a clean interproximal weld of the metal strip to the band 2802 between the teeth. In various embodiments, the slit 2803 may be sealed (e.g., via a laser weld) to thereby seal the PCB 2804 within the band 2802.

FIG. 1K illustrates an example of an alert displayed and/or otherwise provided by user interface 350 of wearable device 300 and/or user interface 450 of user device 400. For example, an alert can be provided when a physiologic measurement (e.g. a pH measurement) exceeds a safety threshold. In some embodiments, system 10 is configured such that a dentist, physician, doctor, medical professional, and/or other clinician ("clinician" herein) that performs installation of intraoral sensor device 100 can manually set customized safety thresholds (e.g. customized per each unique patient). In some embodiments, system 10 includes a default setting that is configured as a safety threshold (e.g. a fixed and/or adjustable setting which triggers an alert when exceeded). FIG. 1L illustrates a depiction of pH data displayed on user interface 350 and/or 450. FIG. 1M depicts a display of data showing the time changing electrical output of the sensor device 100, corresponding to pH changes measured in saliva.

FIG. 1N is a graphical representation of the current through ISFET 1105 channel (I) as a function of time (min). In experiments conducted by applicant, ISFET 1105 is exposed to pH buffers made with standard international union of pure and applied chemistry (IUPAC) recipes. Initially ISFET 1105 is exposed to a 10 mM NaCl solution. The solution is replaced with buffers of varying pH, starting with a pH of approximately 1 and ending with a pH of approximately 12.5. The solution is replaced roughly every 5 minutes, and the current output is continually measured using a data acquisition device.

FIG. 1O is a graphical representation of a calibration curve observed from a pH-based ISFET 1105 of the present inventive concepts. FIG. 1O shows the current through ISFET 1105 channel (I) as a function of the pH of the solution being measured. Once the mathematical equation of the relationship between pH and current is known, the pH of an unknown solution may be inferred based on the output of sensor assembly 110. The equation for the relationship and the RA2 value, indicating linearity, is shown in the top right corner of the figure.

FIG. 1P is a depiction of an array of multiple ISFET 1105 sensors that are sensitive to different analytes that can be included on a single sensor device 100 to sense a multitude of different analytes. In some embodiments, multiple ISFET sensors (sensors 1301 thru 1306 shown) are installed on the supporting printed circuit board (PCB, substrate 1102) to measure a multiplicity of analytes or parameters. The six ISFETs shown in FIG. 1P each utilize a different membrane over the semiconducting channel that displays specificity towards specific analytes. As shown, ISFET 1301 has a membrane specific to protons, ISFET 1302 has a membrane specific to sodium ions, ISFET 1303 has a membrane specific toward calcium molecules, ISFET 1304 has a membrane specific to potassium ions, ISFET 1305 has a membrane specific to fat ions, and ISFET 1306 has a membrane specific toward carbohydrate molecules. Current and voltage is supplied to the ISFETs via the drain electrodes (drains 1-6 shown) via printed traces 1307 on the substrate 1102 (drains 2, 4, and 6 are not shown connected but would be connected). The drain and source electrodes may be constructed from an array of conductive pads plated with gold, silver, platinum, and the like. Current passes through the semiconducting channels, and the output signal (e.g. in the form of voltage between gate and source, voltage between source and drain, and/or current between source and drain) is dependent on the specific analyte concentrations in the solution. The ISFET's gate voltage may be set by a common reference electrode 1308 (e.g. similar to reference electrode 1118 described herein), supplied a voltage via a trace 1307, or each individual ISFET can have its own reference electrode The source and drain pads can be connected to the signal processing circuitry using copper (or other) PCB traces, which can be routed on the top, bottom or through one or more layers of substrate 1102.

FIG. 1Q depicts an exemplary block diagram for an embodiment of a sensor device 100. Sensor device 100 comprises at attachment assembly 180 including a molar band, as well as various electronic components which are mounted upon, or soldered to, substrate 1102 (e.g., a PCB). The substrate 1102 material used can be of one or more layers of laminated fiberglass commonly referred to as "FR4".

Sensor device 100 can comprise a "system on chip" (SOC) integrated circuit that combines the functionality of a microcontroller and a radio transceiver into a single small package. Alternatively, the functionality of the SOC can be implemented with a separate microcontroller and radio transceiver. The SOC sub-parts/modules/peripheral (e.g. components 1127 described herein) can include, but are not limited to, microcontroller, non-volatile memory, volatile memory, analog to digital converters (A/D), power conditioning circuitry, general purpose input and/or output ports, crystal oscillators, low-drop out modules (LDO), and/or a radio transceiver. The microcontroller processor (e.g. processor 150 described herein) can be, for example, a 32 bit, 64 bit, or other type processor, for example running at 64 MHz or other speed, and is based upon an ARM architecture or other architecture. Non-volatile memory is used to store application software which controls the operation of sensor device 100. This memory storage element can be of the Flash memory type, or other, and can be, for example, of 192 Kilobytes (192 KB) in size, or other. Volatile memory can be used to temporarily store measurement or other data. This volatile memory can be of the RAM type, or other, and be of 24 Kilobytes (24 KB) or other. In some embodiments, measurements and/or other data are stored within non-volatile memory using dynamic memory allocation. Sensor device 100 can be configured for low power consumption, particularly while functioning in a "Sleep" or "Stand-By" mode. In some embodiments, the SOC requires only 0.6 microamps or less while in "Sleep" mode, providing for an extended period between power supply 160 charging cycles and/or a minimum of charging pulses from energy harvesting methods. The "front-end" or inputs to the SOC can be an analog to digital (A/D) converter. This converter can be comprised of one or more analog to digital converters which can operate individually and/or they can be multiplexed, such as to provide data into processor 150 for processing. Processor 150 can operate at 200 Kilo Samples Per Second (200 KSBS) or other rate, and it can resolve the analog inputs to 12 Bits or to 1 part of 4,096 parts, or other resolution as required. Sensor device 100 can be configured to optimize current requirements drawn from powers supply 160 for maximum efficiency. This optimization can include sensor device 100 controlling a "switching" DC/DC converter using "Buck" methods when power supply 160 voltage is higher than needed for operation, or using a "Boost" mode when the power supply 160 voltage is lower than desired. Sensor device 100 can also disengage these Buck or Boost modes of a DC/DC switching converter, such as when the input voltage is at nominal levels. Transceiver 170 can be configured to function as both a receiver and a transmitter, and can function as an interface between the SOC and a receiver of an external device. For transmission, transceiver 170 can encode data from the SOC and modulate a radio carrier according to the signaling protocol required. For receiving, transceiver 170 can demodulate the incoming radio carrier signal, decode the signal into data, and send the data to the SOC. Transceiver 170, depending upon the sensor device 100 specifications, can implement a protocol comprising, but not limited to: Bluetooth, Bluetooth Low Energy, Near Field Communication, ZigBee, and/or WiFi protocols. Transceiver 170 can operate over a variety of frequencies including but not limited to: 5 GHz, 2.45 GHz, 915 MHz, 433.920 MHz or other, and, transceiver 170 employ a variety of modulation methods including, but not limited to OOK, AM, FM, SSB, FSK, PSK, GFSK, and MSK. The functionality of transceiver 170 can be expanded upon to include, but not be not limited to: Near Field, Mid Field, and Far Field electric and/or magnetic communications. In various embodiments, the transceiver 170 may be configured to only transmit data one-way. In various embodiments, the transceiver 170 may be configured for two-way communications (e.g., a user may configure settings of the sensor using a mobile device connected via a wireless communications protocol). In various embodiments, the transceiver 170 may convert an analog sensor signal into a higher frequency signal. In various embodiments, the transceiver 170 may transmit sensor data via sound waves (i.e., acoustic energy). In various embodiments, the data may be transmitted via a predetermined frequency of sound wave, such as, for example, 18 kHz. In various embodiments, the sound wave may be outside (e.g., higher than) the audible range of a human ear.

In some embodiments, ISFET 1105 comprises source and drain electrodes (e.g. electrodes 1112 and 1114, respectively, described herein) connected by a semiconducting channel (e.g. channel 1117 described herein), a gate electrode separated from the channel via an electrolyte solution (e.g. solution 1103 described herein), and an analyte-specific membrane (e.g. PEM 1108 described herein) deposited over the gate. The drain current passing through the channel is a function of the intrinsic properties of ISFET 1105, the bias voltages applied to the three ISFET 1105 electrodes, and the ionic potential of the electrolyte solution. In a constant voltage constant current (CVCC) biasing circuit, the current flowing through the semiconducting channel is kept constant, as is the voltage across the source and drain. In this scenario, a change in pH may be measured by a change in output voltage in the circuit.

One or more operational amplifiers (OP-AMPs) function to transduce the microvolt and or microampere level signal changes across the ISFET 1105 drain and source channel which are dependent upon the molecule being sensed and the semiconductor (graphene, silicon, cheese, etc) that is employed. Providing a high input impedance, the OP-AMP functions as a buffer between the ISFET 1105 and the input to the SOC's A/D module. One or more OP-AMPs can be employed for amplification and or to adjust the output voltage or current to the parameters acceptable of the A/D module.

Sensor assembly 110 can be positioned in the patient's mouth for long or short periods of time. Sensor assembly 110 can be positioned in the patient's mouth (e.g. attached to one or more teeth via attachment mechanism 180) during certain activities (e.g. and removed after the activity is complete), such as an activity selected from the group consisting of: sleeping; being in the presence of potential toxins; participating in exercise or other sporting activity; piloting of a vehicle such as a plane; and combinations of these.

Attachment mechanism 180 can include one or more mechanisms configured to attach device 100 to the patient (e.g. to the tooth of the patient). Attachment mechanism 180 can comprise a band that surrounds one or more teeth of the patient, such as a band that surrounds a molar tooth of the patient. Attachment mechanism 180 can be attached to the patient's one or more teeth by one or more of: the patient; a family member or friend of the patient; and/or by a healthcare provider of the patient (e.g., a nurse, dental care provider, and/or clinician of the patient). Additionally or alternatively, the band can be configured as an integral, unitary structure that is sized for placement around the tooth, or as a multi-component structure that is coupled together to form the band. Such multi-component designs can allow for the band to be more easily decoupled and removed for cleaning/repair if desired. For example, the band can be configured as two arcuate pieces that can be mechanically coupled (e.g., tongue and groove mating) together to form the circular band circumscribing the tooth.

Attachment mechanism 180 can be constructed of one, two, three, or more materials; such as one, two, three, or more materials selected from the group consisting of: a metal; a plastic; an elastomer; a shape memory alloy; and combinations thereof. Attachment mechanism 180 can comprise one or more adhesives, for adhesive attachment to one or more teeth, such as a temporary adhesive. Attachment mechanism 180 can comprise a band and/or other attaching component selected from the group consisting of: a malleable attachment element; an attachment element with one or more ridges; an attachment element with one or more hinges; a resiliently biased attachment element (e.g. an element that can be deformed to assume a first shape, such as for insertion around a tooth, and tend to return to its resiliently biased shape); a toothed and/or geared attachment element; a shrinkable attachment element; a stretchable attachment element; an expandable attachment element; a heat-activated attachment element such as an element activated by body heat; an attachment element configured to undergo a phase and/or shape change; and combinations of these. In some embodiments, attachment mechanism 180 comprises a component arranged in a "C-shape" and/or an "H-shape", such as when mechanism 180 comprises: a clasped component; a hinged component; a toothed component; and/or a resiliently biased member. In some embodiments, attachment mechanism 180 comprises one or more jaws, such as when mechanism 180 comprises a resiliently biased member. In some embodiments, attachment mechanism 180 comprises a cap-like component, such as for placement over one or more teeth (e.g. via a temporary adhesive). In some embodiments, attachment mechanism 180 comprises a wedged component, such as a wedged component placed between two teeth and/or a wedged component comprising fingers, flanges, and/or an "H-shape". In some embodiments, attachment mechanism 180 comprises a lingual button, such as a button affixed to the side of one or more teeth. In some embodiments, attachment mechanism 180 comprises a mouth-guard arrangement, such as when sensor device 100 (e.g. at least a recording portion of sensor device 100) is positioned in the patient's mouth only at specific times (e.g. only at night and/or only during sporting activities). In some embodiments, attachment mechanism 180 comprises two or more components that are attachable to each other, such as a first component that is attached to one or more teeth of the patient, and a second component that attaches to the first component (e.g. when sensor device 100 is attached to the second component).

In some embodiments, system 10 comprises one or more safety features, such as when functional element 199 and/or another component of system 10 is configured to detect when sensor device 100 detaches from the patient (e.g. when at least a portion of attachment mechanism 180 and/or at least a portion of sensor assembly 110 undesirably or otherwise detaches from the patient's tooth or other patient location). In these embodiments, if a detachment were to occur, system 10 may enter an alert condition. For example, a system 10 alert condition can result in an action selected from the group consisting of: the patient is alerted, such as via an alert-based functional element 99, 199, 399, and/or 499; power of sensor device 100 and/or another component of system 10 is turned off, such as to prevent energy discharge into the patient; and combinations thereof. For example, functional element 199 can comprise a component selected from the group consisting of: a mechanical switch; an electrical component which monitors a ground or other electrical signal, and/or impedance; a component which monitors a location signal from a smart phone; a component that monitors leakage current; a component that monitors data being out of an acceptable range; a component that identifies a check sum failure; a sensor that monitors a temperature being out of an acceptable range; a sensor that monitors a location being out of range; a component that identifies an unacceptable location change; a component that identifies the physiologic parameter measured by sensor device 100 being out of an acceptable range (e.g. pH and/or a heart signal out of an acceptable range); a sensor configured to detect the patient falling; and combinations of these.

As described herein, sensor device 100 can be configured to perform a data transmission, such as a transmission of data by transceiver 170 that is sent to devices 300 and/or 400, wherein the data transmission is included in an "advertising packet" in a wireless (e.g. Bluetooth) low energy "beacon" configuration, such as a transmission performed without pairing. In this configuration, sensor device 100 can avoid a protocol that includes a syn→syn-ack→ack" handshake, bonding handshake, pairing handshake, or other method of connection acknowledgement between device 100 and devices 300 and/or 400 (e.g. avoids a handshake typically included with GATT communications). This configuration can reduce communication time and/or power used to perform the data transmission.

In some embodiments, sensor device 100 (e.g. at least a portion of sensor device 100 such as at least a portion comprising power supply 160) is configured to be replaced (e.g. a replacement performed by the patient or other person associated with the patient), as described herein. For example, attachment mechanism 180 can comprise a mechanical latch (e.g. attached to a molar band) that is configured to allow the replaceable portion of sensor device 100 to be operably detached and replaced (e.g. with a new portion and/or a portion that has been recharged and/or otherwise changed).

In some embodiments, as shown in FIG. 1, system 10 includes one or more functional elements, such as functional element 99, functional element 199 of sensor device 100 (e.g. a functional element positioned in sensor assembly 110 of sensor device 100), functional element 399 of wearable device 300, and/or functional element 499 of user device 499, each as shown. Functional elements 99, 199, 399, and/or 499 can each comprise one or more sensors, one or more transducers, and/or one or more other functional elements.

In some embodiments, one or more of functional elements 99, 199, 399, and/or 499 comprises a drug and/or other agent delivery device, such as an agent that is provided to the patient based on information produced by system 10 (e.g. data based on measurements made by sensor device 100), such as an agent provided in an emergency medical situation, and/or an agent provided in a closed-loop fashion. For example, functional element 199 of sensor device 100 can comprise an agent delivery device positioned in the patient's mouth, and/or functional elements 99, 399, and/or 499 can comprise a drug delivery device implanted in the patient (e.g. to deliver an agent systemically to the patient), and/or positioned on the patient's skin (e.g. to deliver into the patient's subcutaneous tissue or vascular system via needle, and/or to deliver the agent transdermally).

In some embodiments, one or more functional elements 99, 199, 399, and/or 499 comprises one, two, or more sensor-based functional elements selected from the group consisting of: a temperature sensor (e.g. a temperature sensor configured to measure a patient temperature and/or a temperature of one or more portions of system 10, such as to cause system 10 to enter an alert state when an undesired temperature is detected); a force sensor (e.g. a strain gauge) and/or a pressure sensor (e.g. a sensor configured to determine an undesired force upon and/or pressure within sensor device 100 and/or a tooth of the patient); an accelerometer; a vibration sensor; a chemical sensor; and combinations thereof.

In some embodiments, one or more functional elements 99, 199, 399, and/or 499 comprises one, two, or more transducer-based functional elements configured to deliver an alert when system 10 enters an alert state, as described herein, such as when an undesired pH or undesired physiologic parameter level is detected by sensor device 100, and/or when a component of system 10 enters an undesired state.

In some embodiments, one or more functional elements 99, 199, 399, and/or 499 comprises one, two, or more transducer-based functional elements selected from the group consisting of: a vibrational transducer (e.g. one or more vibrational transducers positioned in device 100 or otherwise in the patient's mouth, and/or in devices 300 and/or 400); a light such as an LED; a heating element; a cooling element; an agitating element; a source of vacuum; a fluid jet (e.g. a fluid jet configured to deliver water or other fluid to remove contamination from one or more components of sensor device 100); and combinations thereof.

In some embodiments, one or more functional elements 99, 199, 399, and/or 499 comprises a visualization device, such as an infrared or visible light camera. In some embodiments, one or more functional elements 99, 199, 399, and/or 499 comprises a source of vacuum. In some embodiments, one or more functional elements 99, 199, 399, and/or 499 comprises a heating element and/or a cooling element. In some embodiments, one or more functional elements 99, 199, 399, and/or 499 comprises an element configured to cause the patient to wake from sleep.

Figure 12:
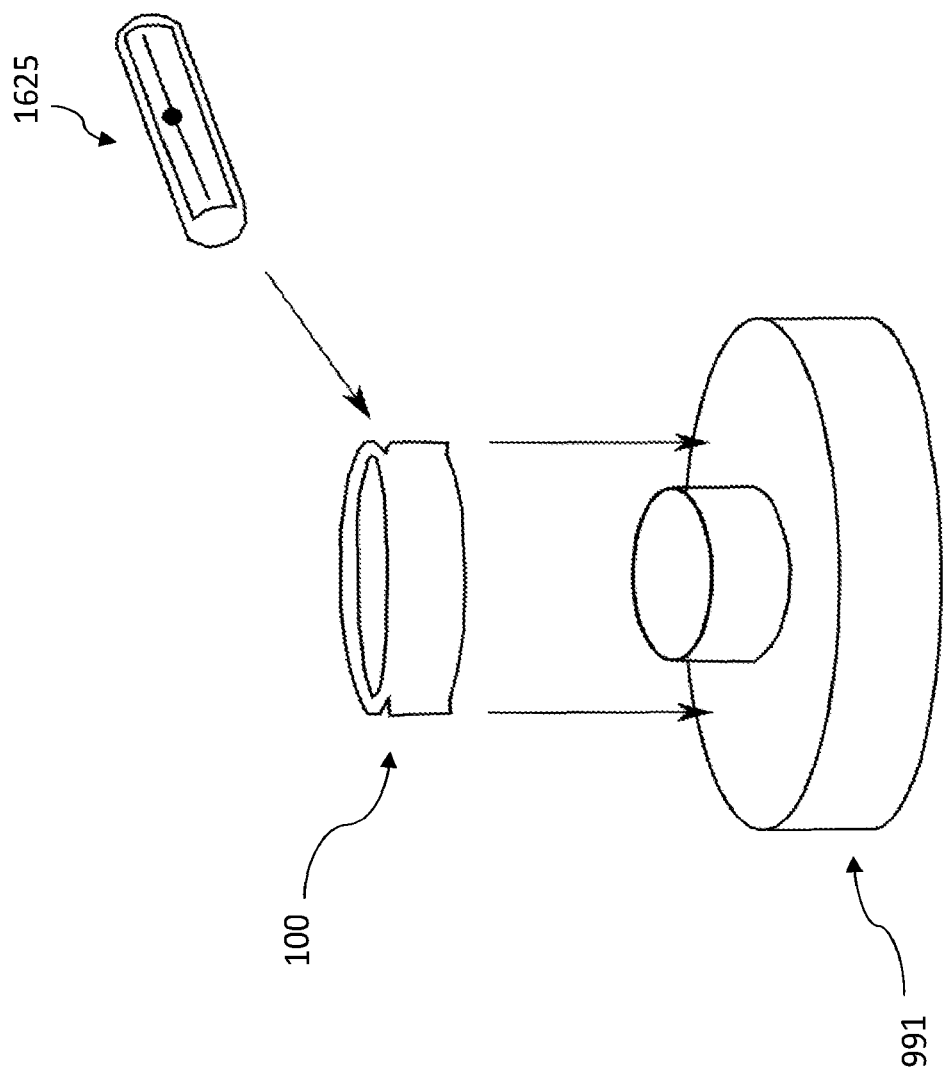
FIG. 12 illustrates a perspective view of a sensor device including a magnetic switch according to embodiments of the present disclosure.
Figure 13A:
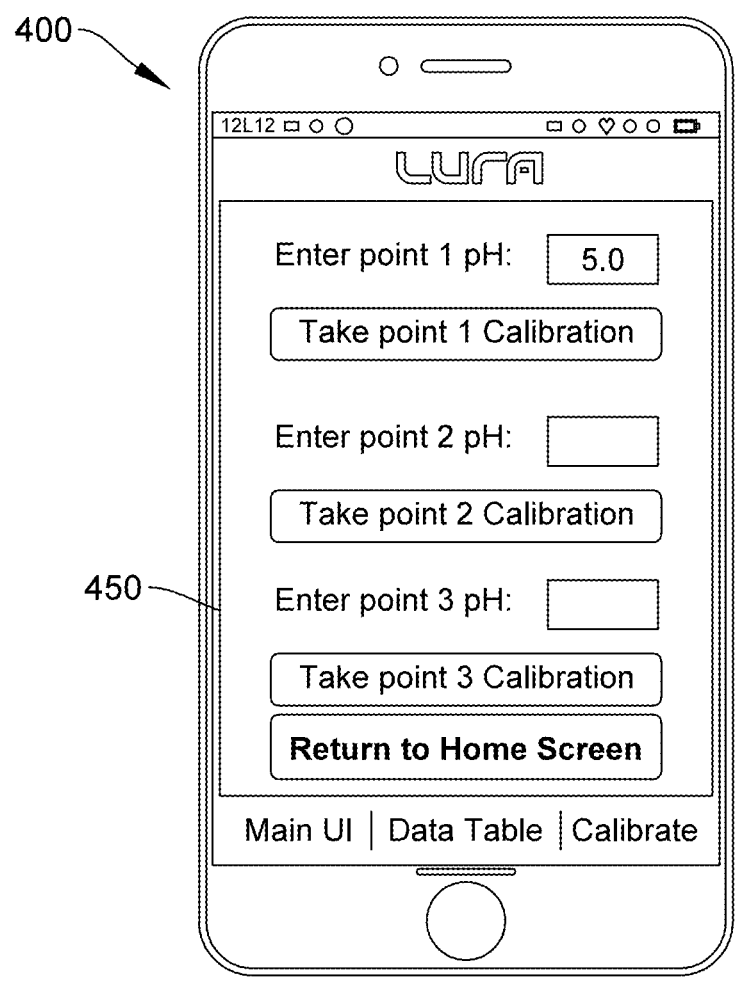
FIGS. 13A-13D illustrated a series of configurations of a user interface of a physiologic parameter recording system according to embodiments of the present disclosure.
Figure 13B:
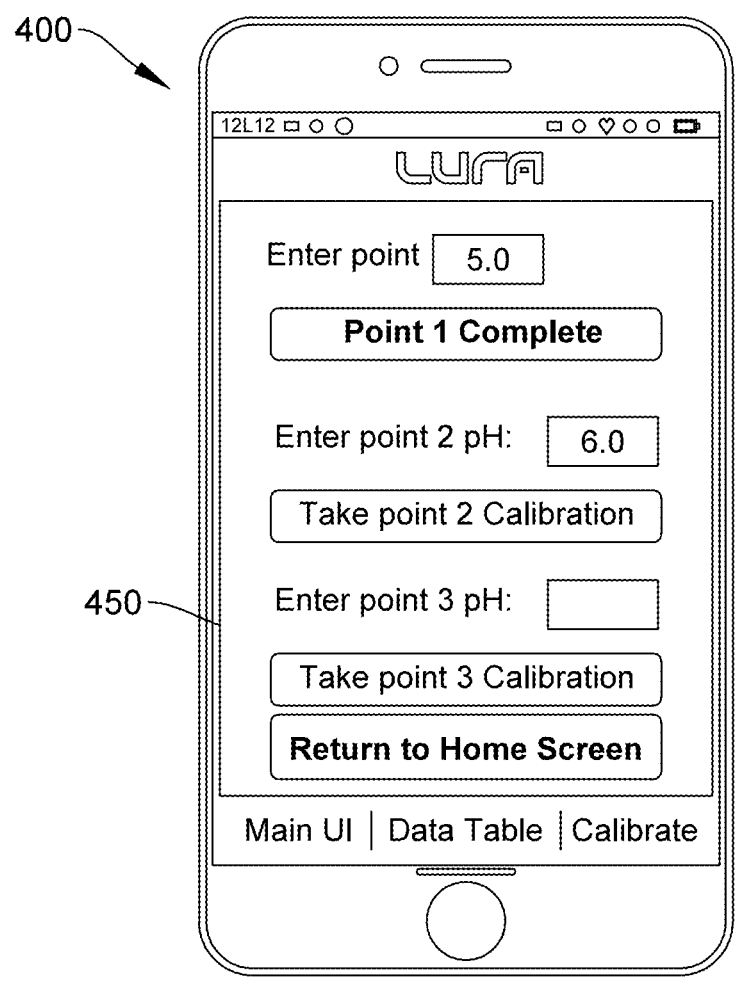
Figure 13C:
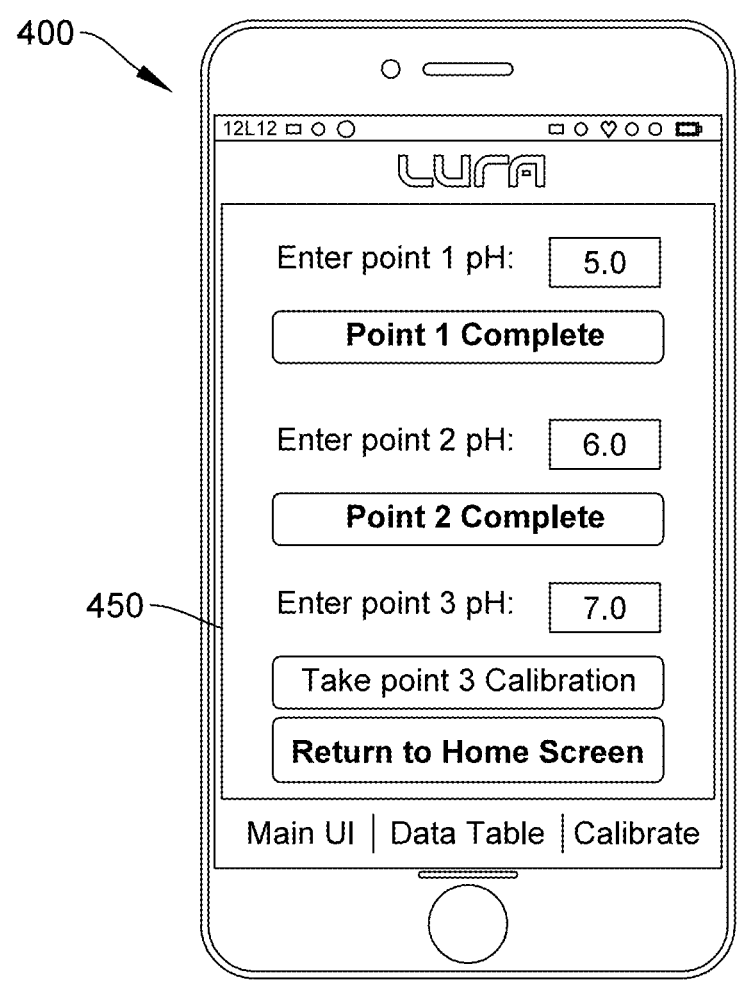
Figure 13D:
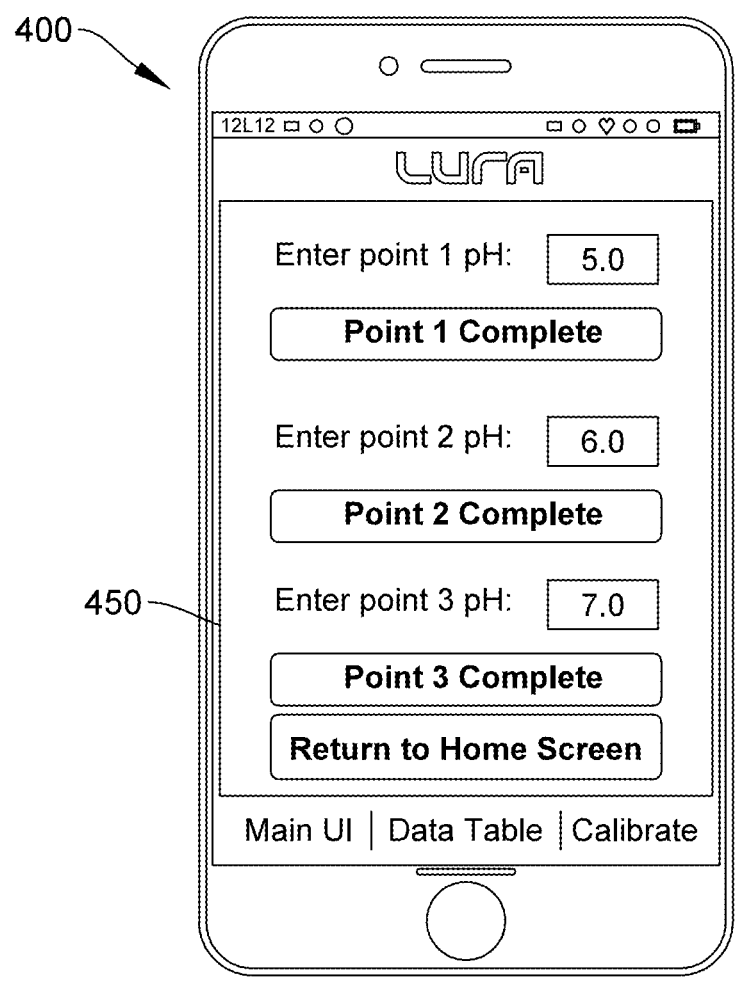

In some embodiments, device 100 includes one or more switches, such as exemplary switch 1625 shown in FIG. 12, that when activated causes device 100 to change from an "off state" (e.g. an unpowered state) to an "on state" (e.g. a powered state), and/or vice versa. Switch 1625 can be used to turn off device 100 after factory testing is complete, prior to storage of device 100, and/or prior to shipping of device 100. Switch 1625 can be used to turn on device 100 prior to, during, or shortly after insertion of device 100 into the patient's mouth. In various embodiments, the switch 1625 may be activated or deactivated by ultraviolet (UV) light. In various embodiments, the device may include one or more (e.g., two) UV-activated reverse fuses that causes a short circuit when exposed to UV light. In various embodiments, one UV switch may be activated during manufacturing while another UV switch (which can be set to a different bandwidth threshold) may be activated at a healthcare provider. In various embodiments, the UV switch may be activated by shining a UV light through a casing on one side of the device.

Switch 1625 can also be configured to be activated (causing device 100 to transition between on and off states) when a physical force is applied to switch 1625. In some embodiments, switch 1625 comprises a conductive element arranged such that when a force is applied to cause the conductive element to connect (e.g. "short") two conductive traces (e.g. of a circuit board) of device 100, where this connection causes device 100 to transition from the inactive state to the active state, or vice versa. For example, a force can be applied to a flexible or otherwise deflectable portion of housing 1106 and/or 1107 to cause switch 1625 to make the connection. In some embodiments, a tool, such as a functional assembly 99 comprising a small pin or other tool, is used to apply the force to cause the deflection. In various embodiments, the switch 1625 may include a deformable portion configured as an on-off control. In various embodiments, the switch 1625 may have a first configuration that corresponds to an 'off' position and may be deformable to a second configuration that corresponds to an 'on' position. In various embodiments, the second configuration may correspond to a shape of a patient's tooth.

In some embodiments, switch 1625 comprises a graspable tab that can be pulled to activate switch 1625, such as a tab that causes one or more insulators to be removed from power supply 160 to connect power supply 160 to the electronic portion of device 100, such that power supply 160 can provide energy to device 100.

In some embodiments, switch 1625 comprises a magnetic switch, such as a switch that is activated by bringing a magnet (e.g. a functional element 99 comprising a magnet) in close proximity to switch 1625. In some embodiments, switch 1625 comprises a magnetic switch of similar construction and arrangement to switch 1625 of FIG. 12 described herein. In various embodiments, a magnet may activate the device (switch the device to the 'on' configuration) when the magnet is directed towards the switch in one direction. In various embodiments, the magnet may deactivate the device (switch the device to the 'off' configuration) when the magnet is directed towards the switch in a different (e.g., opposite) direction.

In some embodiments, switch 1625 can be positioned behind a movable portion of housing 1106 and/or 1107.

In some embodiments, switch 1625 comprises a conductive strip that includes at least segment that includes a split (e.g., a separation) along at least portion, such as to create two conductive strips with a gap in between. A metal place or other conductive component can be rotated or otherwise translated to connect the two conductive strips, creating a switch. In various embodiments, the switch may be a locking tactile switch. In various embodiments, the locking tactile switch may be disposed sideways (e.g., circumferentially along the band) to add minimal thickness to the system. In various embodiments, the casing may include a removable pin in an opening. In various embodiments, the pin may be in contact with a switch such that the switch is kept in the 'off' configuration while in contact with the removable pin. In various embodiments, removing the pin activates the sensor. In various embodiments, the pathway comprises a spring-loaded door configured to close off the opening when the pin is removed, thereby preventing any further power cycling after removal of the pin.

In various embodiments, the system may be powered on/off programmatically. In various embodiments, a physical switch may be used to power on the device. In various embodiments, the device may only be powered off programmatically (i.e., the physical switch will not power the device off). In various embodiments, no physical switch may be present on the device and the device may only be powered on via a mobile application.

In some embodiments, wearable device 300 comprises a transceiver, transceiver 370, that is configured as an "intermediate receiver" of system 10. For example, transceiver 370 can comprise a receiver and/or transmitter, such as a transceiver that receives and/or transmits information (e.g. using Bluetooth protocol) to and/or from devices 100 and/or 400. In these embodiments, device 100 can transmit data to device 300 (e.g. in transmissions of less than 10 seconds, or less than 5 seconds in length) at regular intervals (e.g. 5 minute intervals, 15 minute intervals, and/or 30 minute intervals), and device 300 can subsequently transmit the received data to device 400. Device 300 can continuously attempt to transmit the received data to device 400, such as until receipt of the data transmission is confirmed. Alternatively, device 300 can transmit data at regular or irregular intervals, such as to reduce energy requirements of device 300. Wearable device 300 can comprise a power supply, power supply 360 shown, that is bigger than power supply 160 of device 100. Device 300 can communicate with device 100 via a custom Bluetooth protocol (e.g. a protocol not dictated by commercial phone operating systems). In some embodiments, power supply 360 can comprise a rechargeable battery, such as to be recharged via USB charging, wireless charging, and/or other charging arrangement. In some embodiments, device 300 is configured to store data received from device 100 for an extended period of time, such as a time of at least 1 day, 1 week, 1 month, 3 months, and/or 6 months (e.g. when data of device 300 is configured to be uploaded by a receiving device of a dentist or other clinician of the patient).

In some embodiments, attachment mechanism 180 comprises a construction that is easily removable from the patient's teeth by the patient, such as a construction similar to a dental tray (e.g. those used in teeth aligners, night guards, day guards, and/or retainers). In some embodiments attachment mechanism 180 is configured to perform two functions, such as to maintain device 100 in the patient's mouth, and to perform a second function for the patient, such as to straighten teeth, maintain the position of teeth, address bruxism, and/or provide another dental function. In some embodiments, attachment mechanism comprises an easily removable mechanism, as described herein, and is positioned in the patient's mouth less than 24 hours each day, such as less than 22 hours each day. In some embodiments, attachment mechanism 180 is configured to be positioned in the patient's mouth (e.g. attached to one or more teeth or simply positioned within the patient's mouth), for a relatively short period of time (e.g. less than a couple of hours), such as to test the patient's saliva or perform another test using device 100. In some embodiments, attachment mechanism 180 comprises an orthodontic bracket that is bonded to multiple teeth or a single tooth. For example, attachment mechanism 180 can comprise an orthodontic bracket that is bonded in a region limited to a single side of the patient's tooth (e.g. the cheek side of a patient's tooth).

In some embodiments, device 100 is configured to be positioned in the patient's mouth for an extended period, such as a period of at least 1 month, at least 3 months, and/or at least 6 months. In these embodiments, device 100 can be configured to continuously and/or intermittently (e.g. at 5, 10, and/or 15 minute intervals) record patient data (e.g. pH data), and store the recorded data within device 100 (e.g. within electronic memory of processor 150). At regular or irregular intervals, the recorded data can be transmitted to a separate device (e.g. device 300 and/or device 400), such as when the data is transmitted at a patient checkup or other visit to a dentist or other clinician of the patient. In these embodiments, data can be uploaded from device 100 while device 100 remains in the patient's mouth (e.g. attached to one or more teeth of the patient) and/or after removal of device 100 from the patient's mouth (e.g. detachment from one or more teeth of the patient). The data can be uploaded after a switch (e.g. a switch-based functional element 199) is pressed (e.g. by the clinician), such as an upload of data that is correlated with the patient's medical records (e.g. uploaded to a computer of the clinician or other healthcare provider). The uploaded data can be analyzed, such as via algorithm 155, and records of the analysis can be provided to the clinician and/or patient. The uploaded data can be maintained and stored (e.g. stored in the cloud), similar to other standard patient medical records. In these embodiments, the patient may or may not have a patient-maintained device for uploading the data from device 100 (e.g. avoiding the need for the patient to carry and/or maintain such a device).

In some embodiments, device 400 comprises a cell phone, and device 100 is configured to transmit recorded data (e.g. pH or other recorded data) to device 400 while the patient is using device 400 (e.g. making a phone call, accessing a smart-function of the phone, and/or otherwise holding device 400). For example, when transceiver 470 of device 400 is positioned near transceiver 170 of device 100 (e.g. when the patient is making a phone call and positions transceiver 470 proximate the patient's mouth and/or cheek), device 100 can transfer data to device 400, such as a transmission between device 100 and device 400 performed using near-field communication (NFC). System 10 can be configured to sense the relatively proximity of transceiver 400, such as when algorithm 155 is configured to detect the proximity via: performing an analysis of accelerometer and/or gyroscope data of device 400 (e.g. when functional element 499 comprises an accelerometer and/or gyroscope); detecting a phone call in progress; and combinations of these. For example, algorithm 155 can monitor accelerometer, gyroscope, and/or other movement sensor data to track the motion and/or relative position of device 400. Algorithm 155 can be configured to assess the likelihood that device 400 has been positioned proximate the patient's ear (e.g., taken from a pocket of the patient, a table, or other location and moved to a location proximate the patient's ear). In these embodiments, algorithm 155 can include a bias toward false positives. When algorithm 155 determines that device 400 is proximate device 100 (e.g., when device 400 is proximate the patient's ear or other face location), data transmissions can be attempted. For example, data transmissions can only occur when device 400 is likely to be within appropriate range of device 100, such that periods of data transmission are routinely successful, effectively minimizing power consumption of device 100 and extending battery life of device 100 when compared to standardized transmission intervals of 5 minutes, 10 minutes, 15 minutes, or other preset periods of time). In some embodiments, device 400 repeatedly sends NFC transmissions to device 100, and when sufficient proximity is present, device 100 will respond confirming the proximity, after which data can be transferred from device 100 to device 400. In some embodiments, one of devices 100 or 400 comprises a detectable element (e.g., magnet), and the other of device 100 or 400 comprises a sensor configured to detect proximity of the element (e.g., a magnetic switch or other sensor). After transmission of the data from device 100 to device 400 (e.g., via NFC), the data can subsequently uploaded by device 400 to the cloud or other network based storage system. Use of NFC communications can greatly reduce the requirements (e.g., size) of power supply 160 of device 100.

In some embodiments, a CAD file of one or more of the patient's teeth is created, such as via an intraoral 3D scan and/or a 3D scan of a mold (e.g., an alginate mold) of the patient's teeth. The CAD file can be uploaded into memory storage of the patient's clinician (e.g., dentist) and/or of the supplier of system 10. A customized device 100 (e.g., a customized attachment mechanism 180 and/or other portion of device 100) can be manufactured for that particular patient based on the CAD file, and subsequently shipped to the patient and/or their clinician (e.g., based on address information similarly stored and associated with the CAD file). An alert can be sent to the patient and/or clinician related to delivery, and/or invoicing can automatically be triggered. In some embodiments, replacement devices 100 can be similarly manufactured, delivered, and/or invoiced (e.g., without the need for one or more additional actions by the patient or clinician).

As described herein, system 10 can be configured to measure various physiologic parameters of the patient, such as physiologic parameters that can be measured via analysis of the patient's saliva. In some embodiments, system 10 is configured to monitor a physiologic parameter such as a parameter associated with a viral load and/or a parameter associated with interleukin 6.

In some embodiments, device 100 comprises a temperature sensor (e.g., a functional element 199 comprising a temperature sensor), such as to detect a fever due to illness of the patient (e.g., a fever due to a virus or bacteria), and/or to detect the patient's temperature to assist in family planning (e.g., to provide temperature information associated with ovulation).

In some embodiments, system 10 comprises a temperature monitoring system with device 100 configured to monitor at least the temperature within the mouth of the patient. Device 100 can transmit the patient temperature to a separate device, such as device 300 and/or 400 described herein. System 10 can be configured to allow entry (e.g., via device 400) of patient health information, such as information associated with the temperature information recorded by device 100. The health information can comprise information related to a symptom (e.g., a symptom of an illness). The health information can be stored by system 10 (e.g., in electronic memory and/or a database of system 10), and/or the information can be transmitted by system 10 between components of system 10 or to another device (e.g., a computer network). System 10 can be configured to analyze (e.g., via algorithm 155) the temperature information and compare the information to other information, such as an analysis which correlates information to one or more geographic areas, during one or more time periods. In some embodiments, system 10 comprises multiple sets of devices 100, 300, and/or 400 intended for use with multiple patients, and at least temperature information recorded by the corresponding device 100 of each patient is analyzed as a set of multiple patient data. System 10 can be configured to alert the patient if an undesired condition is detected, such as an undesired condition determined via an analysis of multiple patient information related to one or more geographic areas, such as information related to patient temperature information, patient age information, patient race information, patient sex information, patient genetic information; and/or patient illness information (e.g., past and/or present illness information), such as when these various categories of information are stored in a database or other electronic memory of system 10. In some embodiments, system 10 provides symptom information to the patient. In some embodiments, system 10 provides healthcare provider information to the patient. In some embodiments, system 10 provides patient temperature and/or other patient information to one or more healthcare providers. In some embodiments, system 10 is configured to provide a prompt to the patient or other user, such as a prompt requesting information to be provided by the patient or other user.

In some embodiments, system 10 is configured to measure temperature information of a patient, as described herein, and alert the patient or other user of system 10 when the patient has an undesired temperature, such as a fever.

System 10 can include one or more tools, such as tool 98 shown. In some embodiments, tool 98 comprises one or more beverages or other liquids with a known pH value, each a "calibration liquid", that are used to perform a calibration of system 10 (e.g. a calibration of device 100), such as is described in FIGS. 13A-D.

Figure 2A:
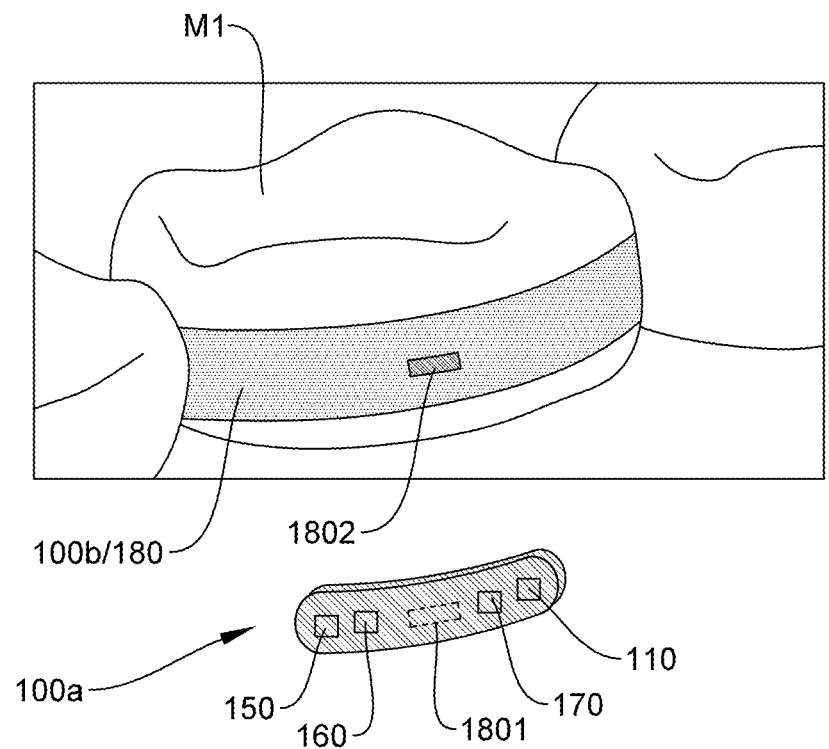
FIGS. 2A-2B illustrate anatomical views of a sensor device according to embodiments of the present disclosure.
Figure 2B:
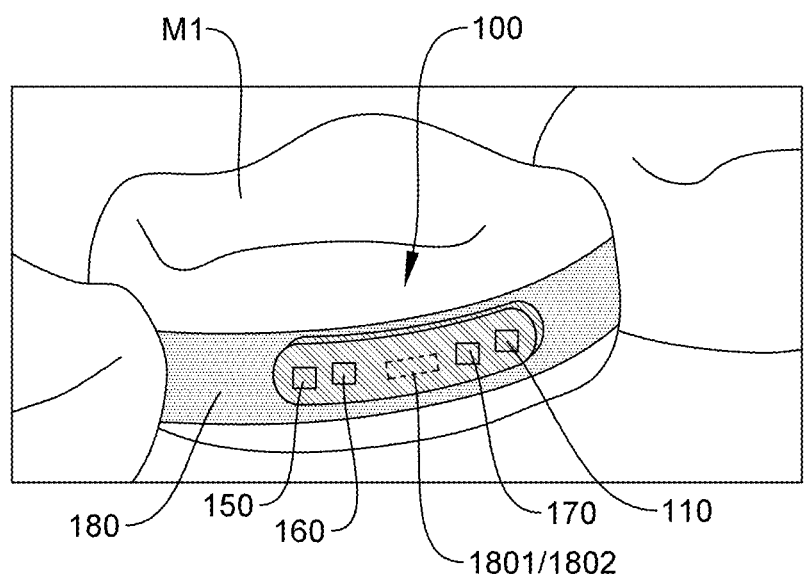

Referring now to FIGS. 2A and 2B, anatomical views of a sensor device prior to full attachment to a tooth of a patient, and after full attachment to the tooth of the patient, respectively, are illustrated, consistent with the present inventive concepts. Sensor device 100 of FIGS. 2A-2B includes various components described in reference to FIG. 1 and otherwise herein, and as shown in the figure. As shown in FIG. 2A, sensor device 100 can comprise a first portion 100a and a second portion 100b. First portion 100a comprises sensor assembly 110, processor, power supply 160, and transceiver 170. First portion 100a further comprises a connecting element 1801. Second portion 100b comprises attachment mechanism 180, which in turn comprises a mating connecting element 1802 that is configured to removably attach to connecting element 1801 of first portion 100a. Second portion 100b has been attached to a tooth of the patient, molar M1. In FIG. 2A, first portion 100a is detached from (e.g. not yet attached to) second portion 100b. In FIG. 2B, first portion 100a has been attached to second portion 100b.

Connecting elements 1801 and 1802 can comprise (e.g. collectively include) mating sets of various connecting elements, such as a connecting element selected from the group consisting of: mating snaps; frictionally engaging elements; male and female mating elements; magnets; mating hook and loop fastener; and combinations of these. In various embodiments, the first portion 100a may be laser sintered to the second portion 100b.

In some embodiments, system 10 comprises multiple first portions 100a, each of which can be configured to sequentially attach to a single second portion 100b, such as when portion 100b is attached to a patient's tooth for days, weeks, and/or months, an initial first portion 100a is attached for a first period of time and one or more additional first portions 100a are attached after a preceding first portion 100a has been removed. In some embodiments, one or more first portions 100a are disposed of after a period of use (e.g. at least one day, or at least one week), such as when an included battery or other power supply 160 has been depleted. Alternatively, one or more first portions 100a can be reused after a first period of use (e.g. after power supply 160 has been replaced or recharged).

Figure 3:
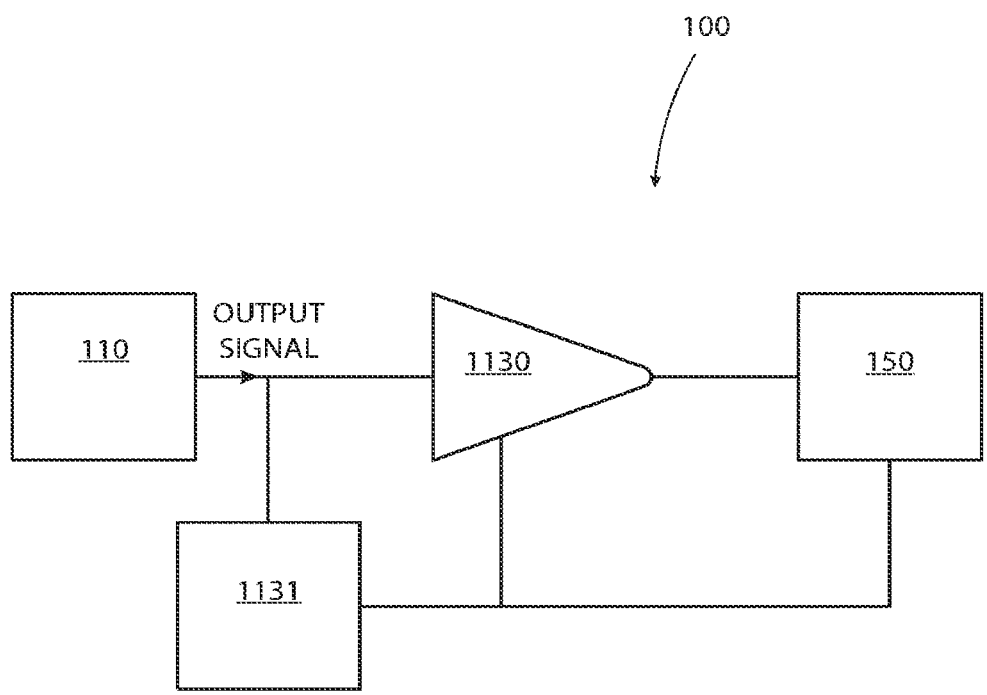
FIG. 3 illustrates a schematic view of a sensor device according to embodiments of the present disclosure.

Referring now to FIG. 3, a schematic view of a sensor device is illustrated, consistent with the present inventive concepts. Sensor device 100 of FIG. 3 includes various components described in reference to FIG. 1 and otherwise herein, and as shown in the figure. Sensor device 100 comprises sensor assembly 110 and processor 150, as described herein. In some embodiments, sensor device 100 is configured to compensate for drift. For example, sensor device 100 can further comprise one or more operational amplifiers, op amp 1130, and one or more sensors, such as drift sensor 1131, each component attached in a feedback loop configuration as shown. Op amp 1130 can be configured to amplify and/or minimize the output signal of sensor assembly 110 (e.g. ISFET 1105) through a feedback loop. If the output signal drifts to an extent where the maximum output exceeds an amplitude threshold (e.g. a voltage threshold, such as 3.3V), the feedback loop can cause op amp 1130 to lower its gain (e.g. to a value less than 1). If drift occurs in the opposite direction, the feedback loop can cause op amp 1130 to increase its gain (e.g. to a value more than 1). The resulting gain of op amp 1130 can be detected by sensor assembly 110 through use of general purpose input-output ports configured to function as analog inputs, and used to calculate a true output value of sensor assembly 110. In some embodiments, sensor assembly 110 comprises op amp 1130 and/or drift sensor 1131.

Figure 4:
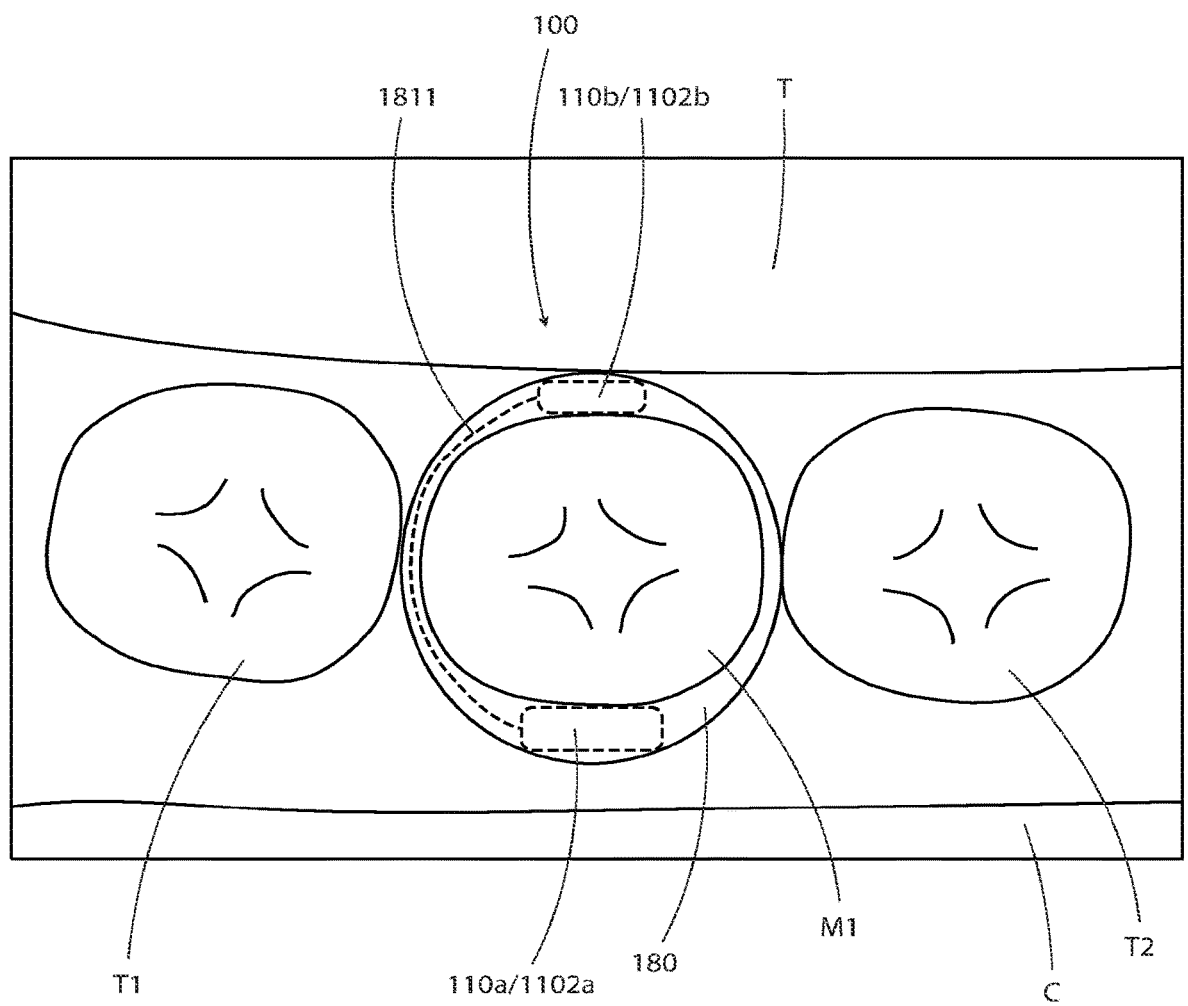
FIG. 4 illustrates an anatomical view of a sensor device attached to a tooth of a patient according to embodiments of the present disclosure.

Referring now to FIG. 4, an anatomical view of a sensor device attached to a tooth of a patient is illustrated, consistent with the present inventive concepts. Sensor device 100 of FIG. 4 includes various components described in reference to FIG. 1 and otherwise herein, and as shown in the figure. Sensor device 100 can be attached to molar M1 via attachment mechanism 180 as shown. Molar M1 is positioned between teeth T1 and T2, also as shown. Sensor device 100 of FIG. 4 further comprises a sensor assembly 110 comprising a first portion 110a and a second portion 110b. Sensor assembly 110a can comprise substrate 1102 comprising a substrate first portion 1102a (e.g. a PCB and/or semiconductor substrate) onto which the components of sensor assembly 110a are operably attached, and a substrate second portion 1102b (e.g. a PCB and/or semiconductor substrate) onto which the components of sensor assembly 110b are operably attached. Sensor assembly portions 110a and 110b can be operably attached by cable 1811, a conduit (e.g. a flexible conduit) comprising one or more wires or traces ("wires" or "traces" herein), optical fibers, flexible PCBs, stretchable PCBs, wave guides, and/or fluid delivery tubes. In some embodiments, sensor assembly portions 110a and 110b are positioned on opposites sides of a tooth, such as on opposite sides of molar M1 as shown, such as when assembly portion 110b is positioned adjacent the patient's tongue T, and assembly portion 110a positioned on the opposite side and adjacent the patient's cheek C, both as shown. In some embodiments, sensor assembly 110 comprises three or more portions (e.g. positioned on three or more locations on one or more teeth of the patient). Division of assembly 110 into two or more portions allows assembly 110 to include additional volume of components, while maintaining all components relatively close to the surface of the tooth to which it is attached (i.e. efficiently minimizing volume of the device, such as minimizing the maximum distance in which assembly 110 radially extends from the attached tooth). In some embodiments, components of sensor device 100 are constructed and arranged to achieve volumetric efficiency as described in reference to FIGS. 10A-10B herein.

Figure 5:
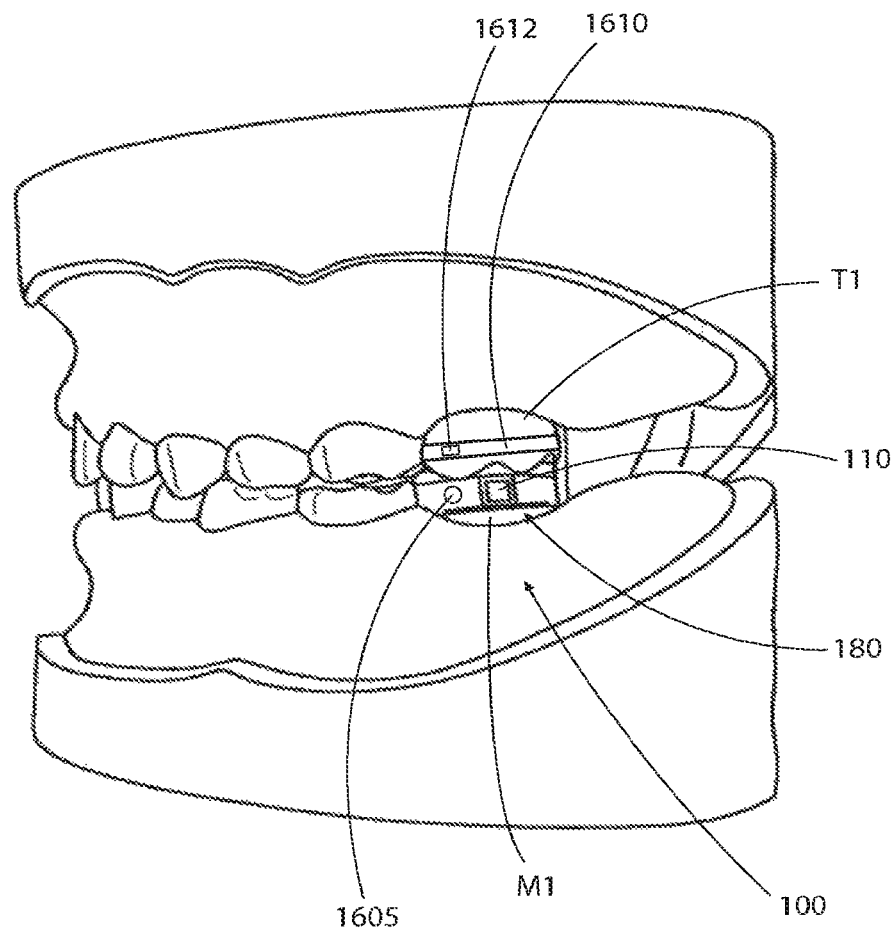
FIG. 5 illustrates an anatomical view of a magnetic field charging assembly of a sensor device according to embodiments of the present disclosure.

Referring now to FIG. 5, an anatomical view of a magnetic field charging assembly of a sensor device is illustrated, consistent with the present inventive concepts. Sensor device 100 of FIG. 5 includes various components described in reference to FIG. 1 and otherwise herein, and as shown in the figure. Sensor device 100 is attached to molar M1 via attachment mechanism 180 as shown. Molar M1 can comprise a molar on the lower jaw of the patient, as shown. Sensor device 100 includes sensor assembly 110, as described herein.

Sensor device 100 can be configured to recharge power supply 160 of sensor device 100 (not shown but positioned proximate molar M1), such as a recharging that occurs during chewing and/or other movement of the patient's teeth. Sensor device 100 of FIG. 5 includes a magnetic field charging assembly comprising charging element 1605, and magnet 1612. Magnet 1612 can be attached to a tooth T1 of the opposite jaw (e.g. a molar or other tooth of the upper jaw as shown) via attachment mechanism 1610 (e.g. a band, adhesive, and/or other tooth-attaching mechanism). Charging element 1605 is configured to create energy via motion of magnet 1612 (e.g. a permanent magnet) relative to charging element 1605, such as recharging energy provided to recharge power supply 160. For example, charging element 1605 can include one or more coils in which a current is generated via motion of magnet 1612 in relative proximity to element 1605 (e.g. current that is generated during chewing and/or other jaw movement that is used to recharge a battery and/or capacitor of power supply 160).

Figure 6:
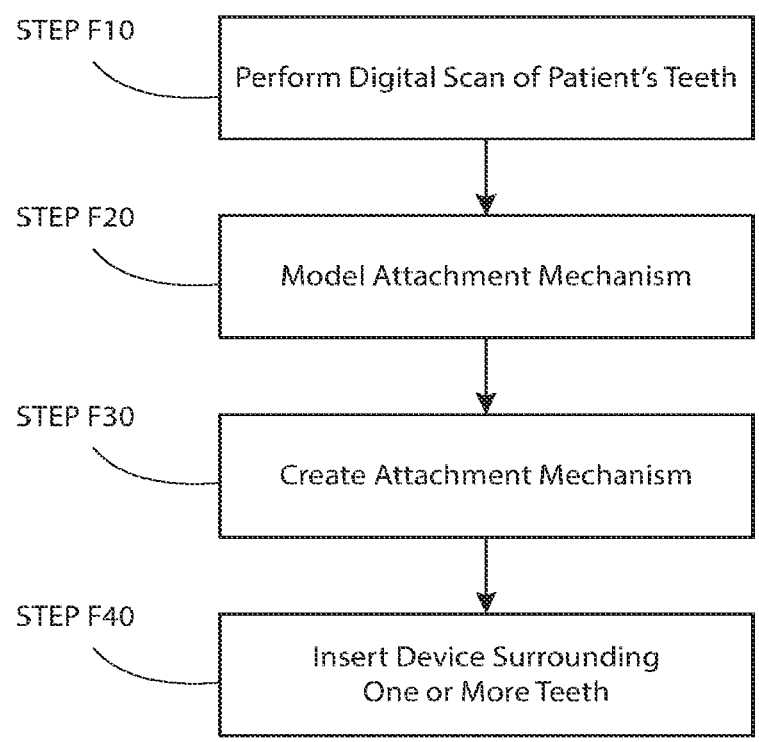
FIG. 6 illustrates a flow chart of a method of manufacture and installation of a sensor device according to embodiments of the present disclosure.

Referring now to FIG. 6, a flow chart of a method of manufacture and installation of a sensor device is illustrated, consistent with the present inventive concepts. The method of FIG. 6 is described using system 10 and its components, as described herein.

In STEP F10, a digital scan of one or more teeth of the patient is performed. For example, a digital image (e.g. an STL/3D model of teeth) can be generated from an intraoral scanner (e.g. functional element 99 comprises an intraoral scanner).

In STEP F20, a design for an attachment mechanism 180 is created. System 10 (e.g. via algorithm 155) can programmatically analyze the digital image created in STEP F10, determine an applicable design (e.g. an optimized geometry and/or component configuration) of attachment mechanism 180 to fit one or more of the patient's teeth. The mechanism 180 design specifications can be sent (e.g. via a wired and/or wireless communication such as the Internet) to a manufacturer of mechanism 180.

In STEP F30, an attachment mechanism 180 is manufactured.

In STEP F40, attachment mechanism 180 is attached to one or more teeth (e.g. a molar) of the patient. In some embodiments, sensor device 100 is attached to attachment mechanism 180 before attachment 180 is attached to the one or more teeth of the patient. Alternatively or additionally, sensor device 100 (e.g. at least a portion of sensor device 100) is attached to attachment mechanism 180 after mechanism 180 is attached to the one or more teeth of the patient.

Referring now to FIGS. 7A and 7B, side sectional, and top transparent views, respectively, of a sensor assembly is illustrated, consistent with the present inventive concepts. Sensor assembly 110 of FIGS. 7A-7B includes various components described in reference to FIG. 1 and otherwise herein, and as shown in the figure. Housing 1106, which is attached to a top surface of substrate 1102 (e.g. a PCB), comprises walls (e.g. walls extending from the top surface of substrate 1102 as shown) that surround ISFET 1105 and reference electrode 1118. The walls of housing 1106 can define the sides of a first chamber, chamber 1125, which surrounds electrode 1118, and the sides of a second chamber, chamber 1126, which surrounds ISFET 1105, each as shown. Diaphragm 1119 (e.g. a ceramic diaphragm) is positioned above reference electrode 1118 such that a solution, solution 1103 shown, is maintained within chamber 1125 and surrounds electrode 1118. Solution 1103 can comprise one or more materials, and it can be configured to perform one or more functions, such as are described in reference to FIG. 8 or otherwise herein.

Positioned on top of diaphragm 1119 is PEM 1108. In some embodiments, PEM 1108 comprises a membrane positioned below diaphragm 1119. In some embodiments, PEM 1108 comprises a first membrane positioned on top of diaphragm 1119, and a second membrane positioned below diaphragm 1119. PEM 1108 can comprise one or more materials, and it can be configured to perform one or more functions, such as are described in reference to FIG. 8 or otherwise herein.

Sensor assembly 110 comprises a fluid channel, channel 1117, that fluidly connects chamber 1126 (including ISFET 1105) to chamber 1125 (including reference electrode 1118). Passage of fluids between chambers 1125 and 1126 includes passage of these fluids through PEM 1108, diaphragm 1119, solution 1103 and fluid channel 1117.

In some embodiments, sensor assembly 110 comprises one or more of a surface modification and/or other coating as described herein. For example, sensor assembly 110 can include coating 1116a shown, which can cover surfaces of at least a portion of chamber 1125 and/or surfaces of components adjacent and/or within chamber 1125. Sensor assembly 110 can include coating 1116b shown, which can cover surfaces of at least a portion of chamber 1126 and/or surfaces of components adjacent and/or within chamber 1126. Coatings 1116a and/or 1116b can comprise a surface treatment and/or a coating, such as a hydrophilic coating (e.g. a superhydrophilic coating), and/or an ion implantation, which can be configured to enhance flow of fluid within chambers 1125 and/or 1126.

Sensor assembly 110 can further include mesh 1115, as described herein. Mesh 1115 can be sized and positioned to reduce food or other undesired solid substances (e.g. toothbrush bristles, food particles, cellular debris) from passing through mesh 1115 into the "working environment" of reference electrode 1118 and ISFET 1105, while allowing fluid and/or protons to pass into that working environment. In some embodiments, coating 1116b (e.g. a hydrophilic coating) is included on at least a portion of mesh 1115, such as to enhanced fluid transfer through mesh 1116 and/or to prevent undesired material (e.g. food, debris, microbes, and the like) from adsorbing to the surface of mesh 1115.

Referring now to FIG. 8, a side sectional view of a sensor device is illustrated, consistent with the present inventive concepts. Sensor device 100 of FIG. 8 includes various components described in reference to FIG. 1 and otherwise herein, and as shown in the figure. Sensor device 100 includes sensor assembly 110 as shown. Sensor assembly 110 of FIG. 8 includes reference electrode 1118 and ISFET 1105. ISFET 1105 can comprise an ion-sensitive field effect transistor (ISFET). In some embodiments, reference electrode 1118 comprises an Ag/AgCl electrode. In some embodiments, reference electrode 1118 comprises one or more wires (e.g. wires comprising Ag/AgCl), and/or one or more pads (e.g. pads comprising Ag/AgCl). For example, reference electrode 1118 can comprise one or more wires protruding from substrate 1102 (e.g. a PCB), such as electrode 1118a shown in FIG. 8. Alternatively or additionally, reference electrode 1118 can comprise a pad positioned on and/or embedded in substrate 1102.

Reference electrode 1118 is positioned within chamber 1125 that is surrounded by a portion of housing 1106, portion 1106a. Similar to the embodiment of FIGS. 7A-7B, chamber 1125 is filled with a solution, solution 1103, which surrounds reference electrode 1118. Solution 1103 can comprise a salt solution that contacts a metal portion of the reference electrode 1118, such as a salt solution of a metal of the reference electrode 1118 (e.g. a potassium chloride salt solution for an Ag/AgCl electrode). Solution 1103 can comprise saturated or super saturated salt solution (e.g. a saturated or super saturated KCl solution). Solution 1103 can comprise an electrolyte fluid or gel. Solution 1103 can further include salt crystals (e.g. suspended KCl salt crystals), such as salt crystals and/or other materials that are configured to maintain saturation. Solution 1103 is contained within chamber 1125 by diaphragm 1119 and/or PEM 1108. PEM 1108 can be configured to allow protons and/or desired molecules or ions to enter chamber 1125. Diaphragm 1119 can comprise ceramic and/or PEEK. Diaphragm 1119 can be configured as a salt bridge. Diaphragm 1119 can comprise one or more coatings, such as a coating comprising a sulfonated tetrafluoroethylene-based fluoropolymer-copolymer coating, a zwitterion coating, and/or a hydrogel coating, such as a coating configured to limit the outward diffusion of solution 1103 (e.g. to limit the outward diffusion of KCl of solution 1103)

In some embodiments, housing 1106 comprises one or more walls which extend from substrate 1102 as shown, creating chamber 1126. The top opening of chamber 1126 can be sealed using mesh 1115. Mesh 1115, diaphragm 1119, the internal surfaces of chamber 1125 and/or 1126, and/or another fluid contacting portion of sensor assembly 110 can include a coating (e.g. an ion implantation or other surface modification, and/or an applied coating), coatings 1116a and/or 1116b shown, and/or other coating 1116 described herein. Coatings 1116a and/or 1116b can comprise a hydrophilic coating. Coatings 1116a and/or 1116b can be configured to cause increased saliva and/or other fluid transfer through mesh 1115 and other surfaces through which these oral fluids make contact, such as to allow oral fluids to contact the transducer components (e.g. ISFET 1105) more easily. The surface treatments can also be configured to provide antifouling and antimicrobial properties.

Mesh 1115 can be sized and positioned to reduce food or other undesired solid substances (e.g. toothbrush bristles) from passing through mesh 1115 into the "working environment" of reference electrode 1118 and ISFET 1105, while allowing fluid and/or protons to pass into that working environment.

Figure 9:
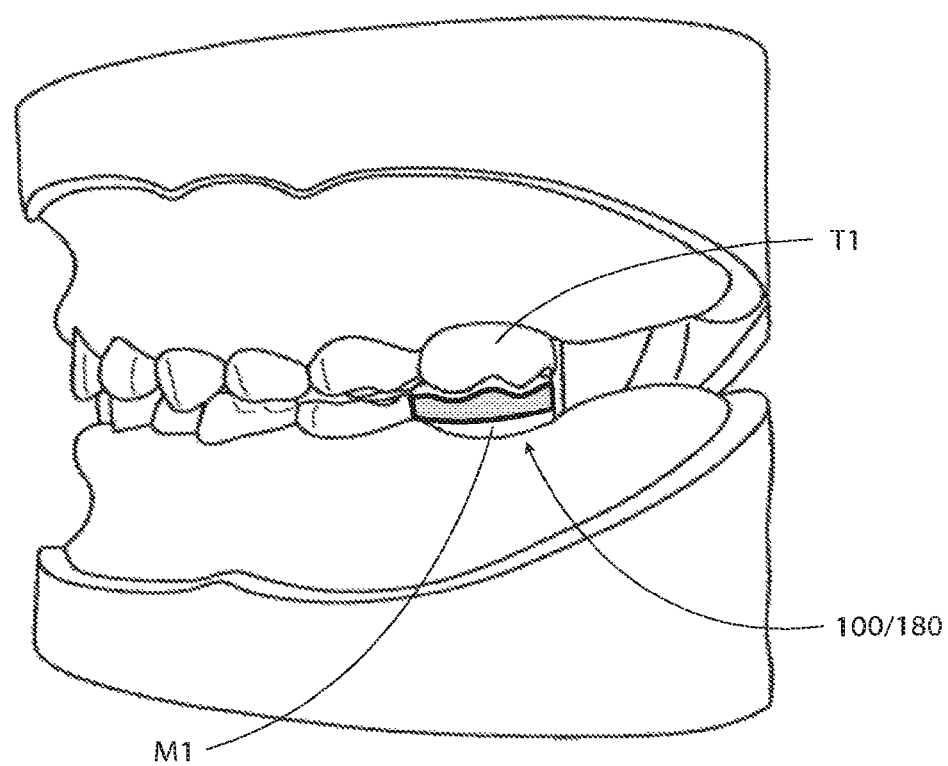
FIGS. 9-9A illustrate an anatomical view of a sensor device positioned on a molar, and a side view of the sensor device, respectively according to embodiments of the present disclosure.
Figure 9A:
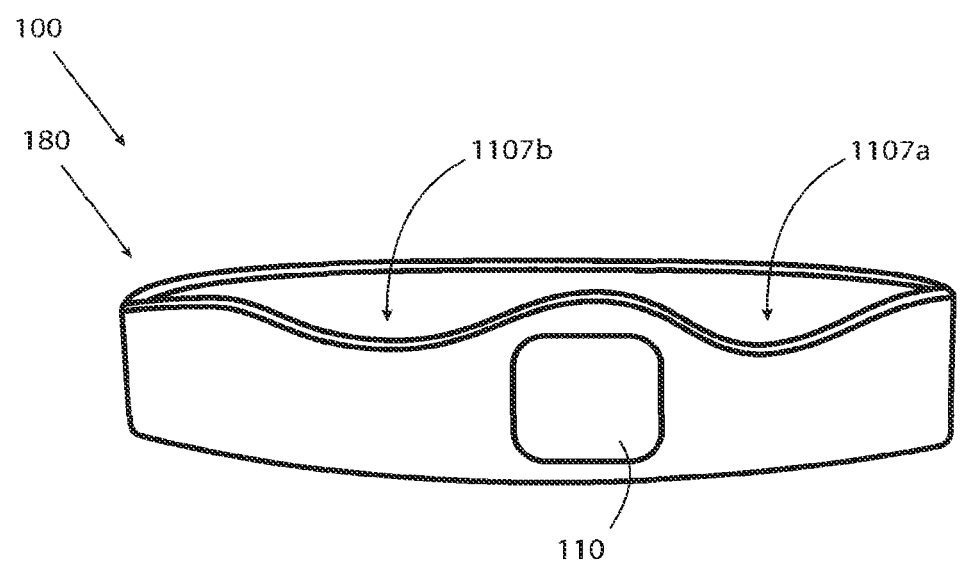

Referring now to FIGS. 9 and 9A, an anatomical view of a sensor device positioned on a molar, and a side view of the sensor device, respectively, are illustrated, consistent with the present inventive concepts. Sensor assembly 110 of FIGS. 9 and 9A includes various components described in reference to FIG. 1 and otherwise herein, and as shown in the figure. As shown in FIG. 9, sensor device 100 comprises attachment mechanism 180 which has attached the other portions of sensor device 100 (e.g. sensor assembly 110) to molar M1. Sensor device 100 includes housing 1107. Housing 1107 can include one or more geometric features that are configured to provide patient comfort, avoid obstruction while chewing and/or biting down, and/or provide a cosmetic effect. For example, housing 1107 can comprise features 1107a and 1107b shown which each comprise a depression in the top surface of housing 1107 (e.g. a reduced height portion of housing 1107) which is geometrically sized and positioned to avoid undesired contact between housing 1107 and extending portions of tooth T1 as shown in FIG. 9. Housing 1107 can comprise numerous features to provide desired benefits to the patient, such as a thinned portion, a radiused portion, a recess, and/or other geometric feature that is different than other portions of housing 1107 proximate the feature.

Figure 10A:
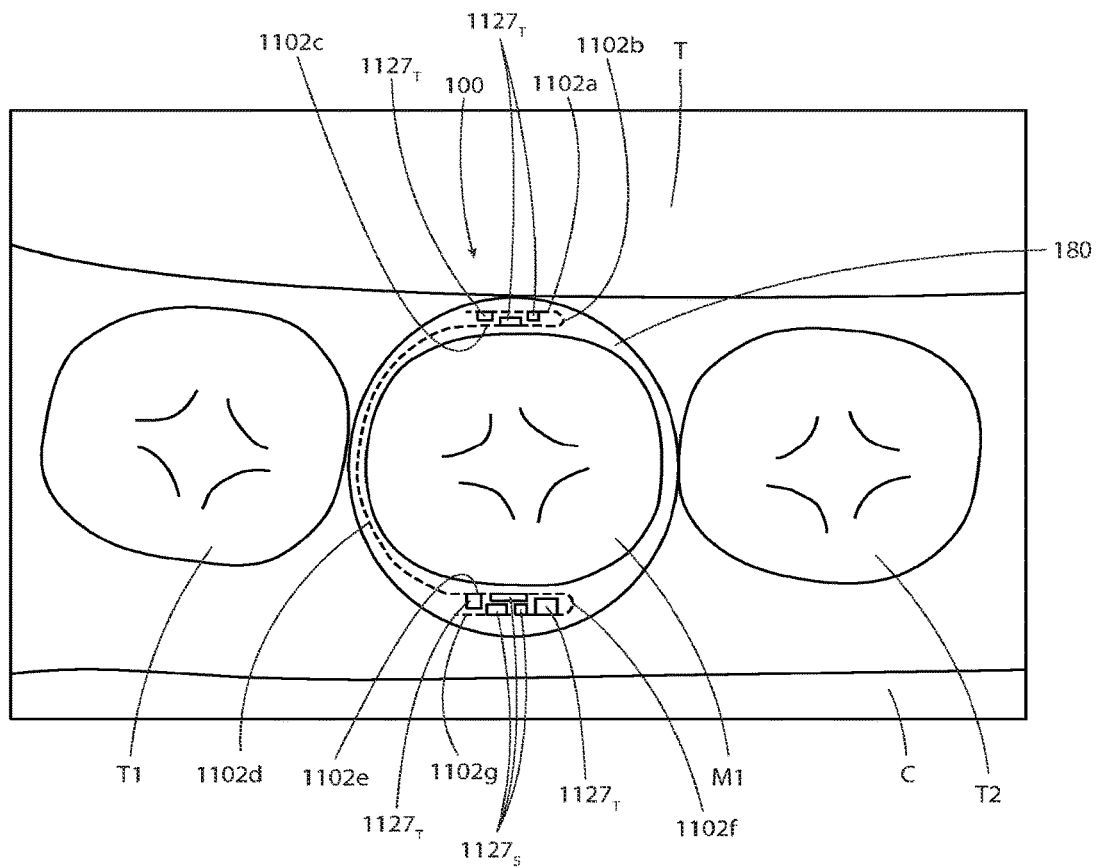
Figure 10B:
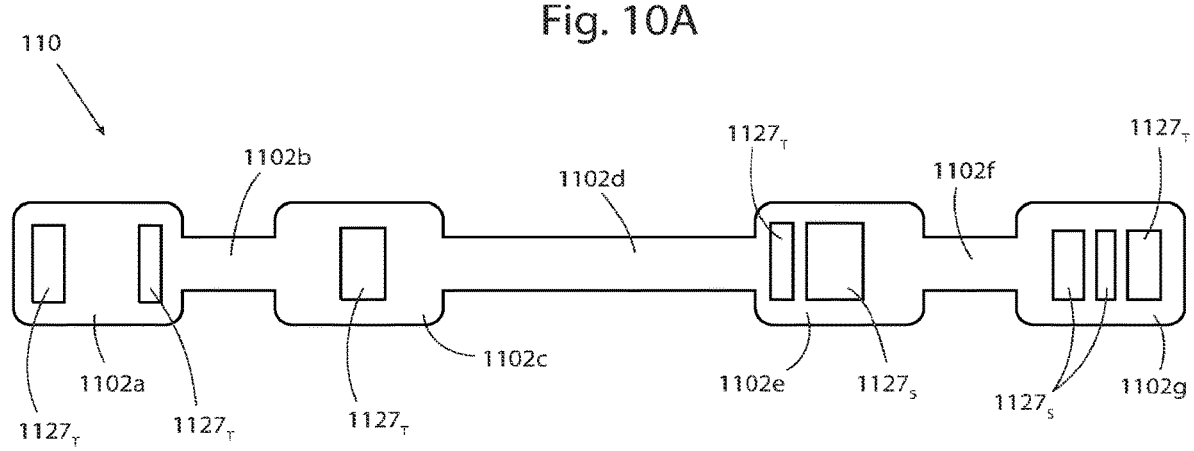

Referring now to FIGS. 10A and 10B, an anatomical view of a sensor device positioned on a molar, and a side view of an electronic assembly of the sensor device, respectively, are illustrated, consistent with the present inventive concepts. Sensor device 100 of FIGS. 10A and 10B includes various components described in reference to FIG. 1 and otherwise herein, and as shown in the figure. As shown in FIG. 10A, sensor device 100 comprises attachment mechanism 180 which has attached the other portions of sensor device 100 (e.g. sensor assembly 110) to molar M1, between tooth T1 and T2. Sensor device 100 includes sensor assembly 110 which includes substrate 1102 onto which various components 1127 (e.g. electronic and/or mechanical components) are attached, such as when substrate 1102 includes one or more PCBs (e.g. flexible and/or rigid PCBs), conductive traces, and/or wires. Components 1127 can comprise various electromechanical components, such as ISFET 1105, reference electrode 1118, and/or other electromechanical components of sensor assembly 110.

Substrate 1102 can comprise various portions, such as portions 1102a-g shown, each with a mounting surface upon which components 1127 can be operably attached (e.g. electrically, mechanically, fluidly, acoustically, and/or chemically attached). In some embodiments, at least portions 1102b, 1102d, and 1102f include flexible and/or stretchable PCBs, and/or other flexible and/or stretchable conduits. Portion 1102d can be of similar construction and arrangement to cable 1811 described herein. Components 1127 can comprise components with a mounted height (e.g. above substrate 1102) that falls into two relative categories, components with a mounted height below a first threshold, components 1127S, and components with a mounted height above the first threshold, components 1127T. Components 1127 can be positioned on substrate 1102, such that when substrate 1102 is arranged in the geometry shown in FIG. 10A, components 1127 on portions 1102a and 1102c are facing each other and efficiently "packed", and components 1127 on portions 1102e and 1102f are facing each other and efficiently packed. Efficient packing can comprise positioning at least two opposing surface portions of two components 1127S in vertical alignment, while avoiding vertical alignment of two components 1127T, such as by avoiding vertical alignment of a component 1127T with any other component (e.g. without an intervening component), as shown in FIG. 10A. The volumetrically efficient packing of sensor assembly 110 reduces the required thickness of sensor assembly 110 on either side of molar M1, such as to improve patient comfort and/or cosmesis, as described herein.

Figure 11A:
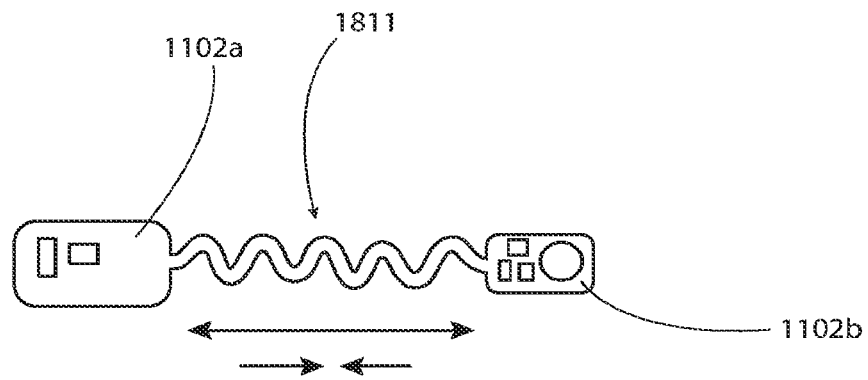
FIGS. 11A-11C illustrate various views of a flexible electronic assembly of a sensor device according to embodiments of the present disclosure.
Figure 11B:
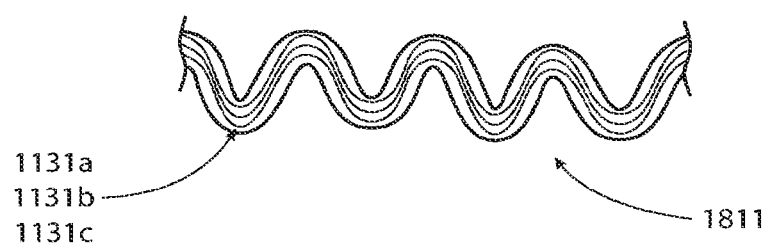
Figure 11C:
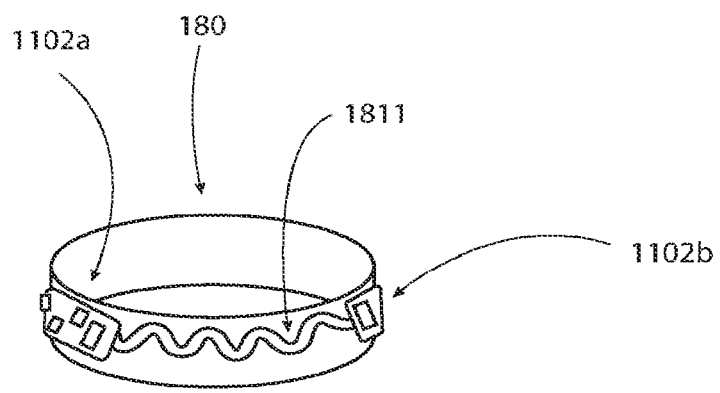

Referring now to FIGS. 11A-11C, a flexible electronic assembly of sensor device 100 is illustrated. Substrate 1102 includes a first portion 1102a and a second portion 1102b that are at least mechanically connected via stretchable connector 1811. Portions 1102a and 1102b can include various electronic and other components as described herein. First portion 1102a can be flexible, or it can comprise one or more flexible portions. Second portion 1102b can be flexible, or it can comprise one or more flexible portions. First portion 1102a can be positioned on the buccal-side of a tooth, such as when second portion 1102b is positioned on the lingual side of a tooth. Connector 1811 can comprise a flexible material and/or a stretchable material. Connector 1811 can comprise the serpentine geometry shown. Alternatively or additionally, connector 1181 can comprise a zigzag geometry, a magazine (e.g. accordion) geometry, a dual wave geometry, and/or a single wave geometry. In some embodiments, the majority of substrate 1102 is flexible and/or stretchable.

As shown in FIG. 11B, connector 1811 can comprise one or more conductive traces ("traces" herein), such as: one or more conductors carrying a system ground, ground trace 1131a; one or more conductors carrying signals, signal trace 1131b; and/or one or more conductors carrying power, power trace 1131c. FIG. 11C shows first portion 1102a, connector 1811, and second portion 1102b positioned about a tooth of the patient, with portion 1102a positioned on the buccal side of the tooth, and portion 1102b positioned on the lingual side of the tooth. In some embodiments, at least a portion of first portion 1102a, at least a portion of connector 1181, and at least a portion of second portion 1102b is flexible and/or stretchable, such that the three components can be positioned on teeth of different sizes (e.g. part of attachment mechanisms 180 that are differently sized and/or configured to be compressed or expanded at least circumferentially). In some embodiments, at least 2 mm, or at least 4 mm of stretch is provided (e.g. collectively by the three components 1102a, 1181, and 1102b stretch to support a circumferential variability of at least 2 mm, or at least 4 mm).

Figure 29:
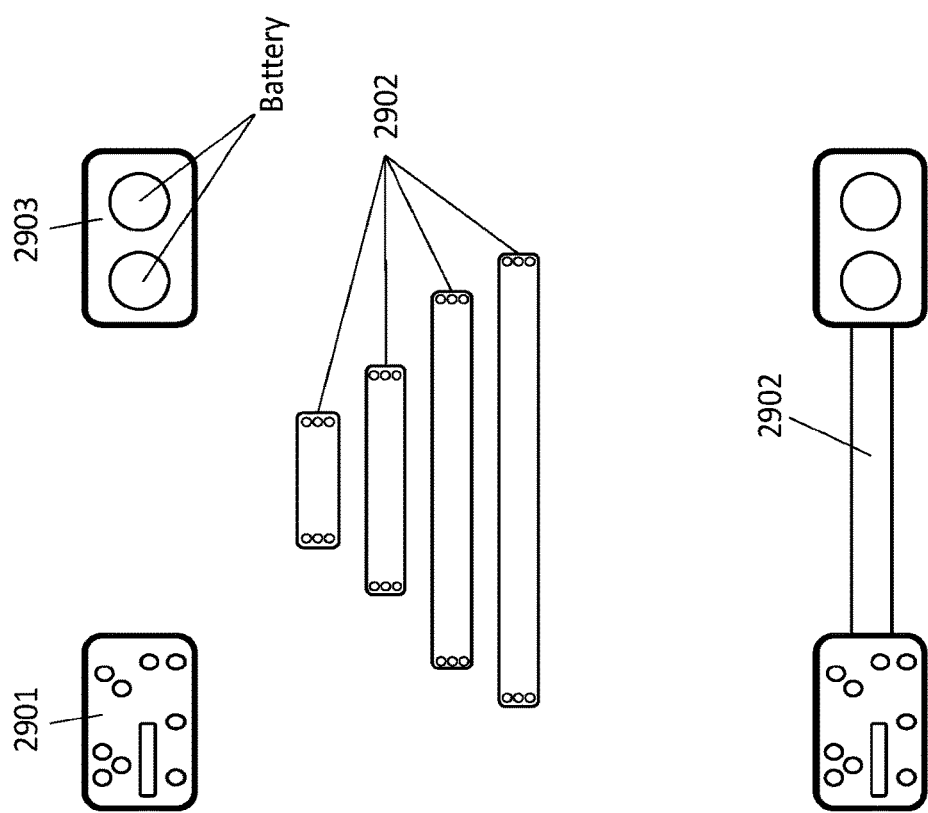
FIG. 29 illustrate various interproximal connectors according to embodiments of the present disclosure.
Figure 30A:
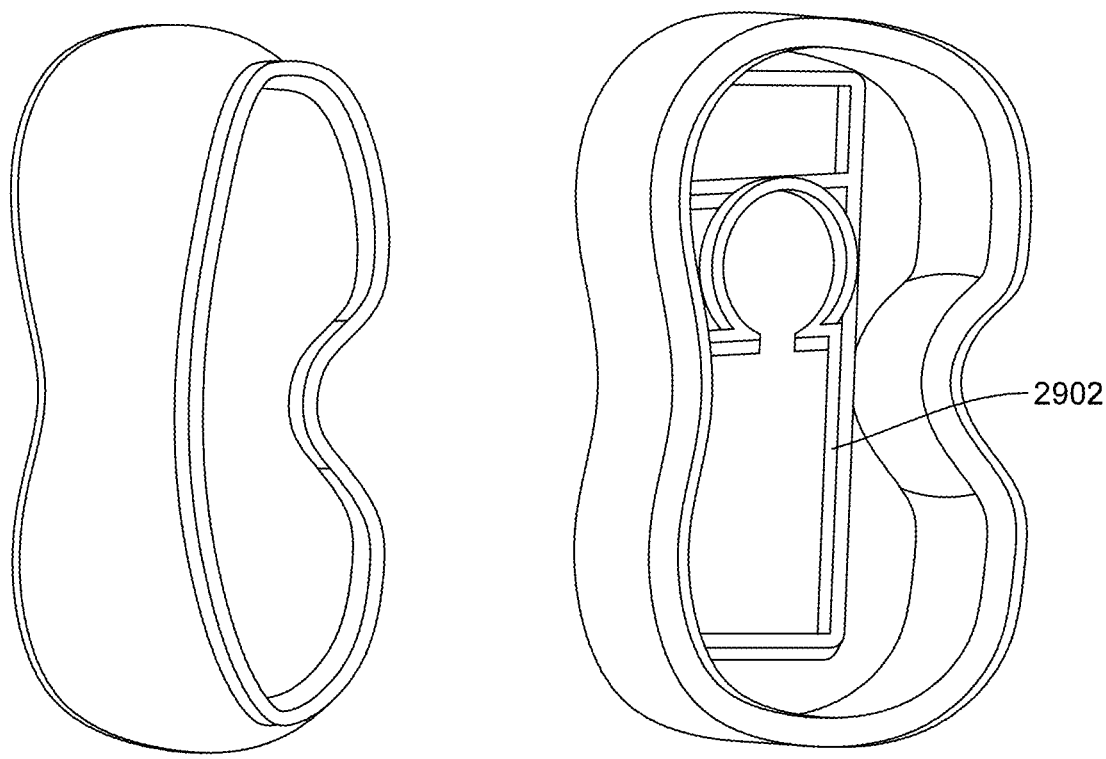
FIGS. 30A-30E illustrate casing internal locator rails according to embodiments of the present disclosure.
Figure 30B:
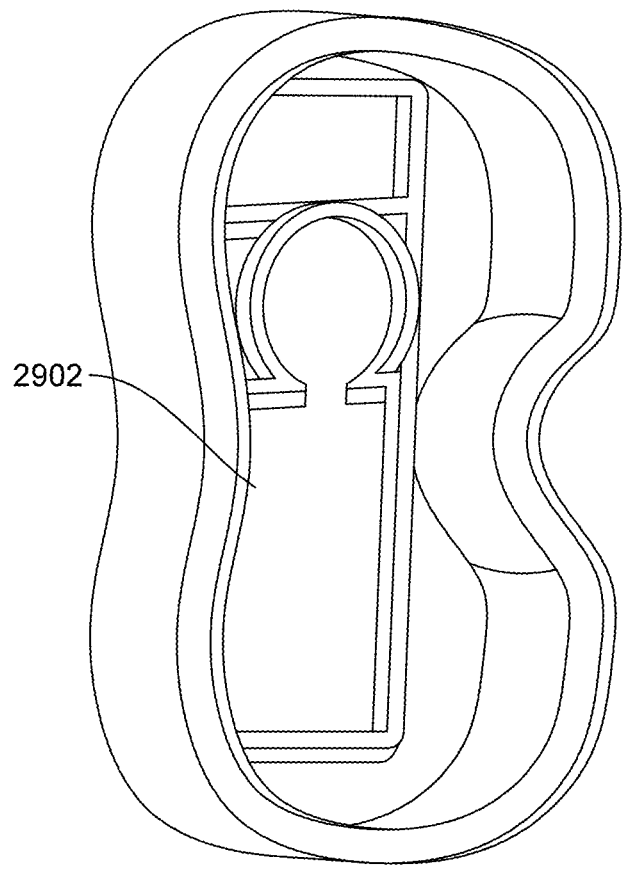
Figure 30C:
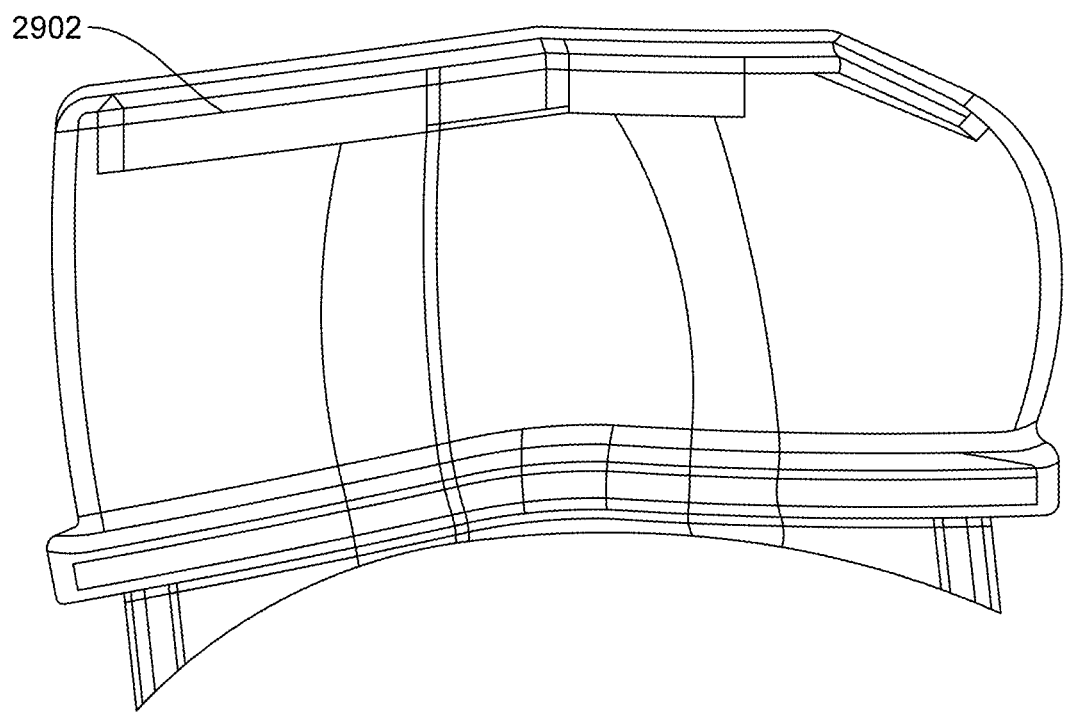
Figure 30D:
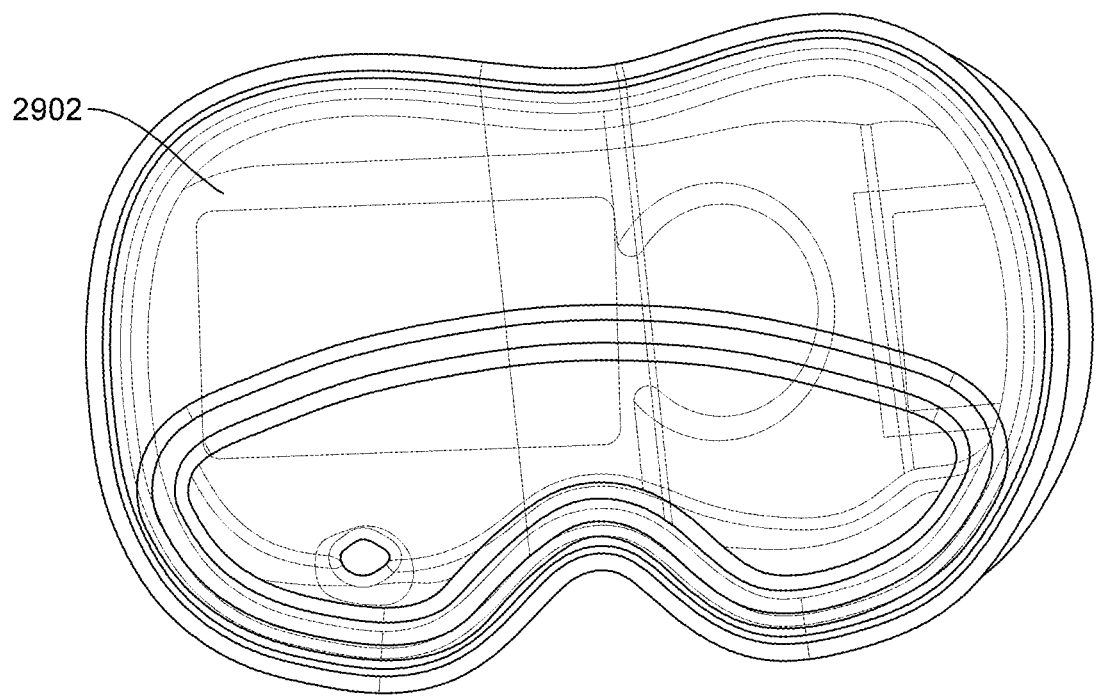
Figure 30E:
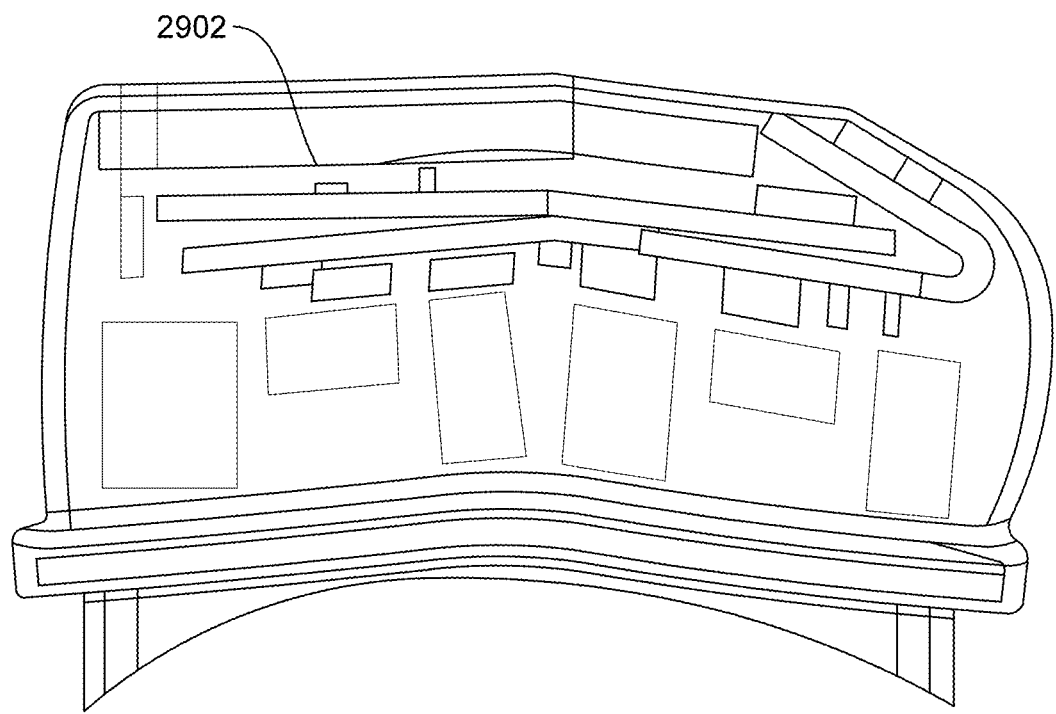
Figure 31:
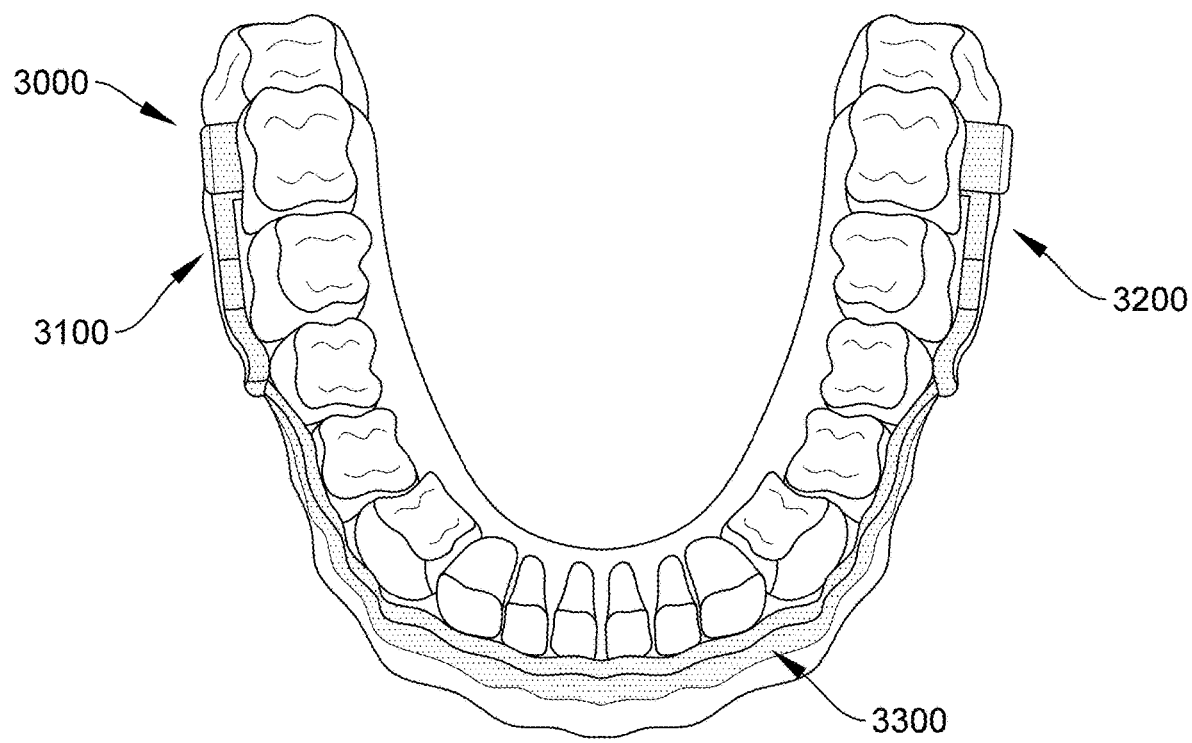
FIGS. 31-34 are illustrations of an exemplary embodiment of the intraoral monitor incorporated into a retainer according to embodiments of the present disclosure.
Figure 32:
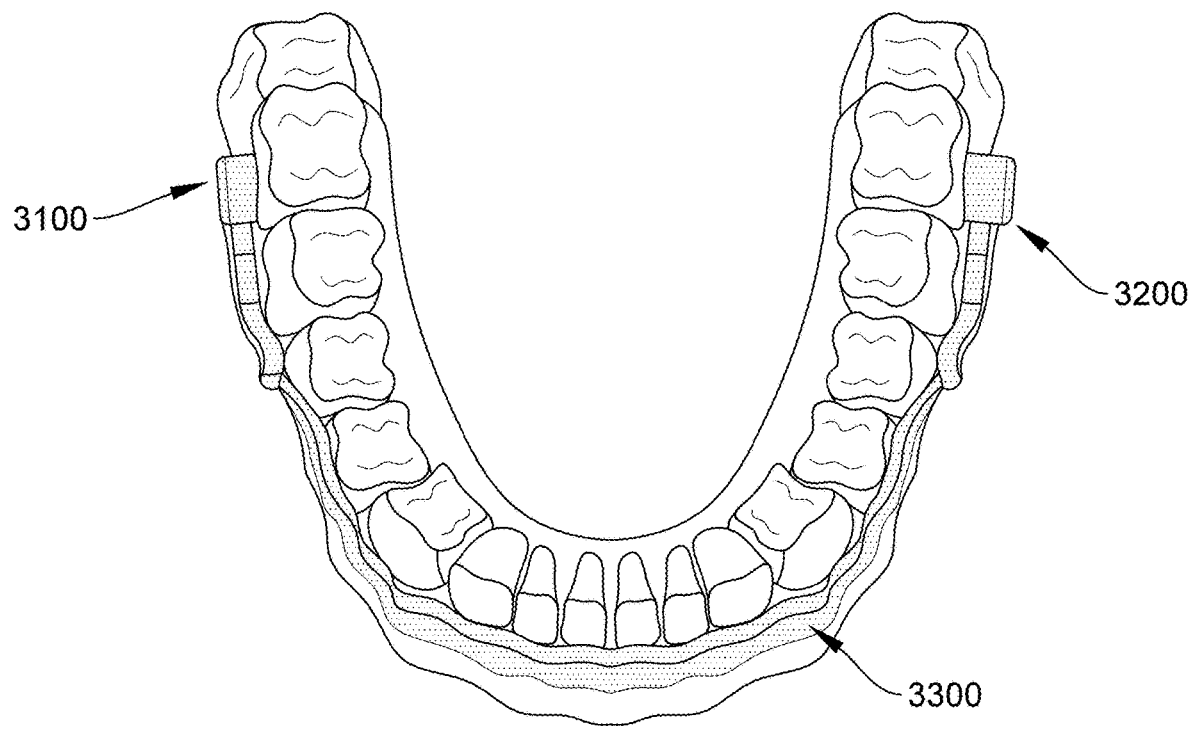
Figure 33:
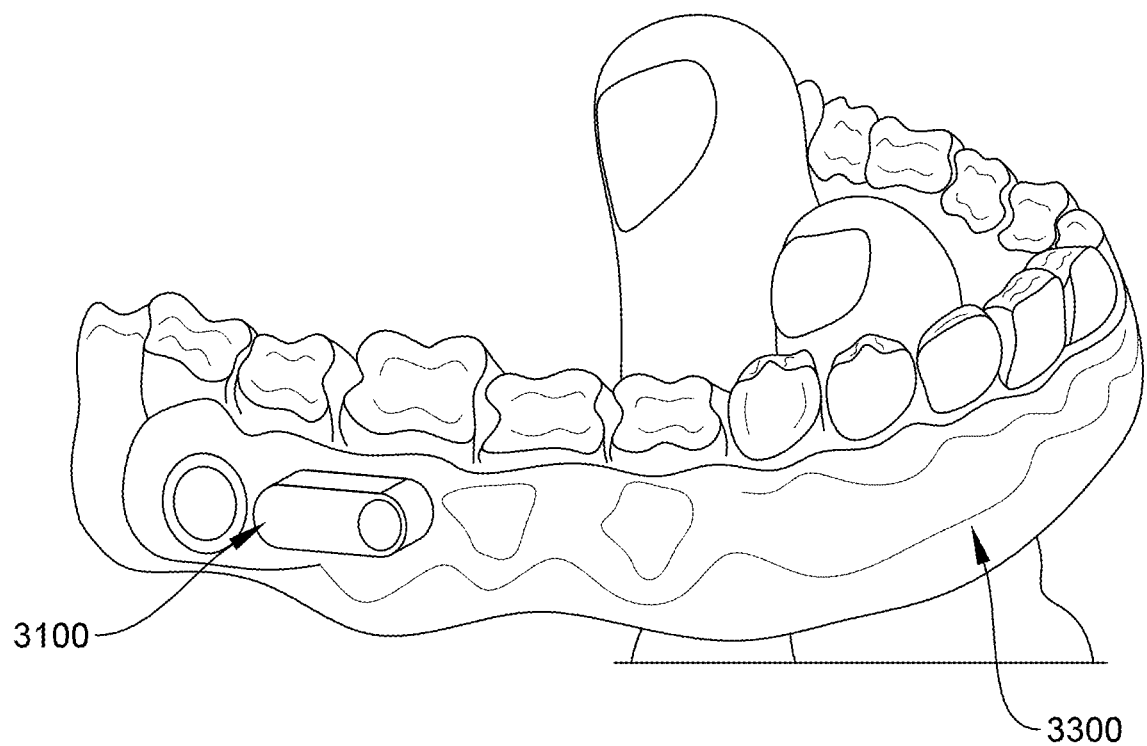
Figure 34:
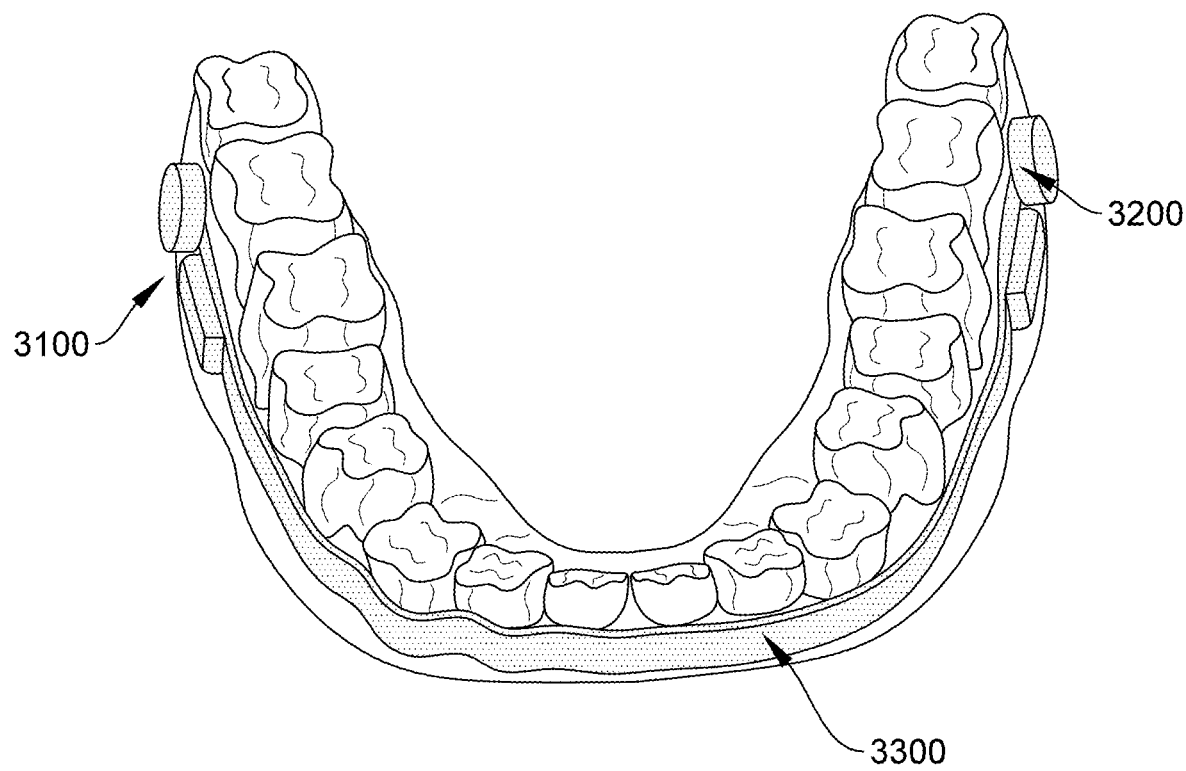

In various embodiments, because different individuals may have different sized teeth, electronics 2901, 2903 may be placed on both the buccal side and lingual side of the tooth. In various embodiments, as shown in FIG. 29, a connector 2902 may extend along the interproximal area of the target tooth providing power/signal between the buccal side and lingual side electronics. In various embodiments, the length of this connector may be sized to fit the target tooth, as a stretchable band material may have durability and performance issues. In various embodiments, interproximal connectors of various lengths are produced and stocked. In various embodiments, when a patient's scan is submitted to a manufacturer, the interproximal connector of the appropriate size may be selected from the prefabricated connectors. In various embodiments, during manufacture, the selected connector of the appropriate size may be soldered to the buccal side electronics and lingual side electronics, and then subsequent manufacturing steps (e.g., coating, packaging, etc.) may be performed. In various embodiments, fully functional sensor devices may be prefabricated with different size connectors such that the prefabricated sensor having the appropriate size connector may be drop shipped at the time of the order.

In various embodiments, a maximum thickness of material between any two teeth (interproximally) may be limited to about 0.5 mm. In various embodiments, the molar band thickness may be preferably about 0.15 mm and the printed circuit board thickness may be preferably about 0.15 mm, so the material to protect and insulate the printed circuit board from oral conditions may be 0.2 mm or less. In various embodiments, plastic milling may produce a thickness of around 0.3 mm, which may be similar to metal 3D printing. In various embodiments, the interproximal area may be required to remain flexible (even if rigid or stretchable) so that the sensor can fit over the tooth. In various embodiments, methods to create thinner layers include electroforming and EDM (electrical discharge machine), but they may be more expensive. In various embodiments, a metal tab or sheet can be placed over the printed circuit board on the interproximal edge and can be sealed to the band in a watertight way by laser welding a line above and below the outline of the printed circuit board. This creates a sealed tube for the PCB, with the inner wall being the molar band and the outer wall being the metal sheet/tab. The metal sheet/tab can be as thin as tin foil (but this will introduce strength problems) to as thick as 0.2 mm. It can be produced out of a biocompatible metal such as stainless steel or Chromium cobalt (CoCr), and the individual tabs can be laser cut from a larger sheet.

In various embodiments, during fabrication, a curable polymer (e.g., UV-curable epoxy) may be applied to any of the components described herein to thereby secure that component within its respective housing. For example, the interproximal connector may be coated with UV-curable epoxy and affixed to a metal band. In various embodiments, the curable polymer may be used to fix a flexible component (e.g., the interproximal connector) in a fixed position or shape. In various embodiments, for metallic components, laser welding may be used to connect components, seal components, or otherwise join metallic components during fabrication. In various embodiments, any gaps along the interproximal connecter may be filled with a potting agent and cured.

In various embodiments, connector 1181 comprises a length to support attachment to the large diameter teeth, and when used with smaller teeth, a wrapping and/or folding process is used to "take up" the extra length of connector 1181.

Referring now to FIG. 12, a perspective view of a sensor device including a magnetic switch is illustrated, consistent with the present inventive concepts. As described in reference to FIG. 1, device 100 can include one or more switches, switch 1625, used to turn device 100 on and/or off (e.g. connect and/or detach power supply 160 to avoid undesired power loss during inactive periods). In the embodiment of FIG. 12, switch 1625 comprise a magnetically activated switch, such as a reed switch that uses magnetic force to open and/or close. When not in use, a magnet (e.g. a functional element 99 comprising a magnet) can be positioned near switch 1625 to maintain device 100 in an off state, such as when a container used to store and/or ship device 100 includes the magnet, and it positions the magnet proximate switch 1625. When removed from the packaging, device 100 will automatically turn on (e.g. not requiring any other action of the clinician or patient).

Referring now to FIGS. 13A-13D, a series of configurations of a user interface of a physiologic parameter recording system is illustrated, consistent with the present inventive concepts. System 10 can include one or more user interfaces, such as user interface of device 400 shown in FIG. 12. User device 400 can comprise a cell phone, or other device with a user interface, such as device 400 described in reference to FIG. 1 and otherwise herein. User interface 450 can be configured to allow the patient or other user of system 10 to perform a calibration routine, such as is illustrated in FIGS. 13A-13D. Device 100 can comprise an intraoral sensor device that requires periodic calibration over time, such as when the output of device 100 drifts over time (e.g. an output of 1000 millivolts for a pH of 4 at day 0 may drift to an output of 1100 millivolts for a pH of 4 at day 30). To compensate for this drift or other potential inaccuracies, system 10 can be configured to allow calibration of device 100. Calibration can be performed over recurring periods of between 7 days and 60 days (e.g. periods of time between 15 days and 30 days). In some embodiments, device 100 is configured to be calibrated by a clinician (e.g. in a clinician's office such as a dental office). Alternatively or additionally, device 100 can be configured to be calibrated at the patient's home (e.g. by the patient without assistance of a clinician). In some embodiments, an initial calibration is performed by a clinician, and subsequent calibrations are performed by the patient. An initial calibration can comprise a three-point calibration, while later calibrations may comprise a single point calibration. Device 400, via user interface 450, can be configured to allow a user to enter a calibration mode, select a calibration option. The patient can drink a liquid with a known pH, a "calibration liquid" herein (e.g. a tool 98 comprising one or more liquids, with known pH values, used for performing a calibration procedure), and then via user interface 450 confirm that the calibration liquid is in place in the patient's mouth, such as to allow up to three points of calibration. Algorithm 155 can map a line of best fit through the points (e.g. three points) and adjust device 100 accordingly. In some embodiments, system 10 (e.g. via device 100, device 300, and/or device 400) alerts the patient that a calibration should be performed (e.g. when a period of time has elapsed since a previous calibration). In these embodiments, at least a portion of algorithm 155 perform the calibration can be included in device 100, within device 300, within device 400, and/or within a computer network (e.g. the cloud). FIGS. 13A-13D illustrate a series of steps in which a user performs a three-point calibration via selection of icons provided by user interface 450.

In various embodiments, the patient or other user of system 10 can use a calibration function (e.g. within the mobile application installed on user device 400) to correct output drift of sensor assembly 110. Over time, ISFET 1105 may experience drift such that upon initial installation pH 7.0 creates a voltage of 1.50 volts, but 30 days following initial installation pH 7.0 creates a voltage of 1.60 volts, or any other voltage which is different from the voltage output that is present during initial installation. Drift is a normal phenomenon demonstrated in the output voltages of ISFET sensors over extended periods of time. Using the calibration function of system 10, the patient or other user can readjust the portion of algorithm 155 (e.g., a portion within device 100) which converts ISFET voltage output to pH values and ensure correct pH values are recorded (e.g. correct values are transmitted to user device 400). System 10 can be configured to allow a patient or other user to perform a one point, two point, and/or three point calibration to correct pH value conversions. The algorithm to convert voltage output to pH values can be modeled as f(x)=M*x+B, where f(x) represents pH as a function of x, the ISFET voltage output, B, a constant value with the unit of pH, and M, a constant value with units of pH/voltage. When performing two-point or three-point point calibrations, system 10 can be configured to allow the user to manually enter pH values of each calibration liquid (e.g. tool 98 comprising a calibration liquid) that the patient will consume. After entering the pH value of the calibration liquid, user device 400 transmits the pH value to sensor device 100. The patient then consumes the calibration liquid and sensor device 100 records and stores the voltage output of ISFET 1105. This process is performed twice for a two-point calibration, and three times for a three-point calibration. Once all pH values and their respective ISFET 1105 voltage outputs have been recorded and stored within sensor device 100, sensor device 100 can perform a linear regression where the x values are ISFET 1105 voltage outputs and y values are the pH values manually entered by the user performing the calibration. The result of the linear regression can be an adjustment to the conversion model explained above, f(x)=M*x+B, with adjusted values for M and B. The process is similar for a one-point calibration, except the user enters only one pH value and the B value of above function is adjusted while the M value remains unchanged. After calibration is completed, the patient or other user can be notified (e.g., via user interface 450 and the mobile application installed upon user device 400) and pH values can be transmitted using the adjusted conversion model.

In some embodiments, tool 98 comprise a consumer product with a known pH, such as a mouthwash or a beverage (e.g. a juice). In some embodiments, user interface 450 allows selection of a consumer liquid to be used as a calibration liquid via a drop-down menu. In some embodiments, user interface 450 comprises a barcode scanner can that identify a consumer product or other product to be used as a calibration fluid. System 10 can include a library of consumer products and their associated pH values, such as to be used as a tool 98 comprising a calibration fluid.

In some embodiments, user device 400 and/or another component of system 10 is configured to alert the patient or other user after a predetermined length of time has expired, such as an alert indicating that a calibration should be performed. The alert can include instructions as to whether a one, two, or three point calibration should be performed (e.g. using the calibration function within the mobile application installed on user device 400). The predetermined length of time between calibrations can be one week, two weeks, three weeks, one month, two months, and/or other periods of time. In some embodiments, calibration is not be necessary because ISFET 1105 is configured to avoid output drift of a significance in which pH accuracy is impaired. In some embodiments, a manual calibration (e.g. using one or more calibration liquids) is not be necessary because intraoral sensor device 100 analyzes ISFET 1105 output data and performs an automated calibration (e.g. a self-calibration) in which compares current ISFET 1105 output data to previously recorded ISFET 1105 output data such that drift may be estimated and compensated for with no intervention from the user.

Figure 14:
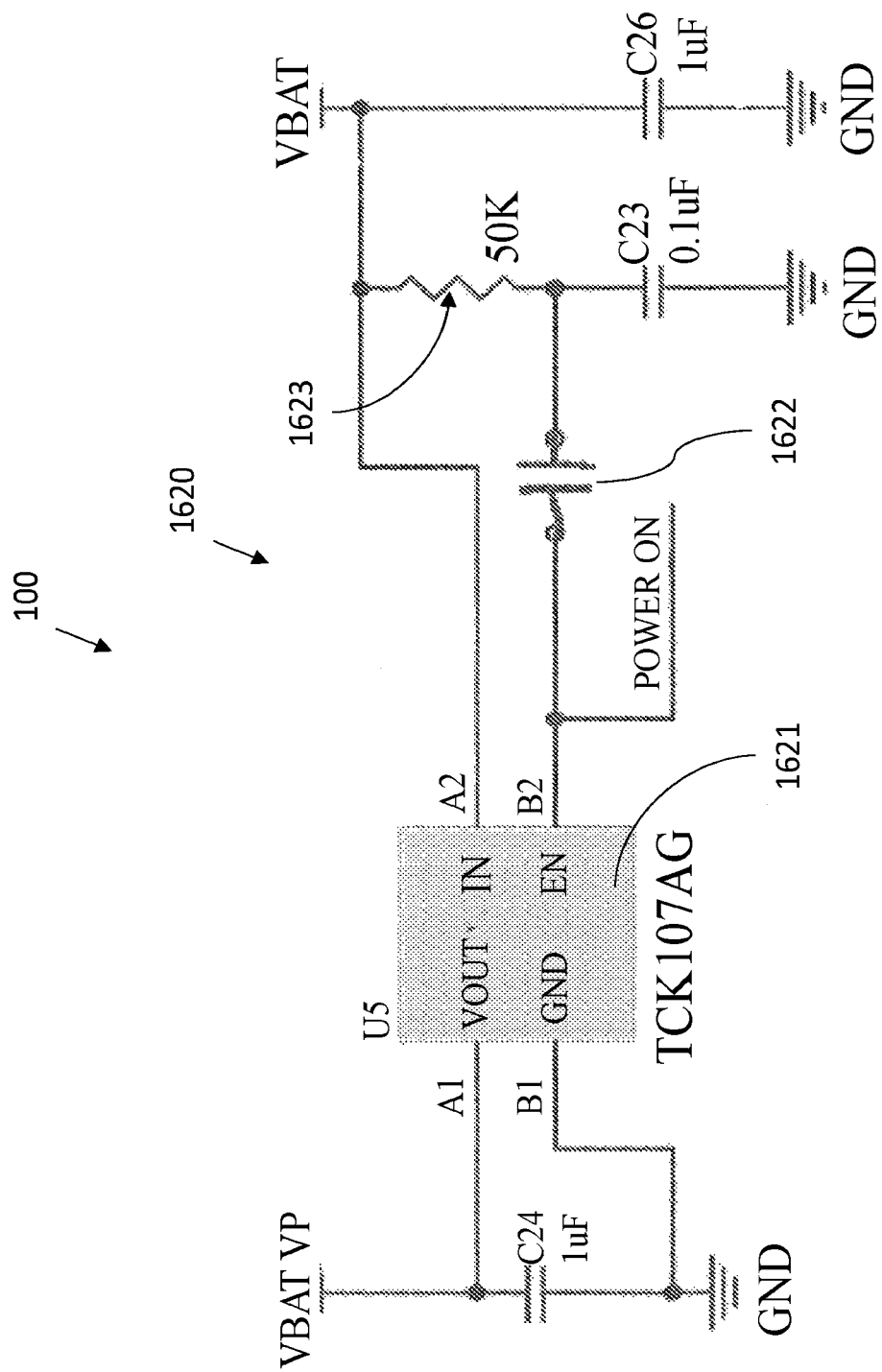
FIG. 14 illustrates a control circuit of a sensor device according to embodiments of the present disclosure.
Figure 18:
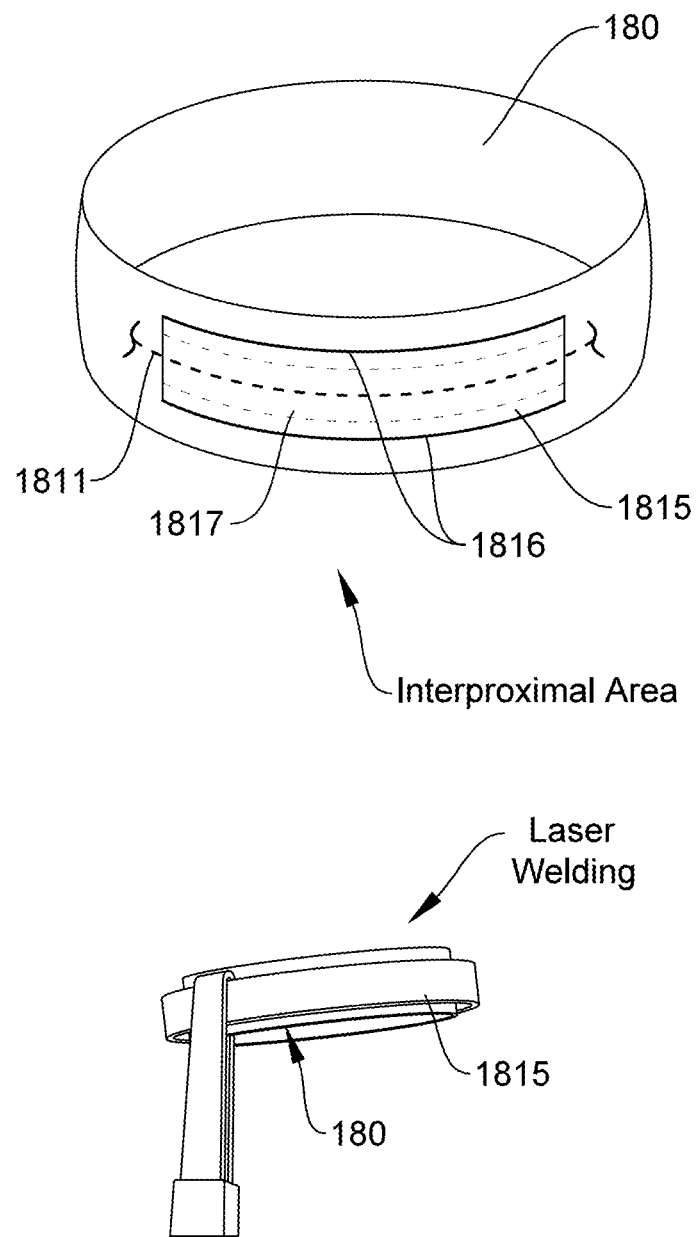
FIG. 18 and FIGS. 18A-18F illustrate a perspective view of an attachment mechanism for a sensor device according to embodiments of the present disclosure.
Figure 18A:
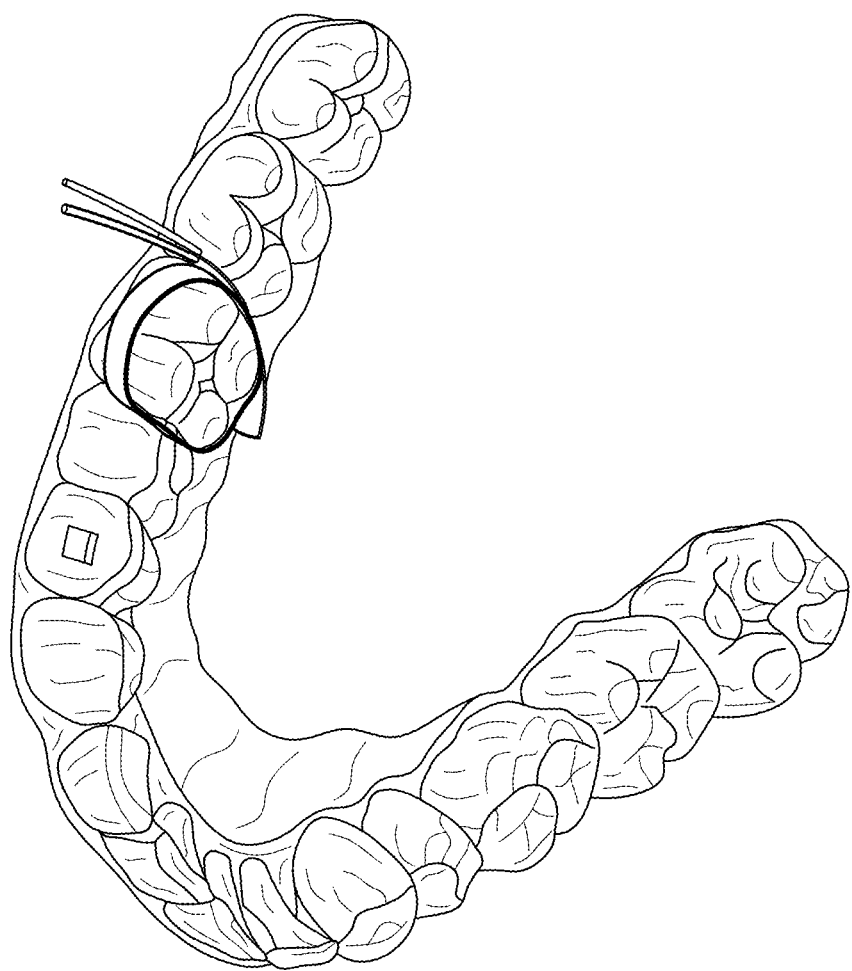
Figure 18B:
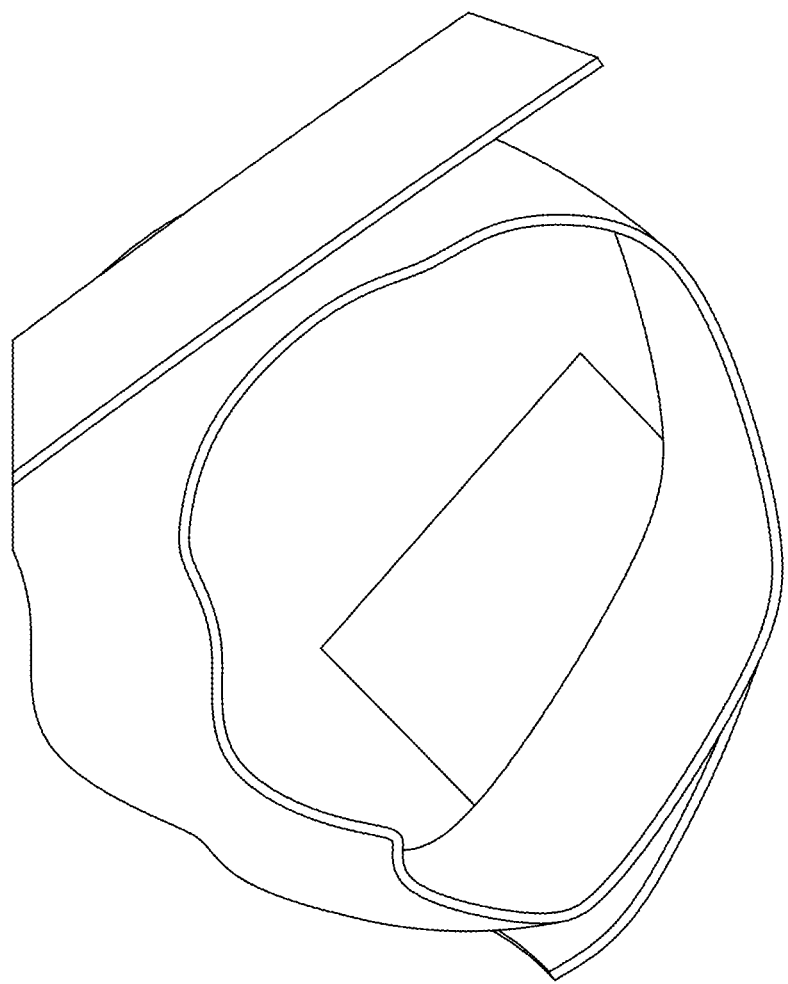
Figure 18C:
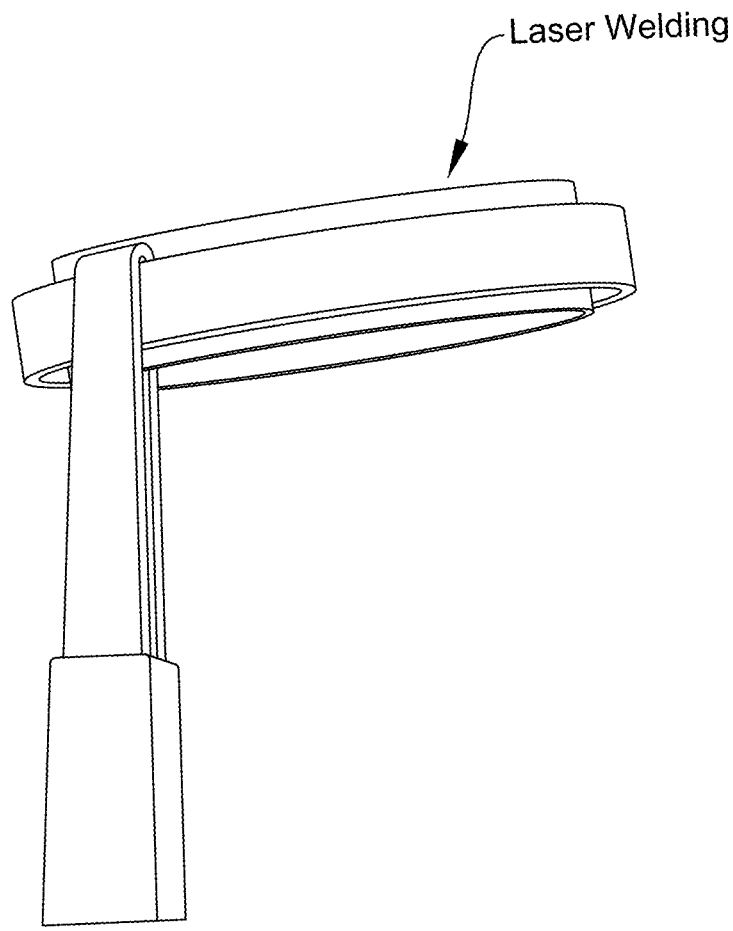
Figure 18D:
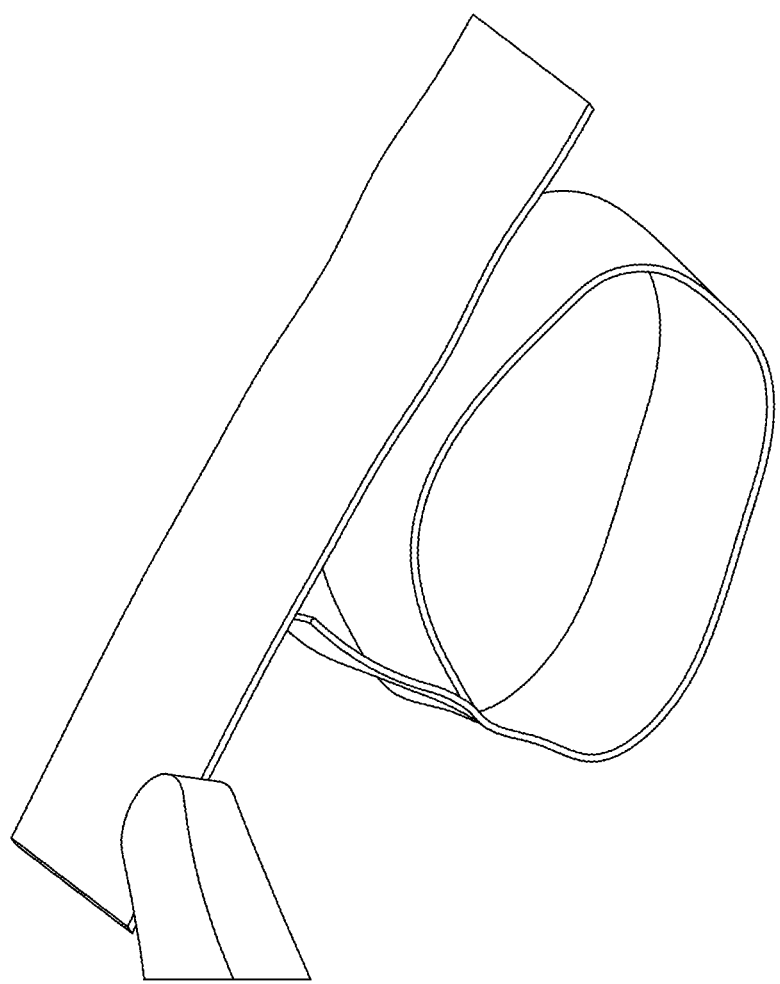
Figure 18E:
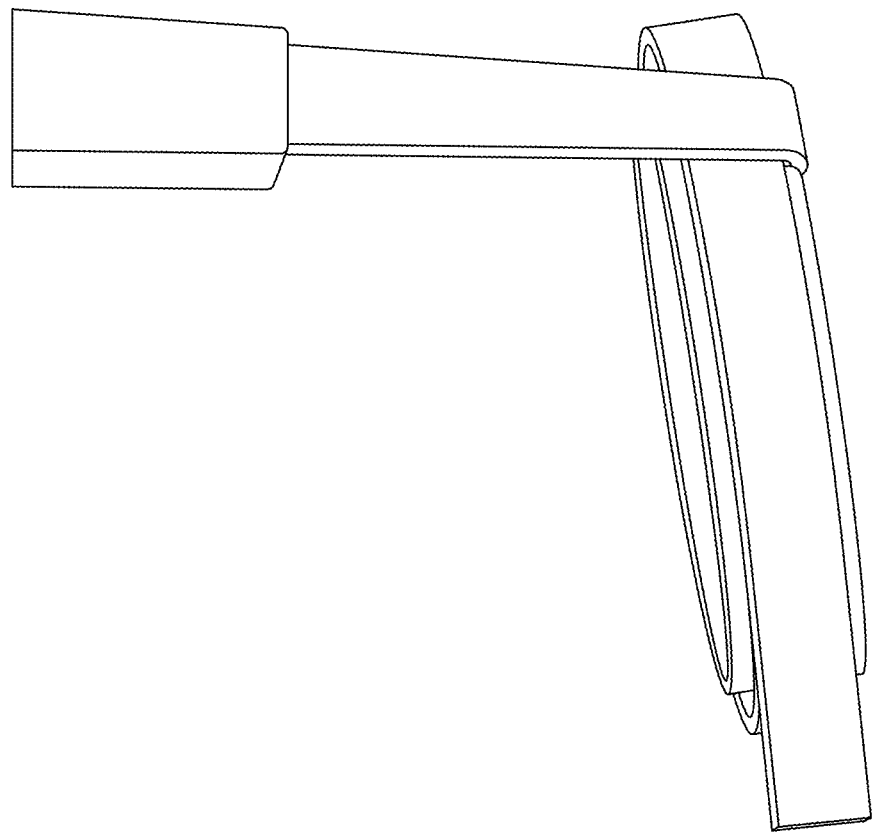
Figure 18F:
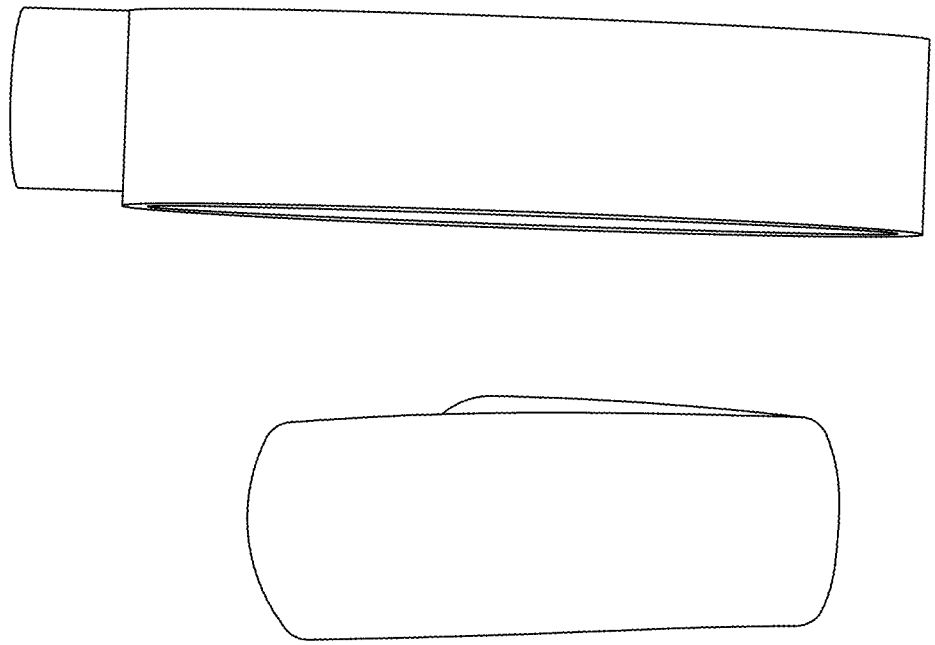

Referring now to FIG. 14, a schematic view of a control circuit of a sensor device is illustrated consistent with the present inventive concepts. As described herein, device 100 can include a switch 1625 (e.g., a mechanical switch, a magnetically-activated switch, and/or other switch or switch assembly) that connects electronic circuitry of device 100 to power supply 160 (e.g., a battery or other power supply), such that device 100 can be stored, shipped, and/or otherwise maintained in an inactive state (e.g., a state that avoids drawing power from power supply 160. In some embodiments, switch 1625 comprises an electronic switching assembly including a capacitor, capacitor 1622 shown, which is included within power control circuit 1620. Capacitor 1622 may be configured with a resistor, resistor 1623 shown, to form an RC circuit that is attached to both the ENABLE pin of a load switch-based integrated circuit, IC 1621 (e.g., IC TCK107AG) and power supply 160. Capacitor 1622 and resistor 1623 can be configured such that the capacitor 1522 charges to a threshold voltage (e.g., 0.5 volts, 0.7 volts, 1.0 volts). Capacitor 1622 and resistor 1623 can be configured such that capacitor 1622 charges to the threshold voltage after a time period, such as a time period of 15 minutes, 30 minutes, or any other period of time following connection to power supply 160. The above threshold voltage which capacitor 1622 will be configured to charge to will be the same threshold voltage required to activate the ENABLE pin of load switch IC 1621. Once capacitor 1622 charges to the appropriate threshold voltage, the ENABLE pin of IC 1621 will become activated and it will connect power supply 160 directly to processor 150 of device 100 (e.g., as described herein) such that processor 150 will turn on to the POWER ON state. Before capacitor 1622 is charged to the threshold voltage, and before the ENABLE pin of IC 1621 is activated, processor 150 will be in an "off" state (POWER OFF state). Once processor 150 transitions to an "on" state (POWER ON state), processor 150 will switch a GPIO output pin (which is also connected to the ENABLE pin of the load switch IC) to the HIGH state, which holds IC 1621 in an activated state. Capacitor 1622 will fully discharge once IC 1621 is enabled. While processor 150 holds the GPIO output pin in a HIGH state to keep IC 1621 activated, processor 150 will read ISFET 1105 output data, convert the ISFET 1105 output to a value (e.g. a pH value), and transmit data to user device 300 and/or wearable device 400, as described herein. Following data transmission, processor 150 will turn the GPIO to a LOW state and deactivate IC 1621, which will disconnect power supply 160 and processor 150, returning processor 150 to the POWER OFF state. This protocol will repeat as capacitor 1622 recharges to the threshold voltage. This protocol will repeat, such as at 10 minute, 15 minute, 30 minute, 1 hour, or other periods of time dependent on the configuration of the RC circuit comprised of capacitor 1622 and resistor 1623. This protocol minimizes power consumption of device 100 because power supply 160 will be entirely disconnected from processor 150 and other power consuming elements of device 100 during the time intervals where capacitor 1622 charges to the threshold voltage. Device 100 will draw minimal amounts of acquiescent current during these time intervals, effectively extending lifetime of power supply 160 and reducing overall device 100 power requirements.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the inventive concepts, which is defined in the accompanying claims.

In various embodiments, one or more components (e.g., a flexible printed circuit board) of the sensor assembly may be coated with a coating. In various embodiments, the coating may be deposited via chemical vapor deposition. In various embodiments, the coating may include any suitable metal. In various embodiments, the coating may include parylene. In various embodiments, the coating may be suitable for: a hydrophobic coating (moisture barriers), Barrier layers (e.g., for filter, diaphragms, valves), sensors in rough environment, corrosion protection for metallic surfaces, reinforcement of micro-structures, protection of plastic, rubber, etc., from harmful environmental conditions, or reduction of friction.

In various embodiments, one or more components (e.g., a flexible printed circuit board) of the sensor assembly (e.g., the ISFET, reference electrode) may be affixed with an adhesive. In various embodiments, the adhesive may be a UV-curable glue.

Referring now to FIGS. 15A-15C, views of an intraoral sensor device including a lock and key mechanism are illustrated. In various embodiments, sensor device 100 includes a first portion 100a and a second portion 100b (e.g., including attachment mechanism 180). In various embodiments, first portion 100a of the sensor device includes a connector 1801 which is configured to attach (e.g., removably attach) to connector 1802 of second portion 100b. Connectors of various sizes are discussed with respect to FIG. 29. In various embodiments, a locking pin 1803 can be slidingly inserted into coaxial holes of connectors 1801 and 1802 to secure the connectors 1801 and 1802 together. In various embodiments, pin 1803 includes threads configured to rotatingly engage the holes of connectors 1801 and 1802.

Referring now to FIGS. 16A-16F, perspective views of a first connector (in an unattached state), a second connector (in an unattached state), and the two connectors attached, are illustrated. In various embodiments, sensor device 100 can include a first portion 100a that includes a connector 1801, and a second portion 100b that includes a connector 1802, where connectors 1801 and 1802 are configured to attach to each other, thereby attaching portions 100a and 100b to each other. FIGS. 16A-16F represent six sets of connectors 1801 and 1802, with the mating geometries shown.

Referring now to FIGS. 17A-17G, perspective views of a first connector (in an unattached state) and a second connector (in an unattached state) are illustrated. In various embodiments, sensor device 100 can include a first portion 100a that includes a connector 1801, and a second portion 100b that includes a connector 1802, where connectors 1801 and 1802 are configured to attach to each other, thereby attaching portions 100a and 100b to each other. FIGS. 17A-17G represent seven sets of connectors 1801 and 1802, with the mating geometries shown. In various embodiments, second portion 100b includes attachment mechanism 180 and attached connector 1802. In various embodiments, first portion 100a includes connector 1801 with the remaining portions of first portion 100a removed for illustrative clarity.

Referring now to FIG. 18 and FIGS. 18A-18F, a perspective view of an attachment mechanism for a sensor device is illustrated. In various embodiments, attachment mechanism 180 of FIG. 18 includes an integral printed circuit board in the interproximal area of the band portion of mechanism 180. In various embodiments, attachment mechanism 180 includes a printed circuit board (PCB) 1811, a cover 1815, a weld 1816, and a channel 1817. In various embodiments, the band portion of attachment mechanism 180 can have a thickness of approximately 0.10 mm-0.25 mm, preferably 0.15 mm. In various embodiments, PCB 1811 may be positioned in channel 1817, where channel 1817 is the space between the band portion of mechanism 180 and cover 1815. In various embodiments, cover 1815 can comprise a metal (e.g. stainless steel or chromium cobalt) and/or or plastic. In various embodiments, cover 1815 provides a seal to mechanism 180 such that contaminants do not come in contact with PCB 1811. In various embodiments, cover 1815 may be welded (e.g., laser welded) to the band portion of mechanism 180. In various embodiments, cover 1815 can have a thickness up to 0.2 mm.

Referring now to FIGS. 19A-19C, three steps of a method of manufacturing a sensor assembly are illustrated. In various embodiments, sensor assembly 110 can include a two-piece housing having a first portion 1141 and a second portion 1142. In various embodiments, first portion 1141 may be made of one or more plastics, and second portion 1142 may be made of one or more metals. In various embodiments, first portion 1141 can include one or more holes 1143. In various embodiments, second portion 1142 can include one or more extending filaments, tabs 1144 shown in an extended state in FIG. 19A. In various embodiments, tabs 1144 can be configured to pass thru a corresponding hole 1143, as shown in FIG. 19B, such as to secure second portion 1142 to first portion 1141, as shown in FIG. 19C. In various embodiments, the distal portion of tab 1144 may be welded (or otherwise affixed) to its proximal portion after passing through hole 1143, such as to further secure (e.g., make permanent) the attachment of second portion 1142 to first portion 1141.

Figure 20:
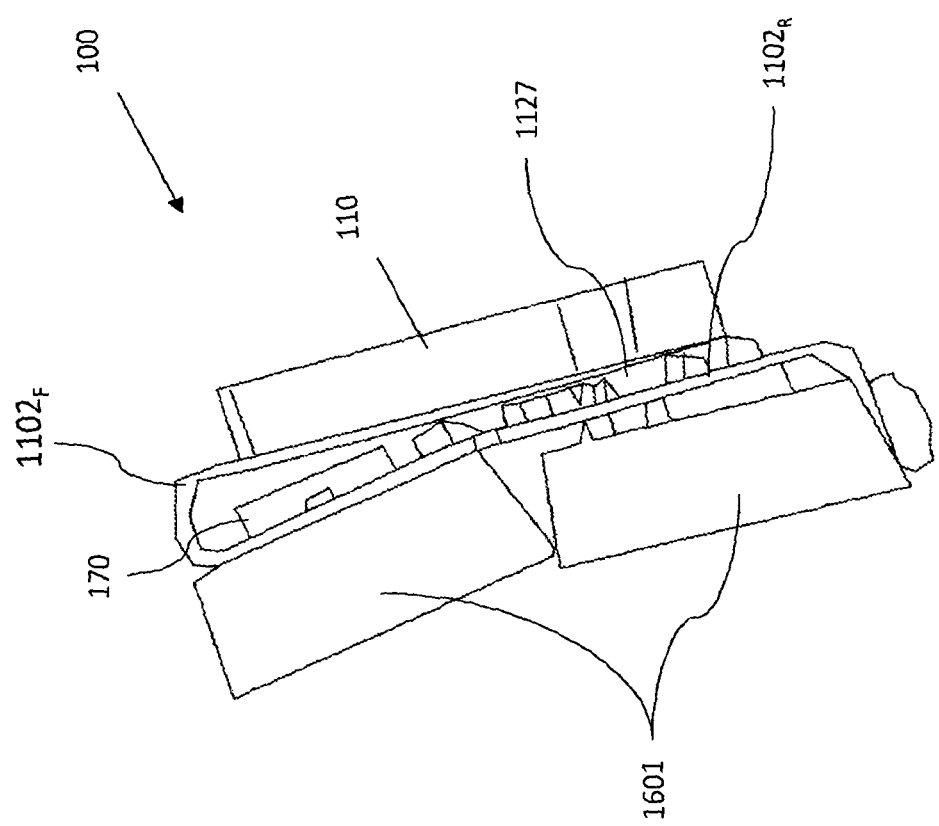
FIG. 20 illustrate a side view of a sensor device according to embodiments of the present disclosure.

Referring now to FIG. 20, a side view of a sensor device is illustrated. In various embodiments, the sensor may not include any components on the bottom side above the RF antenna.

Referring now to FIGS. 21A-21B, perspective views of a sensor device are illustrated. In various embodiments, the sensor housing may include a cap between band portions of the electronics such that the cap overhangs occlusally or gingivally around borders of the band and are fully sealed and/or attached to the band.

Figure 22B:
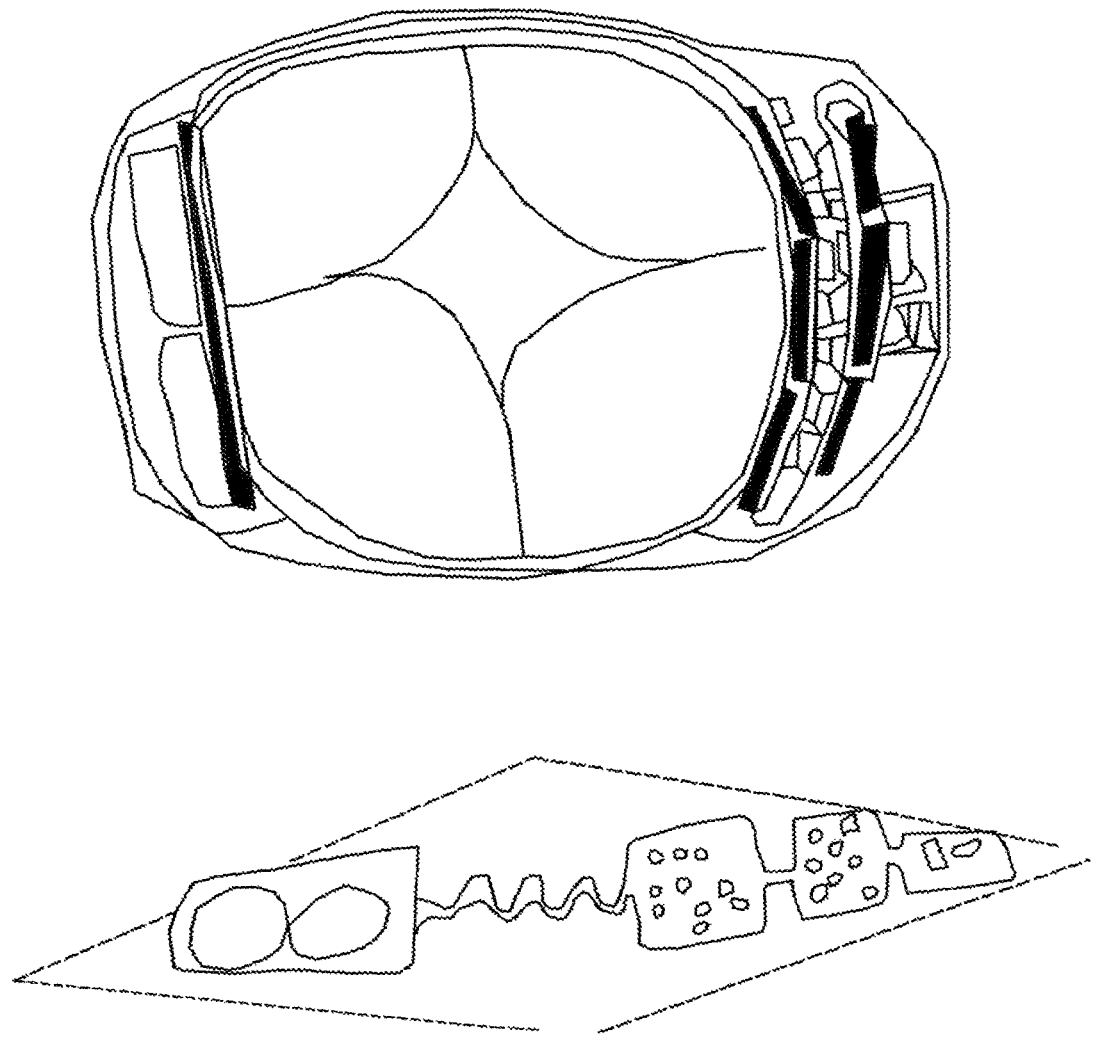
Figure 22C:
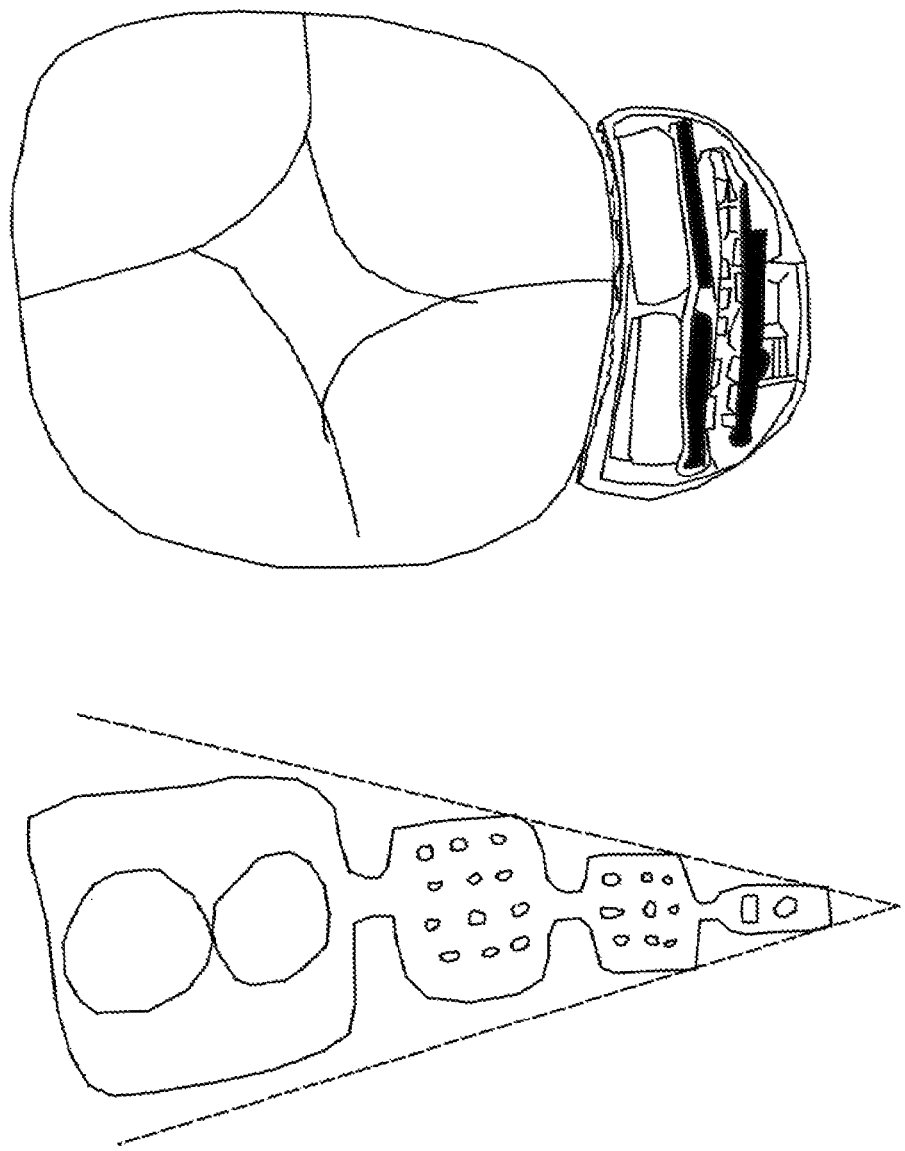

Referring now to FIGS. 22A-22C, schematic views of a sensor device attached to a tooth are illustrated. FIG. 22A illustrates batteries and the sensor on one side, and other electronics on the other side. FIG. 22B illustrates batteries on one side, and the sensor and electronics on the other side. FIG. 22C illustrates batteries, the sensor, and other electronics all on one side.

Referring now to FIGS. 23A-23B, side views of a sensor device with a spring-loaded housing closing feature is illustrated. In various embodiments, the closing feature may include a lock. In various embodiments, the lock may include a tactile switch with a spring-loaded housing closing feature, as described above. In various embodiments, the housing closing feature may be pin-shaped. In various embodiments, the housing closing feature may be removed to thereby close (e.g., seal) the housing.

Figure 24A:
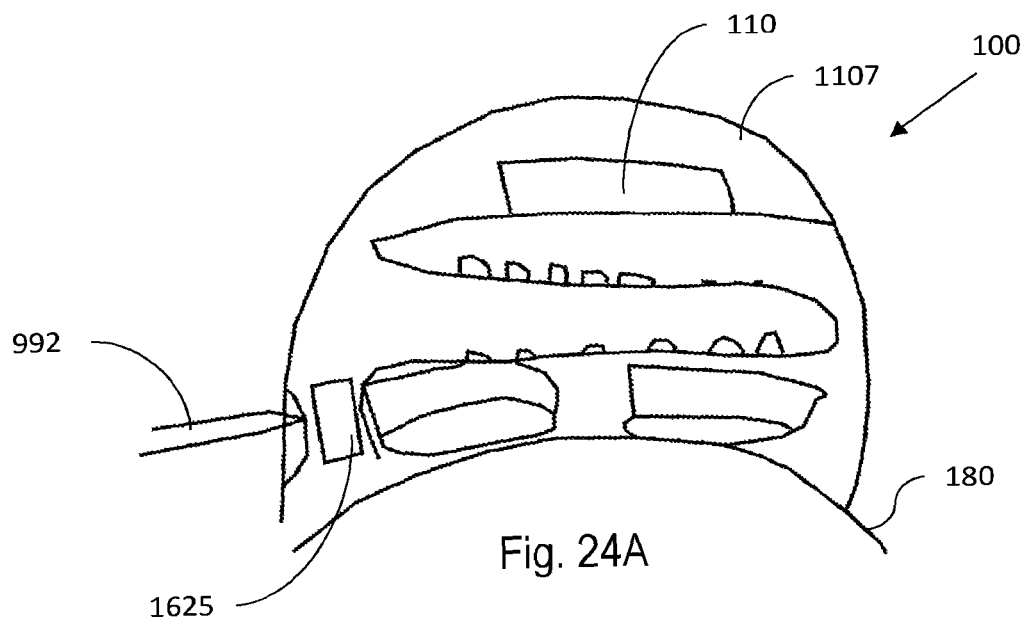
FIGS. 24A-24B illustrate side sectional views of a sensor device according to embodiments of the present disclosure.
Figure 24B:
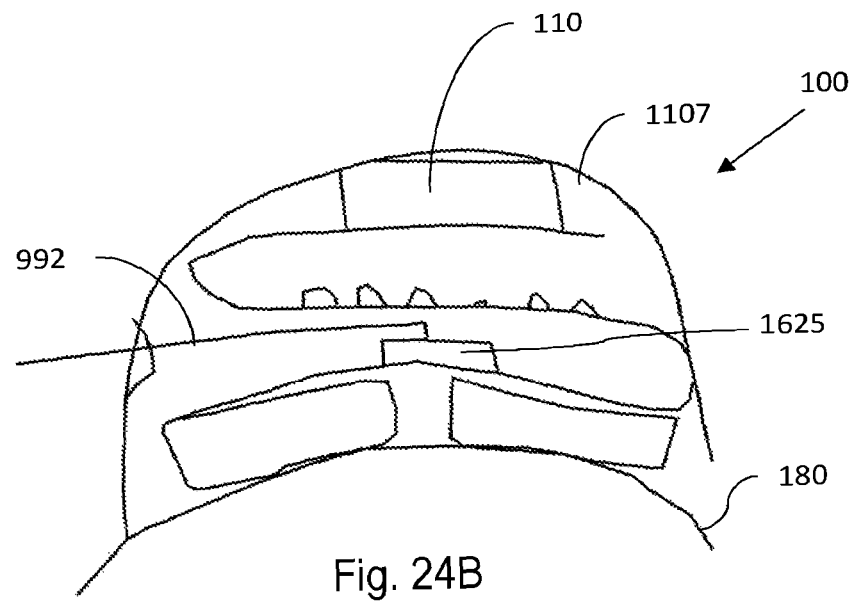

Referring now to FIGS. 24A-24B, side sectional views of a sensor device are illustrated. In various embodiments, the on/off button may be located at any suitable position on the sensor device, such as, for example, on an outwardly facing buccal side of the device for ease of access.

Figure 25A:
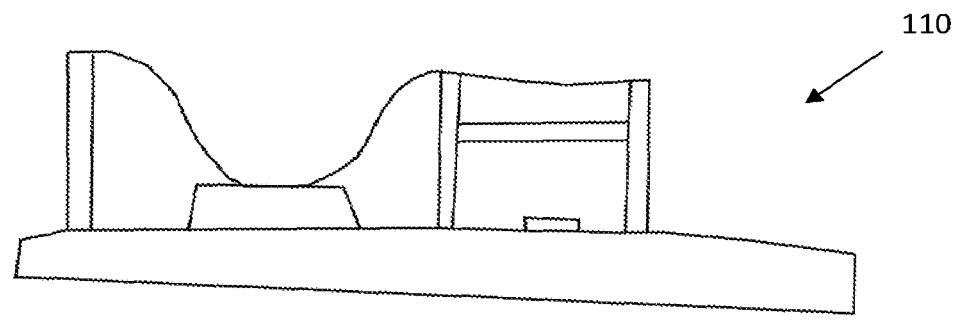
FIGS. 25A-25H illustrate side sectional views of a sensor assembly according to embodiments of the present disclosure.
Figure 25B:
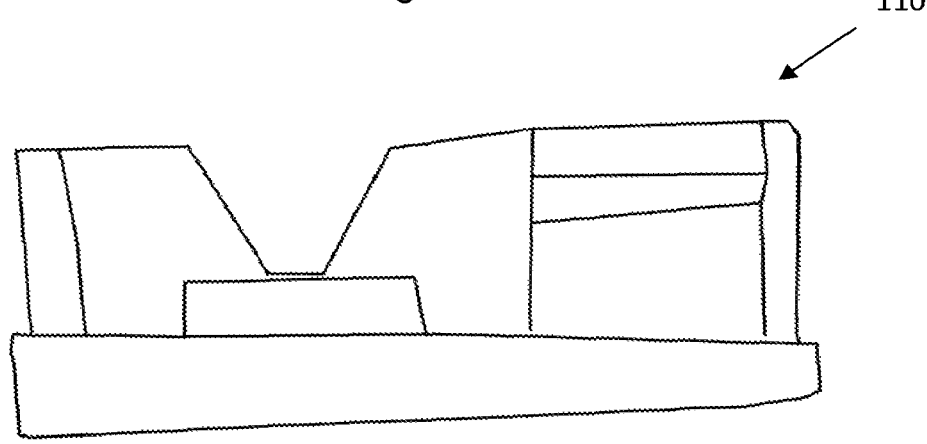
Figure 25C:
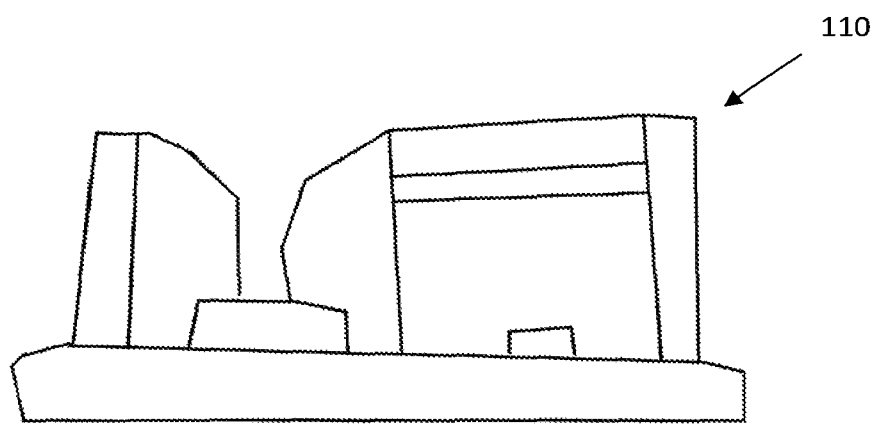
Figure 25D:
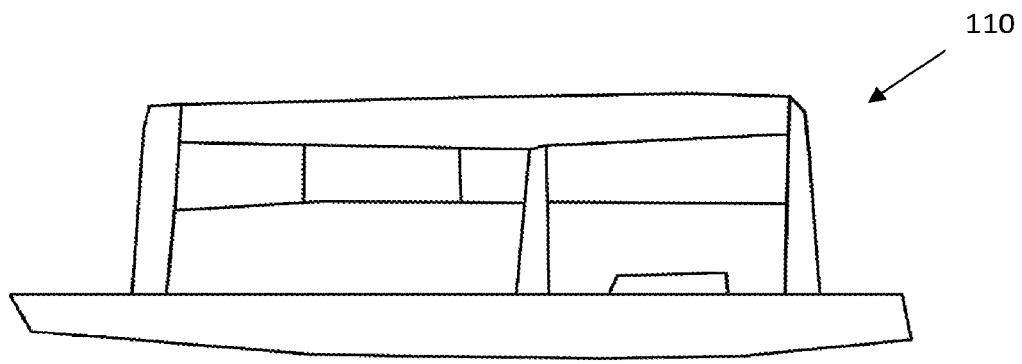
Figure 25E:
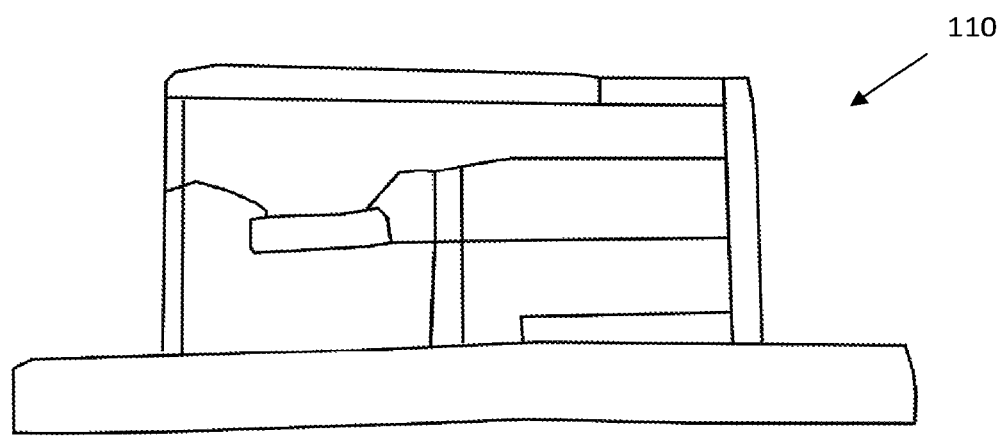
Figure 25F:
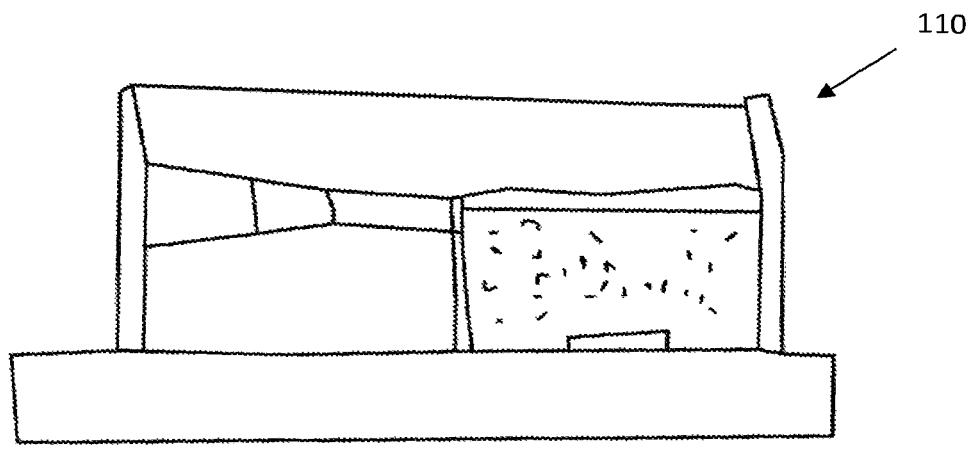
Figure 25G:
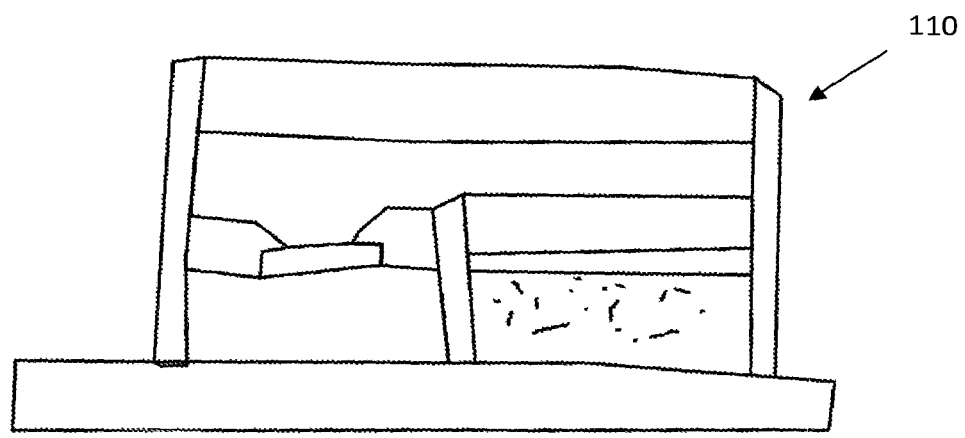
Figure 25H:
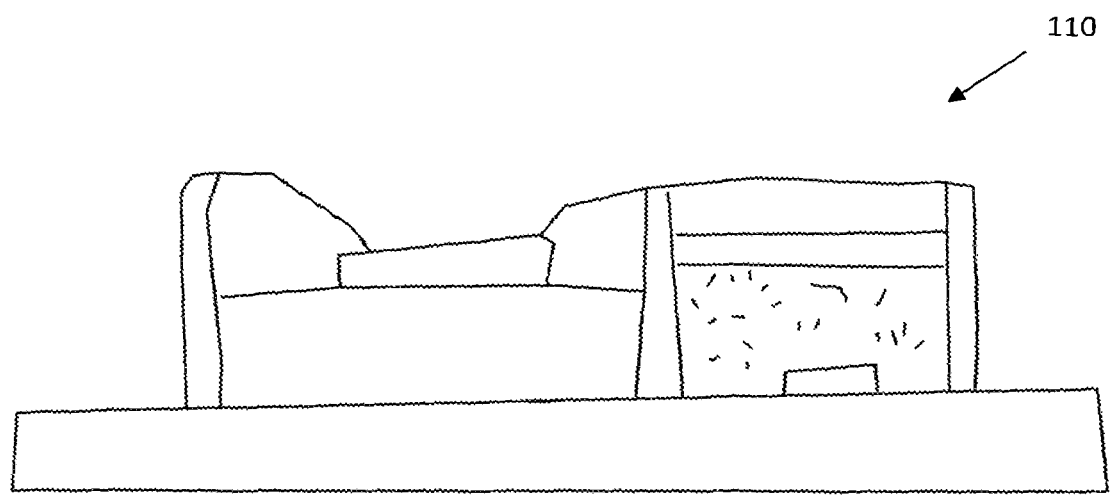

Referring now to FIGS. 25A-2511, side sectional views of a sensor assembly are illustrated.

In various embodiments, the lip of the casing may have a contour that matches the ISFET box walls.

Figure 26A:
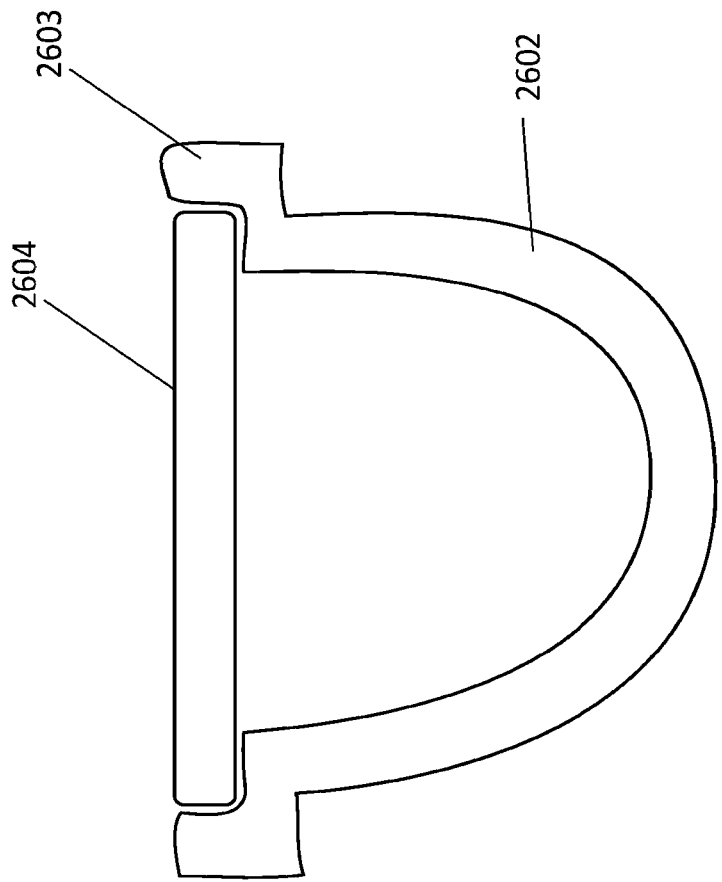
FIGS. 26A-26D illustrate a molar band cap according to embodiments of the present disclosure.
Figure 26B:
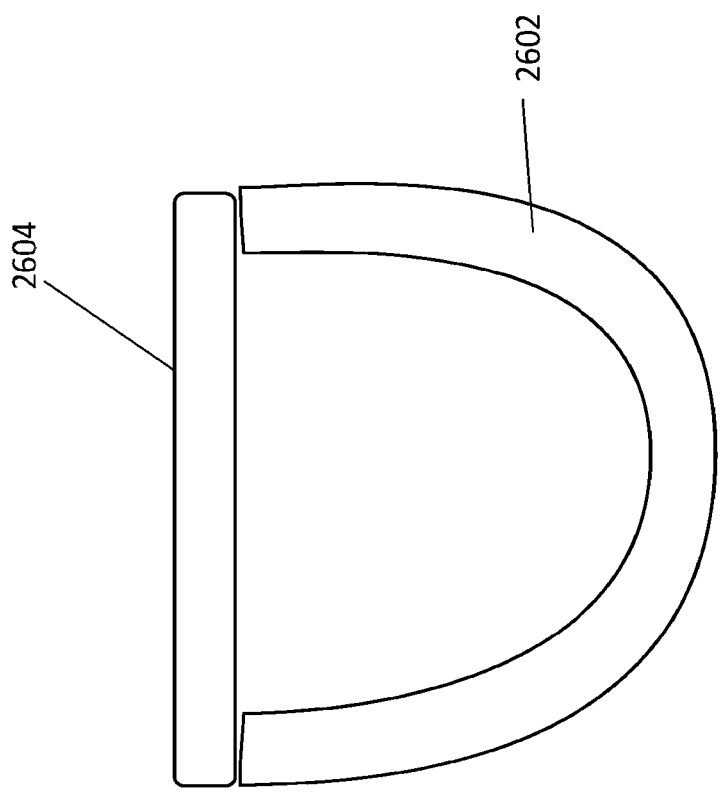
Figure 26C:
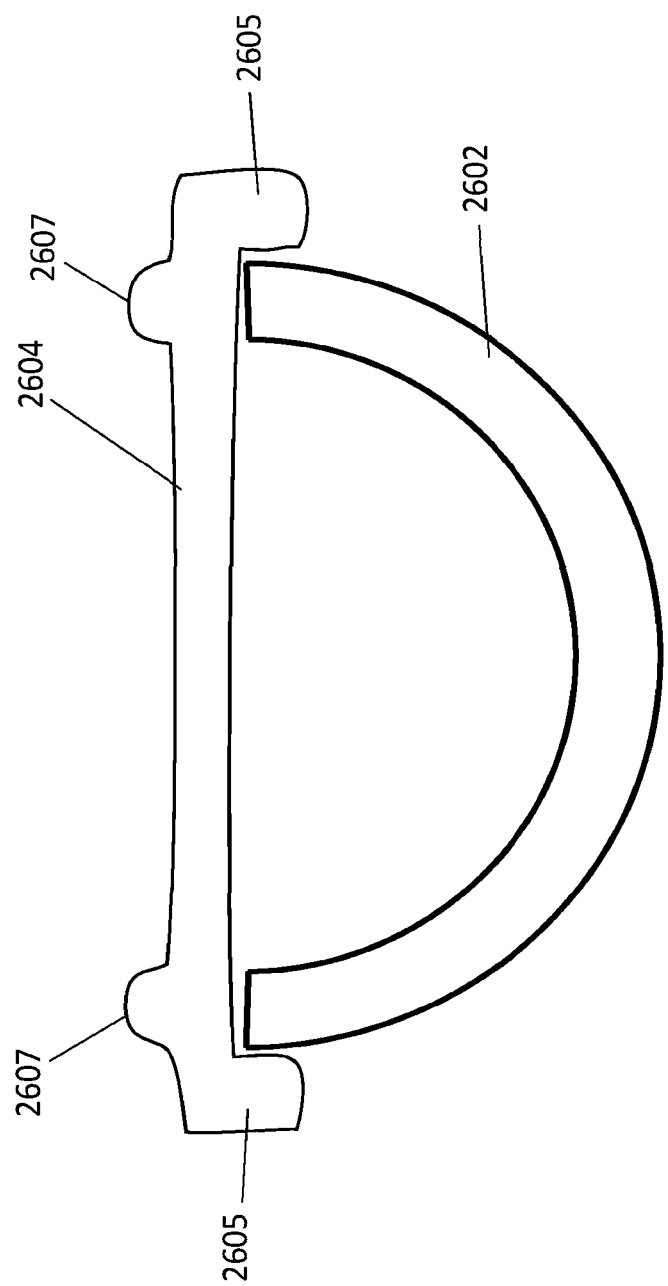

FIGS. 26A-26C illustrate a molar band cap according to embodiments of the present disclosure. In various embodiments, a cap 2604 may be affixed (e.g., welded) onto a case 2602 to fully seal the electronics inside. In various embodiments, the case 2602 and/or the cap 2604 may be made of a metal. In various embodiments, a shelf 2603 may be added to the case 2602 to allow the cap 2604 to rest slightly inside of the case 2602, such that the upper surface of the cap is flush or co-planar with the upper surface of the sidewalls of the shelf 2603. In various embodiments, the cap 2604 may be surrounded on all sides by the shelf 2603. This ensures that the cap 2604 will be positioned correctly, that there will be case material besides and beneath the cap material so a solid weld bond may form at the edge of the cap 2604, and that there will be no holes (i.e., will be sealed). In various embodiments, the shelf 2603 on the case can be completely polished away after the cap is welded to the case, as shown in FIG. 26B. FIG. 26A illustrates a first exemplary cap 2604 where, before welding, the cap 2604 extends to a case edge defined by the shelf 2603. The cap 2603 can be permanently affixed, or removably attached to the case 2602.

FIG. 26C illustrates a second exemplary cap 2604 with a downward lip 2605. In FIG. 26C, the sidewalls of the case 2602 rests inside the cap 2604 instead of vice versa (as shown in FIG. 26A). In various embodiments, the cap 2604 has one or more ridge 2607 on the top surface. In various embodiments, the ridge 2607 may be used to indicate a specific location of laser weld, e.g., the ridges 2607 can be vertically aligned with the sidewalls 2602 of the underlying case 2602.

Figure 26D:
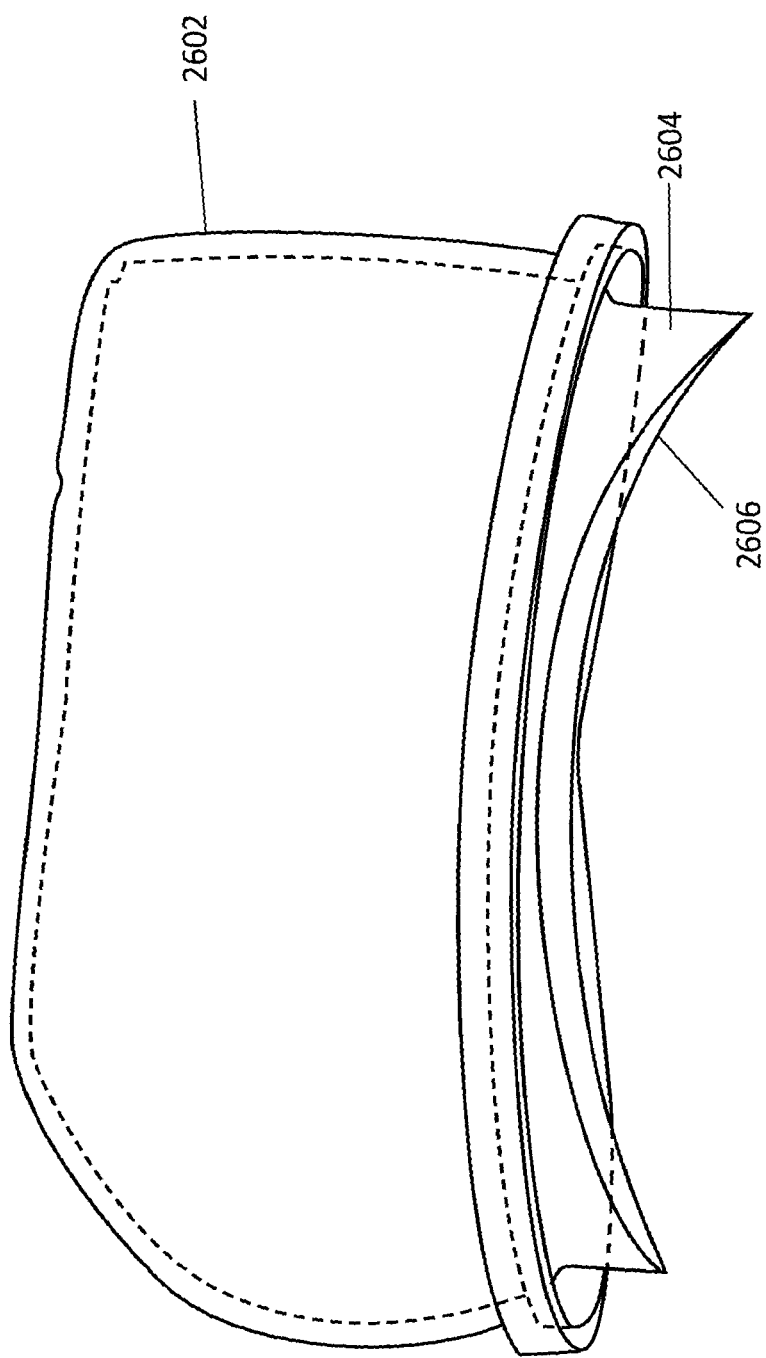

FIG. 26D illustrates a molar band cap 2604 having a cap connector rim 2606 in contact with a band. In various embodiments, because the electronics may be substantially flat, some areas may have a space or gap between the band and the cap of the sensor, especially away from the center of the tooth towards the neighboring teeth. Thus, the cap connector rim 2606 can serve as a downwardly extending skirt that seals this gap. In various embodiments, the cap 2604 may include one or more curved portions configured to coincide with the curvature of the molar band (due to the curvature of the particular tooth on which the band is placed). In various embodiments, caps may be manufactured approximating curvatures of different-sized teeth, as different-sized teeth may have different curvatures. In various embodiments the cap includes a rim of curved metal contacting the molar band. In various embodiments, if the band has less curvature than the cap rim, the rim edge may be easily filed with weld and/or polished away to decrease the curvature. In various embodiments, the rim can be welded to the band from the top, sides, and/or bottom.

FIG. 30A-30E illustrate casing internal locator rails. In various embodiments, when the circuit is loaded into the case, the internal components may need to align with the cutouts for the button, ISFET, and reference electrode. In various embodiments, movement of components when they are loaded may cause the sensor to be misaligned with the holes of the case and further cause issues with saliva contact to the sensor and with sealing the components inside the casing. In various embodiments, locating rails 3002 may be formed in the casing. In various embodiments, the locating rails 3002 may be formed in the inside of the casing. In various embodiments, the locating rails 3002 may border the sensor module and guide the sensor as the sensor is inserted into the casing, allowing a close fit during assembly. In various embodiments, the locating rails 3002 may lock the position of the sensor during subsequent assembly steps so that no movement of the sensor occurs during manufacture.

As shown in FIGS. 31-35, the system 3000 generally includes the circuitry and sensor components for measuring the range of biological parameters as described above. In the embodiment illustrated in FIGS. 31-34, sensors 3100, 3200 can be positioned on the buccal side of both ends of the retainer, with a conductive connector 3300 extending therebetween.

Figure 35:
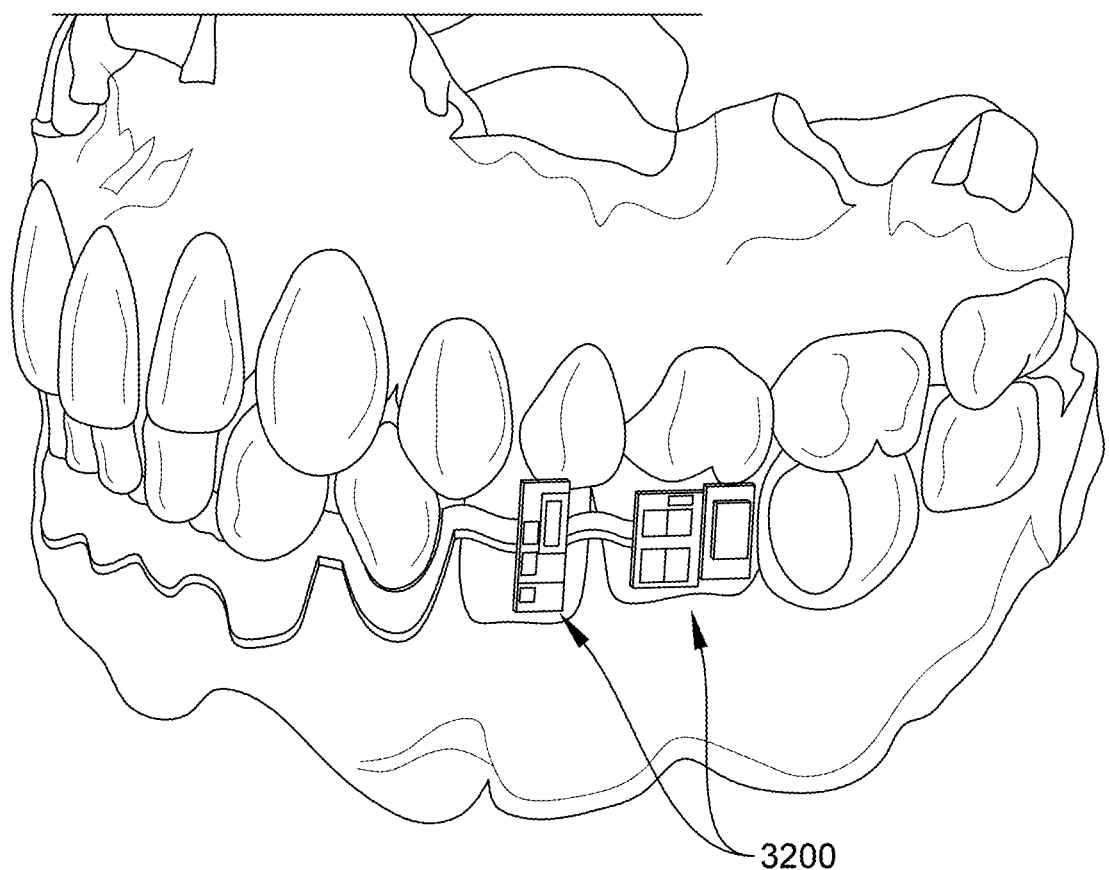
FIGS. 35-36 are schematic representations of an exemplary embodiment of the intraoral monitor (with retainer structure omitted)
Figure 36:
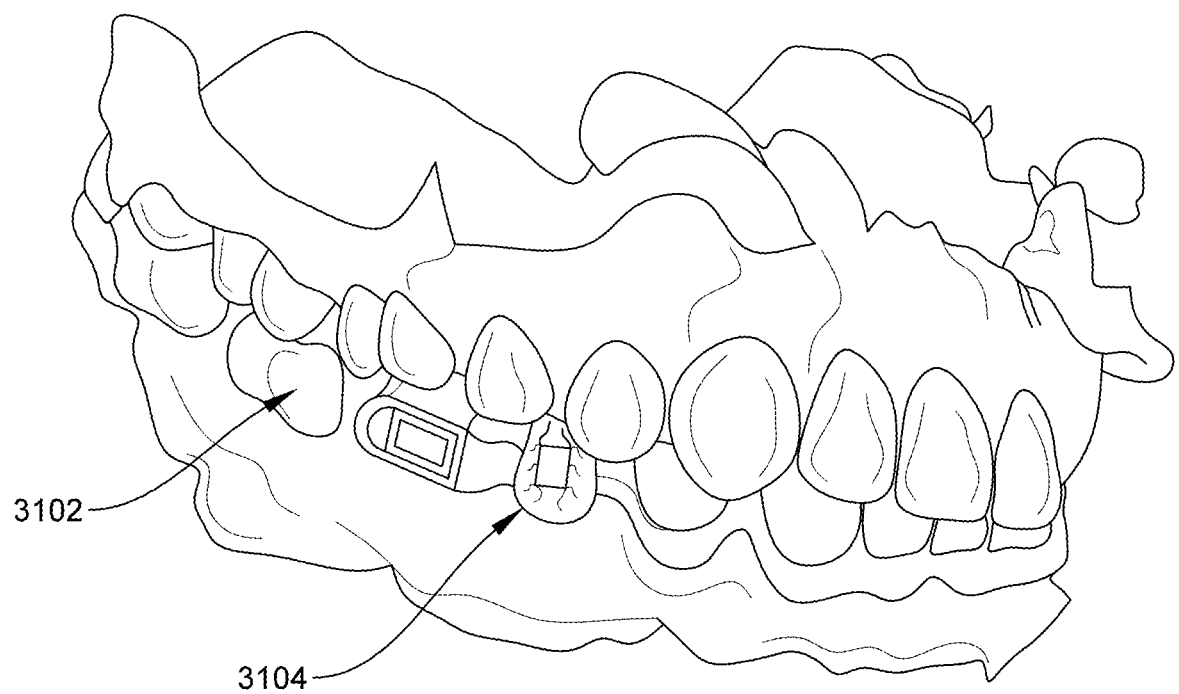
Figure 37C:
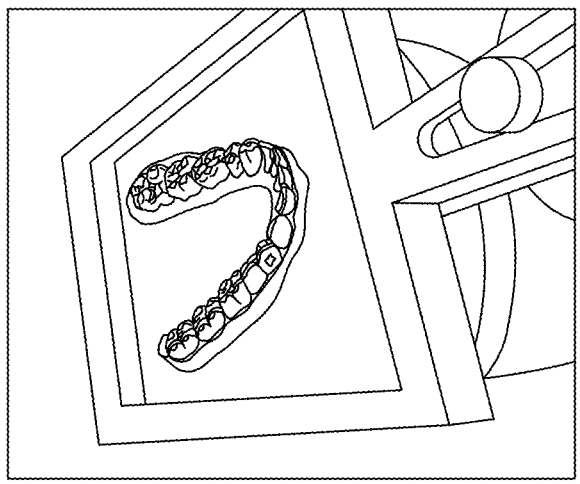
FIGS. 37A-37E are illustrations of exemplary processing steps of forming an inner retainer structure of the intraoral monitor according to embodiments of the present disclosure.
Figure 37B:
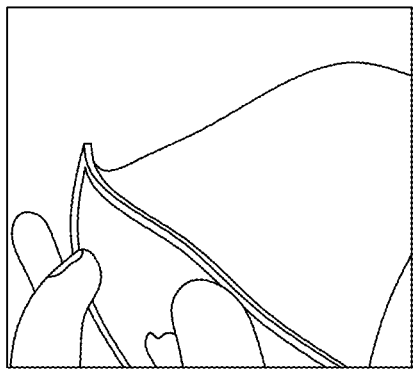
Figure 37E:
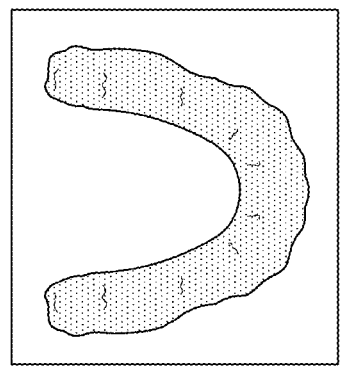
Figure 37A:
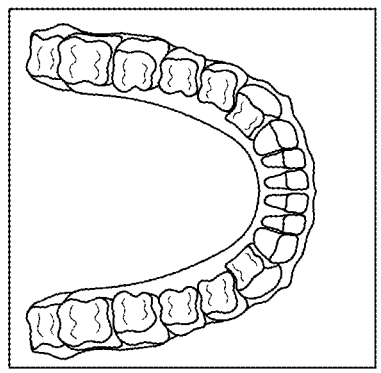
Figure 37D:
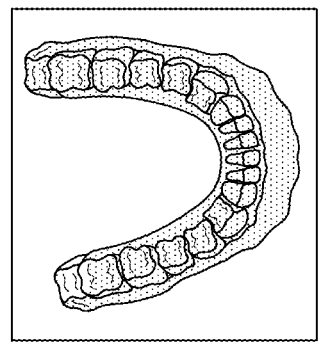

Manufacturing of these devices includes performing a three dimensional in-bite scan or modeling of the user's particular oral anatomy. From this baseline, the various components of the sensors 3100, 3200 (e.g., batteries, antenna, etc.) can be positioned to avoid interference with the user's bite. Additionally, the conductive traces of the circuitry and printed circuit board (PCB) locations are outlined based on this preliminary scan. As shown in FIGS. 35-36, this step can be performed in isolation, e.g., without the material which forms the structure of the retainer being present. The absence of the retainer material is advantageous in that it maximizes the flexibility of the sensor design such that the placement and orientation of the sensor components can be customized to each user's anatomy to ensure there is no occlusion or contact with the opposing teeth, when the user has a closed bite.

In some embodiments, the various sensor components can be distributed over multiple teeth, as shown. For example, the PCB can be positioned so that it is secured to the retainer structure at a location that coincides with, at least one, tooth (e.g., aligned with an underlying tooth rather than bridging the gap between two teeth). In other embodiments, the sensor components can be located on the retainer so as to bridge the gap between adjacent teeth. In the exemplary embodiments illustrated in FIGS. 35-36 and 46-50, the sensor components can be dispersed along the retainer structure to span across three adjacent teeth locations. For example, the battery (alkaline, lithium polymer, etc.) can be located at a first position coinciding with a first tooth location, the ion-sensitive field-effect transistor (ISFET) can be located at a second position coinciding with a second tooth location, and the antenna can be located at a third position coinciding with a third tooth location.

Also, the components can have a variety of angular orientations, or "pitch" as desired in order to provide a complimentary geometry that avoids occlusion/contact with a user's bite. For example, the sensor components can be positioned horizontally, vertically or at an angle. Furthermore, the sensor components can be non-linearly oriented, or offset, such that adjacent sensor components are not straight when travelling from one tooth to the next. In some embodiments, the retainer can include a reinforcing structure (e.g., wire) to increase rigidity and corrective force applied to the teeth; likewise, the circuitry of the connector 3300 can mirror the pattern of the reinforcing wire retainer (if present in the retainer material structure). Additionally, in some embodiments the antenna 3104 is spaced from the battery 3102 (which can include a metallic casing/enclosure) in order to reduce electromagnetic interference, as shown in FIG. 36.

The various embodiments of the device(s) presented herein can be fabricated in a wide variety of ways. As an example, some embodiments of the appliances herein (or portions thereof) can be produced using indirect fabrication techniques, such as by thermoforming over a positive or negative mold. As shown in FIGS. 37A-37E, a mold is provided (37A) and the layer of thermoplastic material (37B) is applied over the mold and vacuum formed (37C) to impart the mold geometry into the retainer (37D), and thereafter the retainer structure can be separated from the mold (37E).

Although the exemplary embodiment shown includes a polymeric retainer structure, the devices disclosed herein can be fabricated with one or more of many materials such as metal, glass, reinforced fibers, carbon fiber, composites, reinforced composites, aluminum, biological materials, and combinations thereof. The device can be shaped in many ways, such as with thermoforming or direct fabrication (e.g., 3D printing, or additive manufacturing). Additionally or alternatively, the appliance can be fabricated with machining such as an appliance fabricated from a block of material with computer numeric control machining.

The appliance can be designed specifically to accommodate the teeth of the user (e.g., the topography of the tooth receiving cavities matches the topography of the user's teeth), and may be fabricated based on positive or negative models of the user's teeth generated by impression, scanning, etc. Alternatively, the appliance can be a generic device configured to receive the teeth, but not necessarily shaped to match the topography of the user's teeth. In some embodiments, only certain teeth received by the retainer structure will be repositioned while other teeth can provide a base or anchor region for holding the retainer structure in place as it applies force against the tooth or teeth targeted for repositioning.

Figure 38:
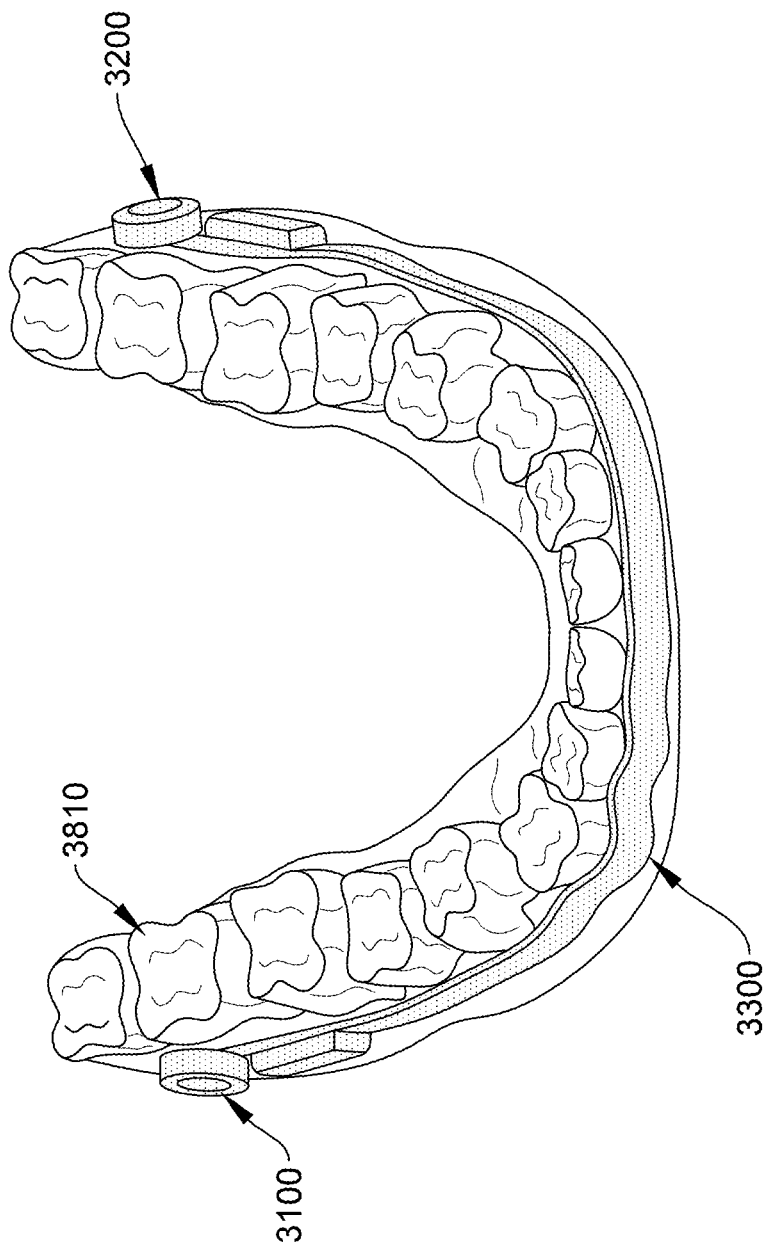
FIG. 38 is an illustration of an exemplary processing step of attaching sensor electronics to the inner retainer structure of the intraoral monitor according to embodiments of the present disclosure.

In some embodiments, a first step is to vacuum form an inner retainer structure that compliments the user's anatomy, as described above. After this first, inner, layer is formed the various electronic components of the sensors 3100, 3200 and conductive connector 3300 are coupled to the first layer 3810 thereby effectively forming a second layer, as shown in FIG. 38. These electronic components can be permanently affixed with an adhesive (e.g., epoxy or glue) which does not adversely affect their conductivity, nor impart any electromagnetic interference.

Figure 39:
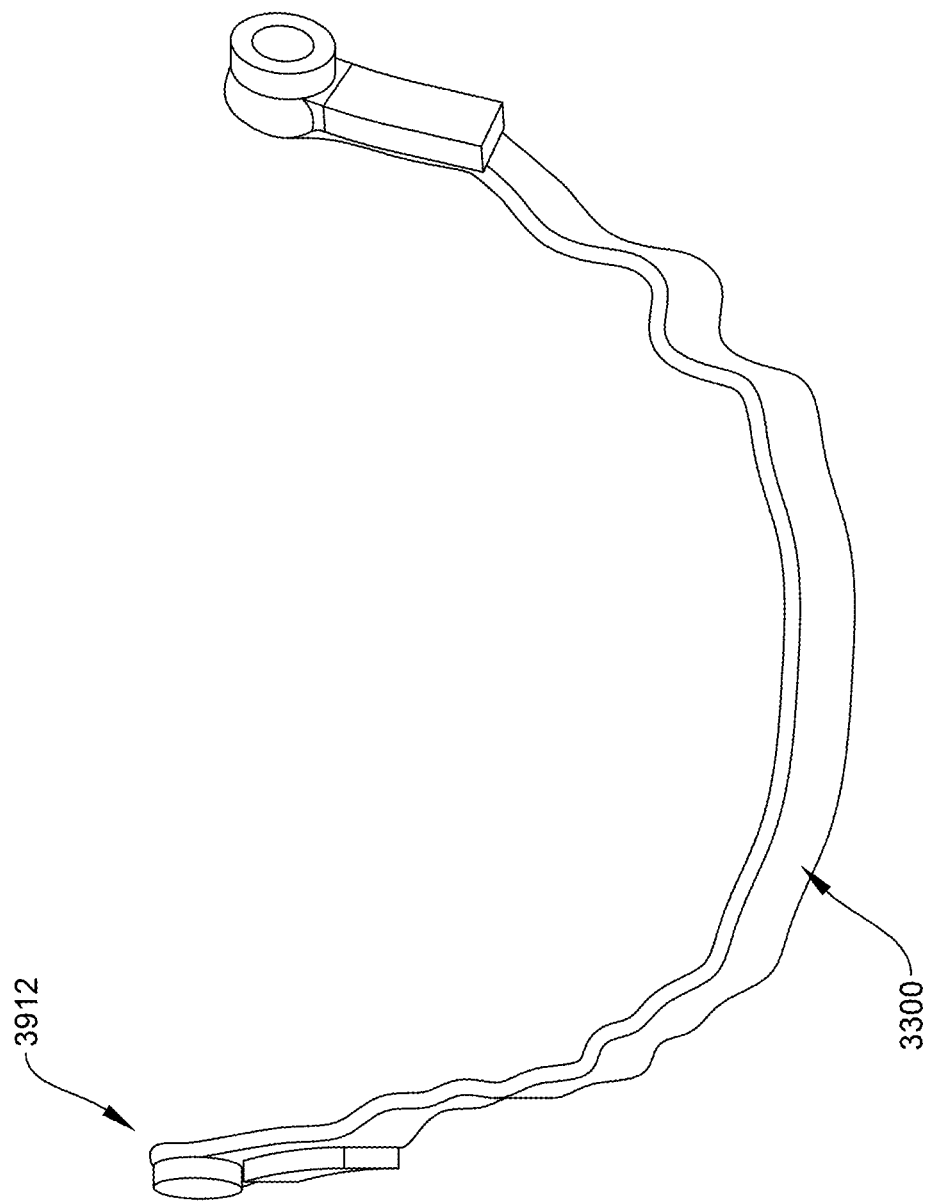
FIG. 39 is an illustration of an exemplary processing step of trimming the sensor electronics and inner retainer structure of the intraoral monitor according to embodiments of the present disclosure.
Figure 40C:
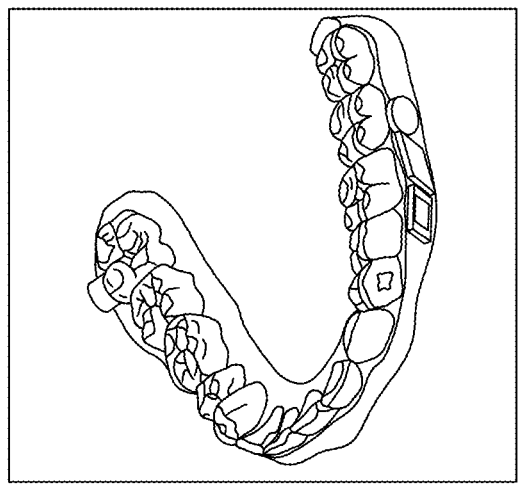
FIGS. 40A-40D are illustrations of exemplary processing steps of attaching the sensor electronics and inner retainer structure assembly of the intraoral monitor to the mold according to embodiments of the present disclosure.
Figure 40B:
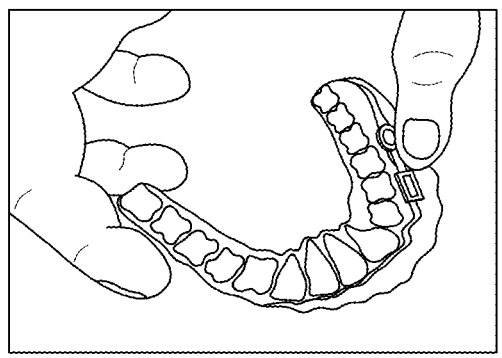
Figure 40A:
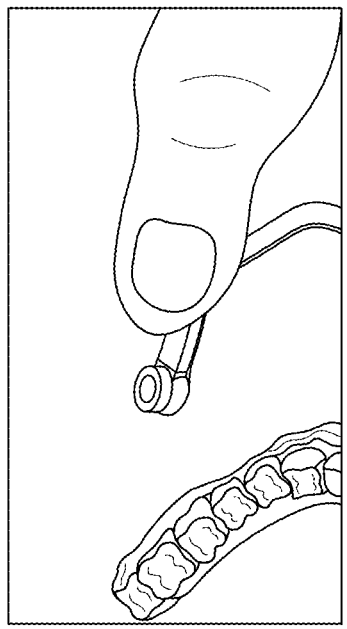
Figure 40D:
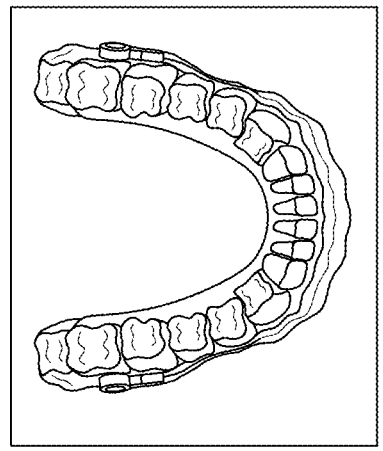

A trimming step can be performed around the perimeter or periphery of the electrical component(s) footprint to separate and remove the retainer material that is not affixed to the sensor electronics, as described above. In other words, the two-layer portion (i.e., inner retainer layer with electronic circuitry attached) is separated from the peripheral portion of the single-layer retainer (i.e., the remainder of the first, inner retainer layer that is free of electronic circuitry), as shown in FIG. 39. This trimming can be performed by a milling apparatus (e.g. CNC Machine) which operates about five distinct axes. In some embodiments, the trim line is offset by approximately 1 mm-2 mm from the electronic component(s) edge(s) or outline. This offset can provide an edge or lip 3912 extending around the entire periphery of the electronic footprint (as shown in FIG. 39). In some embodiments, this lip is only present at select locations.

This two-layer assembly (i.e., first inner retainer layer with attached electronic circuitry) can then be positioned back on the mold, as shown in FIGS. 40A-40D. An additional curing step (e.g., ultraviolet) can be applied at select locations to secure the two-layer assembly to the mold and prevent undesired relative movement.

In some embodiments, a plurality of reference posts, or pegs, can be (temporarily) attached to various electronic components of the sensor and serve as indicia of the location of the underlying components of interest. Also, the post(s) prevent any subsequent coatings (discussed in further detail below) from being applied to the underlying electronics. This is advantageous in that it facilitates establishing an electrical connection after subsequent coating/processing steps are completed. In other words, another vacuum forming operation is to be performed on the two-layer assembly of FIGS. 40A-40D, which applies an outer layer over the entire two-layer assembly—but the presence of this outer layer would prevent electrical contact with the sensor components, so openings to access the underlying electrical components is required. Also, due to the compact construction, it is difficult to machine cut openings in the outer layer as the tooling risks damage to the underlying electrical components. Thus the post(s) can be attached to the desired components, allow for subsequent coating and thermoforming, and then be removed to create an opening above the sensor components to enable electrical connection.

Figure 41:
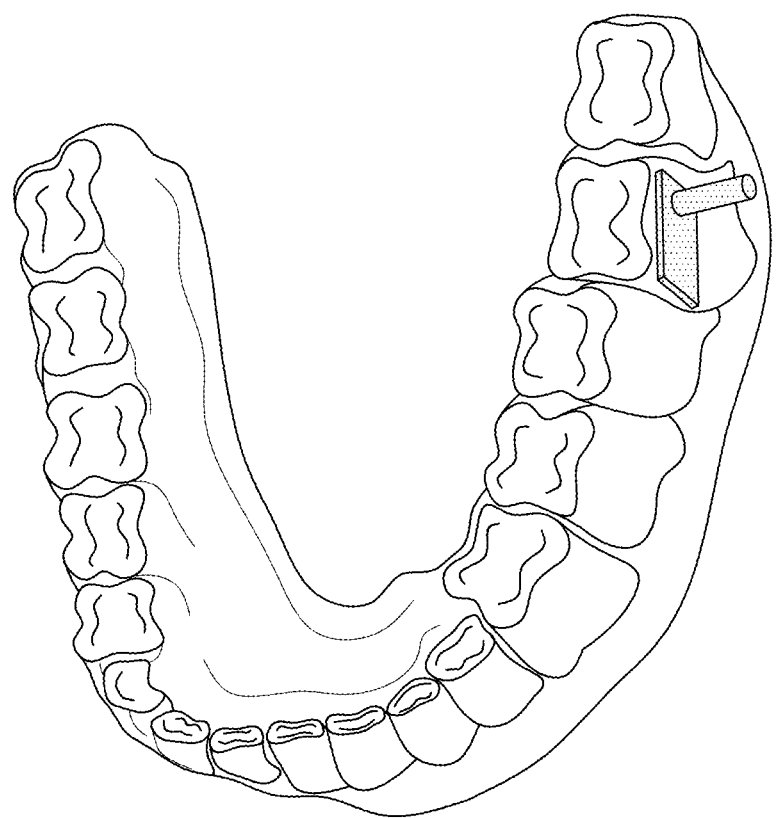
FIG. 41 is an illustration of an exemplary embodiment of the intraoral monitor incorporated into a retainer including posts according to embodiments of the present disclosure.

For example, a reference post can be positioned on top of the sensor(s) 3100, 3200 (e.g. on/off button) and the corresponding reference electrode(s). The posts can extend outwardly (e.g., perpendicular) from the buccal side of the retainer, as shown in FIG. 41. These posts can be shaped in a variety of geometries (e.g., cylindrical, faceted sides, etc.) with the perimeter of the post defining the shape of the access hole (once the post is removed) to the underlying electrical component(s) of the sensor.

Figure 42:
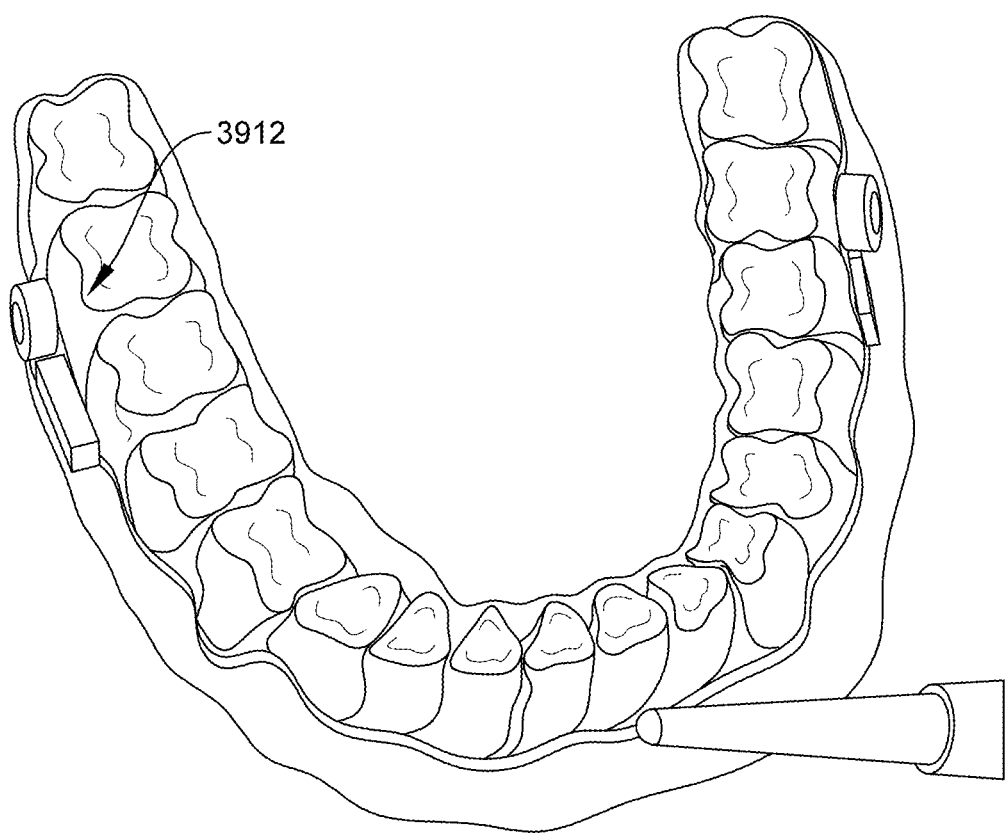
FIG. 42 is an illustration of an exemplary processing step of applying adhesive to the outer surface of the sensor electronics and inner retainer structure of the intraoral monitor according to embodiments of the present disclosure.

Next, an adhesive coating (e.g., epoxy) can be applied to the outer (buccal side) surface about the lip 3912 of the first retainer layer, as shown in FIG. 42. Additionally, the adhesive coating can be applied to the sides of the sensor 3100 and/or any posts that may be present.

Figure 43C:
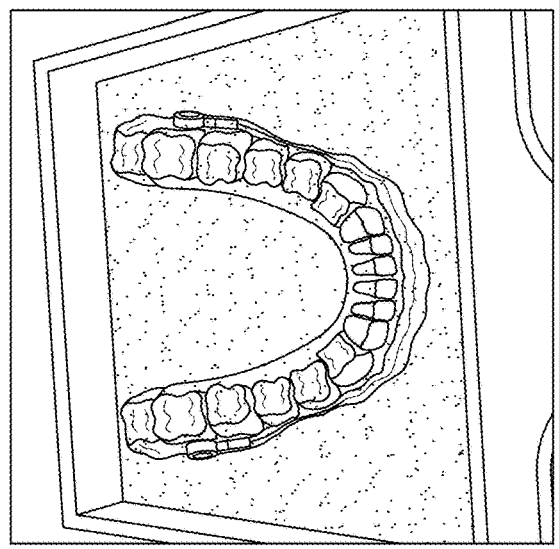
FIGS. 43A-43C are illustrations of exemplary processing steps of forming an outer retainer structure of the intraoral monitor according to embodiments of the present disclosure.
Figure 43B:
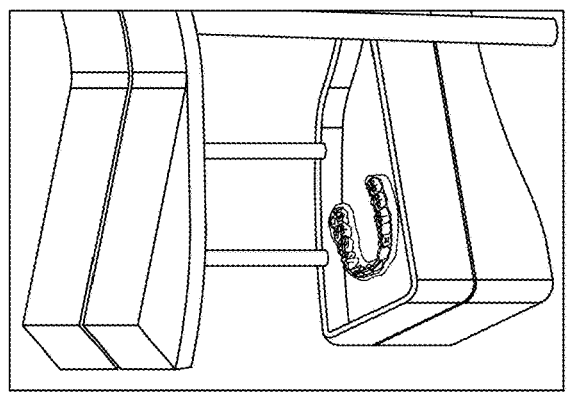
Figure 43A:
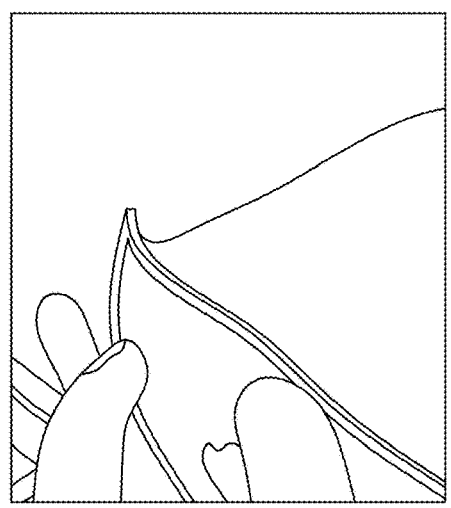

Another layer of the retainer material can be formed around the, trimmed, inner retainer layer and electronic circuitry attached thereto, as shown in FIGS. 43A-43C. This outer layer, upon bonding to the lip 3912 of the inner layer, sandwiches the circuitry therebetween and forms a seal around the electronic components of the device. An additional curing (e.g., ultraviolet) step can then be performed to form a waterproof assembly.

Figure 44B:
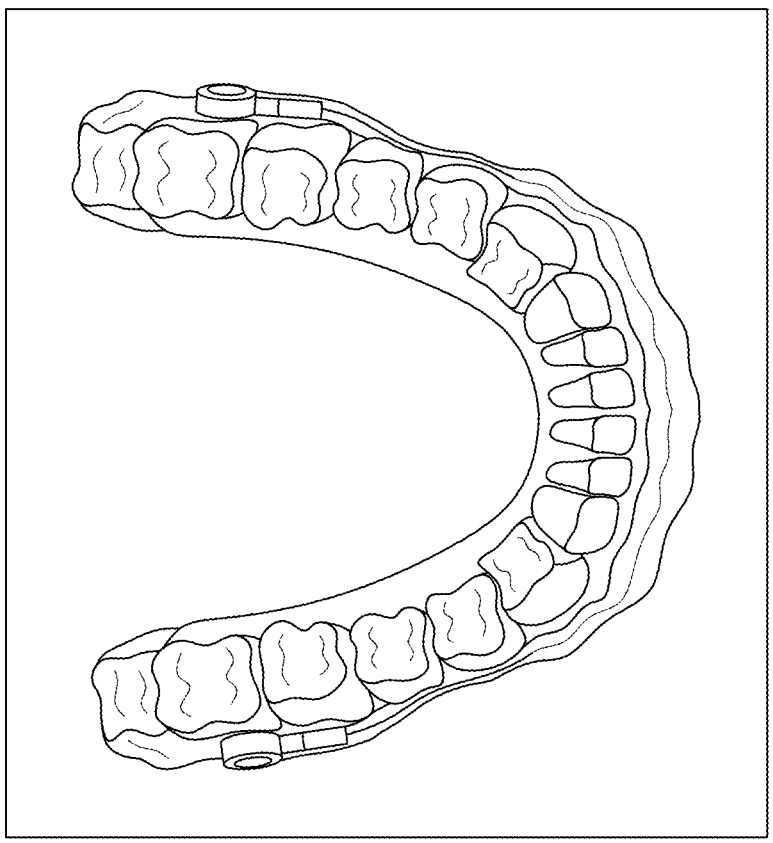
FIGS. 44A-44B are illustrations of an exemplary processing step of trimming the completed retainer structure of the intraoral monitor according to embodiments of the present disclosure.
Figure 44A:
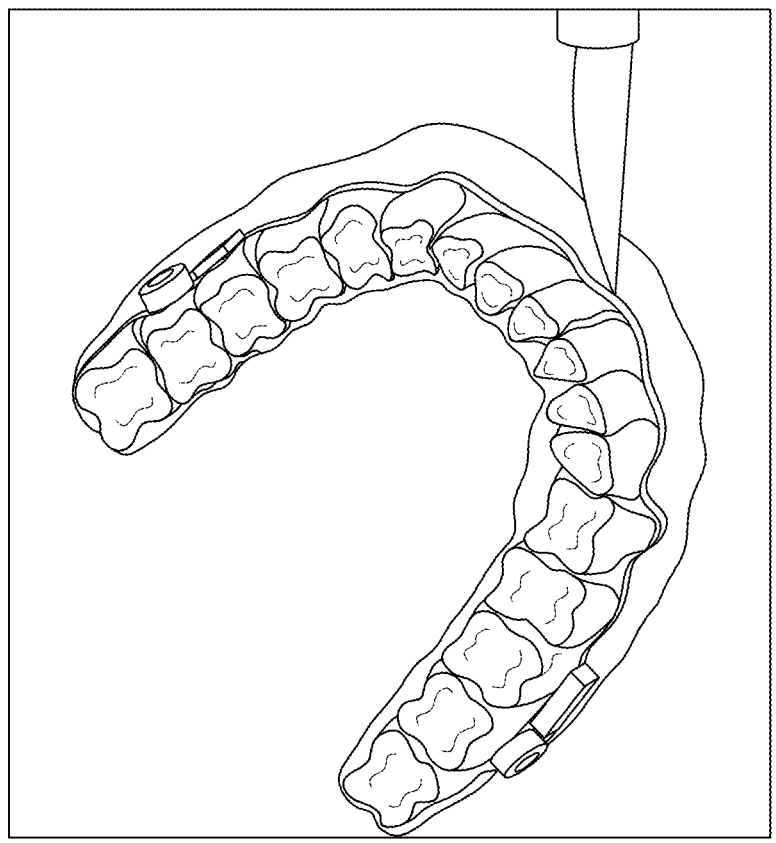
Figure 45B:
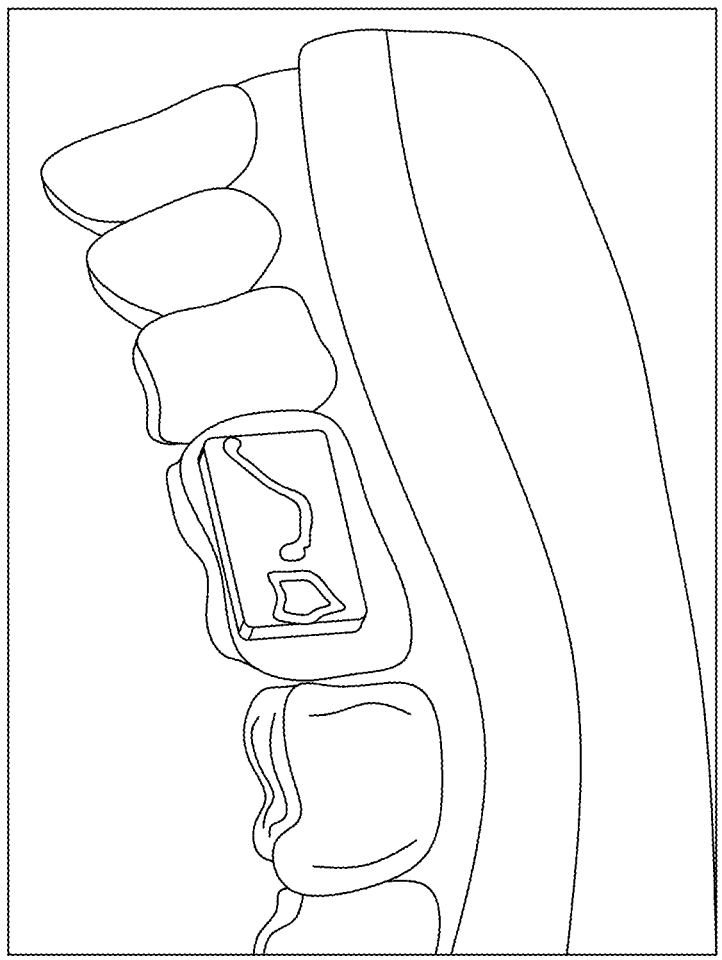
FIGS. 45A-45C are illustrations of an exemplary embodiment of the intraoral monitor incorporated into a retainer after the posts (as shown in FIG. 41) are removed according to embodiments of the present disclosure.
Figure 45A:
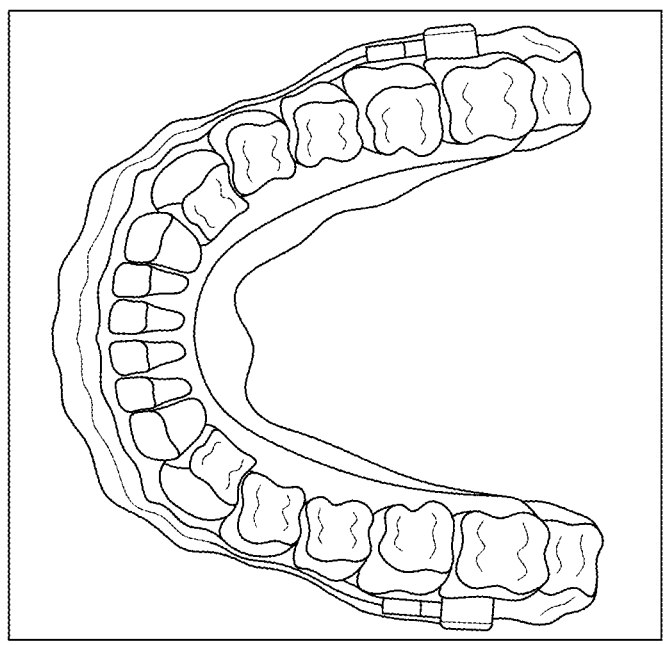
Figure 45C:
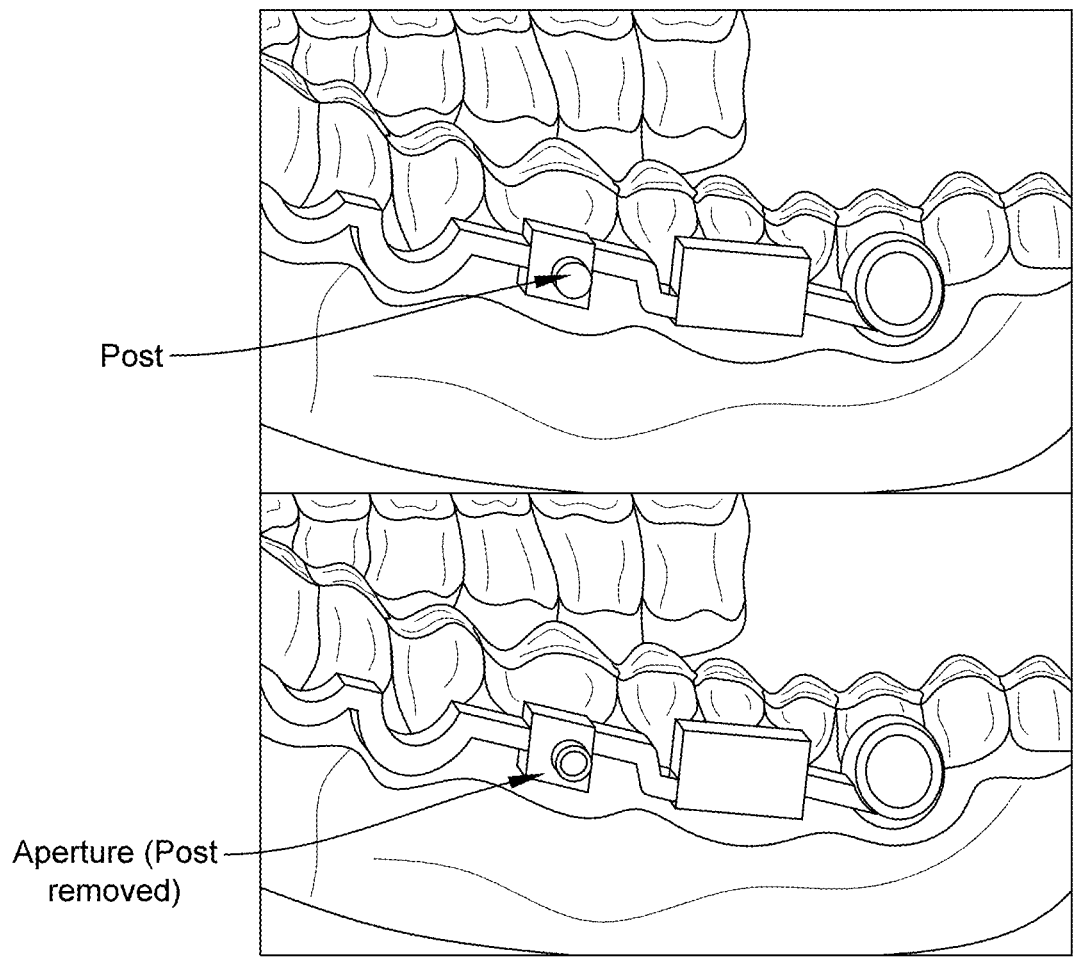
Figure 46C:
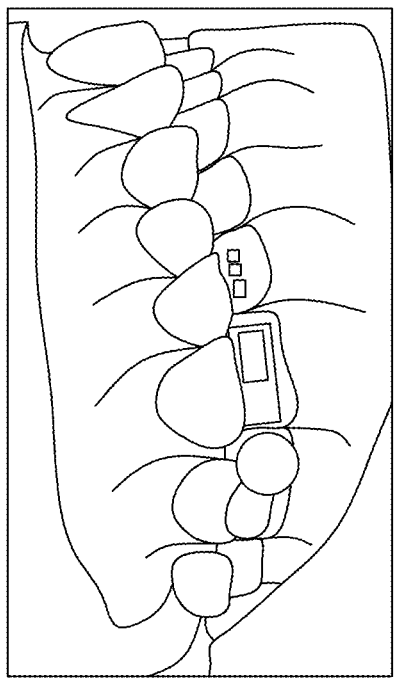
Figure 46A:
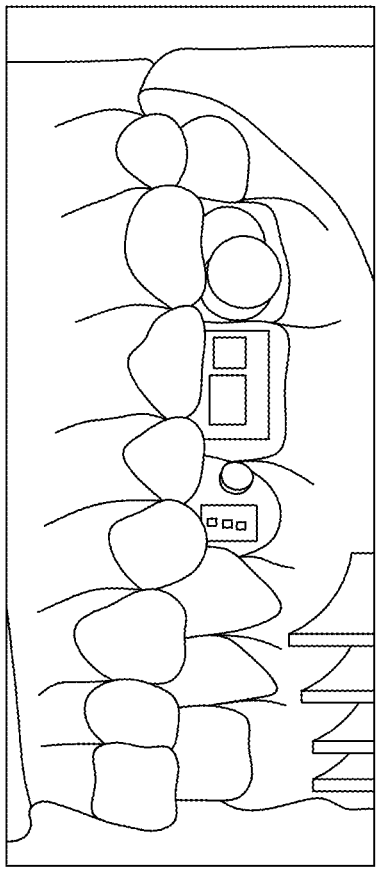
Figure 46B:
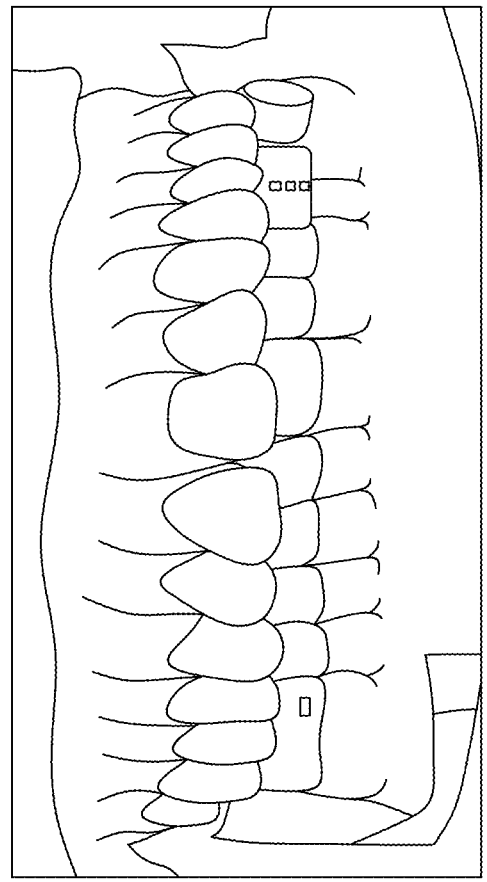
Figure 47A:
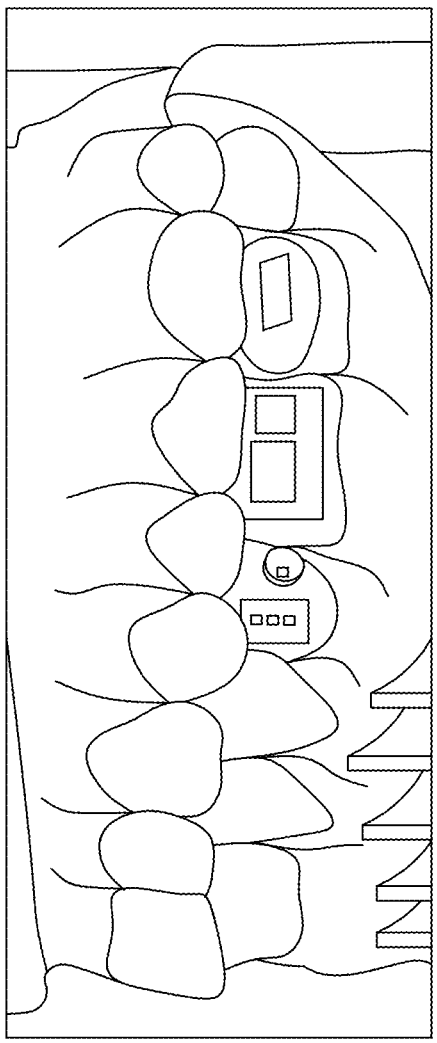
Figure 47B:
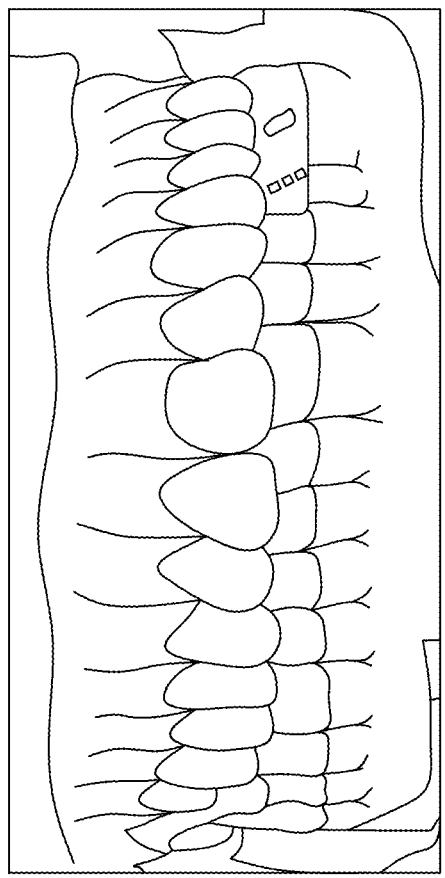
Figure 48A:
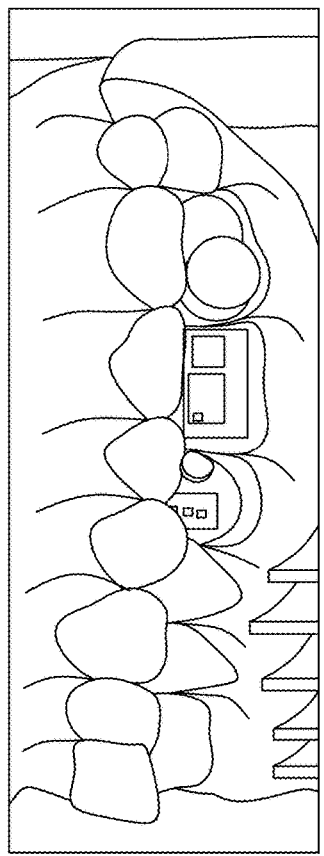
Figure 48B:
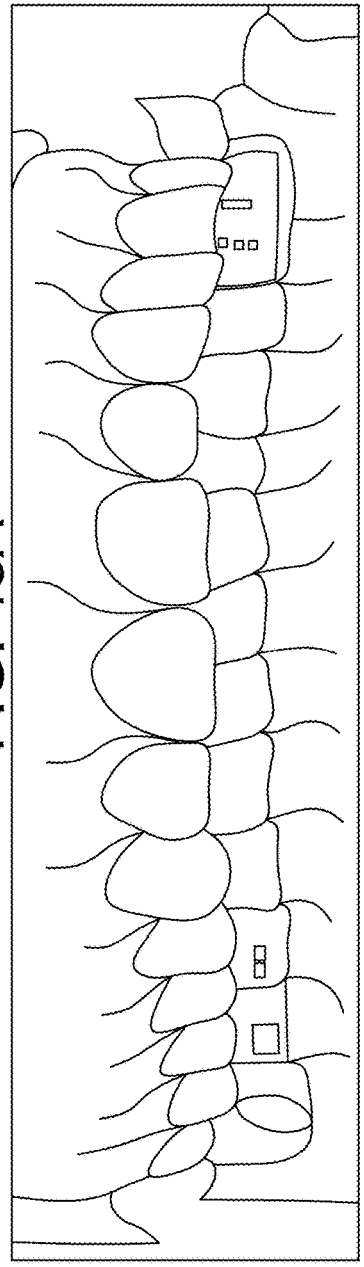
Figure 48C:
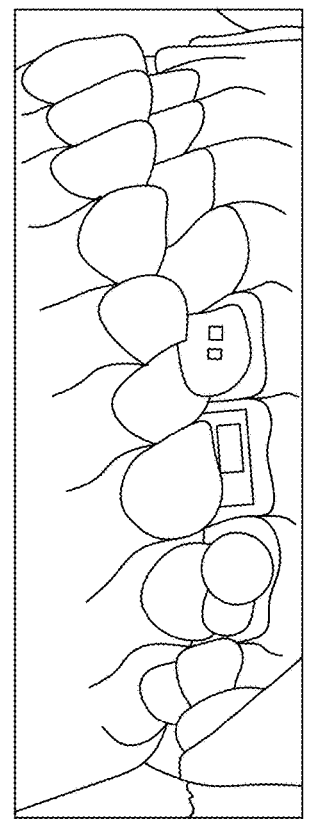
Figure 50C:
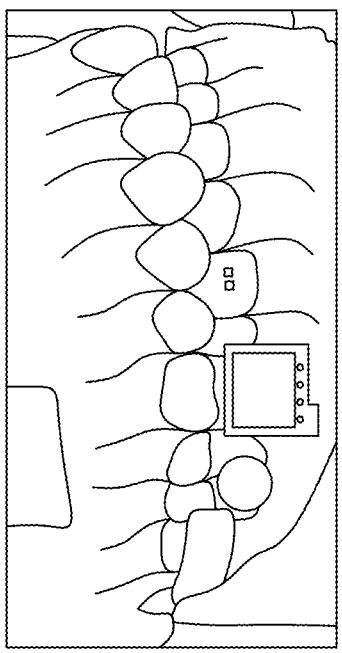
Figure 50A:
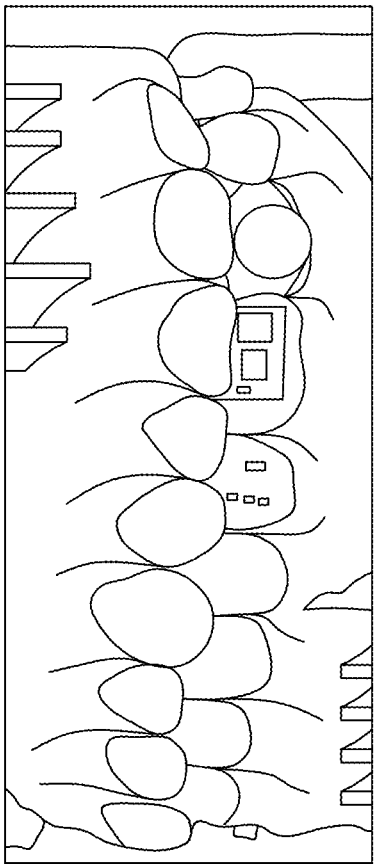
Figure 50B:
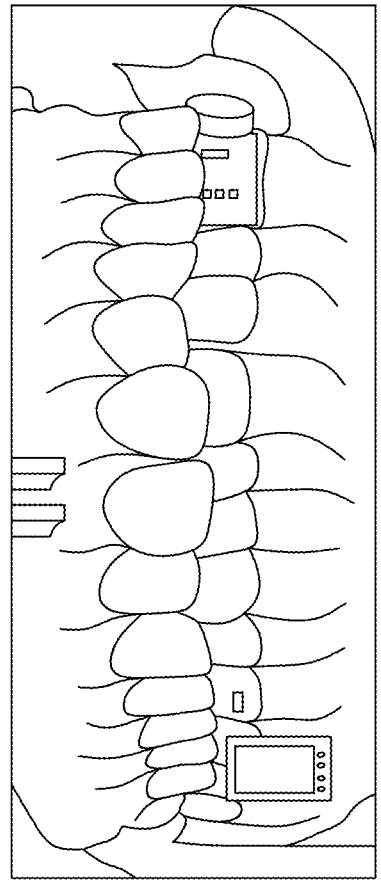

Another trimming operation can be performed on the outer retainer layer along the gingival line to tailor the device with a fitted edge customized to the user's anatomy and maximize comfort, as shown in FIGS. 44A-44B. Also, if present, the posts can be removed by, e.g., cutting the sensor/post interface so that the sensor (or other underlying electrical component) is exposed for operation, as shown in FIGS. 45A-45C. Thereafter, the completed retainer can be removed from the mold, by inserting a tool (e.g., knife) between the mold and the inner layer of the retainer to sever the adhesive bond therebetween and dislodge the device, as shown in FIGS. 46A-46D.

In accordance with another aspect of the disclosure, the devices disclosed herein can be manufactured on a per-order, individual, basis as described in connection with FIGS. 31-50, and/or on a mass production scale including a plurality of devices, as shown in FIGS. 21-24. In some embodiments, the plurality of devices to be manufactured in bulk can be formed with a common geometry (or "bite" profile). Additionally or alternatively, some or each, of the devices to be manufactured in the bulk processing embodiment of FIGS. 51-54 can have distinct profiles geometries that are unique to each user profile.

Figure 51:
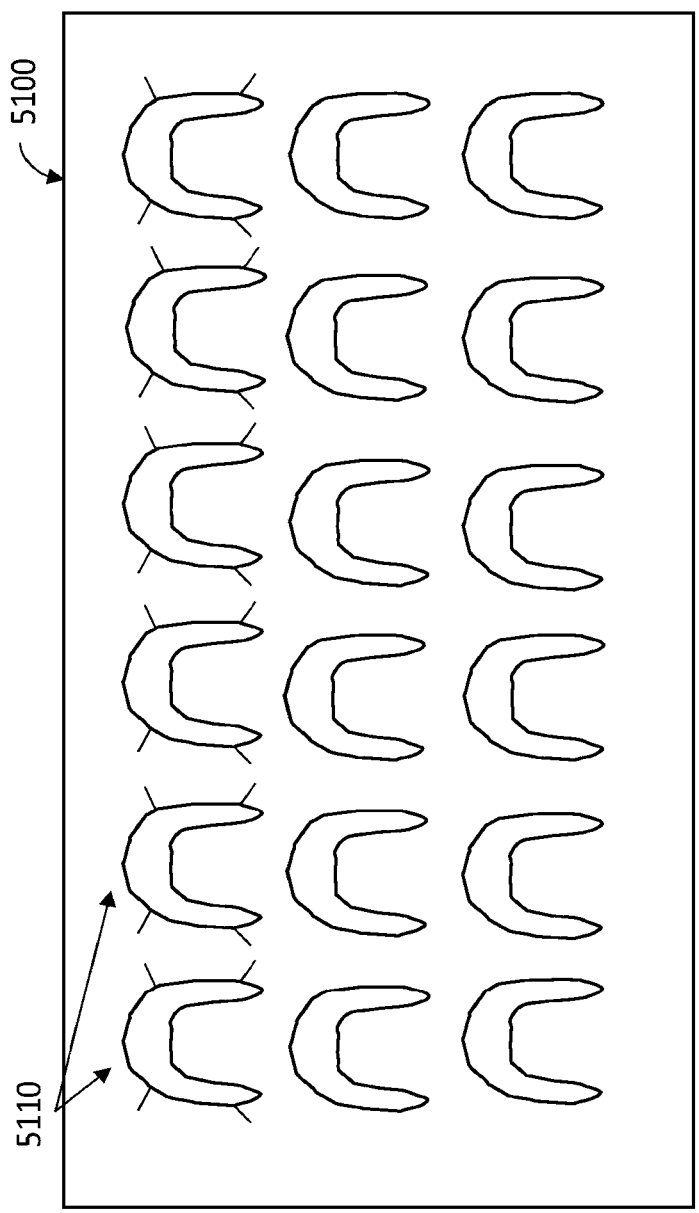
FIGS. 51-54 are schematic representations of a technique for mass production of the intraoral monitors according to embodiments of the present disclosure.
Figure 52:
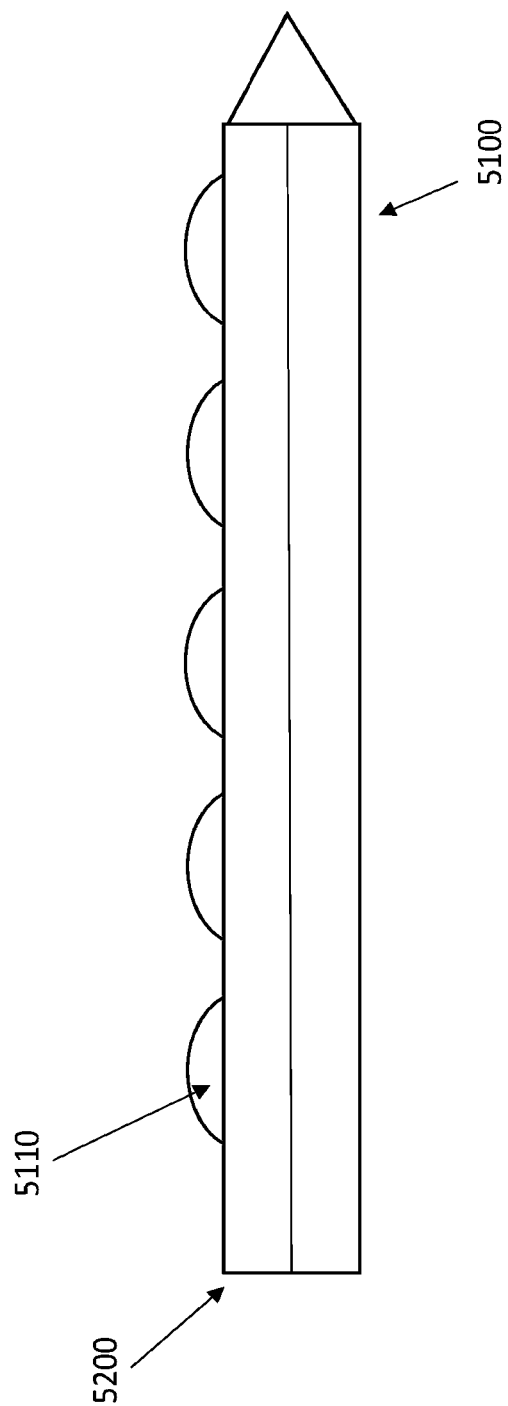

In the exemplary embodiment shown in FIGS. 51-54, an array of dental impressions 5110 from multiple patients can be placed and secured on a vacuum forming bed 5100, as shown in the top view of FIG. 51. A layer of polymer film 5200 can be applied over the impressions 5110 disposed within the vacuum forming bed, as shown in the side view of FIG. 52. This polymer film 5200 can be deposited at elevated temperature and pressed down over all of the impressions 5110 at once, creating a polymer sheet molded around each of the impressions.

Figure 53:
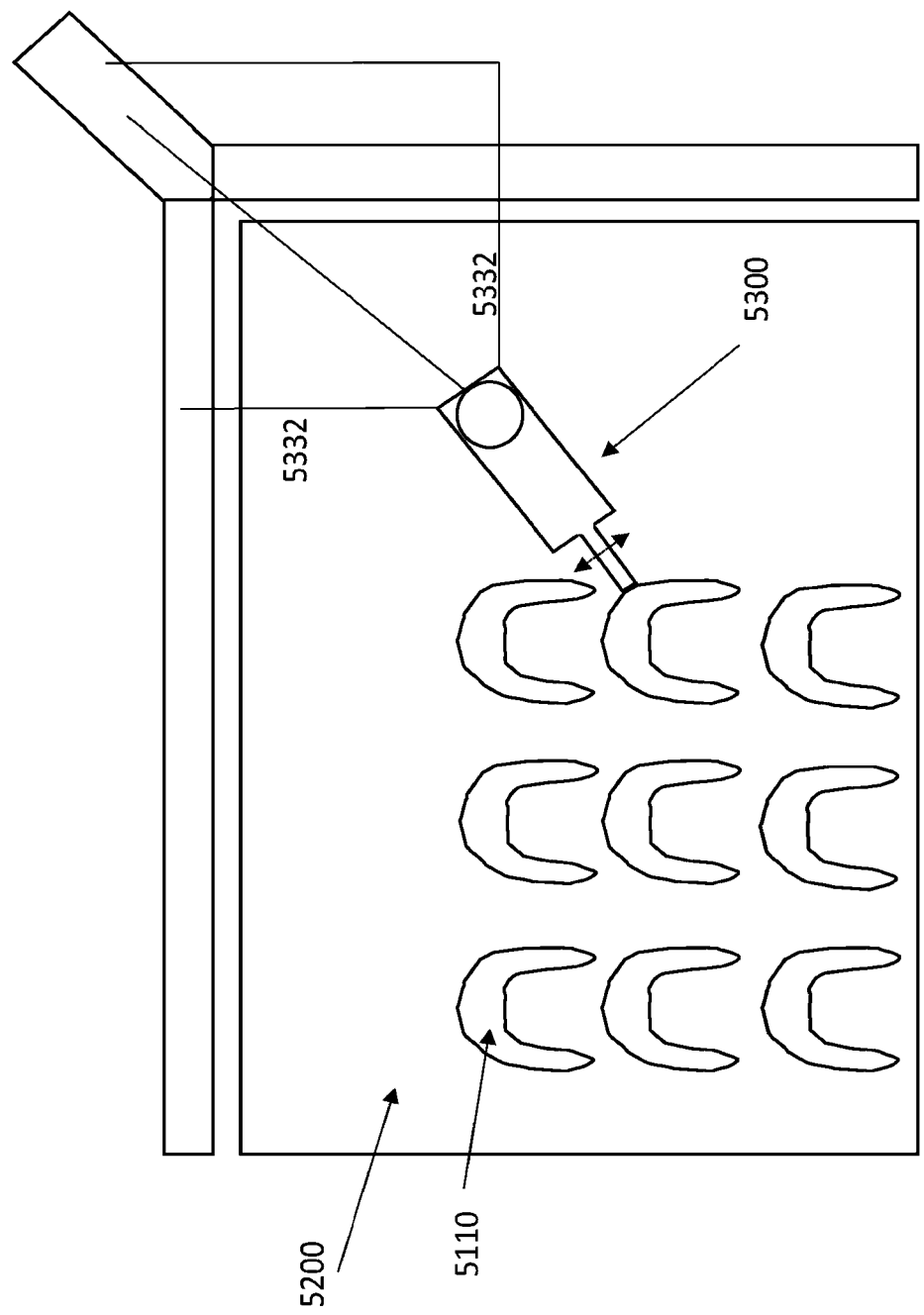

A trimming operation can then be performed on the polymer sheet (which forms the inner retainer layer) along the perimeter/boundary of the impression 5110 to separate it from the remainder of the polymer sheet 5200, as shown in FIG. 53, so that each retainer can be removed from its impression mold. The trimming apparatus 5330 can be mounted to tracks 5332 that permit movement horizontally and vertically (or globally) about the X-Y axis of the array of impressions 5110, as well as articulate angularly around the contour of the retainer (and also about depth or height in the Z-axis). In some embodiments the trimming is performed automatically via computer vision or 3D scanning system overlooking the vacuum forming bed 5200 from above, and a multi-axis (e.g., 3-axis or 5-axis) mill attached to a gantry bordering the vacuum forming bed.

Figure 54:
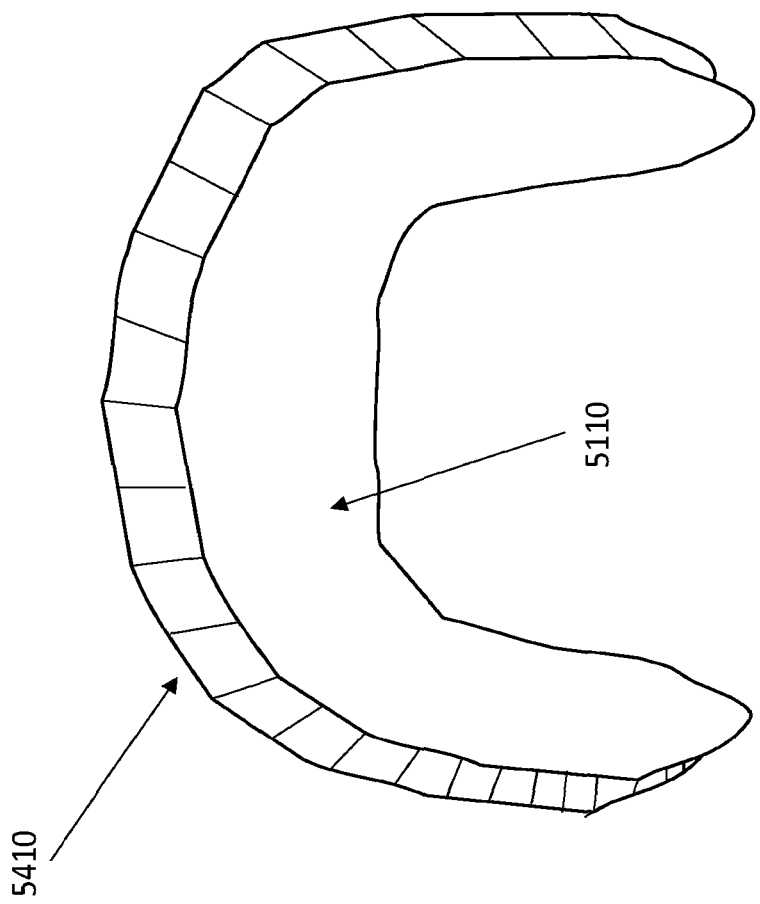

Next, the sensor electronics (e.g., PCB) are fitted into the inner retainer. In some embodiments the sensor electronics are positioned on the inner retainer while the inner retainer is still attached to the impression mold 5110 and residing in the vacuum forming bed 5200. For example, a jig can be employed to position, and press, the sensor electronics between adjacent teeth locations on the retainer to impart a complimentary contour on, e.g., the PCB, and secure it in place, as shown in FIG. 54. To facilitate and expedite bonding, a large ultraviolet lamp can be positioned over the vacuum forming bed 5100 and programmed to automatically activate when all (or predetermined number at select locations) are positioned within range, to simultaneously cure the plurality of PCBs to their respective inner retainers.

As described above with respect to the manufacture of individual retainers in FIG. 39, a trimming operation is performed on the batch of two-layer (polymer+electronics) retainer assemblies. Thereafter the outer retainer layer is formed by repeating the process as described in connection with FIGS. 51-54.

In accordance with another aspect of the present disclosure, all sensor component placement (and pegs) with respect to the retainer layers can be performed automatically by a programmable pick-and-place type gantry apparatus.

A method of forming a retainer including sensor(s) to measure biological variables (e.g., pH) includes thermoforming a first layer of the retainer within a mold (which can be configured with a user's bite profile), removing the first layer of the retainer from the mold and attaching the sensor components (e.g., batteries, PCB, antenna, etc.) to the first layer of the retainer. This subassembly of first retainer layer with sensor circuitry is trimmed to form a lip of the first layer of material extending beyond the boundary edge of the sensor components. Next, a second layer of retainer material is vacuum formed over the first layer and sensor circuitry.

Figure 55:
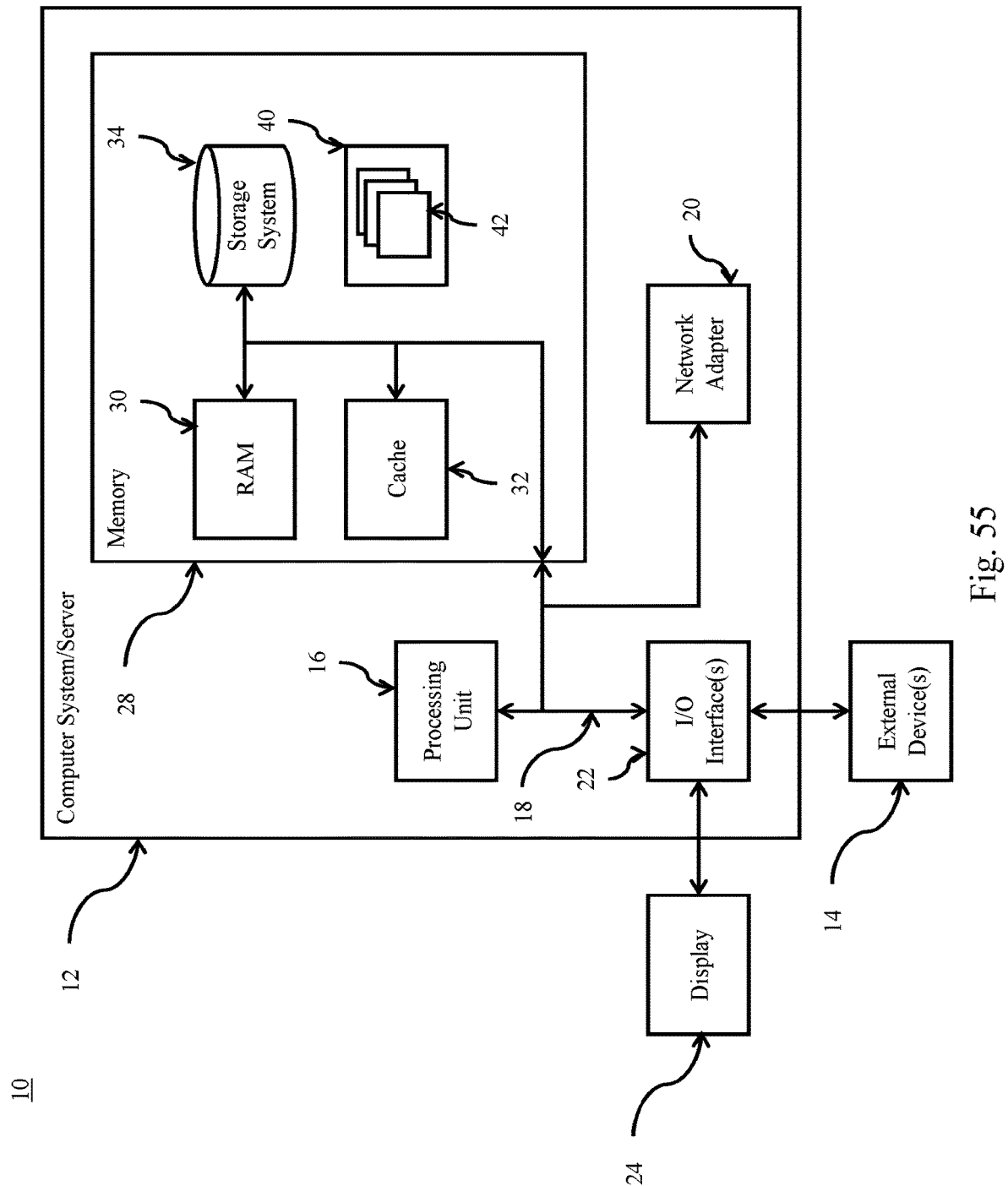
FIG. 55 depicts an exemplary computing node according to embodiments of the present disclosure.

Referring now to FIG. 55, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 55, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of forming an oral device to measure biological variables comprising:
   providing a mold, the mold configured to impart a contour of an oral retainer sized to extend about a plurality of teeth;
   forming a first layer of a retainer with the mold, wherein the first layer of retainer retains the mold contour;
   removing the first layer of the retainer from the mold;
   attaching at least one sensor component to the first layer of the retainer, the at least one sensor component having a profile and defining a boundary edge;
   trimming the first layer of the retainer at a location(s) spaced from the boundary edge of the at least one sensor component to form a lip of the first layer of material extending beyond the boundary edge of the at least one sensor component;
   attaching the first layer of the retainer and at least one sensor component to the mold;
   forming a second layer of the retainer with the mold, wherein the first layer of retainer retains the mold contour, and
   wherein the at least one sensor component is disposed between the first and second layer.

2. The method of claim 1, wherein the lip has a uniform dimension circumscribing the boundary edge of the at least one sensor component.

3. The method of claim 1, wherein the lip has a non-uniform dimension along the boundary edge of the at least one sensor component.

4. The method of claim 1, wherein the lip is disposed at select locations.

5. The method of claim 1, further comprising attaching at least one post to the at least one sensor component, the post(s) attached prior to forming the second layer of the retainer.

6. The method of claim 5, wherein the post(s) extend outwardly in a generally perpendicular direction from the at least one sensor component.

7. The method of claim 5, wherein the post(s) are attached to the on/off button of the at least one sensor.

8. The method of claim 5, further comprising removing the post(s) from the at least one sensor component after forming the second layer of the retainer.

9. The method of claim 8, wherein an aperture is formed in the second layer of the retainer.

10. The method of claim 1, wherein the first and second layers of the retainer are vacuum formed.

11. The method of claim 1, wherein the mold is contoured to the anatomy of an upper jaw of a user.

12. The method of claim 1, wherein the at least one sensor component is disposed at the end(s) of the retainer.

13. The method of claim 1, wherein the at least one sensor component is disposed at the end(s) of the retainer, and an electrical connector extends therebetween.

14. The method of claim 1, wherein the at least one sensor component is disposed along multiple locations coinciding with a plurality of teeth.

15. The method of claim 1, wherein the at least one sensor component is disposed on the buccal side of the retainer.

16. The method of claim 1, wherein each retainer is formed independently and customized to the anatomy of a user.

17. The method of claim 1, wherein a plurality of molds are provided and a plurality of first layers of the retainer are formed simultaneously.

18. The method of claim 17, wherein removing the plurality of first layers of the retainer from the plurality of molds includes trimming the perimeter of each first layers of the retainer.

19. The method of claim 1, wherein the at least one sensor component is a printed circuit board.

20. The method of claim 19, wherein the printed circuit board is configured to have a complimentary contour to the tooth shape of the user.

* * * * *